US011471478B2

(12) United States Patent
Wittkowski

(10) Patent No.: US 11,471,478 B2
(45) Date of Patent: Oct. 18, 2022

(54) USE OF CYCLODEXTRINS IN DISEASES AND DISORDERS INVOLVING PHOSPHOLIPID DYSREGULATION

(71) Applicant: Asdera LLC, New York, NY (US)

(72) Inventor: Knut M. Wittkowski, New York, NY (US)

(73) Assignee: ASDERA LLC, New York, NY (US)

( * ) Notice: Subject to any disclaimer, the term of this patent is extended or adjusted under 35 U.S.C. 154(b) by 0 days.

(21) Appl. No.: 16/647,476

(22) PCT Filed: Sep. 28, 2018

(86) PCT No.: PCT/US2018/051604
§ 371 (c)(1),
(2) Date: Mar. 13, 2020

(87) PCT Pub. No.: WO2019/067269
PCT Pub. Date: Apr. 4, 2019

(65) Prior Publication Data
US 2020/0276225 A1    Sep. 3, 2020

Related U.S. Application Data

(60) Provisional application No. 62/565,053, filed on Sep. 28, 2017, provisional application No. 62/573,658, filed on Oct. 17, 2017, provisional application No. 62/586,826, filed on Nov. 15, 2017, provisional application No. 62/643,694, filed on Mar. 15, 2018, provisional application No. 62/679,912, filed on Jun. 3, 2018.

(51) Int. Cl.
*A61K 31/724* (2006.01)
*A61K 47/54* (2017.01)

(52) U.S. Cl.
CPC .......... *A61K 31/724* (2013.01); *A61K 47/542* (2017.08)

(58) Field of Classification Search
CPC .......................... A61K 31/724; A61K 47/542
USPC ........................................................ 514/58
See application file for complete search history.

(56) References Cited

U.S. PATENT DOCUMENTS

| 6,890,549 | B2 | 5/2005 | Artiss et al. |
| 7,664,616 | B2 | 2/2010 | Wittkowski |
| 7,932,294 | B2 | 4/2011 | Satyam |
| 8,288,378 | B2 | 10/2012 | Kim et al. |
| 9,034,846 | B2 | 5/2015 | Cataldo et al. |
| 2007/0015736 | A1 | 1/2007 | Glausch et al. |
| 2010/0022512 | A1 | 1/2010 | Wisdom et al. |
| 2010/0104634 | A1 | 4/2010 | Kalantri et al. |
| 2011/0172188 | A1 | 7/2011 | Mouthon et al. |
| 2015/0216895 | A1 | 8/2015 | Wittkowski |
| 2015/0284469 | A1 | 10/2015 | Simpson et al. |
| 2015/0002893 | A1 | 11/2015 | Ma |
| 2016/0151410 | A1 | 6/2016 | Ma |
| 2016/0206581 | A1 | 7/2016 | Wittkowski |
| 2017/0044590 | A1 | 2/2017 | Haldar et al. |
| 2017/0216342 | A1 | 8/2017 | Era et al. |
| 2018/0207198 | A1 | 7/2018 | Salome et al. |
| 2020/0000840 | A1 | 1/2020 | Wittkowski |

FOREIGN PATENT DOCUMENTS

| CA | 3076821 | 9/2018 |
| CN | 101704761 | 12/2010 |
| EP | 14841451.9 | 9/2014 |
| EP | 3041577 | 7/2016 |
| EP | 17769520.2 | 3/2017 |
| EP | 3199166 | 8/2017 |
| EP | 18863127.9 | 9/2018 |
| EP | 3432880 | 1/2019 |
| IL | 272912 | 8/2018 |
| IN | 202017008920 | 8/2018 |
| KR | 10-2020-7012367 | 9/2018 |
| NZ | 763623 | 9/2018 |
| SA | 520411435 | 8/2018 |
| WO | WO 2005011710 | 2/2005 |
| WO | WO 2009/136179 A1 | 11/2009 |
| WO | WO 2013016696 | 1/2013 |
| WO | WO 2013064579 | 5/2013 |
| WO | WO 2013163455 | 10/2013 |

(Continued)

OTHER PUBLICATIONS

Szente et al. Fatty Acid-Cyclodextrin Complexes: Properties and Applications. Journal of Inclusion Phenomena and Molecular Recognition in Chemistry 16:339-354, 1993. (Year: 1993).*
Sakurai et al. Dietary α-cyclodextrin reduces atherosclerosis and modifies gut flora in apolipoprotein E-deficient mice. Mol. Nutr. Food Res. 61, 8, 2017, 1600804 (First published: Jan. 19, 2017) (Year: 2017).*
Ceballos et al. Composition of goat and cow milk produced under similar conditions and analyzed by identical methodology. Journal of Food Composition and Analysis 22 (2009) 322-329. (Year: 2009).*
Fenyvesi et al. Cyclodextrins in Food Technology and Human Nutrition: Benefits and Limitations. Critical Reviews in Food Science and Nutrition, 56:1981-2004 (2016). (Year: 2016).*

(Continued)

*Primary Examiner* — Yih-Horng Shiao
(74) *Attorney, Agent, or Firm* — Ballard Spahr LLP

(57) ABSTRACT

In some embodiments, the present disclosure provides certain compositions and methods that may be useful in the treatment and/or prevention of malignant, neurodegenerative, vascular, metabolic, inflammatory, autoimmune, pulmonary, fibrotic, hepatic, lysosomal storage, or viral disease, disorder, or condition, such as carcinomas, Alzheimer's and Parkinson's disease, multiple sclerosis, Paget's disease, or other aspects of aging, such as atherosclerosis or type-2 diabetes. In some such embodiments, compositions are provided that contain at least one cyclodextrin active agent, such as alpha-cyclodextrin, or an analogue or derivative thereof. In some embodiments, the composition is a clathrate of hydroxypropyl-alpha-cyclodextrin and sodium caprate.

14 Claims, 55 Drawing Sheets

Specification includes a Sequence Listing.

(56) References Cited

FOREIGN PATENT DOCUMENTS

| WO | WO 2014022841 | 2/2014 |
|---|---|---|
| WO | WO 2014087778 | 6/2014 |
| WO | PCT/US2014/054421 | 9/2014 |
| WO | WO 2015/002893 | 1/2015 |
| WO | WO 2015/035258 | 3/2015 |
| WO | WO 2015/087016 | 6/2015 |
| WO | WO 2016/047697 | 3/2016 |
| WO | WO 2016/050806 | 4/2016 |
| WO | WO 2016/168772 | 10/2016 |
| WO | PCT/IB2017/000373 | 3/2017 |
| WO | WO 2017/087962 | 5/2017 |
| WO | WO 2017/163128 | 9/2017 |
| WO | PCT/US2018/048414 | 8/2018 |
| WO | PCT/US2018/051604 | 9/2018 |
| WO | WO 2019/067145 | 4/2019 |
| WO | WO 2019/067269 | 4/2019 |

OTHER PUBLICATIONS

Abou Daher, et al. (2017) "Translational Aspects of Sphingolipid Metabolism in Renal Disorders" *Int J Mol Sci* 18.

Agalliu, et al. (2015) "Higher frequency of certain cancers in LRRK2 G2019S mutation carriers with Parkinson disease: a pooled analysis" *JAMA Neurol* 72(1): 58-65.

Agardan NB, et al. (2015) "The Effectiveness of Raloxifene-Loaded Lipsomes and Cochleates in Breast Cancer Therapy," *AAPS PharmSciTech* 17(4): 968-77.

Ahmend and AlSadek (2015) "Galectin-3 as a Potential Target to Prevent Cancer Metastasis" *Clin Med Insights Oncol.* 9: 113-21.

Ahmed, et al. (2011) "Ubiquitin ligase parkin promotes Mdm2-arrestin interaction but inhibits arrestin ubiquitination" *Biochemistry* 50(18): 3749-63.

Alanko and Ivaska (2016) "Endosomes: Emerging Platforms for Integrin-Mediated FAK Signalling" *Trends Cel Biol.* 26(6): 391-8.

Alcalay, et al. (2016) "SCARB2 variants and glucocerebrosidase activity in Parkinson's disease" *NPJ Parkinsons Dis* 2.

Allen, et al. (1979) "A histologica, histochemical, and biochemical study of the macroscopically noral white matter in multiple sclerosis" *J Neurol Sci* 41(1): 81-91.

Allen, I. V. (1981) "The pathology of multiple sclerosis—fact, fiction and hypothesis" *Neuropathol Appl Neurobiol* 7(3): 169-182.

Almahariq, et al. (2013) "A novel EPAC-specific inhibitor suppresses pancreatic cancer cell migration and invasion" *Mol Pharmacol.* 83(1): 122-8.

American Cancer Society (2015) *Cancer Facts & Figures 2015* (Atlanta: American Cancer Society).

Anazi, et al. (2016) "Clinical genomics expands the morbid genome of intellectual disability and offers a high diagnostic yield" *Mol. Psychiatry* 22(4): 615-624.

Andersen, et al. (2016) "P4-ATPases as Phospholipid Flippases-Structure, Function, and Enigmas" *Front Physiol* 7: 275.

Antalis, et al. (2011) "Migration of MDA-MB-231 breast cancer cells depends on the availability of exogenous lipids and cholesterol esterification" *Clin Exp Metastasis* 28(8): 733-41.

Antonell, et al. (2015) "Altered Blood Gene Expression of Tumor-Related Genes (PRKCB, BECN1, and CDKN2A) in Alzheimer's Disease" *Molecular Neurobiology* 53(9): 5902-5911.

Antoniou, et al. (2010) "Common breast cancer susceptibility alleles and the risk of breast cancer for BRCA1 and BRCA2 mutation carriers: implications for risk prediction" *Cancer Res.* 70(23): 9742-54.

Arima, et al. (1992) "Enhanced rectal absorption and reduced local irritation of the anti-inflammatory drug ethyl 4-biphenylylacetate in rats by complexation with water-soluble beta-cyclodextrin derivatives and formulation as oleaginous suppository" *J Pharm Sci* 81(11): 1119-25.

Arbelaez LF, et al. (1997) "Interaction of Matrix Metalloproteinases-2 and -9 with Pregnancy Zone Protein and alpha2-Macroglubulin" *Arch Biochem Biophys* 347:62-8.

Armitage P. (1955) "Test for Linear Trends in Proportions and Frequencies," *Biometrics* 11: 385-86.

Armstrong, et al. (2014) "Lysosomal network proteins as potential novel CSF biomarkers for Alzheimer's disease" *Neuromolecular Med.* 16(1): 150-60.

Baietti, et al. (2012) "Syndecan-syntenin-ALIX regulates the biogenesis of exosomes" *Nat Cell Biol* 14(7): 677-85.

Balla, et al. (2013) "Phosphoinositides: tiny lipids with giant impact on cell regulation" *Physiol Rev.* 93(3): 1019-137.

Banerjee, et al. (2012) "Poly(ethylene glycol)-Prodrug Conjugates: Concept, Design, and Applications" *Journal of Drug Delivery* 2012: a103973.

Bar-On, et al. (2006) "Effects of the cholesterol-lowering compound methyl-beta-cyclodextrin in models of alpha-synucleinopathy" *J Neurochem* 98(4): 1032-45.

Beebe-Dimmer JL, et al. (2015) "Familial clustering of breast and prostate cancer and risk of postmenopausal breast cancer i the Woman's Health Initiative Study," *Cancer,* 121(8): 1254-72.

Bektas, et a. (2005) "A novel acylglycerol kinase that produces lysophosphatidic acid modulates cross talk with EGFR in prostate cancer cells" *J Cell Biol,* 169(5): 801-11.

Ben-Chetrit, et al. (2015) "Synaptojanin 2 is a druggable mediator of metastasis and the gene is overexpressed and amplified in breast cancer" *Sci Signal* 8(360): ra7.

Ben Halima S., et al. (2016) Specific Inhibition of beta-Secretase Processing of the Alzheimer Disease Amyloid Precursor Protein, *Cell Rep* 14(9): 2127-41.

Bereczki, et al. (2016) "Synaptic proteins predict cognitive decline in Alzheimer's disease and Lewy body dementia" *Alzheimers Dement* 12(11): 1149-1158.

Berg J. et al. (2012) "Ca2+-activated Cl-Channels at a Glance" *Journal of Cell Sci* 125: 1367-71.

Berx G, et al. (2009) "Involvement of Members of the Cadherin Superfamily in Cancer" *Cold Spring Harb Perspect Biol* 1: a003129.

Betz, et al. (1997) "Direct interaction of the rat unc-13 homologue Mund3-1 with the N terminus of syntaxin" *J Biol Chem* 272(4): 2520-6.

Bielicki, J. K. (2016) "ABCA1 agonist peptides for the treatment of disease" *Curr Opin Lipidol* 27(1): 40-6.

Bilensoy and Hincal (2009) "Recent advances and future directions in amphiphilic cyclodextrin nanoparticles" *Expert Opin Drug Deliv* 6: 1161-73.

Binkowski-Machut, et al. (2006) "How cyclodextrins can mask their toxic effect on the blood-brain barrier" *Bioorganic & Medicinal Chemistry Letters* 16: 1784-7.

Bishop, D. V. (2010) "Which neurodevelopmental disorders get researched and why?" *PLoS One* 5: e15112.

Blaising, et al. (2014) *Antiviral Research* 107: 84-94.

Boehm-Cagan, et al. (2016) "Differential Effects of apoE4 and Activation of ABCA1 on Brain and Plasma Lipoproteins" *PLoS One* 11(11): e0166195.

Bogie, et al. (2013) "Myelin alters the inflammatory phenotype of macrophages by activating PPARs" *Acta Neuropathol Commun* 1: 43.

Bohdanowicz M, et al. (2013) "Role of phospholipids in endocytosis, phagocytosis, and macrophnocytosis," *Physiol Rev,* 93(1): 69-106.

Booij, L.H. (2009) "Cyclodextrins and the emergence of sugammadex" *Anaesthesia* 64(Suppl 1): 31-7.

Boonyaratanakornkit V., et al. (2001) "Progesterone Receptor Contains a Proline-Rich Motif That Directly Interacts With SH3 Domains and Activates c-Src Family Tyrosine Kinases" *Mol Cell* 8: 269-80.

Bosch A, et al. (2015) "P13K inhibition results in enhanced estrogen receptor function and dependence in hormone receptor-positive breast cancer" *Sci Transl Med* 7(283): 283ra51.

Bosl, W., et al. (2011) "EEG Complexity as a Biomarker for Autism Spectrum Disorder Risk" *BMC Medicine* 9:18.

Bottcher, et al. (2013) "Fabry disease—underestimated in the differential diagnosis of multiple sclerosis?" *PLoS One* 8(8): e71894.

Bouyains., et al. (2010) "The Protein Tyrosine Phosphatases PTPRZ and PTPRG Bind to Distinct Members of the Contactin Family of Neural Recognition Molecules" Proceedings of the National Academy of Sciences 107: 2443-8.

(56) References Cited

OTHER PUBLICATIONS

Bradley, et al. (2015) "Acylglycerophosphate acyltransferase 4 (AGPAT4) is a mitochondrial lysophosphatidic acid acyltransferase that regulates brain phosphatidylcholine, phosphatidylethanolamine, and phosphatidylinositol levels" *Biochimica et Biophysica Acta (BBA)—Molecular and Cell Biology of Lipids* 1851(12): 1566-76.
Bras, et al. (2014) "Genetic analysis implicates APOE, SNCA and suggests lysosomal dysfunction in the etiology of dementia with Lewy bodies" *Human Molecular Genetics* 23(23): 6139-46.
Bresalier, et al. (2015) "Blood-based tests for colorectal cancer screening: do they threaten the survival of the FIT test?" *Dig Dis Sci.* 60(3): 664-71.
Brewster ME, et al. (2007) "Cyclodextrins as pharmaceutical solubilizers." Advanced Drug *Delivery Reviews* 59: 645-66.
Bridges and Saltiel (2015) "Phosphoinositides: Key modulators of energy metabolism," *Biochim Biophys Acta* 1851: 857-66.
Brinkman, et al. (1982) "A dose-ranging study of lecithin in the treatment of primary degeneratie dementia (Alzheimer disease)" *J Clin Psychopharmacol* 2: 281-5.
Brinton RD, et al. (2008) "Progesterone Receptors: Form and Function in Brain" *Front Neuroendocrinol* 29: 313-39.
Bultema, et al. (2012) "BLOC-2, AP-3, and AP-1 proteins function in concert with Rab38 and Rab32 proteins to mediate protein trafficking to lysosome-related organelles" *J Biol Chem* 287(23): 19550-63.
Burghel, et al. (2013) "Identification of candidate driver genes in common focal chromosomal aberrations of microsatellite stable colorectal cancer" *PLoS One* 8(12): e83859.
Busa, W. B. (1988) "Roles for the phosphatidylinositol cycle in early development" *Philos Trans R Soc Lond B Biol Sci* 320(1199): 415-26.
Butt, et al. (2015) "Synergistic effect of pH-responsive folate-functionalized poloxamer 407-TPGS-mixed micelles on targeted delivery of anticancer drugs" *Int J Nanomedicine* 10: 1321-34.
Cai, et al. (2013) "Adenylyl cyclase 6 activation negatively regulates TLR4 signaling through lipid raft-mediated endocytosis" *J Immunol* 191(12): 6093-100.
Cai, et al. (2015) "Deterministic identification of specific individuals from GWAS results" *Bioinformatics* 31(11): 1701-7.
Camilleri, et al. (1994) "beta-Cyclodextrin interacts with the Alzheimer amyloid beta-A4 peptide" *FEBS Lett* 341(2-3): 256-8.
Cammarata, et al. (2015) "High variability of Fabry disease manifestations in an extended Italian family" *Biomed Res Int* 504784.
Campbell, et al. (2013) "Novel 9q34.11 gene deletions encompassing combinations of four Mendelian disease genes: STXBP1, SPTAN1, ENG, and TOR1A" *Genet Med* 14(10): 868-76.
Cao, et al. (2017) "ApoE4-associated phospholipid dysregulation contributes to development of Tau hyper-phosphorylation after traumatic brain injury" *Sci Rep* 7: 11372.
Castro, et al. (2012) "The role of BRCA1 and BRCA2 in prostate cancer" *Asian J Androl.* 14(3): 409-14.
Cataldo, et al. (2000) "Endocytic pathway abnormalities precede amyloid beta deposition in sporadic Alzheimer's disease and Down syndrome: differential effects of APOE genotype and presenilin mutations" *Am J Pathol* 157(1): 277-86.
Cha, et al. (2015) "Loss of parkin promotes lipid rafts-dependent endocytosis through accumulating caveolin-1: implications for Parkinson's disease" *Mol Neurodegener* 10: 63.
Chalbot, et al. (2011) "Blood-cerebrospinal fluid barrier permeability in Alzheimer's disease" *J Alzheimers Dis* 25: 505-15.
Champion, GD, et al. (1978) "Pharmacokinetics of Non-Steroidal Anti-Inflamitory Agents," *Aust Nz J Med* 8 Suppl 1: 94-100.
Chawarska K, et al. (2013) "Decreased Spontaneous Attention to Social Scenes in 6-month-old Infants Later Diagnosed With Autism Spectrum Disorders" *Biol Psychiatry* 74: 195-203.
Chen, et al. (2009) Inhibitors of clathrin-dependent endocytosis enhance TGFbeta signaling and responses *Journal of Cell Science* 122(Pt 11): 1863-71.

Chen, et al. (2011) "GRK5 Promotes F-actin Bundling and Targets Bundles to Membrane Structures to Control Neuronal Morphogenesis" *J Cell Biol* 194: 905-20.
Chen, et al. (2014) "Altered Cholesterol Intracellular Trafficking and the Development of Pathological Hallmarks of Sporadic AD" *J Parkinsons Dis Alzheimers Dis.* 2014: (1)1.
Chen, et al. (2015) "Vav3 oncogene is upregulated and a poor prognostic factor in breast cancer patients" *Oncology Letters* 9(5): 2143-48.
Chen and Yu (2017) "Recent progress in autophagic lysosome reformation" *Traffic* 18: 358-61.
Cheng, et al. (2006) "Cholesterol depletion induces autophagy" *Biochem Biophys Res Commun* 351: 246-52.
Cheng, et al. (2011) "Lipid pathway alterations in Parkinson's disease primary visual cortex" *PLoS One* 6(2): e17299.
Chetty C, et al. (2012) "MMP-9 Induces CD44 Cleavage and CD44 Mediated Cell Migration in Glioblastoma Xenograft Cells" *Cell Signal* 24:549-59.
Chew, et al. (2016) "Endosome and INPP4B" *Oncotarget* 7(1): 5-6.
Chin, et al. (2006) "Protein kinase A-dependent phosphorylation of B/K protein" *Exp Mol Med* 38(2): 144-52.
Choubey, et al. (2014) "BECN1 is involved in the initiation of mitophagy: it facilitates PARK2 translocation to mitochondria" *Autophagy* 10(6): 1105-19.
Chung RH, et al. (2011) "An X Chromosome-Wide Association Study in Autism Families Identifies TBL1X as a Novel Autism Spectrum Disorder Candidate Gene in Males" *Mol Autism* 3: 2.
Cicek MS, et al. (2012) "Colorectal Cancer Linkage on Chromosomes 4q21, 8q13, 12q24, and 15q22," *PLoS One* 7: e38175.
Cichy J, et al. (2003) "The Liberation of CD44" *J Cell Biol* 161:389-43.
Cirrito, et al. (2008) "Endocytosis is required for synaptic activity-dependent release of amyloid-beta in vivo" *Neuron* 58(1): 42-51.
Clear and Smith (2015) "Synthetic Receptors for polar Lipids: Design Priniciples and Applications," in Bradley D. Smith (ed.), *Monographs in Supramolecular Chemistry* (14: Royal Society of Chemistry), 404-36.
Cleveland and Devlin (1988) "Locally Weighted Regression: An Approach to Regression Analysis by Local Fitting" *Journal of the American Statistical Association* 83(403): 596-610.
Coisne, et al. (2016) "Cyclodextrins as Emerging therapeutic Tools in the Treatment of Cholesteol-Associated Vascular and Neurodegenerative Diseases" *Molecules* 21(12): 1748.
Colacurcio and Nixon (2016) "Disorders of lysosomal acidification—The emerging role of v-ATPase in aging and neurodegenerative disease" *Ageing Res Rev* 32: 75-88.
Cole, et al. (2005) "Statins cause intracellular accumulation of amyloid precursor protein, beta-secretase-cleaved fragments, and amyloid beta-peptide via an isoprenoid-dependent mechanism," *J Biol Chem* 280: 18755-70.
Coleman, et al. (2013) "Mammalian P4-ATPases and ABC transporters and their role in phospholipid transport" *Biochim Biophys Acta* 1831(3): 555-74.
Committee for Human Medicinal Producs (CHMP) (2014), "Background review for cyclodextrins used as excipients," *European Medicines Agency*, EMA/CHMO/333892/2013.
Cooper and Shaul "Clathrin-mediated endocytosis and lysosomal cleavage of hepatitis B virus capsid-like core particles" *J Biol Chem* 281: 16563-9, (year 2006).
Coyne, et al. (2007) "Characterization of the interaction between fenamates and hippocampal neuron GABAA receptors", *Neurochemistry International* 51: 440-446.
Crews, et al. (2009) "Role of synucleins in Alzheimer's disease" *Neurotox Res.* 16(3): 306-17.
Cronin, et al. (2015) "Hearing Loss and Otopathology Following Systemic and Intracerebroventricular Delivery of 2-Hydroxypropyl-Beta-Cyclodextrin" *J Assoc Res Otolaryngol* 16(5): 599-611.
Crumling, et al. (2012) "Hearing loss and hair cell death in mice given the cholesterol-chelating agent hydroxypropyl-β-cyclodextrin" *PLoS One* 7(12): e53280.
Cunningham, et al. (2006) "Secreted phospholipase A2 activity in experimental autoimmune encephalomyelitis and multiple sclerosis" *J Neuroinflammation* 3: 26.

(56) References Cited

OTHER PUBLICATIONS

Cunningham, et al. (2008) "Product inhibition of secreted phospholipase A2 may explain lysophosphatidylcholines' unexpected therapeutic properties" *Journal of inflammation (London, England)* 5: 17.

Cuzner and Davison (1973) "Changes in cerebral lysosomal enzyme activity and lipids in multiple sclerosis" *J Neurol Sci* 19(1): 29-36.

Da Costa, et al. (2012) "Identification of six potential markers for the detection of circulating canine mammary tumour cells in the peripheral blood identified by microarray analysis" *J Comp Pathol* 146(2-3): 143-51.

Dai, et al. (2017) "Methyl-beta-cyclodextrin restores impaired autophagy flux in Niemann-Pick C1-deficient cells through activation of AMPL" *Autophagy* 13: 1435-51.

Daleke, et al. (2007) "Phospholipid flippases" *J Biol. Chem.* 282(2): 821-5.

Danthi, et al. (2004) "Cholesterol removal by methyl-beta-cyclodextrin inhibits poliovirus entry" *J Virol.* 78(1): 33-41.

Davidson, et al. (2016) "Efficacy and ototoxicity of different cyclodextrins in Niemann-Pick C disease" *Ann Clin Transl Neurol* 3: 366-80.

Davis ME, et al. (2004) "Cyclodextrin-based pharmaceutics: past, present and future" *Nat Rev Drug Discov* 3: 1023-35 B114.

Day, et al. (2011) "Syntaxins 3 and 4 mediate vesicular trafficking of α5β1 and α3β1 integrins and cancer cell migration" *Int J Oncol* 39(4): 863-71.

Dawson (2008) "Early behavioral intervention, brain plasticity, and the prevention of autism spectrum disorder", *Development and Psychopathology* 20: 775-803.

De Campos, ML, et al. (2012) "Pharmacokinetic Profile of a New Diclofenac Prodrug Without Gastroulcerogenic Effect" *Drug Metab Lett* 6:235-41.

De Schaepdrijver, et al. (2015) "Juvenile animal testing of hydroxypropyl-beta-cyclodextrin in support of pediatric drug development" *Reproductive toxicology (Elmsford, NY)* 56: 87-96.

Decressac, et al. (2013) "TFEB-mediated autophagy rescues midbrain dopamine neurons from alpha-synuclein toxicity" *Proc Natl Acad Sci USA* 110: E1817-26.

Dehay, et al. (2010) "Pathogenic lysosomal depletion in Parkinson's disease" *J Neurosci* 30.

Del Valle, E. M. M. (2004) "Cyclodextrins and their uses" *Process Biochemistry* 39: 1033-46.

Deli, M. A. (2009) "Potential use of tight junction modulators to reversibly open membranous barriers and improve drug delivery" *Biochimica et Biophysica Acta (BBA)—Biomembranes* 1788(4): 892-910.

Deutsch CK, et al. (2003) Brief Report: Cognitive Correlates of Enlarged Head Circumference in Children with Autism *J Autism Dev Disord* 33:209-15.

Di Fiore and von Zastrow (2014) "Endocytosis, Signaling, and Beyond" *Cold Spring Harb Perspect Biol* 6(8): a016865.

Diao, et al. (2013) "Native α-synuclein induces clustering of synaptic-vesicle mimics via binding to phospholipids and synaptobrevin-2/VAMP2" *Elife* 2: e00592.

Disse, et al. (2016) "A Review of the Association Between Parkinson Disease and Malignant Melanoma" *Dermatol Surg.* 42(2): 141-6.

Dong, et al. (2014) "Secretory phospholipase A2-lia upregulates HER/HER2-elicited signaling in lung cancer cells" *Int J Oncol* 45: 978-84.

Dong, et al. (2015) "The enterococcal cytolysin synthetase has an unanticipated lipid kinase fold" *Elife* 4: e07607.

Dong, et al. (2016) "The relevance of ABCA1 R218K polymorphisms and serum ABCA1 protein concentration to Parkinson's disease pathogenesis and classification: a case-control study" *Genes & Genomics* 38: 243-50.

Dooren, et al. (2014) "Derailed intraneuronal signalling drives pathogenesis in sporadic and familial Alzheimer's disease" *Biomed Res Int.* 2014:167024.

Dos Santos, et al. (2017) "Changes in membrane biophysical properties induced by the Budesonide/Hydroxypropyl-β-cyclodextrin complex" *Biochim Biophys Acta Biomembr* 1859(10): 1930-40.

Duchene and Wouessidjewe (1990) "Pharmaceutical Uses of Cyclodextrins and Derivatives" *Drug Development and Industrial Pharmacy* 16(17): 2487-99.

Dysken, et al. (1982) "Lecithin administration in Alzheimer dementia" *Neurology* 32: 1203-4.

Elison JT, et al. (2013) "White Matter Microstructure and Atypical Visual Orienting in 7-month-olds at Risk for Autism" *Am J Psychiatry* 170: 899-908.

Elsabbagh M, et al. (2012) "Infant Neural Sensitivity to Dynamic Eye Gaze Is Associated With Later Emerging Autism" *Curr Biol* 22: 338-42.

Erneux, et al. (2016) "New Functions of the Inositol Polyphosphate 5-Phosphatases in Cancer" *Curr Pharm Des* 22(16): 2309-14. (Abstract).

Etienne, et al. (1981) "Alzheimer disease: lack of effect of lecithin treatment for 3 months" *Neurology* 31: 1552-4. (Abstract).

European Medicines Agency (2017) Annex to the European Commission guideline on 'Excipients in the labeling and package leaflet of medicinal products fo rhuma use,' EMA/CHMP/302620/2017/EN.

Falasca, Marco (ed.) (2012) "Phosphoinositides and Disease," ed. Peter K. Vogt, *Current topics in microbiology and immunology*, Dordrecht: Springer.

Farge, et al. (1999) "Enhancement of endocytosis due to aminophospholipid transport across the plasma membrane of living cells" *Am J Physiol* 276(3 Pt 1): C725-33.

Fauvelle F, et al. (1997) "Mechanism of alphacyclodextrin-induced hemolysis. 1. The two-step extraction of phosphatidylinositol from the membrane" *J Pharm Sci* 86: 935-43.

Feldman, et al. (2014) "Familial coaggregation of Alzheimer's disease and Parkinson's disease: systematic review and meta-analysis" *Neuroepidemiology* 42(2): 69-80.

Feng, et al. (2015) "The associations between Parkinson's disease and cancer: the plot thickens" *Transl Neurodegener* 4: 20.

Fernandez M., et al. (2010) "Flufenamic Acid Suppresses Epileptiform Activity in Hippocampus by Reducing Excitatory Synaptic Transmission and Neuronal Excitability" *Epilepsia* 51: 384-90.

Fernandez-Nogueira, et al. (2016) "Differential expression of neurogenes among breast cancer subtypes identifies high risk patients" *Oncotarget* 7: 5313-26.

Filigheddu, et al. (2007) "Diacylglycerol kinase is required for HGF-induced invasiveness and anchorage-independent growth of MDA-MB-231 breast cancer cells" Anticancer Res 27(3B): 1489-92.

Finn RS, et al. (2016) "Targeting the cyclin-dependent kinases (CDK) 4/6 in estrogen receptorpositive breast cancers" Breast Cancer Res 18(1): 17.

Fisher, RA, The American Statistician, vol. 2, No. 5, Published by Taylor & Francis, Ltd. (1948).

Fisman, et al. (1981) "Double blind study of lecithin in patients with Alzheimer's disease" Canadian journal of psychiatry Revue canadienne de psychiatrie 26: 426-8.

Fogo, A. B. (2003) "Animal models of FSGS: lessons for pathogenesis and treatment" Semin Nephrol. 23(2): 161-71.

Fortin, et al. (2004) "Lipid rafts mediate the synaptic localization of alpha-synuclein" J Neurosci 24: 6715-23.

Frank and Weaver (1976) "Cyclodextrin nephrosis in the rat" Am. J;. Pathol. 83(2): 367-82.

Frere and Slutsky (2016) "Targeting PTEN interactions for Alzheimer's disease" Nat Neurosci 9(3): 416-8.

Frijlink, et al. (1991) "The effect of parenterally administered cyclodextrins on cholesterol levels in the rat" Pharm Res 8: 9-16.

Fujita, et al. "Proinflammatory secreted phospholipase A2 type IIA (sPLA-IIA) induces activation through direct binding to a newly identified binding site (site 2) in integrins alphavbeta3, alpha4beta1, and alpha5beta1" J Biol Chem 290: 259-71, (year 2015).

Fukuda, M. (2013) "The role of synaptotagmin and synaptotagmin-like protein (Slp) in regulated exocytosis," *Madame Curie Regulated Database* [internet].

(56) References Cited

OTHER PUBLICATIONS

Fukuda, M. (2016) "Multiple Roles of VARP in Endosomal Trafficking: Rabs, Retromer Components and R-SNARE VAMP7 Meet on VARP" *Traffic* 17(7): 709-19.
Fulop, et al. (2012) "Aging, immunosenescence and membrane rafts: the lipid connection," *Longev Healthspan* 1: 6.
Garcia-Closas M, et al. (2013) "Genomewide association studies identify four ER negative-specific breast cancer risk loci" *Nat Genet* 45: 392-8.
Gaspar, et al. (2017) "2-Hydroxypropyl-beta-cyclodextrin (HPβCD) reduces age-related lipofuscin accumulation through a cholesterol-associated pathway" *Scientific Reports* 7: 2197.
Gatto, et al. (2015) "Flux balance analysis predicts essential genes in clear cell renal cell carcinoma metabolism" *Sci Rep* 5: 10738.
Gautam, et al. (2014) "β-cyclodextrin and curcumin, a potent cocktail for disaggregating and/or inhibiting amyloids: a case study with α-synuclein" *Biochemistry* 53(25): 4081-3.
Gautman, et al. (2015) "Synaptotagmins interact with APP and promote Aβ generation" *Mol Neurodegener* 10: 31.
Gehan EA (1965) "A generalised Wilcoxon test for comparing arbitrarily singly censored samples" *Biometrika* 52: 203-23.
George, et al. (2016) "Multiple sclerosis risk loci and disease severity in 7,125 individuals from 10 studies" *Neurol Genet* 2(4): e87.
Germain, D. P. (2013) "Fabry disease" *Orphanet J Rare Dis* 5: 30.
Gigerenzer, G. (2004) "Dread risk, Sep. 11, and fatal traffic accidents" *Psychol Sci* 15: 286-7.
Gimpl and Gehrig-Burger (2011) "Probes for studying cholesterol binding and cell biology" *Steroids* 76(3): 216-31.
Goetz, et al. (2011) "Biomechanical remodeling of the microenvironment by stromal caveolin-1 favors tumor invasion and metastasis" *Cells* 146(1): 148-63.
Gonzalez, et al. (2014) "Lysosomal integral membrane protein-2: a new player in lysosome-related pathology" *Mol Genet Metab* 111: 84-91.
González, et al. (2016) "Genetic and Transcriptomic Profiles of Inflammation in Neurodegenerative Diseases: Alzheimer, Parkinson, Creutzfeldt-Jakob and Tauopathies" *Int J Mol Sci.* 17(2): 206.
Gotoh, et al. (2014) "The antitumor effects of methyl-β-cyclodextrin against primary effusion lymphoma via the depletion of cholesterol from lipid rafts" *Biochem Biophys Res Commun.* 455(3-4): 285-9.
Gould, et al. (2005) "2-Hydroxypropyl-beta-cyclodextrin (HP-beta-CD): a toxicology review" *Food Chem Toxicol.* 43(10): 1451-9.
Greenwood, IA, et al. (2007) "Overlapping pharmacology of Ca2+-activated CIS and K+channels," *Trends Pharmacol Sci* 28:1-5.
Grosse et al. (1998) "Antiproliferative effect of methyl-beta-cyclodextrin in vitro and in human tumour xenografted athymic nude mice", *British Jour of Med,* 78: 1165-1169.
Guerra, et al. (2016) "Membrane cholesterol depletion reduces breast tumor cell migration by a mechanism that involves non-canonical Wnt signaling and IL-10 secretion" *Translational Medicine Communications* 1: Article No. 3.
Guerreiro, et al. (2016) "Genome-wide analysis of genetic correlation in dementia with Lewy bodies, Parkinson's and Alzheimer's diseases" *Neurobiol Aging.* 38(214): e7-10.
Guglielmo, R., et al. (2013) "Managing disruptive and compulsive behaviors in adult with autistic disorder with gabapentin," *Journal of Clinical Psychopharmacology* 33: 273-274.
Gunasekara, et al. (2017) "Pulmonary surfactant dysfuntion in pediatric cystic fibrosis: Mechanisms and reversal with a lipid-sequestering drug" *J Cyst Fibros* 16(5): 565-572.
Guo, et al. (2018) "Autophagy in neurodegenerative diseases pathogenesis and therapy" *Brain Pathol* 28: 3-13.
Gupta and Iadecola (2015) "Impaired Aβ clearance: a potential link between atherosclerosis and Alzheimer's disease" *Front Aging Neurosci* 7: 115.
Gurney, et al. (2015) "Phosphodiesterase-4 (PDE4) molecular pharmacology and Alzheimer's disease" *Neurotherapeutics* 12(1): 49-56.

Haddad, et al. (2016) "An exome-wide analysis of low frequency and rare variants in relation to risk of breast cancer in African American Women: the AMBER Consortium" *Carcinogenesis* 37(9): 870-877.
Hall, et al. (2009) "Tensin1 requires protein phosphatase-1 alpha in addition to RhoGAP DLC-1 to control cell polarization, migration, and invasion" *J Biol Chem* 284(50): 34713-22.
Hamon, et al. (2006) "Cooperation between engulfment receptors: the case of ABCA1 and MEGF10" *PLoS One* 1(1): e120.
Hanson, et al. (2016) "Is Cancer Protective for Subsequent Alzheimer's Disease Risk? Evidence from the Utah Population Database," *J Gerontol B Psychol Sci Soc Sci.* 72(6): 1032-1043.
HapMap (2007) "A Second Generation Human Haplotype Map of Over 3.1 Million SNPs" *Nature* 449:851-61.
Harris, C. M. (1981) "Test of the memory-enhancing effect of phosphatidylcholine in humans" Chicago, IL: University of Illinois, 140.
Hashimoto, et al. (2016) "Lysophosphatidic acid activates Arf6 to promote the mesenchymal malignancy of renal cancer" *Nat Commun* 7: 10656.
Hastings, C. (2010) "Request for intrathecal delivery of HPbCD for Niemann-Pick type C patients" *FDA-Filing.*
Hernandez, et al. (2010) "Secreted PLA2 induces proliferation in astrocytoma through the EGF receptor: another inflammation-cancer link" *Neuro-oncology* 12: 1014-23.
Hesketh G.G., et al. (2014) "VARP is recruited on to endosomes by direct interaction with retromer, where together they function in export to the cell surface" *Dev Cell* 29: 591-606.
Higgins and Flicker (2003) "Lecithin for dementia and cognitive impairment" *Cochrane Database Syst Rev:* CD001015.
Hildebrand, JD, et al. (1999) "Shroom, a PDZ Domain-Containing Actin-Binding Protein, Is Required for Neural Tube Morphogenesis in Mice" *Cell* 99: 485-97.
Hipler UC, et al. (2007)"Influence of cyclodextrins on the proliferation of HaCaT keratinocytes in vitro" *J Biomed Mater Res* 83: 70-9.
Hoeffding, W. (1948) "A Class of Statistics with Asymptotically Normal Distribution" *Annals of Mathematical Statistics* 19: 293-325.
Hollingsworth P (1993) "Paediatric Rheumatology: Review the Use of Non-Steroidal Anti-Inflammatory Drugs in Paediatric Rheumatic Diseases," Br J Rheumatol 32: 73-7.
Hopkins, et al. (2016) "Eicosopentaneoic Acid and Other Free Fatty Acid Receptor Agonists Inhibit Lysophosphatidic Acid- and Epidermal Growth Factor-Induced Proliferation of Human Breast Cancer Cells" *J. Clin Med* 5(2).
Hoshino, et al. (2015) "Tumour exosome integrins determine organotropic metastasis" *Nature* 527(7578): 329-35.
Hsu, et al. (2008) "Promoter polymorphisms modulating HSPA5 expression may increase susceptibility to Taiwanese Alzheimer's disease" *J NeuralTransm (Vienna)* 115(11): 1537-43.
Hu, VW, et al. (2006) "Gene Expression Profiling of Lymphoblastoid Cell Lines From Monozygotic Twins Discordant in Severity of Autism Reveals Differential Regulation of Neurologically Relevant Genes" *BMC Genomics* 7: 118.
Huang and London (2013) "Effect of cyclodextrin and membrane lipid structure upon cyclodextrin-lipid interaction" *Langmuir* 29(47): 14631-8.
Hultberg and Olsson (1978) "Diagnostic value of determinations of lysosomal hydrolases in CSF of patients with neurological diseases" *Acta Neurol Scand* 57(3): 201-15.
Hultberg and Olsson (1979) "Lysosomal hydrolases in CSF of patients with multiple sclerosis" *Acta Neurol Scand* 59(1): 23-30.
Hunter DJ, et al. (2007) "A genome-wide association study identifies alleles in FGFR2 associated with risk of sporadic postmenopausal breast cancer" *Nature Genet* 39: 870-4.
Hurley and Odorizzi (2012) "Get on the exosome bus with ALIX" *Nat Cell Biol* 14(7): 654-5.
Iacopetta, et al. (2012) "The Role of Androgen Receptor in Breast Cancer" *Drug Discov Today Dis Mech. Dis Mech.* 9(1-2): e19-e27.
Inabe, et al. (2002) "Vav3 modulates B cell receptor responses by regulating phosphoinositide 3-kinase activation" *J Exp Med* 195(2): 189-200.

(56) References Cited

OTHER PUBLICATIONS

Irie T, et al. (1982) "Cyclodextrin-induced hemolysis and shape changes of human erythrocytes in vitro" *J Pharmacobiodyn* 5: 741-4.

Irie, et al. (1992) "Hydroxypropylcyclodextrins in parenteral use. II: Effects on transport and disposition of lipids in rabbit and humans" *J Pharm Sci.* 81(6): 524-8.

Irie T,et al. (1997) "Pharmaceutical applications of cyclodextrins. III. Toxicological issues and safety evaluation." *JPharm Sci* 86: 147-62.

Ito K, et al. (1994) "Pharmacokinetics of mefenamic acid in preterm infants with patent ductus arteriosus" *Acta Paediatr Jpn* 36:387-91.

Jameson, et al. (2012) "Dye-binding assays forevaluation ofthe effects of small molecule inhibitors on amyloid (aβ) self-assembly" *ACS Chem Neurosci* 3(11): 807-19.

Jain, et al. (2013) "Mutual prodrugs containing bio-cleavable and drug releasable disulfide linkers" *Bioorganic Chemistry,* 49: 40-48.

Jiang, et al. (2015) "Loss of RAB1B promotes triple-negative breast cancer metastasis by activating TGF-β/SMAD signaling" *Oncotarget* 6(18): 16352-65.

Jilani, JA, et al. (1997) "Evaluation of Hydroxyethyl Esters of Mefenamic Acid and Diclofenac as Prodrugs," *Drug Dev Ind Pharm* 23: 319-23.

Jounai, et al. (2011) "NLRP4 negatively regulates autophagic processes through an association with beclin1" *J Immunol* 186(3): 1646-55.

Jung, et al. (2013) "Oncogenicfunction of p34SEI-1 via NEDD4-1-mediated PTEN ubiquitination/degradation and activation of the PI3K/AKT pathway" *Int J Oncol* 43(5): 1587-95.

Kageal, et al. (2010) "Increased expression of the lysosomal cholesterol transporter NPC1 in Alzheimer's disease" *Biochim Biophys Acta* 1801(8): 831-8.

Kamar, et al. (2012) "Membrane cholesterol strongly influences confined diffusion of prestin" *Biophysical Journal* 103(8): 1627-36.

Kameyama, et al. (2017) "Induction of mitophagy-mediated antitumor activity with folate-appended methyl-β-cyclodextrin" *Int J Nanomedicine* 12: 3433-46.

Kanai, et al. (1989) "The effect on the cornea of alpha cyclodextrin vehicle for cyclosporin eye drops" *Transplant Proc.* 21(1 Pt 3): 3150-2.

Kantner and Erben (2012) "Long-term parenteral administration of 2-hydroxypropyl-β-cyclodextrin causes bone loss" *Toxicol Pathol* 40(5): 742-50.

Kawate, et al. (2015) "High levels of DJ-1 protein and isoelectric point 6.3 isoform in sera of breast cancer patients" *Cancer Sci.* 106(7): 938-43.

Kawauchi, et al. (2012) "Cell adhesion and its endocytic regulation in cell migration during neural development and cancer metastasis" *Int J Mol Sci* 13(4): 4564-90.

Keogh, et al. (2015) "A novel de novo STXBP1 mutation is associated with mitochondrial complex I deficiency and late-onset juvenile-onset parkinsonism" *Neurogenetics* 16(1): 65-7.

Kerr, et al. (2011) "Inhibitor and activator: dual functions for SHIP in immunity and cancer" *Ann N Y Acad Sci.*1217: 1-17.

Khalil, et al. (2015) "PINK1-induced mitophagy promotes neuroprotection in Huntington's disease" *Cell Death Dis* 6: e1617.

Khan, MS (2005) "Glyceride Derivatives as Potential Prodrugs: Synthesis, Biological Activity and Kinetic Studies of Glyceride Derivatives of Mefenamic Acid" *Pharmazie* 60: 110-4.

Kilpatrick, et al. (2015) "Genetic and chemical activation of TFEB mediates clearance of aggregated a-synuclein"PLoS One 10: e0120819.

Kim, et al. (2015) "Metastasis-Free Interval Is Closely Related to Tumor Characteristics and Has Prognostic Value in Breast Cancer Patients with Distant Relapse" *J Breast Cancer* 18(4): 371-7.

Kim, et al. (2016) "Fisetin stimulates autophagic degradation of phosphorylated tau via the activation of TFEB and Nrf2 transcription factors" *Sci Rep* 6: 24933.

Kim, et al. (2016) "Evidence that the rab5 effector APPL1 mediates APP-βCTF-induced dysfunction of endosomes in Down syndrome and Alzheimer's disease" *Mol Psychiatry.* 21(5): 707-16.

Kitada, et al. (1998) Mutations in the parkin gene cause autosomal recessive juvenile parkinsonism *Nature* 392(6676): 605-8.

Klavins, et al. (2015) "The ratio of phosphatidylcholines to lysophosphatidylcholines in plasma differentiates healthy controls from patients with Alzheimer's disease and mild cognitive impairment" *Alzheimer's & dementia (Amsterdam, Netherlands)* 1: 295-302.

Koldamova, et al. (2014) "ATP-binding cassette transporter A1: from metabolism to neurodegeneration" *Neurobiol. Dis* 72 Pt A: 13-21.

Kondo, et al. (1996) "Combination effects of alpha-cyclodextrin and xanthan gum on rectal absorption and metabolism of morphine from hollow-type suppositories in rabbits" *Biol Pharm Bull* 19(2): 280-6.

Kojro, et al. (2001) "Low cholesterol stimulates the nonamyloidogenic pathway by its effect on the alpha-secretase ADAM 10" *Proc Natl Acad Sci USA* 98: 5815-20.

Koran, et al. (2014) "Genetic interactions within inositol-related pathways are associated with longitudinal changes in ventricle size" *J Alzheimers Dis* 8(1): 145-54.

Koumangoye, et al. (2011) "Detachment of breast tumor cells induces rapid secretion of exosomes which subsequently mediate cellular adhesion and spreading" *PLoS One* 6(9): e24234.

Krug, et al. (2013) "Sodium caprate as an enhancer of macromolecule permeation across tricellular tight junctions of intestinal cells" *Biomaterials* 34(1): 275-82.

Kunzelmann, et al. (2011) "Anoctamins" *Pflugers Archiv* 462: 195-208.

Kuzuya, et al. (2016) "Identification of the novel activity-driven interaction between synaptotagmin 1 and presenilin 1 links calcium, synapse, and amyloid beta" *BMC Biol* 14: 25.

Kylliainen A., et al. (2006) "Skin Conductance Responses to Another Person's Gaze in Children With Autism" *J Autism Dev Disord* 36:517-25.

Lainhart JE, et al. (2006) "Head Circumference and Height in Autism: A Study by the Collaborative Program of Excellence in Autism" *Am J Med Genet A* 140: 2257-74.

Lane RF, et al. (2012)"Vps10 Family Proteins and the Retromer Complex in Aging-Related Neurodegeneration and Diabetes" *J Neurosci* 32: 14080-6.

Laumonnier F. (2006) "Association of a Functional Deficit ofthe BKCa Channel, a Synaptic Regulator of Neuronal Excitability, With Autism and Mental Retardation" *Am J Psychiatry* 163: 1622-9.

Law, et al. (2016) "Normal Molecular Specification and Neurodegenerative Disease-Like Death of Spinal Neurons Lacking the SNARE-Associated Synaptic Protein Munc18-1" *J Neurosci* 36(2): 561-76.

Le Tourneau C, et al. (2009) "Dose Escalation Methods in Phase I Cancer Clinical Trials" *JNCI Journal of the National Cancer Institute* 101: 708-20.

Lee, et al. (2013) "Dysregulation of cholesterol homeostasis in human prostate cancer through loss of ABCA1" *Cancer Res* 73(3): 1211-8.

Lemonnier, et al. (2012) "A randomised controlled trial of bumetanide in the treatment of autism in children," *Translational Psychiatry,* 2: e202.

Leonova and Galzitskaya (2015) "Role of Syndecans in Lipid Metabolism and Human Diseases" *Adv Exp Med Biol* 855: 241-58.

Leroy-Lechat, et al. (1994) "Evaluation ofthe cytotoxicity of cyclodextrins and hydroxypropylated derivatives" *International Journal of Pharmaceutics* 101(1-2): 97-103.

Levano, et al. (2009) "A genetic strategy involving a glycosyltransferase promoter and a lipid translocating enzyme to eliminate cancer cells" *Glycoconj J* 26(6): 739-48.

Levano, et al. (2012) "Atp8a1 Deficiency is Associated with Phosphatidylserine Externalization in Hippocampus and Delayed Hippocampus-Dependent Learnin" *J Neurochem* 120(2): 302-13.

Li, et al. (1996) "Microglia-derived macrophages in early multiple sclerosis plaques" *Neuropathol Appl Neurobiol* 22(3): 207-15.

Li, et al. (2006) "Elevated levels of cholesterol-rich lipid rafts in cancer cells are correlated with apoptosis sensitivity induced by cholesterol-depleting agents" Am J Pathol 168(4): 1107-18.

Li, C., et al. (2008) "Prioritized Subset Analysis: Improving Power in Genome-Wide Association Studies" *Hum Hered* 65:129-41.

(56) References Cited

OTHER PUBLICATIONS

Li, et al. (2008) "Candidate single-nucleotide polymorphisms from a genomewide association study of Alzheimer disease" *Arch Neurol* 65(1): 45-53.
Li, et al. (2013) "Inhibitory effects of paeoniflorin on lysophosphatidylcholine-induced inflammatory factor production in human umbilical vein endothelial cells" *Int J Mol Med* 31: 493-7.
Li, et al. (2017) "Paeoniflorin Ameliorates Atherosclerosis by Suppressing TLF4-Mediated NF-kappaB Activation" *Inflammation* 40: 2042-51.
Liao, et al. (2015) "A novel small-form NEDD4 regulates cell invasiveness and apoptosis to promote tumor metastasis" *Oncotarget* 6(11): 9341-54.
Lill, et al. (2012) "Comprehensive research synopsis and systematic meta-analyses in Parkinson's disease genetics: The PDGene database" *PLoS Genet* 8(3): e1002548.
Lim S, et al. (2014) "Amyloid-R precursor protein promotes cell proliferation and motility of advanced breast cancer" *BMC Cancer* 14: 928.
Lin, et al. (2013) "Genomic and functional characterizations of phosphodiesterase subtype 4D in human cancers" *Proceedings of the National Academy of Sciences of the United States of America* 110(15): 6109-14.
Lindmark, et al. (1998) "Absorption enhancement through intracellular regulation of tight junction permeability by medium chain fatty acids in Caco-2 cells" *J Pharmacol Exp Ther* 284(1): 362-9.
Little, et al. (1985) "A double-blind, placebo controlled trial of high-dose lecithin in Alzheimer's disease" *J Neurol Neurosurg Psychiatri* 48: 736-42.
Liu, B. (2012) "Therapeutic potential of cyclodextrins in the treatment of Niemann-Pick type C disease" *Clinical lipidology* 7: 289-301.
Liu, et al. (2008) "Osteotropic beta-cyclodextrin for local bone regeneration" *Biomaterials* 29: 1686-92.
Liu, et al. (2008) "Genetic variations and treatments that affect the lifespan of the NPC1 mouse" *J Lipid Res* 49: 663-9.
Liu, et al. (2009) "Reversal of defective lysosomal transport in NPC disease ameliorates liver dysfunction and neurodegeneration in the npc1-/-mouse" *Proc Natl Acad Sci USA* 106(7): 2377-82.
Liu, et al. (2016) "Cation-dependent gold recovery with a-cyclodextrin facilitated by second-sphere coordination" *Journal of the American Chemical Society* 138: 11643-53.
Livak and Schmittgen (2001) "Analysis of relative gene expression data using realtime quantitative PCR and the 2(-Delta Delta C(T)) Method" *Methods* 25: 402-8.
Lizarbe, et al. (2013) "Annexin-phospholipid interactions. Functional implications" *Int J Mol Sci* 14(2): 2652-83.
Llanos, et al. (2015) "The cholesterol-lowering agent methyl-β-cyclodextrin promotes glucose uptake via GLUT4 in adult muscle fibers and reduces insulin resistance in obese mice" *Am J Physiol Endocrinol Metab.* 308(4): E294-305.
Loane, et al. (2011) "Modulation of ABCA1 by an LXR agonist reduces β-amyloid levels and improves outcome after traumatic brain injury" *J Neurotrauma* 28(2): 225-36.
Loftsson T, Brewster ME (1996) "Pharmaceutical applications of cyclodextrins 1. Drug solubilization and stabilization" *J Pharm Sci* 85: 1017-25.
Loftsson T, Brewster ME (2010) "Pharmaceutical applications of cyclodextrins: basic science and product development" *JPharm Pharmacol* 62: 1607-21.
Loftsson T, (2015) "Pharmacokinetics of cyclodextrins and drugs after oral and parenteral administration of drug/cyclodextrin complexes" *J Pharm Pharmacol* 68: 544-55.
Lopez Gonzalez, et al. (2016) "Genetic and Transcriptomic Profiles of Inflammation in Neurodegenerative Diseases: Alzheimer, Parkinson, Creutzfeldt-Jakob and Taupathies" *Int J Mol Sci* 17: 206.
Losel R., et al. (2003) "Nongenomic Actions of Steroid Hormones" *Nat Rev Mol Cell Biol* 4:45-56.
Lowry, et al. (2015) "The Role of Exosomes in Breast Cancer" *Clin Chem* 61(12): 1457-65.
Luo, et al. (2017) "The role of microglia in multiple sclerosis" *Neuropsychiatr Dis Treaet* 13: 1661-67.
Ma, et al. (2008) "PI(3,4,5)P3 and PI(3,4)P2 levels correlate with PKB/akt phosphorylation at Thr308 and Ser473, respectively; PI(3,4)P2 levels determine PKB activity" *Cell Signal* 20(4): 684-94.
Ma, et al. (2017) "Beneficial effects of paeoniflorin on non-alcoholic fatty live disease induced by high-fat diet in rats" *Sci Rep* 7: 44819.
Maarup, et al. (2015) "Intrathecal 2-hydroxypropyl-beta-cyclodextrin in a single patient with Niemann-Pick C1" *Mol Genet Metab* 116(1-2):75-9.
Mahdi (2012) "Design, Synthesis and Hydrolytic Behavior of Mutual Prodrugs of NSAIDs with Gabapentin Using Glycol Spacers," *Pharmaceuticals* 5: 1080-1091.
Majerus and York (2009) "Phosphoinositide phosphatases and disease" *Journal of Lipid Research* 50(Suppl): S249-S54.
Malhotr, et al. (2009) "Vav and Rac activation in B cell antigen receptor endocytosis involves Vav recruitment to the adapter protein LAB" *The Journal of Biological Chemistry* 284(52): 36202-12.
Malkki, H. (2016) "Alzheimer disease: Cancer immunotherapy drug reduces symptoms of Alzheimer disease in mice" *Nat Rev Neurol* 12(3): 126-26.
Mallat, et al. (2010) "Lipoprotein-associated and secreted phospholipases A(2) in cardiovascular disease: roles as biological effectors and biomarkers" *Circulation* 122: 2183-200.
Mann and Whitney (1947) "On a Test of Whether one of Two Random Variables is Stochastically Larger than the Other" *Annals of Mathematical Statistics* 18(1): 50-60.
Martin, T. F. (2015) "PI(4,5)P$_2$-binding effector proteins for vesicle exocytosis" *Biochim Biophys Acta* 1851(6): 785-93.
Martin-Maestro, et al. (2016) "PARK2 enhancement is able to compensate mitophagy alterations found in sporadic Alzheimer's disease" *Hum Mol Genet* 25(4): 792-806.
Martini-Stoica, et al. (2016) "The Autophagy-Lysosomal Pathway in Neurodegeneration: A TFEB Perspective" *Trends Neurosci* 39: 221-34.
Matigian, et al. (2010) "Disease-specific, neurosphere-derived cells as models for brain disorders" *Disease Models & Mechanisms* 3(11-12): 785-98.
Matsuo, et al. (2012) "Effects of cyclodextrin in two patients with Niemann-Pick Type C disease" *Mol Genet Metab* 108(1): 76-81.
Maxwell, et al. (2012) "Attenuation of phosphoinositide 3-kinase δ signaling restrains autoimmune disease" *J Autoimmun* 38(4): 381-91.
Mayer, et al. (2016) "The PI3K/AKT Pathway as a Target for Cancer Treatment" *Annu Rev Med* 67: 11-28.
Mazefsky (2008) "Variability in Adaptive Behavior in Autism: Evidence for the Importance of Family History," *J. Abnorm. Child Psychol.* 36: 591-599.
McCaffery P., et al. (2005) "Macrocephaly and the Control of Brain Growth in Autistic Disorders" *Prog Neurobiol* 77:38-56.
McCleverty, et al. (2007) "Structure of the PTB domain of tensin1 and a model for its recruitment to fibrillar adhesions" *Protein Science: A Publication of the Protein Society* 16(6): 1223-29.
McGranahan, et al. (2015) "Clonal status of actionable driver events and the timing of mutational processes in cancer evolution" *Sci Transl Med.* 7(283): 283ra51-83ra51.
McGurk, et al. (1996) "Reactivity of mefenamic acid 1-o-acyl glucuronide with proteins in vitro and ex vivo" *Drug Metab Dispos* 24:842-9.
McKeown and Allen (1977) "Lysosomal involvement in the pathogenesis of multiple sclerosis [proceedings]" *Biochem Soc Trans* 5(5): 1416-8.
McKeown and Allen (1979) "The fragility of cerebral lysosomes in multiple sclerosis" *Neuropathol Appl Neurobiol* 5(5): 405-15.
McKew, et al. (2014) "Cyclodextrin for the Treatment of Lysosomal Storage Diseases," WO: US Health.
Medina and Ballabio (2015) "Lysosomal calcium regulates autophagy" *Autophagy* 11: 970-1.
Mellman I, et al. (2013) "Endocytosis and Cancer" *Cold Spring Harbor Perspectives in Biology* 5(12).
Merkus, et al. (1991) "Absorption enhancing effect of cyclodextrins on intranasally administered insulin in rats" *Pharm Res* 8: 588-92.

(56) References Cited

OTHER PUBLICATIONS

Michailidou, et al. (2013) "Large-scale genotyping identifies 41 new loci associated with breast cancer risk" *Nat Genet* 45(4): 353-61.
Michel, et al. (2012) "Design and evaluation of cyclodextrin-based delivery systems to incorporate poorly soluble circumin analogs for the treatment of melanoma" *Eur J Pharm Biopharm* 81: 548-56.
Mikhael A, et al. (1992) "Synthesis of Some NewFenamic and Naphthalene Propionic Acid Esters of Pharmacological Activities" *Egyptian Journal of Pharm Sci* 33: 149-166.
Miller, et al. (2013) "Genes and pathways underlying regional and cell type changes in Alzheimer's disease" *Genome Med* 5(5): 48.
Minn, et al. (2005) "Genes that mediate breast cancer metastasis to lung" *Nature* 436(7050): 518-24.
Mitra, et al. (2012) "Rab25 in cancer: a brief update" *Biochem Soc Trans* 40(6): 1404-8.
Miyajima, et al. (1985) "Complex Formation Between Di- and Monophosphatidylcholines and Cyclodextrins in Water" *Chem Pharm Bull (Tokyo)* 33(6): 2587-90.
Mizushima, et al. (2011) "Autophagy: Renovation of Cells and Tissus" *Cell* 147(4): 736.
Mohammad N, et al. (2014) "Cholesterol depletion by methyl-R-cyclodextrin augments tamoxifen induced cell death by enhancing its uptake in melanoma" *Mol Cancer A* 3: 204.
Moloudizargari, et al. (2017) "Autophagy, its mechanisms and regulation: Implications in neurodegenerative diseases" *Ageing Res Rev* 40: 64-74.
Monnaert V, et al. (2004) "Behavior of alpha- beta-, and gamma-Cyclodextrins and Their Derivatives on an in Vitro Model of Blood-Brain Barrier" *Journal of Pharmacology and Experimental Therapeutics* 310: 745-51.
Moon, et al. (2008) "Physico-chemical modifications of conjugated linoleic acid for ruminal protection and oxidative stability" *Nutrition & Metabolism* 5: Article 16.
Moors, et al. (2017) "Therapeutic potential of autophagy-enhancing agents in Parkinson's disease" *Mol Neurodegener* 12: 11.
Moran, et al. (2006) "Whole genome expression profiling of the medial and lateral substantia nigra in Parkinson's disease" *Neurogenetics* 7(1): 1-11.
Morris, R. G. M. (1981) "Spatial localization does not require the presenceof local cues" *Learning and Motivation* 12(2): 239-60.
Mosesson, et al. (2008) "Derailed endocytosis: an emerging feature of cancer" *Nat Rev Cancer* 8(11): 835-50.
Moskvina, et al. (2013) "Analysis of genome-wide association studies of Alzheimer disease and of Parkinson disease to determine if these 2 diseases share a common genetic risk" *JAMA Neurol.* 70(10): 1268-76.
Motoyama, et al. (2015) "Evaluation of antitumor effects of folate-conjugated methyl-β-cyclodextrin in melanoma" *Biol Pharm Bull* 38(3): 374-9.
Nalls, et al. (2014) "Large-scale meta-analysis of genome-wide association data identifies six new risk loci for Parkinson's disease" *Nat Genet* 46(9): 989-93.
Ng, TM, et al. (2013) "Comparison of Bumetanide- and Metolazone-Based Diuretic Regimens to Furosemide in Acute Heart Failure," *J Cardiovasc Pharmacol Ther* 18: 345-53.
Nicholls, et al. (2014) "Varespladib and cardiovascular events in patients with an acute coronary syndrome: the VISTA-16 randomized clinical trial" *JAMA* 311: 252-62.
NIH (2015) "Study of 2-hydroxpropyl-13-cyclodextrin (VTS-270) to Treat Niemann-Pick Type CI (NPC1) Disease" ClinicalTrialsgov: NCT02534844.
Nishimura, et al. (2003) "Overexpression of ROCK in human breast cancer cells: evidence that ROCK activity mediates intracellular membrane traffic of lysosomes" *Pathol Oncol Res* 9(2): 83-95.
Nishimura, et al. (2006) "A role of LIM kinase 1/cofilin pathway in regulating endocytic trafficking of EGF receptor in human breast cancer cells" *Histochem Cell Biol* 126(5): 627-38.

Nociari, et al. (2014) "Beta cyclodextrins bind, stabilize, and remove lipofuscin bisretinoids from retinal pigment epithelium" *Proceedings of the National Academy of Sciences* 111: E1402-E8.
Nordestgaard, et al. (2015) "Loss-of-function mutation in ABCA1 and risk of Alzheimer's disease and cerebrovascular disease" *Alzheimers & Dementia* 11(12): 1430-38.
O'Neill, C. (2013) "PI3-kinase/Akt/mTOR signaling: impaired on/off switches in aging, cognitive decline and Alzheimer's disease" *Exp Gerontol.* 48(7): 647-53.
O'Reilly, et al. (2015) "The fate of chemoresistance in triple negative breast cancer (TNBC)" *BBA Clin* 3: 257-75.
Ohtani Y, et al. (1989) "Differential effects of a-, R- and ?-cyclodextrins on human erythrocytes" *European Journal of Biochemistry* 186: 17-22.
Okada, et al. (1995) "Inhibition of Human Vascular Smooth Muscle Cell Migration and Proliferation by B-Cyclodextrin Tetradecasulfate" *The Journal of Pharmacology and Experimental Therapeutics* 273(2): 948-954.
Ono N, et al. (2001) "A moderate interaction of maltosyl-alphacyclodextrin with Caco-2 cells in comparison with the parent cyclodextrin" *Biol Pharm Bull* 24: 395-402.
Ooms Lisa M, et al. (2015) "The Inositol Polyphosphate 5-Phosphatase PIPP Regulates AKT1-Dependent Breast Cancer Growth and Metastasis" *Cancer Cell* 28: 155-69.
Ottinger et al.: (2014) "Collaborative Development of 2-Hydroxypropyl-[beta]-Cyclodextrin for the Treatment of Niemann-Pick Type CI Disease" *Current Topics in Medicinal Chemestry* 14(3):330-339.
Ozonoff S., et al. (2005) "Parental report of the early development of children with regressive autism the delays-plus-regression phenotype" *Autism* 9: 461-86.
Pahnke, et al. (2014) "Alzheimer's and ABC transporters—new opportunities for diagnostics and treatment" *Neurobiol Dis* 72 Pt A: 54-60.
Palaniyandi, et al. (2012) "Human Breast Cancer Stem Cells Have Significantly Higher Rate of Clathrin-Independent and Caveolin-Independent Endocytosis than the Differentiated Breast Cancer Cells" *Journal of cancer science & therapy* 4(7): 214-22.
Pandey P, et al. (2016) "Amyloid precursor protein and amyloid precursor-like protein 2 in cancer" *Oncotarget* 7(15): 19430-44.
Park, et al. (2002) "Inclusion complex of conjugated linoleic acid (CLA) with cyclodextrins" *J Agric Food Chem* 50(10): 2977-83.
Parnell, et al. (2015) "The future of EPAC-targeted therapies: agonism versus antagonism" *Trends in Pharmacological Sciences* 36(4): 203-14.
Pearson, et al. (2008) "How to interpret a genome-wide association study" *JAMA.* 299(11): 1335-44.
Pecheur, et al. (2016) "The Synthetic Antiviral Drug Arbidol Inhibits Globally Prevalent Pathogenic Viruses" *Journal of virology* 90: 3086-92.
Peinado, et al. (2011) "The secreted factors responsible for pre-metastatic niche formation: old sayings and new thoughts" *Semin Cancer Biol* 21(2): 139-46.
Peng, ST, et al, (2007) "CD44 Crosslinking-Mediated Matrix metalloproteinase-9 Relocation in Breast Tumor Cells Leads to Enhanced Metastasis" *Int J. Oncol* 31: 1119-26.
Peretz A, et al. (2007) "A Tale of Switched Functions: From Cyclooxygenase Inhibition to M-channel Modulation in New Diphenylamine Derivatives" *PLoS One* 2: e1332.
Perrett, et al. (2015) "The endosomal pathway in Parkinson's disease" *Mol Cell Neurosci.* 66(Pt A): 21-28.
Perrin, et al. (1978) "beta-Cyclodextrin as an aid to peritoneal dialysis. Renal toxicity of beta-cyclodextrin in the rat" Research communications in chemical pathology and pharmacology 19: 373-6.
Persaud, et al. (2011) "Nedd4-1 binds and ubiquitylates activated FGFR1 to control its endocytosis and function" *EMBO J* 30(16): 3259-73.
Person TA, et al., (2008) "How to Interpret a Genome-Wide Association Study" *JAMA* 299: 1335-44. Abstract.
Pfeffer, S. Z. (1999) "Motivating endosome motility" *Nat Cell Biol* 1(6): E145-E47.
Picollo, et al. (2015) "TMEM16 proteins: unknown structure and confusing functions" *J Mol Biol* 427(1): 94-105.

(56) References Cited

OTHER PUBLICATIONS

Pinho, et al. (2016) "Gene Expression Differences in Peripheral Blood of Parkinson's Disease Patients with Distinct Progression Profiles" *PLoS One* 11(6): e0157852.
Pinto D, et al. (2010) "Functional Impact of Global Rare Copy Number Variation in Autism Spectrum Disorders" *Nature* 466:368-72.
Pitha J, Szente L (1982) "Cyclodextrins and Congeners in Parenteral Applications" In: Proceedings of the First International Symposium on Cyclodextrins. Springer Netherlands, 457-66.
Plaza-Zabala, et al. (2017) "Autophagy and Microglia: Novel Partners in Neurodegeneration and Aging" *Int J Mol Sci* 18(3): 598.
Poser, et al. (2015) "Phosphoinositides in endocytosis" *Biochim Biophys Acta* 1851(6): 794-804.
Pourmand, et al. (2007) "Role of PTEN gene in progression of prostate cancer" *Urol J* 4(2): 95-100.
Prakasch AS, Abbott PJ (2001) "Cellular targeting strategies for drug design and delivery" *Nat Rev Drug Discov* 9: 29-42.
Prasad, eta l. (2014) "Synthesis of Prodrugs of Mefenamic Acid and their In Vivo Evaluation," *Intl Jour of Pharmacy and Pharmaceutical Sci* 6: 437-442.
Pringsheim T, et al. (2008) "Acute treatment and prevention of menstrually related migraine headache: evidence-based review" *Neurology* 70: 1555-63.
Prinz and Priller (2014) "Microglia and brain macrophages in the molecular age: from origin to neuropsychiatric disease" Nat Rev Neurosci 15(5): 300-12.
"Public Assessment Report for paediatric studies submitted in accordance with Article 45 of Regulation (EC) No. 1901/2006, as amended; Mefenamic Acid;" UK/W/037/pdWS/001 (Sep. 17, 2012).
Pugazhendi, et al. (2017) "Association of ATG16L1 gene haplotype with inflammatory bowel disease in Indians" *PLoS One* 12: e0178291.
Puthiyedth, et al. (2016) "Identification of Differentially Expressed Genes through Integrated Study of Alzheimer's Disease Affected Brain Regions" *PLoS One* 11(4): e0152342.
Raghu, et al. (2010) "Localization of uPAR and MMP-9 in lipid rafts is critical for migration, invasion and angiogenesis in human breast cancer cells" *BMC Cancer* 10: 647.
Rainero, et al. (2015) "Ligand-Occupied Integrin Internalization Links Nutrient Signaling to Invasive Migration" *Cell Rep* 10: 398-413.
Rajendran, et al. (2010) "Subcellular targeting strategies for drug design and delivery" *Nat Rev Drug Discov* 9(1): 29-42.
Rajewski and Stella (1996) "Pharmaceutical applications of cyclodextrins. 2. In vivo drug delivery" *J Pharm Sci* 85: 1142-69.
Rastogi and Clausen (1980) "Loss of lysosomal neutral proteinase from leucocytes induced by the action of multiple sclerosis-specific brain antigens" *Clin Exp Immunol* 42(1): 50-6.
Reitz, C. (2012) "The role of intracellular trafficking and the VPS10d receptors in Alzheimer's disease" *Future Neurol* 7(4): 423-31.
Renukuntla, et al. (2013) "Approaches for enhancing oral bioavailability of peptides and proteins" *International journal of pharmaceutics* 447(0): 75-93.
Resnik, et al. (2015) "Highly Selective Anti-Cancer Activity of Cholesterol-Interacting Agents Methyl-β-Cyclodextrin and Ostreolysin A/Pleurotolysin B Protein Complex on Urothelial Cancer Cells" *PLoS One* 10(9): e0137878.
Richler J., et al. (2006) "Is There a 'Regressive Phenotype' of Autism Spectrum Disorder Associated With the Measles-Mumps-Rubella Vaccine? A CPEA Study" *J Autism Dev Disord* 36:299-316.
Riekkinen, et al. (1972) "Neurochemical and morphological studies on demyelination in multiple sclerosis with special reference to etiological aspects" J Neurol 203(2): 91-104.
Risbridger, et al. (2010) "Breast and prostate cancer: more similar than different" *Nat Rev Cancer.* 10(3): 205-12.
Rivera, et al. (2010) "Sorting nexin 6 interacts with breast cancer metastasis suppressor-1 and promotes transcriptional repression" *J Cell Biochem* 111(6): 1464-72.
Rivero-Rios, et al. (2015) "Alterations in late endocytic trafficking related to the pathobiology of LRRK2-linked Parkinson's disease" *Biochem Soc Trans* 43(3): 390-5.
Rivers, et al. (2012) "Neuroprotective effect of hydroxypropyl-β-cyclodextrin in hypoxia-ischemia" *Neuroreport.* 23(3): 134-8.
Robinson AJ, et al. (2005) "Multivalent Interactions of calcium/ calmodulin-dependent Protein Kinase II With the Postsynaptic Density Proteins NR2B, densin-180, and alpha-actinin-2" *J Biol Chem* 280: 35329-36.
Rocks, et al. (2012) "Curcumin-cyclodextrin complexes potentiate gemcitabine effects in an orthotopic mouse model of lung cancer" *Br J Cancer* 107(7): 1083-92.
Rocks, et al. (2012) "Dye-binding assays for evaluation of the effects of small molecule inhibitors on amyloid (aβ) self-assembly" *CS Chem Neurosci* 3(11): 807-19.
Rodal SK, et al. (1999) "Extraction of Cholesterol with Methyl-R-Cyclodextrin Perturbs Formation of Clathrin-coated Endocytic Vesicles" *Molecular Biology of the Cell* 10: 961-74.
Rodrigues, et al. (2016) "Aβ-Induced Synaptic Alterations Require the E3 Ubiquitin Ligase Nedd4-1" *J Neurosci* 36(5): 1590-5.
Rohatgi and Shaw (2016) "An autophagy-independent function for Beclin 1 in cancer" *Mol Cell Oncol* 3(1): e1030539.
Roka E, et al. (2015) "Evaluation of the Cytotoxicity of alpha-Cyclodextrin Derivatives on the Caco2 Cell Line and Human Erythrocytes" *Molecules* 20: 20269-85.
Rossi, et al. (2005) "Identification of inactivating mutations in the JAK1, SYNJ2, and CLPTM1 genes in prostate cancer cells using inhibition of nonsense-mediated decay and microarray analysis" *Cancer Genet Cytogenet* 161(2): 97-103.
Rouzier, et al. (2005) "Microtubule-associated protein tau: a marker of paclitaxel sensitivity in breast cancer" *Proc Natl Acad Sci U S A.* 102(23): 8315-20.
Runowicz CD, et al. (2016) "American Cancer Society/American Society of Clinical Oncology Breast Cancer Survivorship Care Guideline" *J Clin Oncol* 34: 611-35.
Russell, et al. (2012) "Amyloid-β acts as a regulator of neurotransmitter release disrupting the interaction between synaptophysin and VAMP2" *PLoS One* 7(8): e43201.
Rutter, M, et al. (1999) "Quasi-autistic Patterns Following Severe Early Global Privation. English and Romanian Adoptees (ERA) Study Team" *J Child Psychol Psychiatry* 40: 537-49.
Saegusa, et al. (2008) "Pro-inflammatory secretory phospholipase A2 type IIA binds to inegrins alphavbeta3 and alph4beta1 and induces proliferation of monocytic cells in an integrin-dependent manner" *J Biol Chem* 283: 26107-15.
Sahay, et al. (2015) "The LPA1/ZEB1/miR-21-activation pathway regulates metastasis in basal breast cancer" *Oncotarget* 6(24): 20604-20.
Sakane and Kanoh (1997) "Molecules in focus: diacylglycerol kinase" *Int J Biochem Cell Biol* 29(10): 1139-43.
Sakurai, et al. (2017) "Dietary α-cyclodextrin reduces atherosclerosis and modifies gut flora in apolipoprotein E-deficient mice" *Mol Nutr Food Res* 61(8).
Salminen, et al. (2013) "Impaired autophagy and APP processing in Alzheimer's disease: The potential role of Beclin 1 interactome" *Prog Neurobiol* 106-107: 33-54.
Salter and Stevens (2017) "Microglia emerge as central players in brain disease" *Nat Med* 23(9): 1018-27.
Samadder et al. (2011) "An Active Endocytosis Pathway Is Required for the Cytotoxic Effects of Glycosylated Antitumor Ether Lipids." *Anticancer Research* 31(11): 3809-3818.
Sarnie and Xu (2014) "Lysosomal exocytosis and lipid storage disorders" *J Lipid Res* 55(6): 995-1009.
Sanchez, et al. (2011) "Methyl-β-cyclodextrins Preferentially Remove Cholesterol From the Liquid Disordered Phase in Giant Unilamellar Vesicles" *J. Membr. Biol.* 241(1): 1-10.
Sanders SJ, et al. (2011) "Multiple Recurrent De Novo CNVs, Including Duplications of the 7q11.23 Williams Syndrome Region, Are Strongly Associated With Autism" *Neuron* 70:863-85.
Santos, et al. (2017) "Changes in membrane biophysical properties induced by the Budesonide/Hydroxypropyl-β-cyclodextrin complex" *Biochim Biophys Acta Biomembr.* 1859(10): 1930-40.

(56) References Cited

OTHER PUBLICATIONS

Saunders, et al. (1997) "Measurement of total phospholipids in urine of patients treated with gentamicin" *Br J Clin Pharmacol* 43(4): 435-40.
Sardiello, M. (2016) "Transcription factor EB: from master coordinator of lysosomal pathways to candidate therapeutic target in degenerative storage diseases" *Ann N Y Acad Sci* 1371: 3-14.
Sato J., et al. (1997) "Urinary Excretion of Mefenamic Acid and Its Metabolites Including Their Esterglucuronides in Preterm Infants Undergoing Mefenamic Acid Therapy" *Biol Pharmacol Bull* 20:443-5.
Schimanski, et al. (2010) "Expression of the lipid transporters ABCA3 and ABCA1 is diminished in human breast cancer tissue" *Horm Metab Res* 42(2): 102-9.
Schluth-Bolard C, et al. (2013) "Cryptic Genomic Imbalances in De Novo and Inherited Apparently Balanced Chromosomal Rearrangements: Array CGH Study of 47 Unrelated Cases" Eur *J Med Genet* 9: e1003449.
Schmid SL, et al. (2013) "Cell biology: Lipid switches and traffic control" *Nature* 499: 161-2.
Schork AJ, et al. (2013) "All SNPs Are Not Created Equal: Genome-Wide Association Studies Reveal a Consistent Pattern of Enrichment Among Functionally Annotated SNPs" *PLoS Genet* 9: e1003449.
Schreij, et al. (2015) "Endocytic membrane trafficking and neurodegenerative disease" *Cell Mol Life Sci* 73(8): 1529-45.
Schroeder and McNiven (2014) "Importance of endocytic pathways in liver function and disease" *Compr Physiol* 4: 1403-17.
Schwyzer and Henzi (1983) "Multiple sclerosis: plaques caused by 2-step demyelination?" *Med Hypotheses* 12(2): 129-42.
Seaman and Freeman (2014) "Analysis of the Retromer complex-WASH complex interaction illuminates new avenues to explore in Parkinson disease" *Commun Integr Biol* 7: e29483.
Sekine, et al. (2010) "High-density lipoprotein induces proliferation and migration of human prostate androgen-independent cancer cells by an ABCA1-dependent mechanism" *Mol Cancer Res* 8(9): 1284-94.
Sengelaub CA, et al. (2015) "PTPRN2 and PLCR1 promote metastatic breast cancer cell migration through P1(4,5)P2-dependent actin remodeling" *EMBO J.* 35(1):62-76.
Settembre, et al. (2011) "TFEB links autophagy to lysosomal biogenesis" *Science* 332: 1429-33.
Shah K., et al. (2014) "Formulation and Evaluation of Suspensions: Mefenamic Acid Prodrugs" *Pak J Pharm Sci* 27:917-23.
Shaikh, et al. (2012) "Permeability Enhancement Techniques for Poorly Permeable Drugs: A Review" *J Appl Pharmacol Sci* 2: 34-9.
Shao, et al. (1992) "Cyclodextrins as nasal absorption promoters of insulin: mechanistic evaluations" *Pharmaceutical Research* 9: 1157-63.
Shen, et al. (2013) "Phagocytic receptor signaling regulates clathrin and epsin-mediated cytoskeletal remodeling during apoptotic cell engulfment in C. elegans" *Development* 140(15): 3230-43.
Sherva, et al. (2011) "Identification of novel candidate genes for Alzheimer's disease by autozygosity mapping using genome wide SNP data" *J Alzheimers Dis* 23(2): 349-59.
Sherva, et al. (2014) "Genome-wide association study of the rate of cognitive decline in Alzheimer's disease" *Alzheimers Dement* 10(1): 45-52.
Shimizu, et al. (2008) "IL-4-induced selective clearance of oligomeric beta-amyloid peptide(1-42) by rat primary type 2 microglia" *J Immunol* 181(9): 6503-13.
Shimoda Y, et al. (2009) "Contactins: Emerging Key Roles in the Development and Function of the Nervous System" *Cell Adh Migr* 3:64-70.
Shishido, et al. (2015) "Antifungal activity improved by coproduction of cyclodextrins and anabaenolysins in Cyanobacteria" *Proc Natl Acad Sci USA* 112: 13669-74.
Shityakov S, et al. (2016) "Evaluation of the potential toxicity of unmodified and modified cyclodextrins on murine blood-brain barrier endothelial cells" *J Toxicol Sci* 41: 175-84.

Shulga, et al. (2010) "Molecular species of phosphatidylinositol-cycle intermediates in the endoplasmic reticulum and plasma membrane" *Biochemistry* 49(2): 312-7.
Shvartsman, et al. (2006) "Cyclodextrins but not compactin inhibit the lateral diffusion of membrane proteins independent of cholesterol" *Traffic* 7: 917-26.
Sim, et al. (2012) "Ontology-based federated data access to human studies information" *AMIA Annu Symp Proc* 2012: 856-65.
Simons, et al. (1998) "Cholesterol depletion inhibits the generation of beta-amyloid in hippocampal neuons" *Proc Natl Acad Sci USA* 95: 6460-4.
Sjöblom, et al. (2006) "The consensus coding sequences of human breast and colorectal cancers" *Science* 314(5797): 268-74.
Small and Petsko (2015) "Retromer in Alzheimer disease, Parkinson disease and other neurological disorders" *Nat Rev Neurosci* 16(3): 126-32.
Smoller, et al. (2013) "Identification of risk loci with shared effects on five major psychiatric disorders: a genome-wide analysis," *Lancet* 381: 1371-9.
Soderberg, et al. (1992) "Lipid composition in different regions of the brain in Alzheimer's disease/senile dementia of Alzheimer's type" *J Neurochem* 59(5): 1646-53.
Sole-Domenech, et al. (2016) "The endocytic pathway in microglia during health, aging and Alzheimer's disease" *Ageing Res Rev* 32: 89-103.
Solecki, D. J. (2012) "Sticky situations: recent advances in control of cell adhesion during neuronal migration" *Curr Opin Neurobiol* 22(5): 791-8.
Song, et al. (2004) "Meta-analysis: apolipoprotein E genotypes and risk for coronary heart disease" *Ann Intern Med* 141: 137-47.
Song W, et al. (2014) "2-Hydroxypropyl-R-cyclodextrin promotes transcription factor EB-mediated activation of autophagy: implications for therapy" *J Biol Chem* 289: 10211-22.
Splawski, et al. (2004) "CaV1.2 kCalcium Channel Dysfunction Causes a Multisystem Disorder Including Arrhythmia and Autism," *Cell,* 119: 19-31.
Stella VJ, et al. (2008) "Cyclodextrins" *Toxicol Pathol* 36: 30-42.
Storch, et al. (2007) "Localization of the human breast cancer resistance protein (BCRP/ABCG2) in lipid rafts/caveolae and modulation of its activity by cholesterol in vitro" *J Pharmacol Exp Ther.* 323(1): 257-64.
Strandvik, B. (2010) "Fatty acid metabolim in cystic fibrosis" *Prostaglandins, leukotrienes, and essential fatty acids* 83: 121-9.
Sullivan, et al. (2017) "Autophagy-Lysosome Dysfunction in Amytrophic Lateral Sclerosis and Frontotemporal Lobar Degeneration," in Sharma, P. (ed) *Lysosomes—Associated Diseases and Methods to Study their Function.* Rijeka: InTech, 63-91.
Swaminathan, et al. (2016) "BECN1/Beclin 1 sorts cell-surface APP/amyloid β precursor protein for lysosomal degradation" *Autophagy* 12(12): 2404-19.
Symeonides, et al. (2017) "FAK-inhibition opens the door to checkpoint immunotherapy in Pancreatic Cancer" *J Immunother Cancer* 5: 17.
Szejtli J, et al. (1981) "Influencing of resorption and side-effects of salicylic acid by complexing with beta-cyclodextrin" *Pharmazie* 36: 283-6.
Szente and Fenyvesi (2017) "Cyclodextrin-Lipid Complexes: Cavity Size Matters" *Structural Chemistry* 28: 479-92.
Takagi t, et al. (2006) "Schnurri-2 Mutant Mice Are Hypersensitive to Stress and Hyperactive" *Brain Res* 1108:88-97.
Takahashi, et al. (2000) "Cdk5 and munc-18/p67 co-localization in early stage neurofibrillary tangles-bearing neurons in Alzheimer type dementia brains" *J Neurol Sci* 172(1): 63-9.
Takahashi S, et al. (2016) "Susceptibility of outer hair cells to cholesterol chelator 2-hydroxypropyl-R-cyclodextrine is prestin-dependent" *Sci Rep* 6: 21973.
Tan, et al. (2003) "Plasma total cholesterol level as a risk factor for Alzheimer disease: the Framingham Study" *Archives of internal medicine* 163: 1053-7.
Tan, et al. (2014) "Decreased rabphilin 3A immunoreactivity in Alzheimer's disease is associated with Aβ burden" *Neurochem Int* 64: 29-36.

(56) References Cited

OTHER PUBLICATIONS

Tan, et al. (2017) "Autophagy and its implication in human oral diseases" *Autophagy* 13:225-36.
Tall AR, et al. (1975) "Studies on Ponstan (Mefenamic Acid): I. Gastro-intestinal Blood Loss; II. Absorbtion and Excretion of a New Formulation" *J Int Med Res* 3:176-82.
Tatusova and Madden (1999) "BLAST 2 Sequences, a new tool for ocmparing protein and nucleotide sequences," *FEMS microbiology letters* 174: 247-50.
Telarico and Perl (2012) "The role of endocytic recycling in autoimmunity" *Methods Mol Biol* 900: 91-107.
Teng KK, et al. (2010) "Understanding Proneurotrophin Actions: Recent Advances and Challenges" *Developmental Neurobiology* 70:350-9.
Tettey, et al. (2014) "Vascular comorbidities in the onset and progression of multiple sclerosis" *J Neurol Sci* 347: 23-33.
The Merck Manual, (1992) 1403-1404, 1488-1494.
Thomas P, et al. (2012) "Membrane Progesterone Receptors: Evidence for Neuroprotective, Neurosteroid Signaling and Neuroendocrine Functions in Neuronal Cells" *Neuroendrocrinology* 96: 162-71.
Tiribuzi, et al. (2011) "Lysosomal β-galactosidase and β-hexosaminidase activities correlate with clinical stages of dementia associated with Alzheimer's disease and type 2 diabetes mellitus" *J Alzheimers Dis* 24(4): 785-97.
Tomas, et al. (2014) "EGF receptor trafficking: consequences for signaling and cancer" *Trends in Cell Biology* 24(1): 26-34.
Tomlinson, et al. (2015) "Identification of distinct circulating exosomes in Parkinson's disease" *Ann Clin Transl Neurol* 2(4): 353-61.
Tonks NK (2006) "Protein Tyrosine Phosphatases: From Genes, to Function, to Disease" *Nat Rev Mol Cell Biol* 7:833-46.
Trasino, et al. (2009) "Ligand, receptor, and cell type-dependent regulation of ABCA1 and ABCG1 mRNA in prostate cancer epithelial cells" *Mol Cancer Ther* 8(7): 1934-45.
Tsigelny, et al. (2008) "Mechanisms of hybrid oligomer formation in the pathogenesis of combined Alzheimer's and Parkinson's diseases" *PLoS One* 3(9): e3135.
Tukey, JW(1962) "The Future of Data Analysis" *Ann Math Stat* 33(1): 1-67.
Tukey, John W. (1977) Exploratory data analysis (Reading, Mass.: Addison-Wesley).
Tukey JW (1980) "We Need Both Exploratory and Confirmatory" *American Statistician* 34: 23-5.
Tulpule and Dringen (2013) "Formaldehyde in brain: an overlooked player in neurodegeneration?" *Journal of Neurochemistry* 127(1): 7-21.
Tuvia, et al. (2014) "A Novel Suspension Formulation Enhances Intestinal Absorption of Macromolecules Via Transient and Reversible Transport Mechanisms" *Pharmaceutical Research* 31(8): 2010-21.
Valencia, et al. (2013) "Striatal synaptosomes from Hdh140Q/140Q knock-in mice have altered protein levels, novel sites of methionine oxidation, and excess glutamate release after stimulation" *J Huntingtons Dis* 2(4): 459-75.
Valenza, et al. (2015) "Disruption of astrocyte-neuron cholesterol cross talk affects neuronal function in Huntington's disease" *Cell Death Differ* 22(4): 690-702.
Valnegri P, et al. (2011) "The X-linked Intellectual Disability Protein IL1RAPL1 Regulates Excitatory Synapse Formation by Binding PTPδ and RhoGAP2" *Hum Mol Genet* 20:4797-809.
Van der Mark, et al. (2013) "P4 ATPases: flippases in health and disease" *International Journal of Molecular Sciences* 14(4): 7897-922.
Van Dijk, et al. (2013) "Changes in endolysosomal enzyme activities in cerebrospinal fluid of patients with Parkinson's disease" *Mov Disord* 28(6): 747-54.
Van Dooren, et al. (2014) "Derailed intraneuronal signalling drives pathogenesis in sporadic and familial Alzheimer's disease" *Biomed Res Int*, 167024.
Van Ommen, et al. (2004) "Disposition of 14C-alpha-cyclodextrin in germ-free and conventional rats" *Regul Toxicol Pharmacol* 39 Suppl 1: 57-66.
Van Spronsen M, et al. (2010) "Synapse Pathology in Psychiatric and Neurologic Disease" *Current Neurology and Neuroscience Reports* 10: 207-14.
Van Weering, et al. (2012) "SNX-BAR-mediated endosome tubulation is co-ordinated with endosome maturation" *Traffic* 13(1): 94-107.
Vance JE (2012) "Dysregulation of cholesterol balance in the brain: contribution to neurodegenerative diseases" *Disease Models and Mechanisms* 5: 746-55.
Vance JE, et al. (2014) "Niemann-Pick C disease and mobilization of lysosomal cholesterol by cyclodextrin" *Journal of Lipid Research* 55: 1609-21.
Vecsernyes M, et al. (2014) "Cyclodextrins, blood-brain barrier, and treatment of neurological diseases." *Arch Med Res* 45: 711-29.
Venuti MC, et al. (1989) "Synthesis and Biological Evaluation of omega-(N,N,N-trialkylammonium)alkyl Esters and Thioesters of Carboxylic Acid Nonsteroidal Antiinflammatory Agents" *Phar Res* 6:867-73.
Viaud, et al. (2016) "Phosphoinositides: Important lipids in the coordination of cell dynamics" *Biochimie* 125: 250-58.
Vilarino-Guell, et al. (2014) "DNAJC13 mutations in Parkinson disease" *Hum Mol Genet* 23(7); 1794-801.
Vite, et al. (2015) "Intracisternal cyclodextrin prevents cerebellar dysfunction and Purkinje cell death in feline Niemann-Pick type C1 disease" *Sci Transl Med* 7(276): 276ra26.
Von Tresckow, et al. (2004) "Depletion of cellular cholesterol and lipid rats increases shedding of CD30" *Journal of Immunology* 172: 4324-31.
Wadman, M. (2016) "Battle over rare disease drug ensnares NIH" *Science* 354(6308): 18-19.
Wagner, et al. (2008) "Dietary alpha-cyclodextrin lowers low-density lipoprotein cholesterol and alters plasma fatty acid profile in low-density lipoprotein receptor knockout mice on a high-fat diet" *Metabolism* 57(8): 1046-51.
Walenbergh, et al. (2015) "Weekly Treatment of 2-Hydroxypropyl-β-cyclodextrin Improves Intracellular Cholesterol Levels in LDL Receptor Knockout Mice" *Int J Mol Sci.* 16(9): 21056-69.
Walter, et al. (2001) "Phosphorylation regulates intracellular trafficking of beta-secretase" *J Biol Chem* 276(18): 14634-41.
Wang, et al. (2004) "Mutational Analysis of the Tyrosine Phosphatome in Colorectal Cancers" *Science* 304:1164-6.
Wang, et al. (2009) "Common Genetic Variants on 5p14.1 Associate With Autism Spectrum Disorders" *Nature* 459: 528-33.
Wang, et al. (2014) "Dysregulation of protein trafficking in neurodegeneration" *Molecular Neurodegeneration* 9: Article 31.
Wang, et al. (2015) "A pivotal role of FOS-mediated BECN1/Beclin 1 upregulation in dopamine D2 and D3 receptor agonist-induced autophagy activation" *Autophagy* 11(11): 2057-73.
Wang, et al. (2015) "Polymorphisms within ASTN2 gene are associated with age at onset of Alzheimer's disease" *J Neural Transm (Vienna)* 122(5): 701-8.
Wang, et al. (2017) "Endo-lysosomal dysfunction: a converging mechanism in neurodegenerative diseases" *Curr Opin Neurobiol* 48: 52-8.
Ward, et al. (2010) "2-hydroxypropyl-beta-cyclodextrin raises hearing threshold in normal cats and in cats with Niemann-Pick type C disease" *Pediatr. Res* 68(1): 52-6.
Waschbusch, et al. (2014) "LRRK2 transport is regulated by its novel interacting partner Rab32" *PLoS One* 9(10): e111632.
Waugh, M. (2015) "PIPs in Neurological Diseases" *Biochim Biophys Acta.* 1851(8): 1066-82.
Weber, G. F. (2015) "Molecular Analysis of a Recurrent Sarcoma Identifies a Mutation in FAF1" *Sarcoma*, 839182.
Wei X, et al. (2011) "Exome Sequencing Identifies GRIN2A as Frequently Mutated in Melanoma" *Nat. Genet* 43: 442-6.
Wei, et al. (2015) "Annexin A4 and cancer" *Clin Chim Acta* 447: 72-8.
Weng, et al. (2013) "Genome-wide discovery of genetic variants affecting tamoxifen sensitivity and their clinical and functional validation" *Annals of Oncology* 24(7): 1867-73.

(56) References Cited

OTHER PUBLICATIONS

Whyte, et al. (2017) "Endo-lysosomal and autophagic dysfunction: a driving factor in Alzheimer's disease?" *J Neurochem* 140: 703-17.
Wilcoxon F (1954) "Individual comparisons by ranking methods" *Biometrics* 1: 80-3.
Wilkinson, et al. (2012) "Ibuprofen attenuates oxidative damage through NOX2 inhibition in Alzheimer's disease" *Neurobiology of Aging* 33(1): 197.
Willshaw, et al. (2004) "Identification of a novel protein complex containing annexin A4, rabphilin and synaptotagmin" *FEBS Lett* 559(1-3): 13-21.
Wilson, et al. (2010) "Astn2, a novel member of the astrotactin gene family, regulates the trafficking of ASTN1 during glial-guided neuronal migration" *The Journal of Neuroscience* 30(25): 8529-40.
Wilton, D. C. (2005) "Phospholipases A2: structure and function" *European Journal of Lipid Science and Technology* 107: 193-205.
Winder CV, et al. (1962) "Anti-inflammatory, Antipyretic and Antinociceptive Properties of N-(2,3-xylyl)anthranilic Acid (Mefenamic Acid)" *J. Pharmacol Exp Ther* 138:405-13.
Winder CV, et al. (1966) "Experimental Observations on Flufenamic, Mefenamic, and Meclofenamic Acids. I. Pharmacology" *Rheumatology* VIII: 7-49.
Winslow, et al. (2010) "α-Synuclein impairs macroautophagy: implications for Parkinson's disease" *J Cell Biol* 190(6): 1023-37.
Wittkowski, et al. (1988) "Friedman-Type Statistics and Consistent Multiple Comparisons for Unbalanced Designs with Missing Data" *Journal of the American Statistical Association* 83: 1163-70.
Wittkowski, et al. (2004) "Combining several ordinal measures in clinical studies" *Stat Med* 23: 1579-92.
Wittkowski, et al. (2008) "A novel computational biostatistics approach implies impaired dephosphorylation of growth factor receptors as associated with severity of autism" *Transl Psychiatri* 4: e354.
Wittkowski KM, et al. (2013) "From single-SNP to wide-locus: genome-wide association studies identifying functionally related genes and intragenic regions in small sample studies" *Pharmacogenomics* 14: 391-401.
Wittkowski, et al. (2014) "A novel computational biostatistics approach implies impaired dephosphorylation of growth factor receptors as associated with severity of autism" *Transl. Psychiatry* 4(1): e354.
Wittkowski, et al. (2018) "Complex polymorphisms in endocytosis genes suggest alpha-cyclodextrin as a treatment for breast cancer" *PLoS One* 13: e0199012.
Wood, H. (2016) "Anticancer drug prevents nucleation of toxic amyloid-β42 aggregates" *Nat Rev Neurol* 12: 126.
Woolley, et al. (2015) "Phosphoinositide signaling in cancer: INPP4B Akt(s) out" *Trends Mol Med*. 21(9): 530-32.
Wu, JY, et al. (2005) "Association of Duchenne Muscular Dystrophy With Autism Spectrum Disorder" *J Child Neurol* 20: 790-5.
Yamaguchi, et al. (2009) "Lipid rafts and caveolin-1 are required for invadopodia formation and extracellular matrix degradation by human breast cancer cells" *Cancer Res* 69: 8594-602.
Yamaguchi, et al. (2015) "Targeting cholesterol with β-cyclodextrin sensitizes cancer cells for apoptosis" *FEBS Lett* 589(24 Pt B): 4097-105.
Yamashita, et al. (2015) "Outer Hair Cell Lateral Wall Structure Constrains the Mobility of Plasma Membrane Proteins" *PLoS Genet* 11(9): e1005500.
Yang, et al. (2004) "Paeoniflorin: an antihyperlipidemic agent from Paeonia lactiflora" *Fitoterapia* 75: 45-9.
Yang, et al. (2008) "Attenuation of MPTP neurotoxicity by rolipram, a specific inhibitor of phosphodiesterase IV" *Exp Neurol* 211(1): 311-4.
Yang, et al. (2013) "Elevated expression of syntenin in breast cancer is correlated with lymph node metastasis and poor patient survival" *Breast Cancer Res* 15(3): R50.
Yao, et al. (2006) "An essential role for beta-actin mRNA localization and translation in Ca2+-dependent growth cone guidance" *Nat Neurosci* 9(10): 1265-73.

Yao, et al. (2010) "MicroRNA-related cofilin abnormality in Alzheimer's disease" *PLoS One* 5(12): e15546.
Yao, et al. (2012) "Neuroprotection by cyclodextrin in cell and mouse models of Alzheimer disease" *Journal of Experimental Medicine* 209(13): 2501-13.
Yao, et al. (2016) "The role of annexin A4 in cancer" *Front Biosci (Landmark Ed)* 21: 949-57.
Yarla, et al. (2016) "Phospholipase A2 Isoforms as Novel Targets for Prevention and Treatment of Inflammatory and Oncologic Diseases" *Curr Drug Targets* 17: 1940-62.
Yau, HJ, et al. (2010) "Flufenamic Acid Decreases Neuronal Excitability Through Modulation of Voltage-Gated Sodium Channel Gating" *J Physiol* 588: 3869-82.
Yokoo M, et al. (2015) "2-Hydroxypropyl-R-Cyclodextrin Acts as a Novel Anticancer Agent" *PLoS One* 10: e0141946.
Yoshimura, Y, et al. (2013) "The Brain's Response to the Human Voice Depends on the Incidence of Autistic Traits in the General Population" *PLoS One* 8: e80126.
Yoshitomi, et al. (1987) "Effect of triglyceride on small intestinal absorption of cefoxitin in rats" *J Pharm Pharmacol* 39(11): 887-91.
Yu, et al. (2015) "Cooperative interactions of LPPR family members in membrane localization and alteration of cellular morphology" *Journal of Cell Science* 128(17): 3210-22.
Xin-Ming, et al. (2008) "Osteotropic beta-cyclodextrin for local bone regeneration" *Biomaterials*. 29(11): 1686-92.
Zarzycki, et al. (2009) "Interaction of native alpha-cyclodextrin, beta-cyclodextrin and gamma-cyclodextrin and their hydroxypropyl derivatives with selected organic low molecular mass compounds at elecated and subambienttemperature under RP-HPLC conditions" *J Pharm Sci* 86: 935-43.
Zhang, et al. (2006) "Metastatic potential of mouse Lewis lung cancer cells is regulated via ganglioside GM1 by modulating the matrix metalloprotease-9 localization in lipid rafts" *J Biol Chem*. 281(26): 18145-55.
Zhang, et al. (2013) "PTEN mutation, methylation and expression in breast cancer patients" *Oncology Letters* 6(1): 161-68.
Zhang, et al. (2014) "Endothelial PINK1 mediates the protective effects of NLRP3 deficiency during lethal oxidant injury" *The Journal of Immunology* 192(11): 5296-304.
Zhang, et al. (2015) "The Role of Retromer in Alzheimer's Disease," *Molecular Neurobiology* 53: 4201-4209.
Zhao, et al., (2016) "Candidate Antimetastasis Drugs Suppress the Metastatic Capacity of Breast Cancer Cells by Reducing Membrane Fluidity", *Cancer Research* 76: 2037-2049.
Zhiyu, et al. (2016) "The inflammasome: an emerging therapeutic oncotarget for cancer prevention" *Oncotarget* 7(31): 50766.
Zhu, et al. (2012) "Mutations in a P-type ATPase gene cause axonal degeneration" *PLoS Genetics* 8(8): e1002853.
Zhu, et al. (2016) "Association of Parkinson's Disease GWAS-Linked Loci with Alzheimer's Disease in Han Chinese" *Mol Neurobiol* 54(1): 308-318.
Zimmer, et al. (2016) "Cyclodextrin promotes atherosclerosis regression via macrophage reprogramming" *Sci Transl Med*. 8(333): 333ra50.
Zoller M. (2011) "CD44: Can a Cancer-Initiating Cell Profit From an Abundantly Expressed Molecule?" *Nat Rev Cancer* 11: 254-67.
Zou, et al. (2011) "Association of Upregulated Ras/Raf/ERK1/2 Signaling With Autism" *Genes Brain Behav* 10:615-24.
Zuko, A, et al. (2011) "Contactins: Structural Aspects in Relation to Developmental Functions in Brain Disease" *Adv Protein Chem Struct Biol* 84: 143-80.
International Search Report and Written Opinion dated Sep. 28, 2018 by the International Searching Authority for International Application No. PCT/IB2017/000373, filed on Mar. 20, 2017 and published as WO 2017/163128 on Sep. 28, 2017 (Applicant—Asdera, LLC) (16 Pages).
International Preliminary Report on Patentability dated Sep. 25, 2018 by the International Searching Authority for International Application No. PCT/IB2017/000373, filed on Mar. 20, 2017 and published as WO 2017/163128 on Sep. 28, 2017 (Applicant—Asdera, LLC) (12 Pages).
European Search Report and Written Opinion dated Nov. 11, 2019 by the European Patent Office for EP Application No. 17769520.2,

(56) References Cited

OTHER PUBLICATIONS filed on Mar. 20, 2017 and published as EP3432880 on Jan. 30, 2019 (Applicant—Asdera LLC) (25 Pages).
International Search Report and Written Opinion dated Dec. 22, 2014 by the International Searching Authority for International Application No. PCT/US2014/054421, filed on Sep. 5, 2013 and published as WO/2015/035258 on Mar. 12, 2015 (Applicant—The Rockefeller University) (16 Pages).
International Preliminary Report on Patentability dated Mar. 8, 2016 by the International Searching Authority for International Application No. PCT/US2014/054421, filed on Sep. 5, 2013 and published as WO/2015/035258 on Mar. 12, 2015 (Applicant—The Rockefeller University) (9 Pages).
European Search Report and Written Opinion dated May 30, 2017 by the European Patent Office for EP Application No. 14841451.9, filed on Sep. 5, 2014 and published as EP3041577A1 on Jul. 13, 2016 (Applicant—Univ Rockefeller) (13 Pages).
Communication pursuant to Article 94(3) EPC dated Jun. 19, 2019 by the European Patent Office for EP Application No. 14841451.9, filed on Sep. 5, 2014 and published as EP3041577A1 on Jul. 13, 2016 (Applicant—Univ Rockefeller) (11 Pages).
International Search Report and Written Opinion dated Apr. 4, 2019 by the International Searching Authority for International Application No. PCT/US2018/048414, filed on Aug. 28, 2018 and published as WO 2019/067145 on Apr. 4, 2019 (Applicant—Asdera, LLC) (17 Pages).
International Preliminary Report on Patentability dated Mar. 31, 2020 by the International Searching Authority for International Application No. PCT/US2018/048414, filed on Aug. 28, 2018 and published as WO 2019/067145 on Apr. 4, 2019 (Applicant—Asdera, LLC) (10 Pages).
International Search Report and Written Opinion dated Feb. 24, 2020 by the International Searching Authority for International Application No. PCT/US2018/051604, filed on Aug. 28, 2018 and published as WO 2019/067269 on Apr. 4, 2019 (Applicant—Asdera, LLC) (18 Pages).
International Preliminary Report on Patentability dated Mar. 31, 2020 by the International Searching Authority for International Application No. PCT/US2018/051604, filed on Aug. 28, 2018 and published as WO 2019/067269 on Apr. 4, 2019 (Applicant—Asdera, LLC) (9 Pages).
Requirement for Restriction dated Nov. 4, 2019 by the U.S. Patent and Trademark Office for U.S. Appl. No. 16/086,946, filed Sep. 20, 2018 and published as US 2020-0000840 A1 on Jan. 2, 2020 (Applicant—Asdera, LLC) (7 Pages).
Response to Requirement for Restriction filed on Feb. 3, 2020 with the U.S. Patent and Trademark Office for U.S. Appl. No. 16/086,946, filed Sep. 20, 2018 and published as US 2020-0000840 A1 on Jan. 2, 2020 (Applicant—Asdera, LLC) (8 Pages).
Response to Office Action filed on Aug. 5, 2020 with the U.S. Patent and Trademark Office for U.S. Appl. No. 16/086,946, filed Sep. 20, 2018 and published as US 2020-0000840 A1 on Jan. 2, 2020 (Applicant—Asdera, LLC) (7 Pages).
Non-final Office Action dated Apr. 24, 2020 by the U.S. Patent and Trademark Office for U.S. Appl. No. 16/086,946, filed Sep. 20, 2018 and published as US 2020-0000840 A1 on Jan. 2, 2020 (Applicant—Asdera, LLC) (16 Pages).
Response to Office Action filed on Jul. 24, 2020 with the U.S. Patent and Trademark Office for U.S. Appl. No. 16/086,946, filed Sep. 20, 2018 and published as US 2020-0000840 A1 on Jan. 2, 2020 (Applicant—Asdera, LLC) (18 Pages).
Requirement for Restriction dated Oct. 6, 2016 by the U.S. Patent and Trademark Office for U.S. Appl. No. 14/916,665, filed Mar. 4, 201616 and published as US 2016-0206581 A1 on Jul. 21, 2016 (Applicant—Asdera, LLC) (9 Pages).
Response to Requirement for Restriction filed on Feb. 6, 2017 by the U.S. Patent and Trademark Office for U.S. Appl. No. 14/916,665, filed Mar. 4, 201616 and published as US 2016-0206581 A1 on Jul. 21, 2016 (Applicant—Asdera, LLC) (8 Pages).

Non-final Office Action dated Jun. 28, 2017 by the U.S. Patent and Trademark Office for U.S. Appl. No. 14/916,665, filed Mar. 4, 201616 and published as US 2016-0206581 A1 on Jul. 21, 2016 (Applicant—Asdera, LLC) (9 Pages).
Response to Office Action filed on Oct. 30, 2017 by the U.S. Patent and Trademark Office for U.S. Appl. No. 14/916,665, filed Mar. 4, 201616 and published as US 2016-0206581 A1 on Jul. 21, 2016 (Applicant—Asdera, LLC) (15 Pages).
Final Office Action dated Mar. 27, 2018 by the U.S. Patent and Trademark Office for U.S. Appl. No. 14/916,665, filed Mar. 4, 201616 and published as US 2016-0206581 A1 on Jul. 21, 2016 (Applicant—Asdera, LLC) (10 Pages).
Response to Office Action filed on Sep. 27, 2018 by the U.S. Patent and Trademark Office for U.S. Appl. No. 14/916,665, filed Mar. 4, 201616 and published as US 2016-0206581 A1 on Jul. 21, 2016 (Applicant—Asdera, LLC) (16 Pages).
Non-final Office Action dated Dec. 13, 2018 by the U.S. Patent and Trademark Office for U.S. Appl. No. 14/916,665, filed Mar. 4, 201616 and published as US 2016-0206581 A1 on Jul. 21, 2016 (Applicant—Asdera, LLC) (11 Pages).
Response to Office Action filed on Jun. 13, 2019 by the U.S. Patent and Trademark Office for U.S. Appl. No. 14/916,665, filed Mar. 4, 201616 and published as US 2016-0206581 A1 on Jul. 21, 2016 (Applicant—Asdera, LLC) (18 Pages).
Final Office Action dated Oct. 18, 2019 by the U.S. Patent and Trademark Office for U.S. Appl. No. 14/916,665, filed Mar. 4, 201616 and published as US 2016-0206581 A1 on Jul. 21, 2016 (Applicant—Asdera, LLC) (14 Pages).
Response to Office Action filed on Dec. 18, 2019 by the U.S. Patent and Trademark Office for U.S. Appl. No. 14/916,665, filed Mar. 4, 201616 and published as US 2016-0206581 A1 on Jul. 21, 2016 (Applicant—Asdera, LLC) (12 Pages).
Advisory Action dated Dec. 27, 2019 by the U.S. Patent and Trademark Office for U.S. Appl. No. 14/916,665, filed Mar. 4, 201616 and published as US 2016-0206581 A1 on Jul. 21, 2016 (Applicant—Asdera, LLC) (3 Pages).
Response to Office Action filed on Dec. 30, 2019 by the U.S. Patent and Trademark Office for U.S. Appl. No. 14/916,665, filed Mar. 4, 201616 and published as US 2016-0206581 A1 on Jul. 21, 2016 (Applicant—Asdera, LLC) (12 Pages).
Non-final Office Action dated Jun. 17, 2020 by the U.S. Patent and Trademark Office for U.S. Appl. No. 14/916,665, filed Mar. 4, 201616 and published as US 2016-0206581 A1 on Jul. 21, 2016 (Applicant—Asdera, LLC) (9 Pages).
Notice of Non-Compliant Amendment dated Jul. 31, 2020 with the U.S. Patent and Trademark Office for U.S. Appl. No. 16/086,946, filed Sep. 20, 2018 and published as US 2020-0000840 A1 on Jan. 2, 2020 (Applicant—Asdera, LLC) (2 Pages).
Notice of Non-Compliant Amendment filed on Aug. 5, 2020 with the U.S. Patent and Trademark Office for U.S. Appl. No. 16/086,946, filed Sep. 20, 2018 and published as US 2020-0000840 A1 on Jan. 2, 2020 (Applicant—Asdera, LLC) (9 Pages).
Comerford et al. (2011) "The beneficial effects of α-cyclodextrin on blood lipids and weight loss in healthy humans," *Obesity* 19(6): 1200-1204.
Khan et al. (2010) "Cancer and metastasis: prevention and treatment by green tea," *Cancer Metastasis Review* 29: 43 5-445.
Tanyi et al. (2003) "Role of decreased levels of lipid phosphate phosphatase-1 in accumulation of lysophosphatidic acid in ovarian cancer," *Clinical Cancer Research* 9: 3534-3545.
Final Office Action dated Oct. 27, 2020 by the U.S. Patent and Trademark Office for U.S. Appl. No. 16/086,946, filed Sep. 20, 2018 and published as US 2020-0000840 A1 on Jan. 2, 2020 (Applicant—Asdera, LLC) 21 Pages).
Ajisaka, N. et al. (2002) "Effects of medium-chain fatty acid-cyclodextrin complexes on ruminal methane production in vitro" *Animal Science Journal* 73: 479-484.
Coisne, C. et al. (2016) "Cyclodextrins as emerging therapeutic tools in the treatment of cholesterol-associated vascular and neurodegenerative diseases," *Molecules* 21: 1748.
Furune, T. et al. (2014) "A study on the inhibitory mechanism for cholesterol absorption by α-cyclodextrin administration," *Beilstein J. Org. Chem.* 10: 2827-2835.

(56) References Cited

OTHER PUBLICATIONS

Hadaruga, N. G. et al. (2010) "Water content of fatty acid/cyclodextrin nanoparticles," *Journal of Agroalimentary Processes and Technologies* 16(2): 230-235.
Kimura, Y. et al. (1998) "Physico-chemical properties of fatty acids for assessing the threshold concentration to enhance the absorption of a hydrophilic substance," *Biosci. Biotechnol. Biochem.* 62(3): 443-447.
Maher, S. et al. (2009) "Safety and efficacy of sodium caprate in promoting oral drug absorption: from in vitro to the clinic," *Advanced Drug Delivery Reviews* 61(15): 1427-1449.
Trichard, L. et al. (2007) "α-Cyclodextrin/oil beads as a new carrier for improving the oral bioavailability of lipophilic drugs," *Journal of Controlled Release* 122: 47-53.
U.S. Appl. No. 62/310,774, filed Mar. 20, 2016, Knut M. Wittkowski.
U.S. Appl. No. 16/086,946 (US 2020/0000840 A1), filed Mar. 20, 2016 (Jan. 2, 2020), Knut M. Wittkowski.
U.S. Appl. No. 61/874,979, filed Sep. 6, 2013, Knut Wittkowski.
U.S. Appl. No. 61/911,998, filed Dec. 4, 2013, Knut Wittkowski.
U.S. Appl. No. 61/919,501, filed Dec. 20, 2013, Knut Wittkowski.
U.S. Appl. No. 14/916,665 (US 2016/0206581 A1), filed Sep. 5, 2014 (Jul. 21, 2016), Knut Wittkowski.
U.S. Appl. No. 62/551,193, filed Aug. 28, 2017, Knut Wittkowski.
U.S. Appl. No. 62/565,053, filed Sep. 28, 2017, Knut Wittkowski.
U.S. Appl. No. 62/573,658, filed Oct. 17, 2017, Knut Wittkowski.
U.S. Appl. No. 62/586,826, filed Nov. 15, 2017, Knut Wittkowski.
U.S. Appl. No. 62/643,694, filed Mar. 15, 2018, Knut Wittkowski.
U.S. Appl. No. 62/679,912, filed Jun. 3, 2018, Knut Wittkowski.
U.S. Appl. No. 16/643,494, filed Feb. 28, 2020, Knut Wittkowski.
Qiu et al. (2017) "Applications of cyclodextrins in cancer treatment," J Incl Phenom Macrocycl Chem 89(2): 1-18.
Yewale, C. et al "Oral Absorption Promoters: Opportunities, Issues, and Challenges" Crit. Rev. Ther. Drug Carr. Syst., vol. 32, No. 5, pp. 363-387. (2015).

\* cited by examiner

Clustering Analysis

MβCD, but not αCD protect A2E

Exocytosis / Lysosomal Function

Endocytosis in Alzheimer's Disease

HPβCD Clearance of a-Syn

A: TFEB

Control　　　HPβCD　　　HPβCD-cholesterol

B: a-syn-GFP

Control　　　HPβCD　　　HPβCD-cholesterol

HTT: HPαCD improves Bodyweight

A Sex = Female

B Sex = Male

SOD1: HPαCD improves Bodyweight

A Sex = Female

B Sex = Male

FPLC Standard curves

| Study | Gene | IPV6 | IPV1 | Othr | Mbrn | PI/EC | MPK | Ncls |
|---|---|---|---|---|---|---|---|---|
| CGEM | PRKCQ | 6.70 | | | | | PRKCQ | |
| CGEM | TRPM3 | 6.26 | | | TRPM3 | | | |
| CGEM | BUB3 | 6.20 | 6.20 | | | | | BUB3 |
| CGEM | SCARB2 | 6.02 | 5.57 | | | SCARB2 | | |
| CGEM | FGFR2 | 6.00 | 4.89 | | FGFR2 | | | |
| CGEM | POLR1A | 5.95 | | | | | | POLR1A |
| CGEM | GNG7 | 5.89 | | | GNG7 | | | |
| CGEM | VWA3B | 5.86 | | VWA3B | | | | |
| CGEM | SYK | 5.85 | | | SYK | | | |
| CGEM | MSL3 | 5.81 | | | | | | MSL3 |
| CGEM | CALN1 | 5.79 | | | CALN1 | | | |
| CGEM | ATP8B1 | 5.58 | | | | ATP8B1 | | |
| CGEM | TCF15 | 5.49 | | | | | | TCF15 |
| CGEM | LPPR1 | 5.48 | 4.65 | | | LPPR1 | LPPR1 | |
| CGEM | HAS2 | 5.44 | 4.63 | | HAS2 | | | |
| CGEM | NUP54 | 5.42 | | | | | | NUP54 |
| CGEM | BRCAT49 | 5.38 | 4.46 | BRCAT49 | | | | |
| CGEM | KCND3 | 5.38 | | | KCND3 | | | |
| CGEM | MDGA1 | 5.37 | | MDGA1 | | | | |
| CGEM | SYT17 | 5.36 | | | | SYT17 | | |
| CGEM | SYNJ2 | 5.30 | | | | SYNJ2 | | |
| CGEM | MACROD2 | 5.22 | | | | | | MACROD2 |
| CGEM | SHANK2 | 5.14 | | | SHANK2 | | | |
| CGEM | AK5 | 5.13 | 4.24 | AK5 | | | | |
| CGEM | LYZL1 | 5.12 | | | LYZL1 | | | |
| CGEM | MMRN1 | 5.09 | 4.95 | MMRN1 | | | | |
| CGEM | CTNNBL1 | 5.08 | | | | | | CTNNBL1 |
| CGEM | SAMHD1 | 5.06 | | | | | | SAMHD1 |
| CGEM | MEGF11 | 5.06 | | | | MEGF11 | | |
| CGEM | NLRP4 | 5.04 | | | | NLRP4 | | |
| CGEM | DMRTB1 | 5.03 | | | | | | DMRTB1 |
| CGEM | ZMAT4 | 5.02 | | | | | | ZMAT4 |
| CGEM | ALPP | 5.00 | | ALPP | | | | |
| CGEM | ABCA1 | 4.99 | | | | ABCA1 | | |
| CGEM | SCMH1 | 4.98 | | | | | | SCMH1 |
| CGEM | LPHN3 | 4.98 | 4.18 | | LPHN3 | | | |
| CGEM | DGKQ | 4.97 | | | | DGKQ | | |
| CGEM | HNF1B | 4.97 | | | | | | HNF1B |
| CGEM | SMARCAL1 | 4.95 | 4.81 | BRCAT54 | | | | SMARCAL1 |
| CGEM | BRCAT54 | 4.95 | 4.81 | BRCAT54 | | | | |
| CGEM | AGPAT4 | 4.94 | | | | AGPAT4 | | |
| CGEM | PTCD3 | 4.52 | 4.47 | PTCD3 | | | | |
| CGEM | BMPR1B | 4.89 | 4.47 | BMPR1B | | | | |
| CGEM | FBXO38 | 4.29 | 4.29 | | | | | FBXO38 |
| CGEM | PARK2 | 4.86 | 4.24 | PARK2 | | | | |
| CGEM | ANO4 | 4.21 | 4.21 | | ANO4 | | | |
| CGEM | ABO | 4.24 | 4.19 | ABO | | | | |
| CGEM | DAP | 4.28 | 4.19 | DAP | | | | |
| CGEM | STXBP1 | 4.59 | 4.11 | | | STXBP1 | | |
| CGEM | SLC5A3 | 4.09 | 4.09 | | | SLC5A3 | | |
| CGEM | MRGPRE | 4.49 | 4.07 | | MRGPRE | | | |
| CGEM | NTSR1 | 4.82 | 4.06 | | NTSR1 | | | |
| CGEM | MRPL35 | 4.04 | 4.04 | MRPL35 | | | | |

FIG. 49A

| Study | Gene | IPV6 | IPV1 | Othr | Mbrn | PI/EC | MPK | Ncls |
|---|---|---|---|---|---|---|---|---|
| EPIC | SOHLH2 | 8.58 | 5.42 | | | | | SOHLH2 |
| EPIC | AGPAT3 | 6.59 | 4.73 | | | AGPAT3 | | |
| EPIC | CELF2 | 6.51 | 4.11 | | | | | CELF2 |
| EPIC | STARD13 | 6.48 | 4.56 | | STARD13 | | | |
| EPIC | PCSK5 | 6.37 | | | PCSK5 | | | |
| EPIC | mirLET7BHG | 6.33 | 4.68 | mirLET7BHG | | | | |
| EPIC | ATP8A1 | 6.28 | 4.87 | | | ATP8A1 | | |
| EPIC | CHD3 | 6.13 | 5.66 | | | | | CHD3 |
| EPIC | TNS1 | 5.88 | 4.19 | | TNS1 | | | |
| EPIC | TRAPPC9 | 5.85 | 4.38 | | | | TRAPPC9 | |
| EPIC | CDKAL1 | 5.82 | 4.34 | | | | | CDKAL1 |
| EPIC | TAS2R1 | 5.57 | | | TAS2R1 | | | |
| EPIC | TMEM132C/D | 5.50 | | TMEM132C/D | | | | |
| EPIC | SIX2 | 5.49 | 4.05 | | | | | SIX2 |
| EPIC | GLB1 | 5.40 | | GLB1 | | | | |
| EPIC | SPATA19 | 5.35 | 4.13 | SPATA19 | | | | |
| EPIC | ASTN2 | 5.33 | | ASTN2 | | | | |
| EPIC | CHMP7 | 5.27 | | | | CHMP7 | | |
| EPIC | PRKCQ | 5.26 | | | | | PRKCQ | |
| EPIC | E2F3 | 5.24 | | | | | | E2F3 |
| EPIC | NEFL/M | 5.23 | | | NEFL/M | | | |
| EPIC | NCCRP1 | 5.21 | | | | | | NCCRP1 |
| EPIC | FLT3 | 5.16 | | | FLT3 | | | |
| EPIC | EPHB1 | 5.15 | 4.12 | | EPHB1 | | | |
| EPIC | CFAP36 | 5.14 | 4.08 | CFAP36 | | | | |
| EPIC | GRIA1 | 5.13 | | | GRIA1 | | | |
| EPIC | RASD2 | 5.08 | | | RASD2 | | | |
| EPIC | COL3A1 | 5.08 | | COL3A1 | | | | |
| EPIC | RARB | 5.06 | | | | | | RARB |
| EPIC | SLC43A3 | 5.05 | | SLC43A3 | | | | |
| EPIC | VAV3 | 5.05 | | | | VAV3 | | |
| EPIC | HMGXB4 | 5.04 | | | | | | HMGXB4 |
| EPIC | VWC2L | 5.03 | 4.32 | VWC2L | | | | |
| EPIC | PRKAG2 | 5.02 | | | | | PRKAG2 | |
| EPIC | LZTS1 | 5.00 | | | | | | LZTS1 |
| EPIC | LARGE | 5.00 | | LARGE | | | | |
| EPIC | LSMD1 | 4.98 | | LSMD1 | | | | |
| EPIC | IGSF9B | 4.93 | | IGSF9B | | | | |
| EPIC | ACAN | 4.90 | | | ACAN | | | |
| EPIC | SDCBP2 | 4.88 | | | | SDCBP2 | | |
| EPIC | KPNA3 | 4.77 | 4.77 | KPNA3 | | | | |
| EPIC | OR52K2 | 4.64 | 4.26 | OR52K2 | | | | |
| EPIC | GPHN | 4.63 | 4.24 | | GPHN | | | |
| EPIC | BMP7 | 4.22 | 4.22 | | BMP7 | | | |
| EPIC | RAPGEF4 | 3.68 | 4.20 | | | RAPGEF4 | | |
| EPIC | TNFRSF10A | 4.20 | 4.20 | | TNFRSF10A | | | |
| EPIC | MICAL2 | 3.90 | 4.18 | MICAL2 | | | | |
| EPIC | SFRS8 | 3.57 | 4.16 | | | | | SFRS8 |
| EPIC | PNOC | 4.81 | 4.06 | | PNOC | | | |
| EPIC | USP44 | | | USP44 | | | | |

FIG. 49B

| Study | Gene | IPV6 | IPV1 | Othr | Mbm | PI/EC | MPK | Ncls |
|---|---|---|---|---|---|---|---|---|
| PBCS | DOCK8 | 7.74 | 5.83 | | DOCK8 | | | |
| PBCS | NCOR2 | 6.83 | | | | | | NCOR2 |
| PBCS | CACNA1C | 6.59 | 4.95 | | CACNA1C | | | |
| PBCS | MEGF11 | 6.39 | 4.07 | | | | MEGF11 | |
| PBCS | GPC6 | 6.22 | 4.82 | | GPC6 | | | |
| PBCS | PTENP1 | 6.14 | | | | PTENP1 | | |
| PBCS | CDH4 | 6.06 | 4.60 | CDH4 | | | | |
| PBCS | CLLU1 | 6.05 | | CLLU1 | | | | |
| PBCS | RGS3 | 5.97 | 5.80 | | RGS3 | | | |
| PBCS | TMCC3 | 5.70 | | TMCC3 | | | | |
| PBCS | SSTR4 | 5.63 | | | SSTR4 | | | |
| PBCS | EDN1 | 5.43 | | | EDN1 | | | |
| PBCS | ANAPC13 | 5.39 | | | | | | ANAPC13 |
| PBCS | TRPC3 | 5.35 | 4.86 | | TRPC3 | | | |
| PBCS | COL11A1 | 5.34 | 4.15 | COL11A1 | | | | |
| PBCS | PRH1 | 5.33 | 4.27 | PRH1 | | | | |
| PBCS | EEA1 | 5.32 | 4.46 | | | EEA1 | | |
| PBCS | RBM23 | 5.22 | 4.48 | | | | | RBM23 |
| PBCS | HAPLN3 | 5.22 | 4.13 | | HAPLN3 | | | |
| PBCS | PTPRG | 5.21 | 5.08 | | PTPRG | | | |
| PBCS | RNASE11 | 5.21 | | RNASE11 | | | | |
| PBCS | ANXA4 | 5.17 | 4.42 | | | ANXA4 | | |
| PBCS | CADM2 | 5.14 | 4.39 | CADM2 | | | | |
| PBCS | CDK18 | 5.13 | | | | | | CDK18 |
| PBCS | SLC13A3 | 5.12 | | SLC13A3 | | | | |
| PBCS | KIF25 | 5.11 | | KIF25 | | | | |
| PBCS | MMD2 | 5.07 | | MMD2 | | | | |
| PBCS | TRIM36 | 5.05 | | TRIM36 | | | | |
| PBCS | PAX2 | 5.05 | | | | | | PAX2 |
| PBCS | GLIS2 | 5.02 | | | | | | GLIS2 |
| PBCS | CYB5RL | 5.02 | | CYB5RL | | | | |
| PBCS | ISM1 | 5.00 | 3.83 | | | | | ISM1 |
| PBCS | BAG1 | 4.99 | 4.45 | BAG1 | | | | |
| PBCS | ZNF98 | 4.98 | 4.19 | ZNF98 | | | | |
| PBCS | ZFAT | 4.98 | | | | | | ZFAT |
| PBCS | SDK1 | 4.95 | | | SDK1 | | | |
| PBCS | TRMT11 | 4.95 | 4.29 | TRMT11 | | | | |
| PBCS | HDAC4 | 4.92 | | | | | | HDAC4 |
| PBCS | MDF1 | 4.91 | | | | | | MDF1 |
| PBCS | TFAP2A | 4.91 | | | | | | TFAP2A |
| PBCS | HLA-C | 4.91 | | HLA-C | | | | |
| PBCS | FHIT | 4.61 | 4.48 | | | | | FHIT |
| PBCS | UNC13C | 4.91 | 4.41 | | | UNC13C | | |
| PBCS | CHIT1 | 4.42 | 4.41 | CHIT1 | | | | |
| PBCS | SYNDIG1 | 4.38 | 4.38 | | SYNDIG1 | | | |
| PBCS | SLC25A26 | 4.74 | 4.28 | SLC25A26 | | | | |
| PBCS | RAB32 | 4.84 | 4.14 | | | RAB32 | | |
| PBCS | A2BP1 | 4.12 | 4.12 | | | | | A2BP1 |
| PBCS | N4BP3 | 4.59 | 4.07 | | | N4BP3 | | |

FIG. 49C

USE OF CYCLODEXTRINS IN DISEASES AND DISORDERS INVOLVING PHOSPHOLIPID DYSREGULATION

RELATED APPLICATIONS

This application is a national stage filing under 35 U.S.C. § 371 of International Application No. PCT/US2018/051604, filed Sep. 18, 2018, which claims the benefit of priority to U.S. Provisional Application No. 62/679,912, filed Jun. 3, 2018, U.S. Provisional Application No. 62/643,694, filed Mar. 15, 2018, U.S. Provisional Application No. 62/586,826, filed Nov. 15, 2017, U.S. Provisional Application No. 62/573,658, filed Oct. 17, 2017, and U.S. Provisional Application No. 62/565,053, filed Sep. 28, 2017. The entire contents of the aforementioned applications are incorporated by reference in their entireties.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_37927_0003U8. The size of the text file is 58,647 bytes, the text file was created on Feb. 12, 2020.

BACKGROUND

As the human population is aging, the prevalence of age-related conditions, including, but not limited to, cancers and neurodegenerative diseases increases, yet interventions to prevent or treat these conditions are lacking or have undesirable side effects. Currently, about 5 million US individuals have Alzheimer's disease and about 1 million have Parkinson's disease. As life expectancy increases, the prevalence of neurodegenerative diseases or disorders also increases. Ten percent of people age 65 and older and 15% of people age 75 or older have Alzheimer's disease. Alzheimer's disease also disproportionately affects women, who comprise two thirds of Americans with Alzheimer's disease. Alzheimer's disease is also more likely to affects members of African American and Hispanic communities than Caucasian communities. Patients with Alzheimer's disease have few treatment options. Several recent phase 3 studies of BACE1 inhibitors have failed. Similarly, patients with Parkinson's disease initially benefit from treatment of motor symptoms (levodopa), but become non-responsive over time.

Breast cancer (BCa) is the most common non-cutaneous malignancy in women. In 2016, 246,660 U.S. women were newly diagnosed, and 3,100,000 U.S. women lived with breast cancer. After lung cancer has been declining 30% since 1990, breast cancer is the second most deadly cancer, causing 40,290 deaths in 2015, 17,010 before the age of 65 (most from metastases to bone, lung, and brain). As women with a family history of breast cancer have a two-fold risk of developing breast cancer, (American Cancer Society (2015)) a substantial portion of breast cancer risk is expected to be inherited, yet the known complexes of 'cancer growth genes' PIK3CA/PTEN as well as DNA damage repair genes BRCA1/BRCA2/PALB2 and MRE11A/RAD50/NBN/RINT1, explain only 10% of the incidence.

Treatments of malignant diseases or disorders are also limited and suffer from numerous drawbacks. Treatments generally include local therapy (for instance: surgery with or without radiation in breast cancer, surgery or radiation in prostate cancer) and adjuvant systemic therapy (hormonal therapy, chemotherapy, and biologic agents) for cancer cells that may have spread. Radiation and chemotherapy often cause substantial side-effects including, but not limited to, nausea and hair loss. Hormone therapy for prostate cancer includes anti-androgens. For some hormone-receptor-positive forms of breast cancer, selective estrogen receptor modulators (SERM), such as tamoxifen and raloxifene, and aromatase inhibitors, such as exemestane and anastrozole, can interfere with disease progression. Monoclonal antibodies, such as trastuzumab and pertuzumab, are approved for the treatment of HER2 positive cancer. For patients with triple-negative breast cancer (absence of estrogen, progesterone, and the Her2/neu receptor), treatment options are limited.

A common thread between neurodegenerative disorders and malignancies are lysosomal dysfunction. Lysosomal dysfunction is implicated in a diverse range of disorders and diseases, including genetic diseases. In some cases, high levels of endocytosis have been suggested as a pleiotropic factor in the etiology underlying malignant and neurodegenerative processes, including, but not limited to, a role of endocytosis in cancer, and "deranged" endocytosis in Alzheimer's disease, where endocytic pathway abnormalities precede $A\beta$ deposition and inhibition of endocytosis reduces amyloid precursor protein ("APP") internalization and immediately lowers $A\beta$ levels in vivo.

While sufficient levels of endocytosis are necessary in early life, high levels of endocytosis may become detrimental with age. Enlarged macrophages have been identified in atherosclerosis, steatohepatitis, and cystic fibrosis, and high levels of endocytosis can increase accumulation of lipids in macrophages. Activation of the early endocytic pathway has been observed in autoimmune-diseases, such as systemic lupus erythematosus (SLE), inflammatory bowel disease (IBD), and arthritis. Attenuation of phosphoinositides (PIPs), which regulate endocytosis, restrains autoimmune disease and phosphoinositides have also been linked to several genetic diseases. Impaired phospholipid (PL) efflux increases accumulation of lipids in macrophages (MΦs) and enlarged macrophages have been identified in atherosclerosis, steatohepatitis, and cystic fibrosis (CF). Inhibition of signaling by the phosphoinositide-3 kinase (PI3K) has been shown to benefit inflammatory and autoimmune diseases as well as hematological malignancies. Several attempts to modulate specific phosphatases or kinases, however, have failed to result in successful therapies. Hence, in spite of strong evidence for involvement of endo-/pinocytosis in all these diseases and for involvement of phosphoinositides, effective modulators of endocytosis are lacking.

Activation of the early endocytic pathway can lead to accumulation of lipids in macrophages and enlarged macrophages have been identified in atherosclerosis, steatohepatitis, and cystic fibrosis. Activation of the early endocytic pathway has been observed in autoimmune-diseases, such as systemic lupus erythematosus (SLE), inflammatory bowel disease, and arthritis. Attenuation of phosphoinositides restrains autoimmune disease. Broadly acting [cyclin-dependent kinase (CDK)] inhibitors yielded largely disappointing results, and only a small number of patients benefit from phosphoinositide 3-kinase (PI3K) inhibitors. Overall, dysregulation of phospholipids has been linked to poor quality of life with aging.

Because overactive endocytosis has been linked to cancers, neurodegenerative diseases, and other pathological conditions, the same treatment that prevents metastases in cancer could also prevent accumulation of undegraded macromolecules in neurodegenerative diseases and many other age-related conditions, including formation of foam cells in atherosclerosis via macropinocytosis. Yet, effective treatments to regulate endocytosis are lacking. Therefore, there is a need for effective treatments for the symptoms of disorders and diseases that involve dysfunction involving endocytosis, phagocytosis, pinocytosis, and lysosomal pathways.

The lipid-carrier molecule β-cyclodextrin (β-CD) is "generally recognized as safe" (GRAS) as food additives and the more water-soluble derivative 2-hydroxypropyl-β-cyclodextrin (HP-β-CD, HPβCD) is frequently used as an excipient to form water soluble compounds with lipophilic drugs. In vitro and in animal models, HP-β-CD has been shown to exert some of its effect by reducing lysosomal dysfunction (LYD) and improving autophagy (AΦ), another common factor in the etiology of age-related conditions. In humans, HP-β-CD has been used for the treatment of Niemann-Pick disease type C (NPC), where its function is to reduce the aggregation of cholesterol, a lipid molecule, in lysosomes (LYs). Again, the mechanism of action is unknown. Clinical applications of HP-β-CD have been limited, however, because depriving the ear's outer hair cells of cholesterol may cause permanent hearing loss.

It has not yet been appreciated that derivatives of the smaller α-cyclodextrin (α-CD, αCD) and its derivatives, such as hydroxypropyl-α-cyclodextrin (HP-α-CD, HPαCD), which are too small to fit cholesterol, may effectively treat malignancies and neurodegenerative disorders without the undesirable side effects, such the hearing loss caused by beta-cyclodextrin.

SUMMARY

Through the application of computational biostatistics and decision strategies to data from genome-wide association studies (GWAS), we have identified functionally related collections of genes and determined that endocytosis, which is controlled by phosphoinositides (PIP) comprising those generated by the PI cycle, is involved in the metastases process of certain types of cancers such as breast or prostate cancer. In this regard, we established that breast cancer risk is conferred not only by (rare) variations in DNA damage repair genes, such as BRCA1/2, but more frequently by a global dysregulation of the PI cycle and that endocytosis, which is known to be controlled by the PI cycle, is a critical component of local spread, migration, and invasion of cancer cells. See e.g., Example 1. Thus, in one aspect, provided herein are methods of targeting the PI cycle as a means for treating diseases or conditions causing a dysfunctional lysosomal pathway and/or elevated endocytosis, phagocytosis, or pinocytosis in a subject, in which the diseases or condition may be caused by e.g., aberrant expression of a gene or combination of genes as identified e.g., by the novel GWAS approach (see e.g., Example 1) described herein. Such diseases or conditions include e.g., breast cancer (BCa), Alzheimer's disease (AD), Parkinson's disease (PD), Huntington's disease (HD), multiple sclerosis (MS), amyotrophic lateral sclerosis (ALS), coronary artery disease (CAD), and Niemann-Pick type C disease (NPC). See e.g., Examples 2, 3, 6, and 7.

Therapeutic agents known to have effects against animal models of carcinomas, neurodegenerative and several other age-related diseases are beta-cyclodextrins. These include e.g., methyl-β-cyclodextrin (M-β-CD) and HP-β-CD. See e.g., J Membr Biol. 2011 May, 241(1): 1-10; The Journal of Experimental Medicine, 209 (13), 2501-13, and the discussion set forth in Example 5. Traditionally, beta-cyclodextrins were believed to remove and to extract cholesterol (Chol) from cell membranes and/or organelles. For example, the scavenging of cholesterol and/or binding directly to Aβ or α-synuclein was believed to be the mode of action for β-CDs in AD and PD. See The Journal of Experimental Medicine, 209 (13), 2501-13. Although β-CDs have therapeutic potential, they are ototoxic, i.e., cause damage to the ear which can result in permanent hearing loss. See J Assoc Res Otolaryngol, 16 (5), 599-611.

Here, having for the first time identified the implication of phospholipid supply to the PI cycle for lysosomal function (see e.g., Example 1), the scavenging of cholesterol can no longer be viewed as the primary mechanism upon which cyclodextrins such as β-CDs function. See e.g., Example 1. Rather, our data show that cyclodextrins act by scavenging phospholipids and, thereby, regulate endocytosis, which reduces lysosomal stress and improves autophagy. For example, we have also found that α-CD restores what has been called "derailed" endocytosis in breast cancer, "deranged" endocytosis in AD and "defective" endocytosis in PD. See e.g., Example 4. We have also noted that α-CD is more efficient than β-CD in solubilizing phospholipids (see Example 8). Therefore, in one aspect, provided herein are methods of using α-cyclodextrins (e.g., α-CD or HP-α-CD) for treating a subject having a disease, disorder, or condition that involves impaired lysosomal function. Such diseases and disorders are described herein and include e.g., breast cancer (BCa), Alzheimer's disease (AD), Parkinson's disease (PD), Huntington's disease (HD), multiple sclerosis (MS), amyotrophic lateral sclerosis (ALS), coronary artery disease (CAD), and Niemann-Pick type C disease (NPC)

In addition to the above findings, we have further realized that the absorption of alpha-cyclodextrins (e.g., HP-α-CD) from the intestine can be improved by the complexation with fatty acids. For example, we have demonstrated that a composition comprising a clathrate of HP-α-CD and medium chain fatty acids substantially improved absorption. Accordingly, in one aspect, provided herein are pharmaceutical compositions comprising an alpha-cyclodextrin (e.g., HP-α-CD) and a medium chain fatty acid (e.g., capric acid), as well as and their use for treating a disease or disorder that involves impaired lysosomal function and autophagy. Such diseases and disorders are described herein and include e.g., breast cancer (BCa), Alzheimer's disease (AD), Parkinson's disease (PD), Huntington's disease (HD), multiple sclerosis (MS), amyotrophic lateral sclerosis (ALS), coronary artery disease (CAD), and Niemann-Pick type C disease (NPC).

In yet another aspect, we further identified that pharmaceutical compositions comprising an alpha-cyclodextrin (e.g., HP-α-CD) and a medium chain fatty acid (e.g., capric acid) can be used to treat diseases involving inflammation. See e.g., Example 16. Therefore, in one aspect, provided herein are pharmaceutical compositions comprising an alpha-cyclodextrin (e.g., HP-α-CD) and a medium chain fatty acid (e.g., capric acid) for use in treating inflammatory diseases.

Additional aspects are further described below and in the Detailed Description and Examples sections of the application. The description in each of the sections of this patent application is intended to be read in conjunction with the other sections. Furthermore, the various embodiments described in each of the sections of this patent application can combined in various different ways, and all such combinations are intended to fall within the scope of the present disclosure.

In one aspect, the present disclosure provides a method of treating a malignant, neurodegenerative, vascular, metabolic, inflammatory, autoimmune, pulmonary, fibrotic, hepatic, lysosomal storage, or viral disease, disorder, or condition in a subject, the method comprising administering to the subject an effective amount of a cyclic oligosaccharide (e.g., α-cyclodextrin (α-CD)), or an analogue or derivative thereof (e.g., HP-α-CD), either alone or in combination with one or more additional active agents. In another aspect, the present disclosure provides a composition comprising α-CD, or an analogue or derivative thereof (e.g., HP-α-CD), for use in the treatment of an epithelial cancer (carcinoma) or the treatment of Parkinson's, Alzheimer's, or Huntington's disease. In one aspect, the composition comprising HP-α-CD further comprises a medium-length chain fatty acid (MCFA), e.g., fatty acids having an aliphatic tail of 6-12 carbon atoms. In one aspect, the HP-α-CD and medium-length chain fatty acid (MCFA) in the composition form a clathrate. In such clathrates, the MCFAs are guests of HP-α-CD. In one the MCFA in the composition is caprate or caprylate or is a salt thereof such as sodium caprate.

In one aspect, the present disclosure provides a method of improving one or more indicators or symptoms of a malignant, neurodegenerative, vascular, metabolic, inflammatory, autoimmune, pulmonary, fibrotic, hepatic, lysosomal storage, or viral disease, disorder, or condition in a subject, the method comprising administering to a subject exhibiting one or more indicators or symptoms of a malignant, neurodegenerative, vascular, metabolic, inflammatory, autoimmune, pulmonary, fibrotic, hepatic, lysosomal storage, or viral disease, disorder, or condition, an effective amount of α-CD, or an analogue or derivative thereof (e.g., HP-α-CD), either alone or in combination with one or more additional active agents. Suitable indicators include, but are not limited to, results of a blood test (including, but not limited to circulating tumor DNA and/or prostate-specific antigen), an x-ray evaluation, the result of a physical examination (including, but not limited to a palpable tumor), a psychiatric evaluation, or a tissue biopsy for histological evaluation and/or determination of hormone receptor status. In one aspect, a symptom or indicator is selected from the group consisting of survival, disease-free survival, distant metastasis-free survival, results of a blood test (including, but not limited to circulating tumor DNA and prostate-specific antigen), an x-ray evaluation, the result of a physical examination (including, but not limited to a palpable tumor), or a tissue biopsy for histological evaluation. In one embodiment, the "improving" comprises an increase of at least 1% in a measurement of the one or more indicators or symptoms. In another aspect, the present disclosure provides a composition comprising α-CD, or an analogue or derivative thereof (e.g., HP-α-CD), for use in the treatment of an epithelial cancer (carcinoma) or the treatment of Parkinson's, Alzheimer's, or Huntington's disease. In one aspect, the composition comprising HP-α-CD further comprises a medium-length chain fatty acid (MCFA), e.g., fatty acids having an aliphatic tail of 6-12 carbon atoms. In one aspect, the HP-α-CD and medium-length chain fatty acid (MCFA) in the composition form a clathrate. In such clathrates, the MCFAs are guests of HP-α-CD. In one the MCFA in the composition is caprate or salt thereof such as sodium caprate.

In some embodiments, the disclosure relates to a method of restoring the synthesis of sphingomyelin in a subject in need thereof, the method comprising administering a cyclodextrin (e.g., α-CD), or an analogue or derivative thereof (e.g., HP-α-CD), either alone or in combination with one or more additional active agents. In one aspect, the present disclosure provides a method of improving one or more indicators or symptoms of a malignant, neurodegenerative, vascular, metabolic, inflammatory, autoimmune, pulmonary, fibrotic, hepatic, lysosomal storage, or viral disease, disorder, or condition in a subject in need thereof, the method comprising administering to a subject exhibiting one or more indicators or symptoms of a malignant, neurodegenerative, vascular, metabolic, inflammatory, autoimmune, pulmonary, fibrotic, hepatic, lysosomal storage, or viral disease, disorder, or condition, an effective amount of α-CD, or a salt, analogue or derivative thereof (e.g., HP-α-CD), either alone or in combination with one or more additional active agents. Suitable indicators include, but are not limited to, results of a blood test (including, but not limited to circulating tumor DNA and/or prostate-specific antigen), an x-ray evaluation, the result of a physical examination (including, but not limited to a palpable tumor), a psychiatric evaluation, or a tissue biopsy for histological evaluation and/or determination of hormone receptor status. In one aspect, a symptom or indicator is selected from the group consisting of survival, disease-free survival, distant metastasis-free survival, results of a blood test (including, but not limited to circulating tumor DNA and prostate-specific antigen), an x-ray evaluation, the result of a physical examination (including, but not limited to a palpable tumor), or a tissue biopsy for histological evaluation. In one embodiment, the "improving" comprises an increase of at least 1% in a measurement of the one or more indicators or symptoms.

In one aspect, the present disclosure provides a method of treating and/or preventing focal segmental glomerulosclerosis (FSGS) and nephrotic swelling in a subject in need thereof the method comprising administering to the subject an effective amount of α-CD, a salt or an analogue or derivative thereof (e.g., HP-α-CD), either alone or in combination with one or more additional active agents. In some embodiments, the disclosure relates to a method of treating and/or preventing kidney damage caused by excess or dysfunctional sphingolipid catabolism in a subject in need thereof, the method comprising administering to the subject an effective amount of α-CD, or a salt, an analogue or derivative thereof (e.g., HP-α-CD), either alone or in combination with one or more additional active agents. In some embodiments, the disclosure relates to a method of restoring the synthesis of sphingomyelin in a subject in need thereof, the method comprising administering α-CD, or an analogue or derivative thereof (e.g., HP-α-CD or salt thereof), either alone or in combination with one or more additional active agents.

In other embodiments the compositions described herein comprise resorption enhancers known in the art including, but not limited to bile salts (sodium glycocholate, sodium deoxycholate, sodium taurocholate, sodium fusidate, sodium glycodeoxycholate, sodium taurodihydrofusidate), surfactants (sodium lauryl sulfate, lysophosphatidylcholine (LPC), dioctyl sodium sulfosuccinate, laurenth-9, polysorbate, polyethyleneglycol-8-laurate, glyceryl monolaurate, glyceryl monocaprylate/caprate, glyceryl dicaprylate/caprate, saponin), fatty acids and derivatives (sorbitan laurate, sodium caprate, sucrose palmitate, lauroyl choline, sodium myristate, palmitoyl carnitine), glycerides (phospholipids, monohexanoin, medium chain glycerides), chelators (ethylene diamine tetraacetate (EDTA), disodium EDTA), salicylates (salicylic acid, sodium methoxysalicylate, acetylsalicylic acid), polymers or polysacharides (chitosan and chitosan derivatives, dextran, polyvinyl pyrrolidone (PVP), polycarbophil, sodium carboxymethylcellulose and their derivatives, inulin, pectin, chondroitin sulfate), others (azone, benzalkonium chloride, phenothiazines, nitric acid donors, menthol), newer (zonula occluden toxin, poly-1-arginines, soybean derivative glucosides, citicholine, amino acid peptides). See (Deli M A (2009) Biochimica et Biophysica Acta (BBA)—Biomembranes 1788:892-910; Renukuntla J, Vadlapudi A D, et al. (2013) Int J Pharm 447:75-93; Shaikh I, Derle N D, et al. (2012) J Appl Pharmacol Sci 2:34-9).

In some embodiments, the cyclodextrin is administered to the subject at a dose of about 2500 mg/kg α-CD bi-weekly (≈700 mg/kg/d), the same dose used for HP-β-cyclodextrin in two children with NPC for "over a year, with no discernable side effects" for a "targeted concentration of 0.1-1.0 mM." (INDs 104,114 and 104,116, approval date: 2009 Jul. 13). In other embodiments, the dose will be adjusted over time to the highest dose not causing renal adverse events or hemolysis in the patient. In some embodiments, the cyclodextrin, such as α-CD, is administered to the subject at a dose of at least about 100 mg, at least about 200 mg, at least about 500 mg, at least about 1000 mg, at least about 2000 mg, at least about 5000 mg, or at least about 10,000 mg. In some embodiments, the cyclodextrin, such as α-CD, is administered to the subject at a dose in the range of from about 1 to about 10,000 mg, from about 1 to about 7,500 mg, from about 1 to about 5,000 mg, from about 1 to about 2,500 mg, from about 1 to about 1,000 mg, from about 1 to about 500 mg, from about 1 to about 200 mg, from about 200 to about 10,000 mg, from about 200 to about 4,000 mg, from about 200 mg about 2,000 mg, about 200 to about 1,000 mg, or about 200 to about 500 mg per day. In some such embodiments, each of the dosages described above is mg/kg/day. Additional dosages that may be used are provided in the Detailed Description section of this patent application.

In some embodiments, the present disclosure provides a method of treating and/or preventing Huntingdon's disease, Alzheimer's disease, Parkinson's disease, multiple sclerosis, in a subject in need thereof, the method comprising administering to the subject an effective amount of α-CD, or an analogue or derivative thereof (e.g., HP-α-CD), either alone or in combination with one or more additional active agents. In some embodiments, the present disclosure provides a method of treating and/or preventing a malignant, neurodegenerative, vascular, metabolic, inflammatory, autoimmune, pulmonary, fibrotic, hepatic, lysosomal storage, or viral disease, disorder, or condition in a subject not exhibiting disease-specific indicators or symptoms, except indicators of the subject to belong to an at-risk subpopulation. In some embodiments, the indicator will be age. In some embodiments, the indicator will be more than 30, 40, 50, or 60 years of age.

In some embodiments the present disclosure provides a method of treating or preventing a malignant, neurodegenerative, vascular, metabolic, inflammatory, autoimmune, pulmonary, fibrotic, hepatic, lysosomal storage, or viral disease, disorder, or condition in a subject in need of treatment, the method comprising administering to the subject an effective amount of a drug reducing extracellular phospholipid. In some embodiment the malignant, neurodegenerative, vascular, metabolic, inflammatory, autoimmune, pulmonary, fibrotic, hepatic, lysosomal storage, or viral disease, disorder, or condition will be an epithelial cancer (carcinoma). In some embodiments the malignant, neurodegenerative, vascular, metabolic, inflammatory, autoimmune, pulmonary, fibrotic, hepatic, lysosomal storage, or viral disease, disorder, or condition will be breast cancer. In another embodiment the malignant, neurodegenerative, vascular, metabolic, inflammatory, autoimmune, pulmonary, fibrotic, hepatic, lysosomal storage, or viral disease, disorder, or condition will be Alzheimer's disease. In some embodiments the malignant, neurodegenerative, vascular, metabolic, inflammatory, autoimmune, pulmonary, fibrotic, hepatic, lysosomal storage, or viral disease, disorder, or condition will be Parkinson's disease. In some embodiments, the malignant, neurodegenerative, vascular, metabolic, inflammatory, autoimmune, pulmonary, fibrotic, hepatic, lysosomal storage, or viral disease, disorder, or condition will be Huntington's disease. In some embodiments, malignant, neurodegenerative, vascular, metabolic, inflammatory, autoimmune, pulmonary, fibrotic, hepatic, lysosomal storage, or viral disease, disorder, or condition will be non-alcoholic steatohepatitis (NASH).

In some embodiments, the present disclosure provides various combinations of treatments, including pharmaceutical compositions. In some embodiments, cyclodextrins are used in combination with established pharmaceutical, radiological, or surgical interventions comprising cytotoxic interventions, receptor antagonists, monoclonal antibodies, radiation therapy, removal of tumor tissue, and the like.

In one embodiment, the subject is a human. In another embodiment the subject is an adult human. In some embodiments, the subject is in need of the treatment and/or has been identified as having a risk of developing a disease or disorder resulting from one or a plurality of cellular defects caused by lysosomal dysfunction. In some embodiments, the disclosure relates to a composition comprising an effective amount of a clathrate of HP-α-CD and a salt, such as sodium caprate. In some embodiments, the molar ratio of HP-α-CD to the fatty acid is from about 0.5 to about 5. In some embodiments, the molar ratio of HP-α-CD to the fatty acid is from about 2.0 to about 1.0. In some embodiments, the molar ratio of HP-α-CD to the fatty acid is from about 1.5 to about 1.0. In some embodiments, the molar ratio of HP-α-CD to the fatty acid is from about 1.0 to about 1.0.

In some embodiments, the disclosure relates to a pharmaceutical composition comprising an effective amount of a clathrate of HP-α-CD and a salt, such as sodium caprate, wherein the composition is free or substantially free of beta-cyclodextrin and/or α-CD. In some embodiment, the disclosure relates to a method of treating any disorder disclosed herein by administering an effective amount of a pharmaceutical composition comprising (i) one or a plurality of α-cyclodextrin, derivative thereof, or a salt thereof and (ii) a fatty acid molecule, each of (i) and (ii) at an amount in weight to form a clathrate of the one or a plurality of α-cyclodextrin, derivative thereof, or a salt thereof. In some embodiments, the clathrate is from about 80 to 90% in weight of one or a plurality of α-cyclodextrin, derivative thereof, or a salt thereof, and from about 10% to about 20% in weight of the fatty acid. In some embodiments, the clathrate is from about 85% in weight of one or a plurality of α-cyclodextrin, derivative thereof, or a salt thereof, and about 15% in weight of the fatty acid. In some embodiments, the fatty acid is capric acid or a salt thereof.

The disclosure relates to a method of treating and/or preventing Alzheimer's disease in a subject in need thereof, the method comprising administering an effective amount of a pharmaceutical composition comprising one or a plurality of alpha-cyclodextrins, a derivatives, salt thereof or combinations thereof to the subject. The disclosure relates to a method of treating and/or preventing Parkinson's disease in a subject in need thereof, the method comprising administering an effective amount of a pharmaceutical composition comprising one or a plurality of alpha-cyclodextrins, a derivatives, salt thereof or combinations thereof to the subject. The disclosure relates to a method of treating and/or preventing Huntington's disease in a subject in need thereof, the method comprising administering an effective amount of a pharmaceutical composition comprising one or a plurality of alpha-cyclodextrins, a derivatives, salt thereof or combinations thereof to the subject. The disclosure relates to a method of treating and/or preventing amyotrophic lateral sclerosis (ALS) disease in a subject in need thereof, the method comprising administering an effective amount of a pharmaceutical composition comprising one or a plurality of alpha-cyclodextrins, a derivatives, salt thereof or combinations thereof to the subject. The disclosure relates to a method of treating and/or preventing multiple sclerosis (MS) disease in a subject in need thereof, the method comprising administering an effective amount of a pharmaceutical composition comprising one or a plurality of alpha-cyclodextrins, a derivatives, salt thereof or combinations thereof to the subject. In some embodiments, any of the disclosed methods, the pharmaceutical composition comprises an effective amount of a clathrate of the one or a plurality of alpha-cyclodextrins, a derivatives, salt thereof or combinations thereof, wherein the clathrate comprises a medium-length chain of fatty acid or salt thereof and the one or a plurality of alpha-cyclodextrins, a derivatives, salt thereof or combinations thereof. In some embodiments, the one or a plurality of alpha-cyclodextrins, a derivatives, salt thereof or combinations thereof and the fatty acid are in a weight/weight ratio from about 15% weight fatty acid and about 85% weight of the one or a plurality of alpha-cyclodextrins, a derivatives, salt thereof or combinations thereof in the clathrate. In some embodiments, the weight:weight ratio of fatty acid to α-cyclodextrin is sufficient for absorption into the blood.

The disclosure relates to a method of treating and/or preventing inflammation in a subject in need thereof, the method comprising administering an effective amount of a pharmaceutical composition comprising one or a plurality of alpha-cyclodextrins, a derivatives, salt thereof or combinations thereof to the subject. The disclosure also relates to a method of treating and/or preventing local metastases of a breast cancer or prostate cancer characterized by dysfunctional or deficient endocytosis caused by dysfunction or deficiency of any genes identified in the disclosure related to endocytosis. The disclosure also relates to a method of treating and/or preventing local metastases of a breast cancer or prostate cancer characterized by dysfunctional or deficient lysosomal function caused by dysfunction or deficiency of any genes identified in the disclosure related to lysosomal function. in a subject in need thereof, the method comprising administering an effective amount of a pharmaceutical composition comprising one or a plurality of alpha-cyclodextrins, a derivatives, salt thereof or combinations thereof to the subject.

In some embodiments, the disclosure relates to a method of reducing phospholipid levels in the blood of a subject, the method comprising administering an effective amount of a pharmaceutical composition comprising one or a plurality of alpha-cyclodextrins, a derivatives, salt thereof or combinations thereof to the subject. In some embodiments, the method of reducing phospholipid levels in the blood is accomplished without scavenging lysophopholipids. The disclosure also relates to a method of activating autophagy, the method comprising administering an effective amount of a pharmaceutical composition comprising one or a plurality of alpha-cyclodextrins, a derivatives, salt thereof or combinations thereof to the subject. In some embodiments, the method of improving or activating autophagy is accomplished without causing lysosomal dysfunction.

1 mM HPαCD v. 1 mM HPβCD, p=0.0001
1 mM HPαCD v. 2 mM HPβCD, p=0.0252 4 mM HPαCD v.
4 mM HPβCD, p=0.0442

(Modified from (Wittkowski K M, Dadurian C, et al. (2018) PLoS One 13:e0199012)

Figure 36:
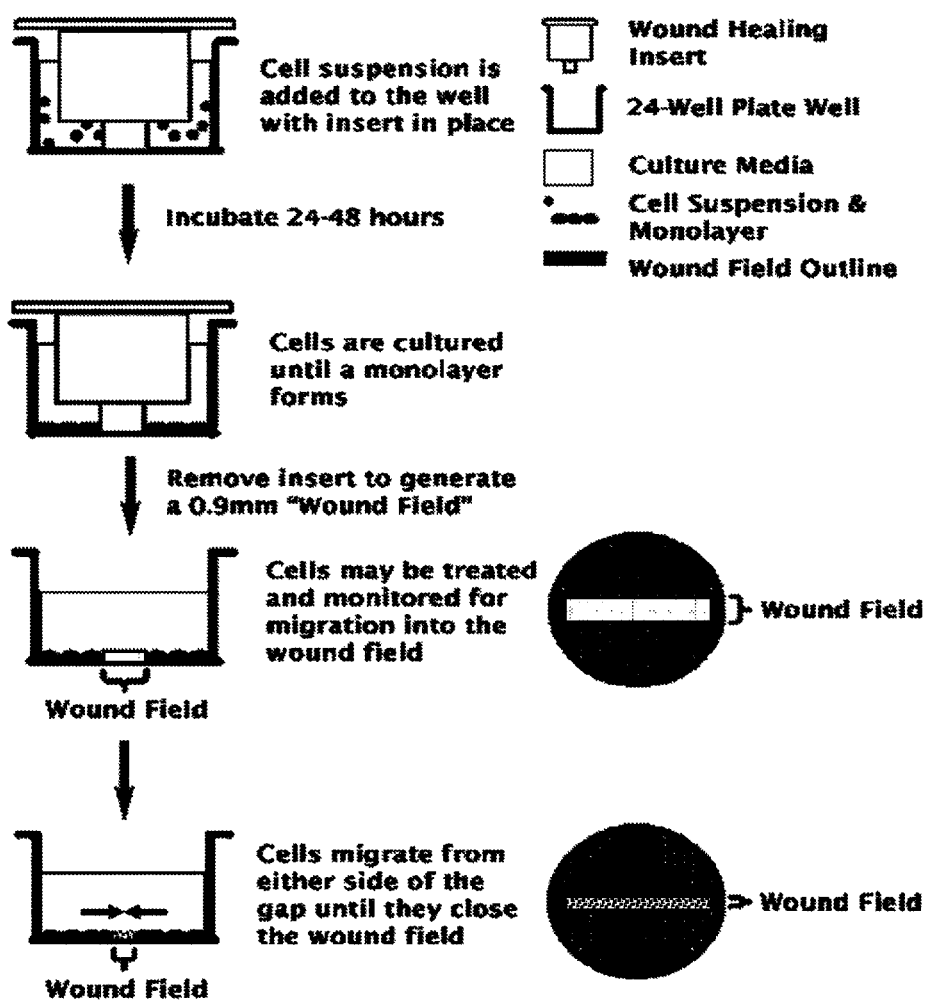

FIG. 36: Wound Healing Assay: Modified from Cell BioLabs Inc., Assay CBA-120

Figure 37:
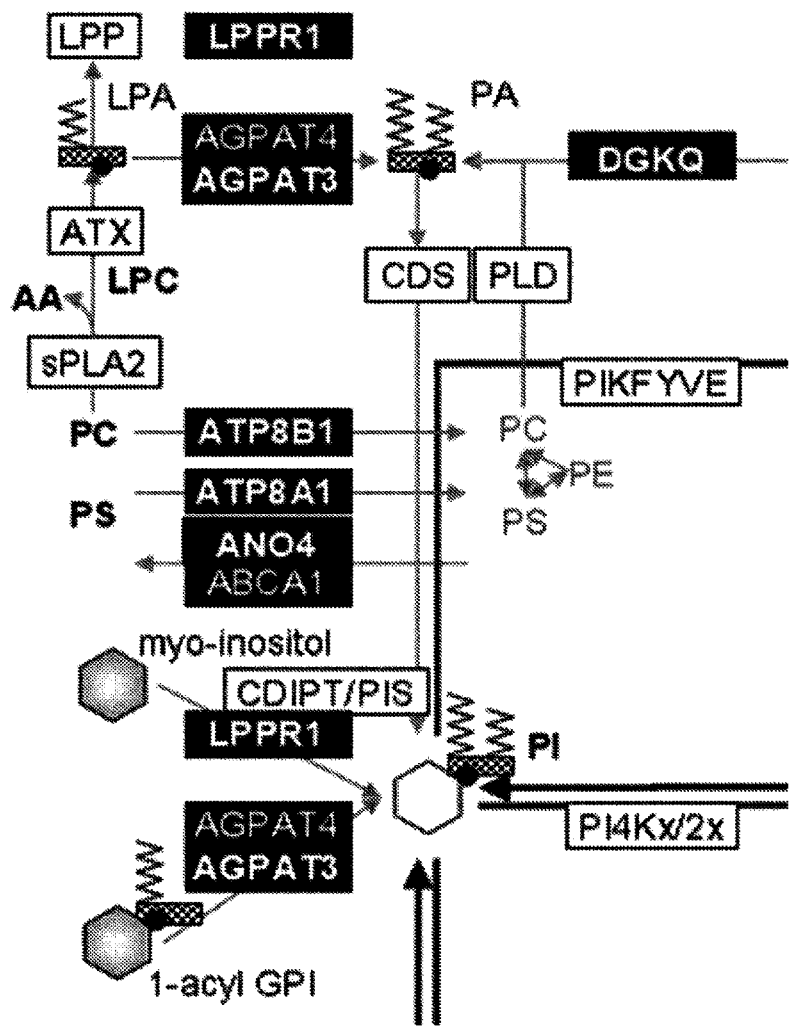

FIG. 37: Impact of PL selectivity: (upper left corner of FIG. 12, see FIG. 12 for legends) HP-α-CD only scavenged PC (and, potentially PI), but not lysophospholipids including, but not limited to, LPC and LPA, upstream of sPLA2, which splits PC into LPC and arachidonic acid (AA).

Figure 38A:
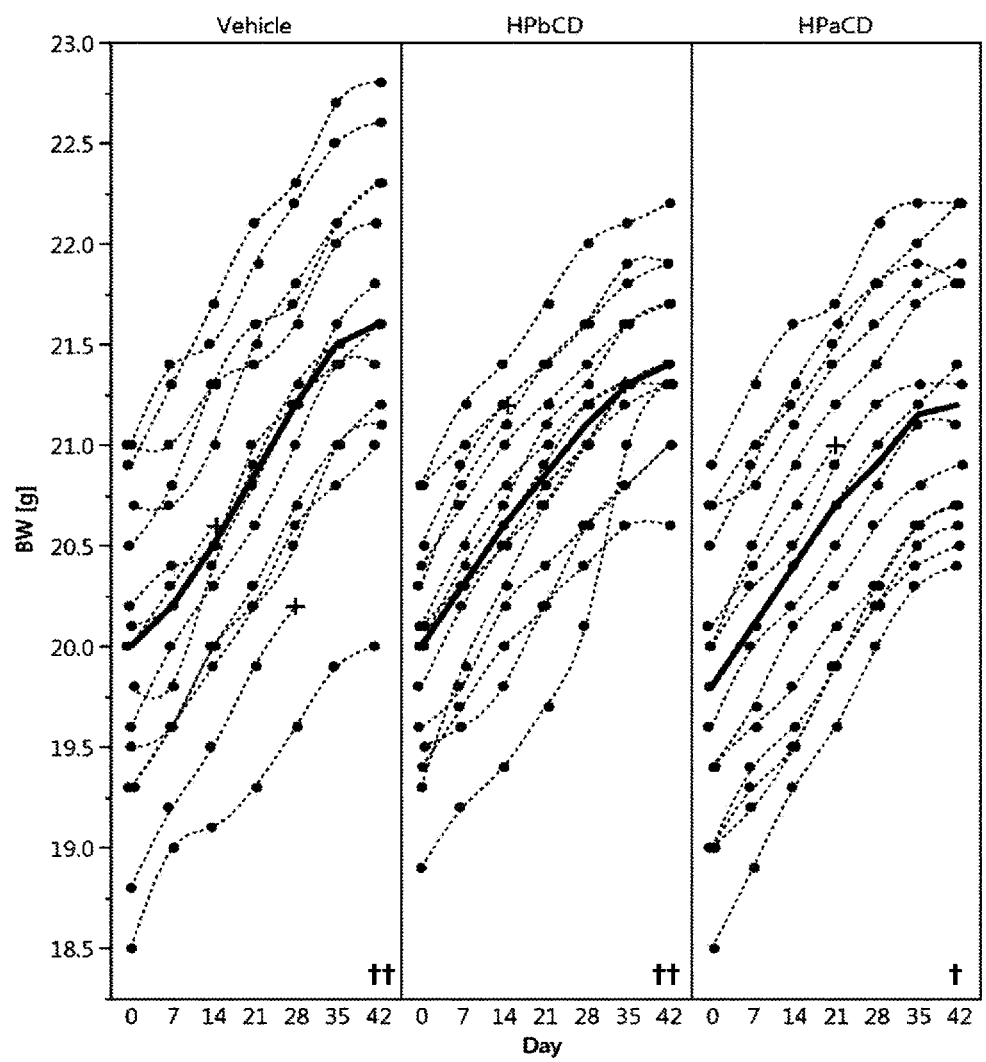
Figure 38B:
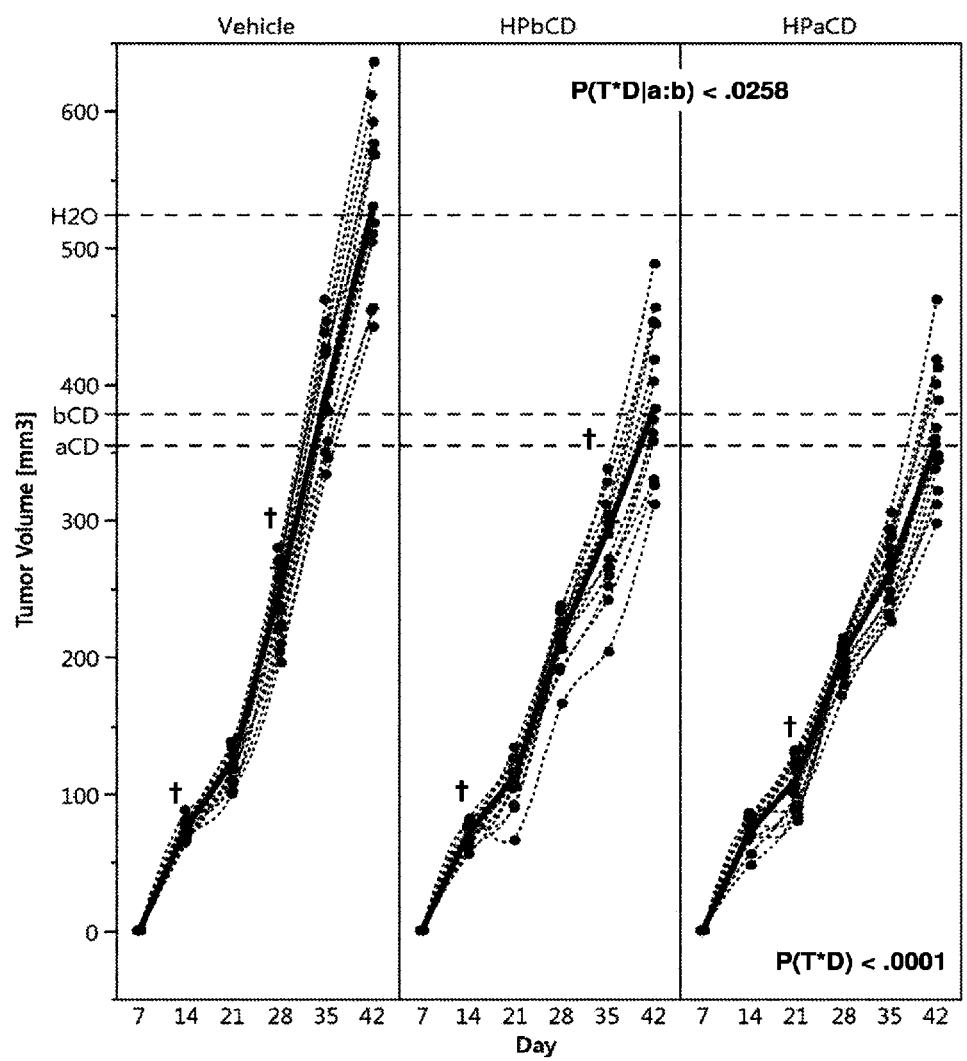

FIG. 38a and FIG. 38b: BCa Body Weight (A) and Tumor Volume (B) by Treatment. Individual curves and medians are shown. A: 't' at the bottom and '+' in the curves indicates death for unknown reason. B: Both HP-α-CD and HP-β-CD are effective (overall treatment effect Day*Treatment (D*T) <0.001, ANOCA with Mice as a random factor). HP-α-CD is more effective than HP-β-CD (pairwise treatment effect Day*Treatment (D*Tla:b)=0.0258, ANOCA with mice as a random factor).

Figure 39:
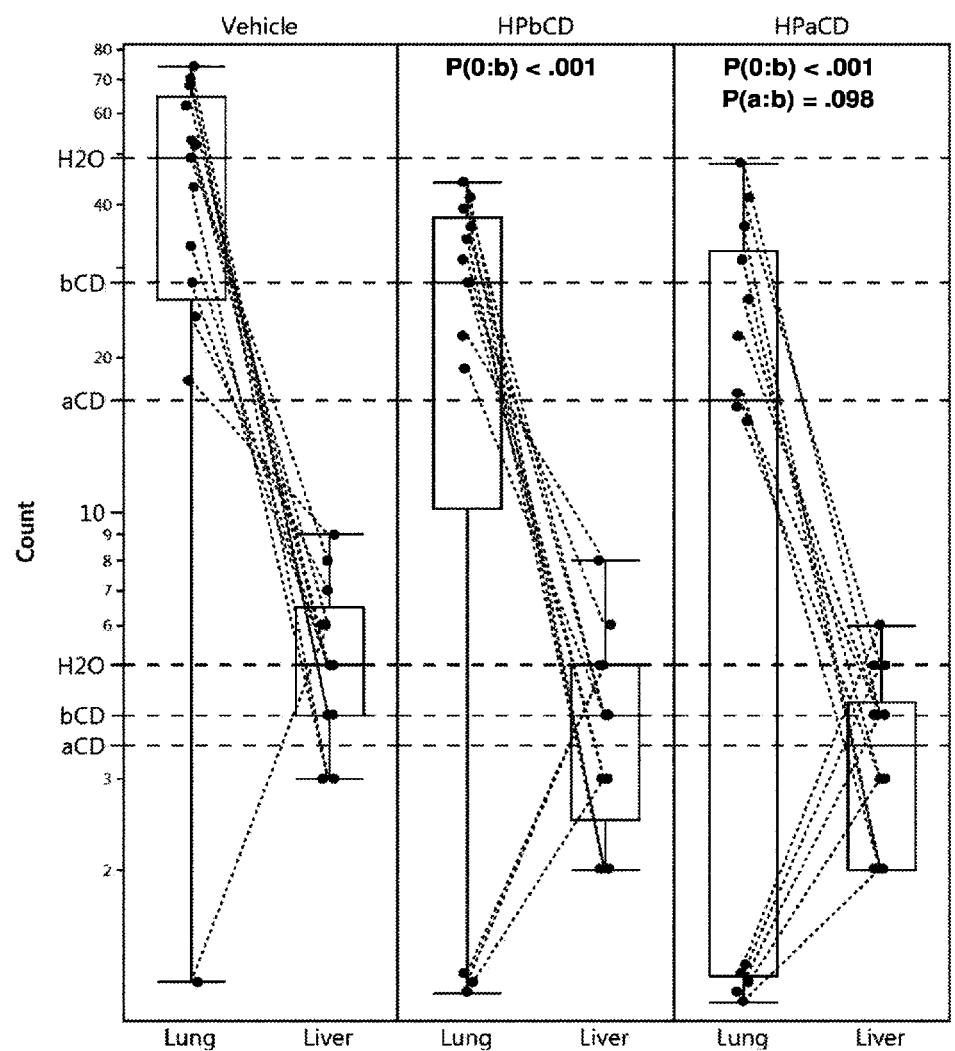

FIG. 39: BCa Lung and Liver Metastases. P-values are from pairwise comparisons of bivariate (lung/liver) data via u-statistics for multivariate data (Wittkowski K M, Lee E, et al. (2004) Stat Med 23:1579-92)

Figure 40:
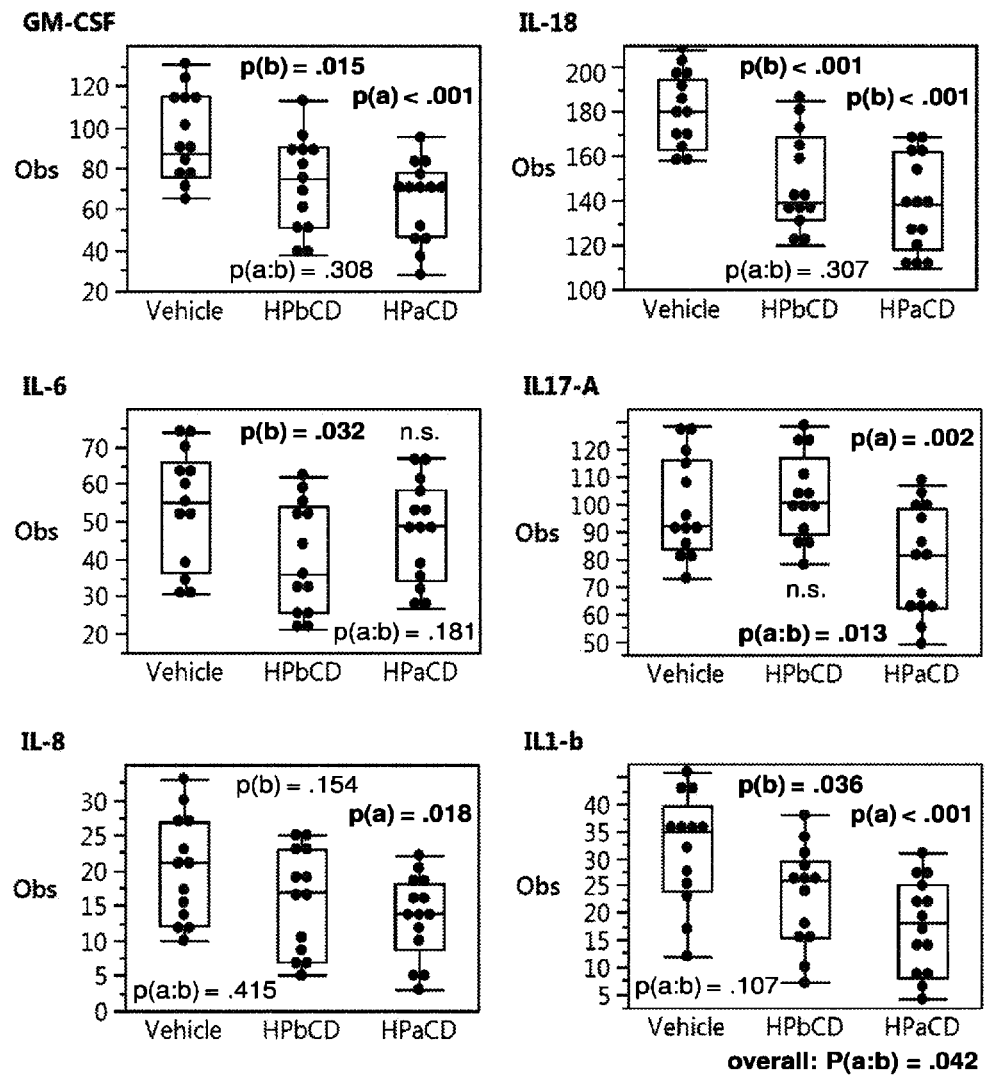

FIG. 40: BCa Plasma Cytokines. Individual P-values are derived from two sample t-tests p(b): HP-β-CD v. Vehicle, p(a): HP-α-CD v. Vehicle, p(a:b): HP-α-CD v. HP-β-CD. Overall P-value for all six cytokines is calculated via u-statistics for multivariate data (Wittkowski K M, Lee E, et al. (2004) Stat Med 23:1579-92)

Figure 41:
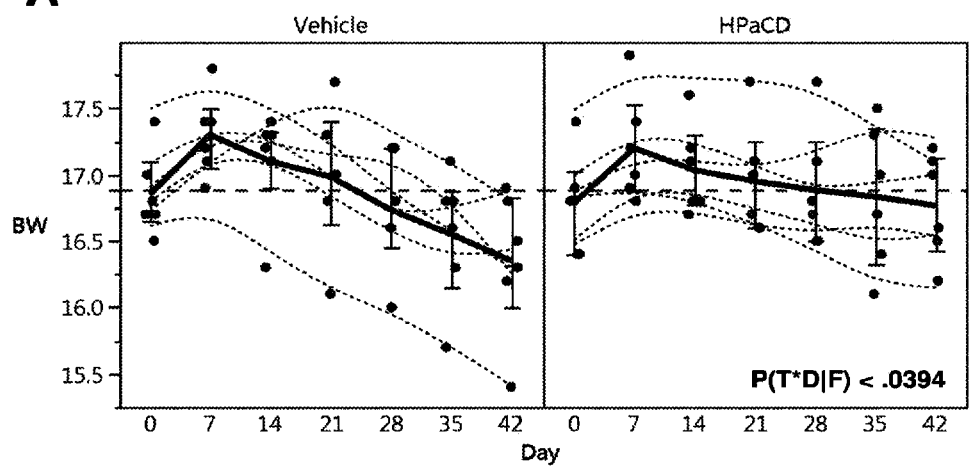
Figure 41:
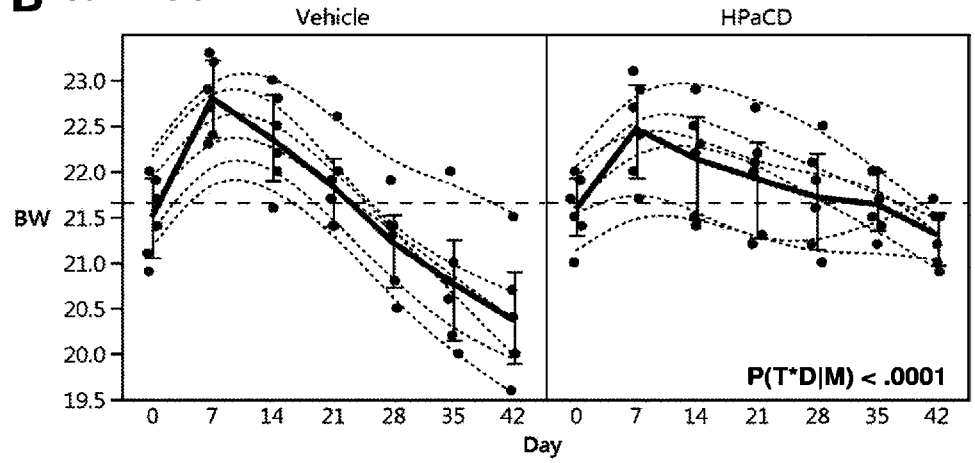

FIG. 41: HTT Mice: Bodyweight. Estimates are means±SD, P-values for Treatment*Day interaction (P(T*D)) overall and by sex (F: female, M: male) are derived from mixed model ANOVA with mice as random factor.

Figure 42:
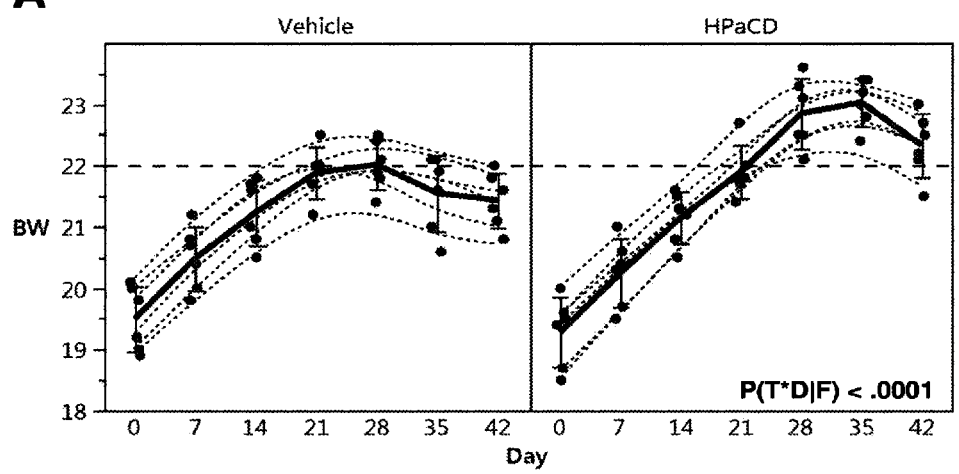
Figure 42:
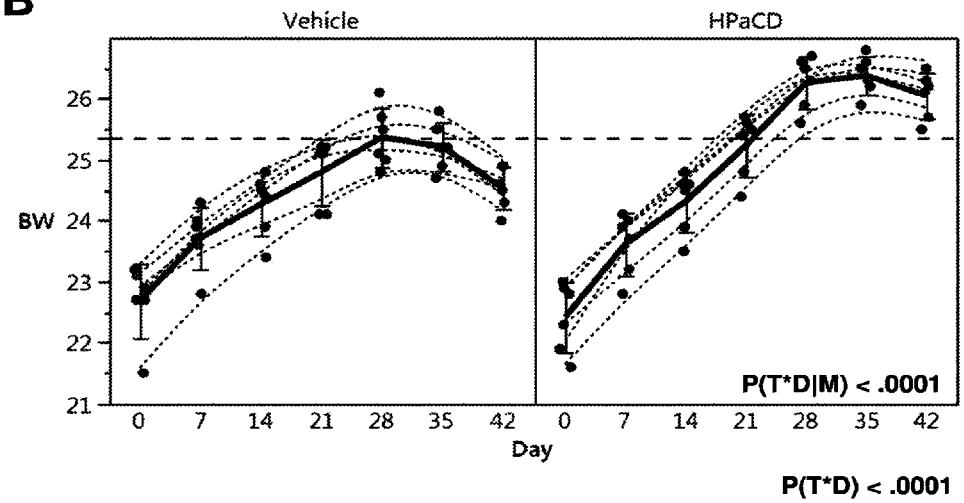

FIG. 42: SOD1 Mice: Bodyweight. Estimates are means±SD, P-values for Treatment*Day interaction (P(T*D)) overall and by sex (F: female, M: male) are derived from mixed effects ANOVA with mice as a random factor.

Figure 43:
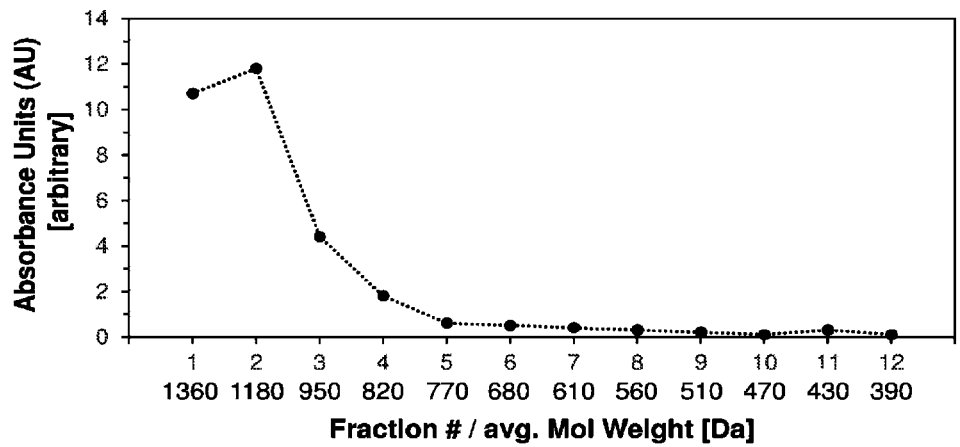
Figure 43:
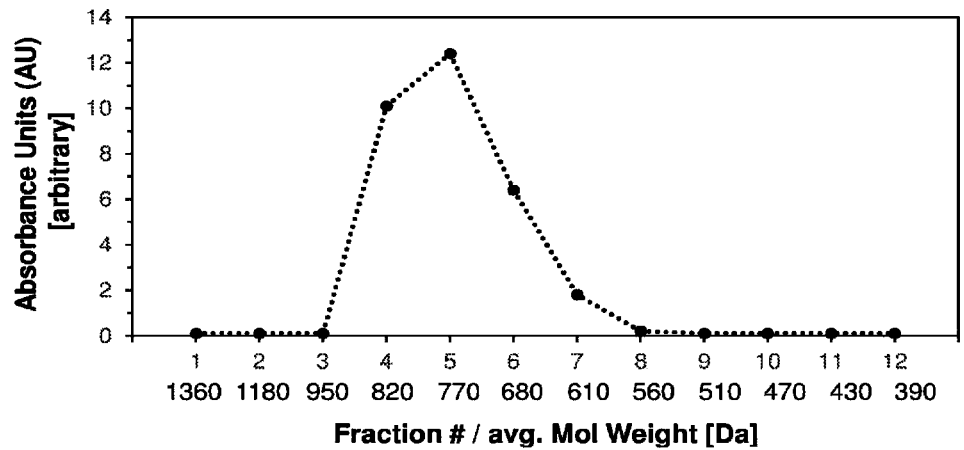

FIGS. 43A and 43B: FPLC Standard curves for the type of FPLC columns used. 43A) HP-α-CD (HPαCD, 1180 Da) is confirmed to be measured mostly in Fraction 2 (nominally 1060-1267 Da). 43B) Phosphatidylcholine (PC) is confirmed to be measured mostly in Fraction 5 (nominally 734-795 Da).

Figure 44:
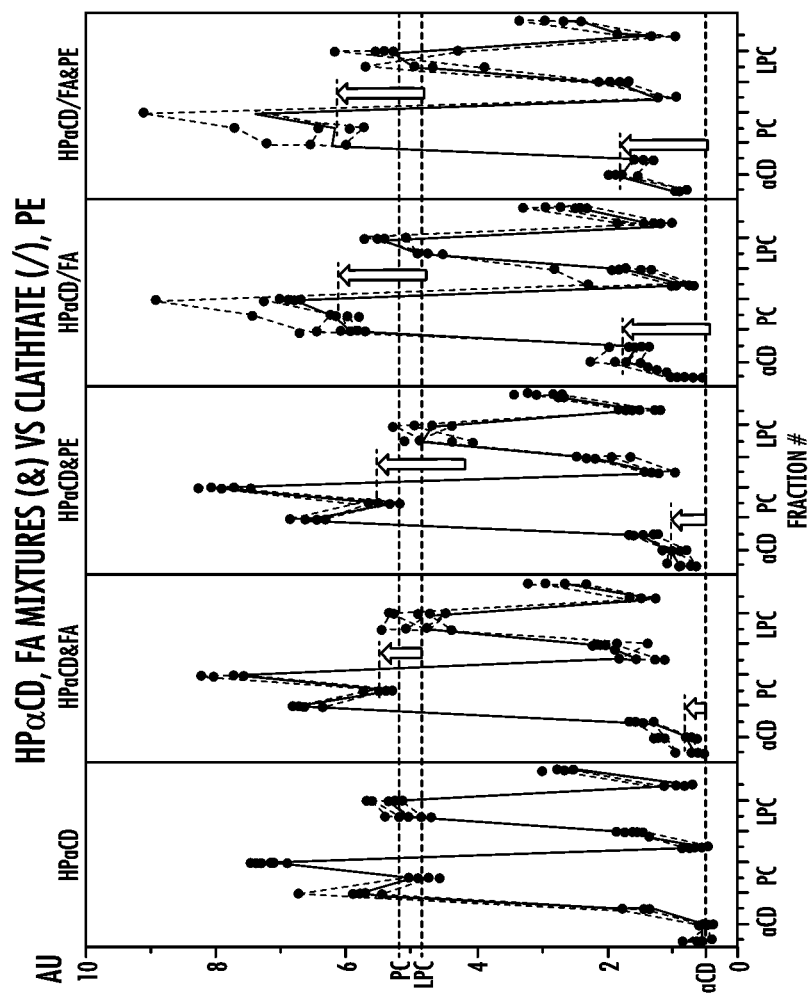

FIG. 44: HPαCD, FA mixtures (&) v. clathrate. FPLC of morning urine 8 h after intake of different HP-α-CD preparations containing 15 g HP-α-CD each as the active substance as well as different forms of penetration enhancers. HPaCD: HP-α-CD only (n=5). HPaCD&FA: a mixture of HPaCD and 10% w/w sodium caprate and the permeation enhancing oily suspension (PE) proposed in (Tuvia S, Pelled D, et al. (2014) Pharmaceutical Research 31:2010-21) (n=5). HPaCD/FA: HP-α-CD/FA clathrate (n=5). HPaCD/FA&PE (n=4): The clathrate mixed with the above penetration enhancer. Axes: as in FIG. 43. Y-axis with labels added: aCD, PC, and LPC indicate the median amount of substrate identified in the HP-α-CD fraction 2 (1060-1267 Da), the phosphatidylcholine fraction 5 (724-795 Da), and the lysophosphatidyl choline fractions 9 and 10 (450-534 Da). The fractions referred to on the y-axis are indicated by the same labels on the x-axis. The upward open arrows indicate the difference between the corresponding median for HP-α-CD (horizontal line) and the median for each of the four mixtures and/or clathrates, respectively, (short horizontal dotted lines).

Figure 45:
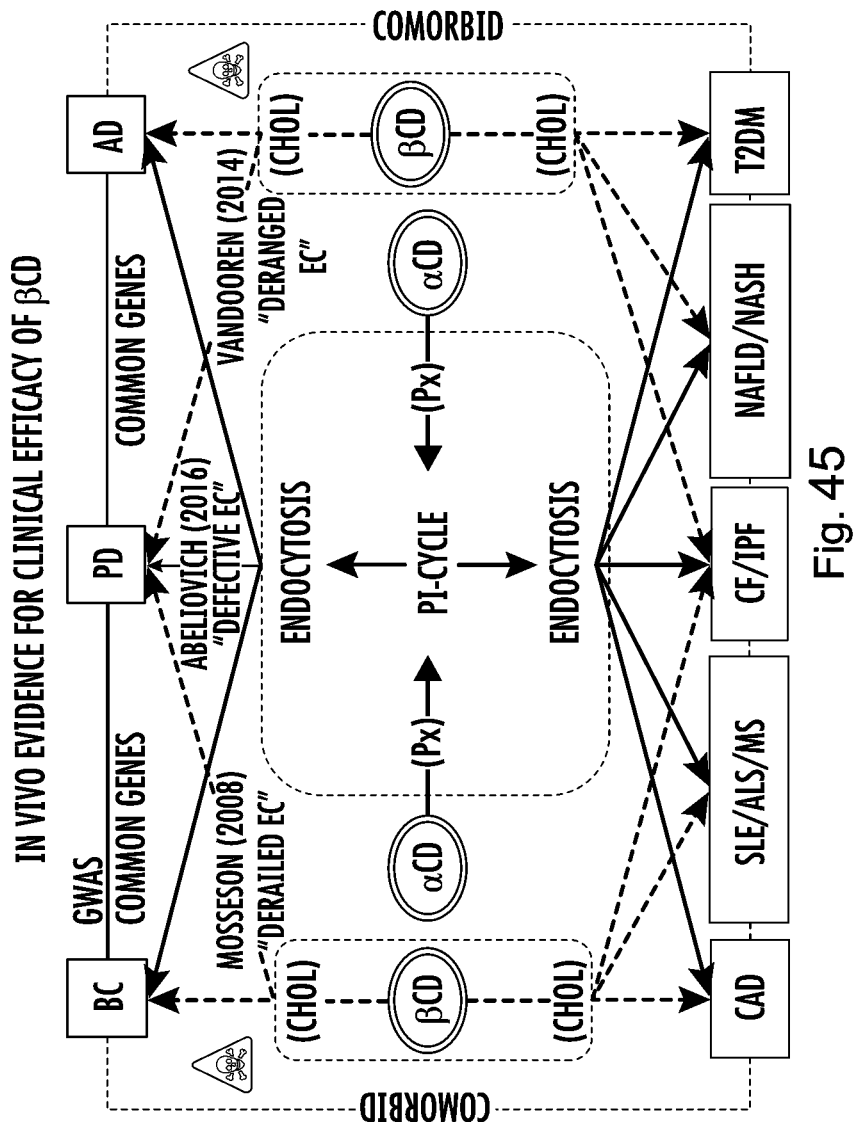

FIG. 45: In vivo Evidence for Clinical Efficacy of βCDs. Efficacy of β-CD in animal models of breast cancer, Parkinson's disease, Alzheimer's disease, CAD, systemic lupus erythematosus/ALS/MS, cystic fibrosis/IPF, NAFLD/NASH, and T2DM was consistently attributed to the ability of β-CD to scavenge cholesterol (Chol, dashed arrows), which carries the now well-known risk of cholesterol-mediated ototoxicity. The mechanism by which depletion of cholesterol should improve the various phenotypes, however, was rarely explained. Clinical results also showed phospholipid upregulation in several of these diseases. β-CDs, however, also scavenge phospholipids (phospholipids) and, thus, also downregulate the PI cycle (center), which directly benefits the various disease phenotypes (solid arrows).

Figure 46:
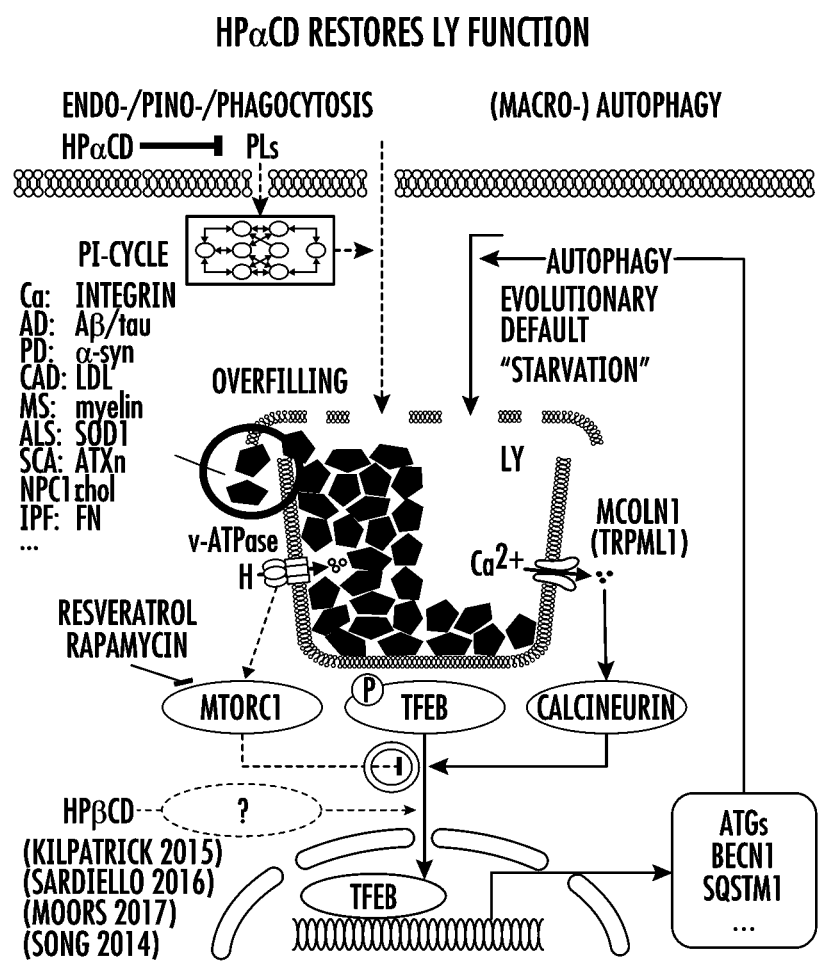

FIG. 46: HP-α-CD Restores LY Function: (update of FIG. 26). HP-β-CD has been shown to activate transcription factor EB (TFEB), yet the mechanism of action is unknown (Kilpatrick K, Zeng Y, et al. (2015) PLoS One 10:e0120819; Song W, Wang F, et al. (2014) J Biol Chem 289:10211-22; Sardiello M (2016) Ann N Y Acad Sci 1371:3-14; Moors T E, Hoozemans J J, et al. (2017) Mol Neurodegener 12:11). The unexpected genetics results (Example 2) confirmed by the urinalysis results (Example 16) identified the mechanism. It is not direct activation that activated the translocation of TFEB to the nucleus, but scavenging of phospholipids, which reduces autophagy and prevents the overfilling lysosome from activating MTORC1, the target of the anti-aging drugs resveratrol and rapamycin, thereby preventing translocation of TFEB from being inhibited. As a result the aggregation of various proteins in amyloid-beta amd tau in Alzheimer's disease, α-synuclein in Parkinson's disease, LDL in CAD, Ataxins in spinocerebellar ataxia (SCA), myelin in MS, SOD1 in ALS, and others is prevented. Adapted from (Kim S, Choi K J, et al. (2016) Sci Rep 6:24933; Medina D L, Ballabio A (2015) Autophagy 11:970-1; Sardiello M (2016) Ann N Y Acad Sci 1371:3-14; Moors T E, Hoozemans J J, et al. (2017) Mol Neurodegener 12:11; Martini-Stoica H, Xu Y, et al. (2016) Trends Neurosci 39:221-34)

Figure 47:
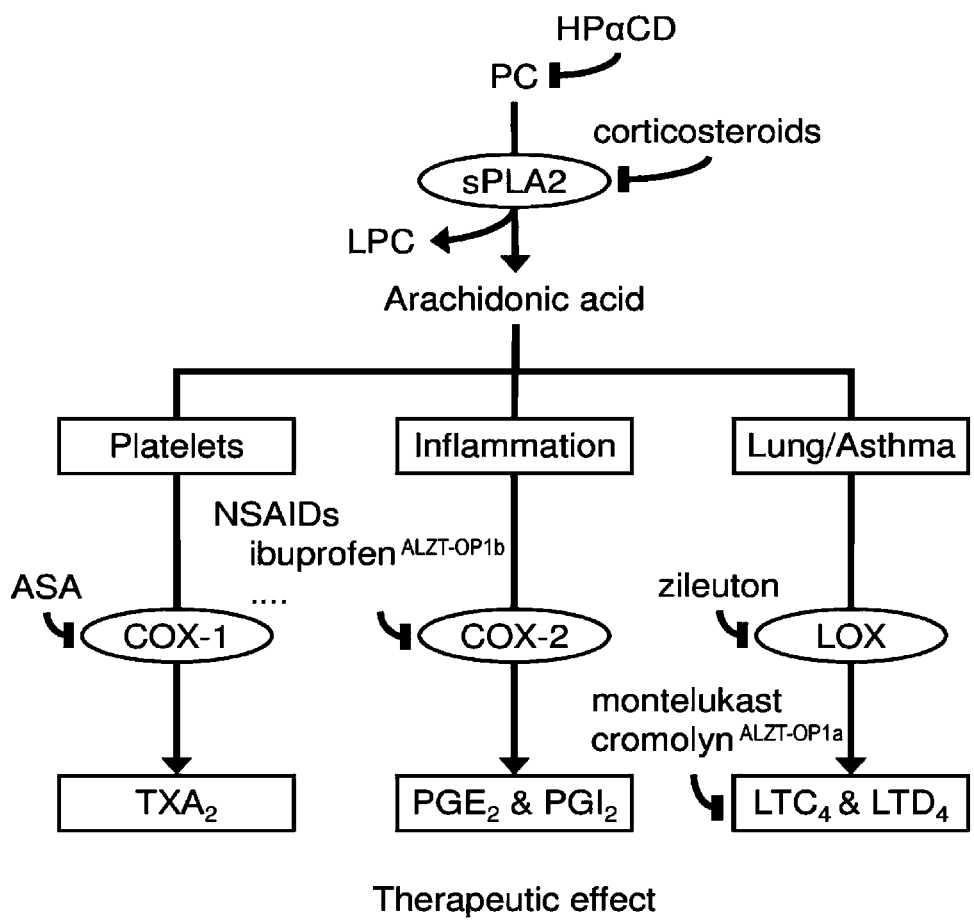

FIG. 47: HP-α-CD Reduces Inflammation: Effects of α-CD on arachidonic acid (AA) and known drugs with similar effects downstream of arachidonic acid. By restricting PC, rather than blocking sPLA2, the effect of α-CD is better tolerated than the effect of corticosteroids. The combination of ibuprofen and cromolyn is tested as the dry-powder inhaler ALZT-OP1 (Elmaleh D (2017)). In contrast, by downregulating all three pathways, α-CD prevents the compensatory activation seen in the not targeted pathways with ASA, NSAIDs, or LOX inhibitors. Also in contrast to α-CD, no effect on endocytosis is expected and, thus, no synergistic anti-inflammatory benefit from also improving autophagy. (modified from http://tmedweb.tulane.edu/pharmwiki/doku.php/introduction_to_eicosanoids).

Figure 48:
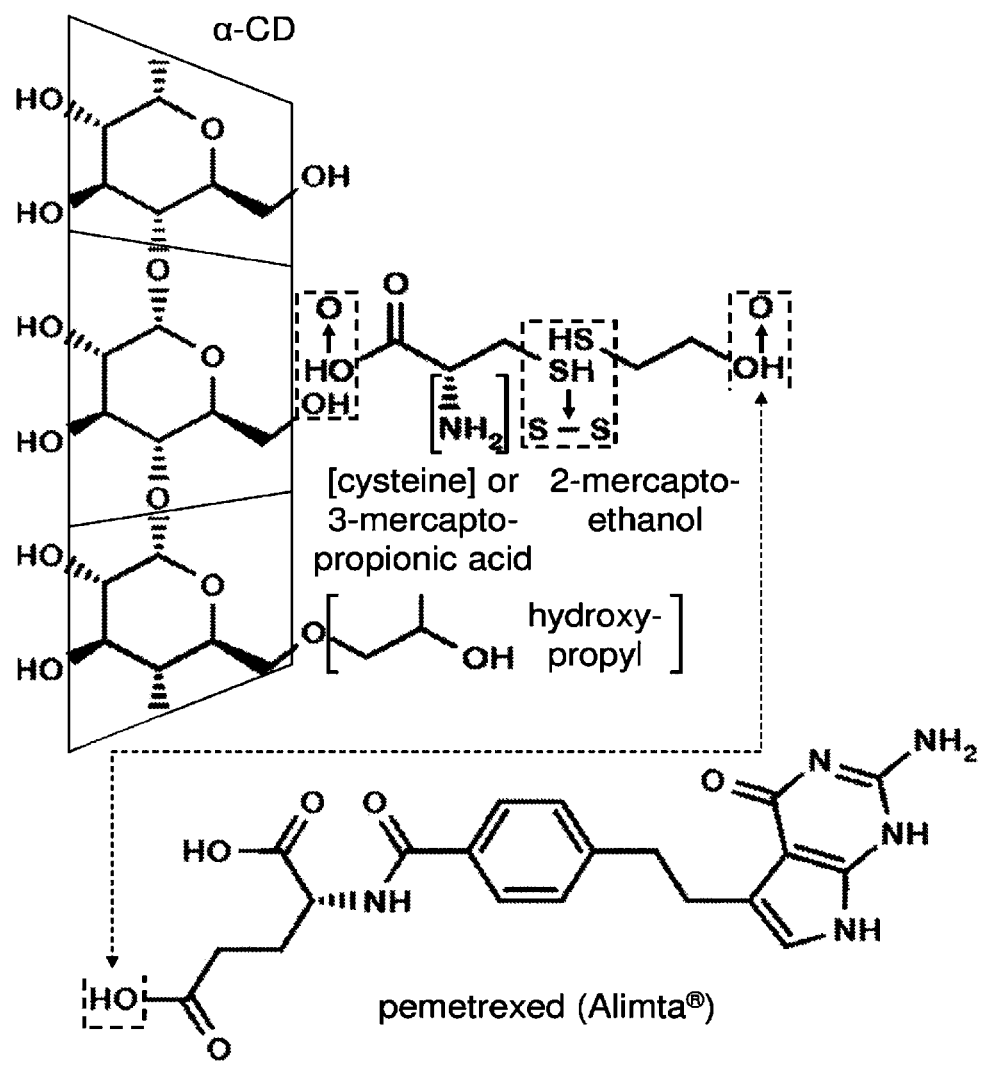

FIG. 48: α-CD/Pemetrexed Compounds: To target the compound to the neighborhood of cancer cells, which have folate-receptors, α-CD (or a derivative, such as HP-α-CD, with hydroxypropyl) can be linked, as a non-limiting example, to pemetrexed with a disulfide linker that is bound to both the α-CD and pemetrexed via an ester. The disulfide linker could be formed by either cysteine or 3-maercapto-propionic acid and 2-mercapto-ethanol. The ester or disulfide links (dashed boxes) can be formed by methods well established, such as those described in (Michel D, Chitanda J M, et al. (2012) Eur J Pharm Biopharm 81:548-56) and (Hunter R, Stellenboom N, et al. (2008) Synlett 252-4) (removing one $H_2O$, each to form an O from two OH), and (Butt A M, Mohd Amin M C, et al. (2015) Int J Nanomedicine 10:1321-34) (removing $H_2$ to form an S—S from two SH).

FIG. 49A, 49B, 49C: Genetic Analysis: Table 4 (FIGS. 49A through 49C) depicts the genetic analysis performed through IPV6/IPV1: −log 10(p-value) in muGWAS/ssGWAS.

DETAILED DESCRIPTION OF EMBODIMENTS

The present disclosure is based, in part, on the discovery of certain disease-relevant collections of genes based on a reanalysis of three independent sets of breast cancer genetic data, which are available for analysis from the National Institutes of Health's dbGaP collection. This reanalysis differed from the earlier analyses by using a novel computational biostatistics method, which incorporates knowledge about genetics into the method itself. (Wittkowski K M, Sonakya V, et al. (2014) Transl Psychiatry 4:e354) As described in detail in the Examples, this method addresses the following four points, which prior analyses of the same data using conventional bioinformatics approaches failed to consider: (i) non-additive relationships between risk alleles and incidence, (ii) cis-epistatic interaction, (iii) correlation between significance and minor allele frequency or "MAF" and (iv) non-randomization bias. It also addresses multiplicity adjustment for diplotype length, a problem arising from the use of a wide-locus approach. By addressing these points, the same strategy previously identified two novel collections of autism-specific genes now identified another novel collection of genes related to endocytosis and lysosomal function. (Wittkowski K M, Sonakya V, et al. (2014) Transl Psychiatry 4:e354)

Figure 12:
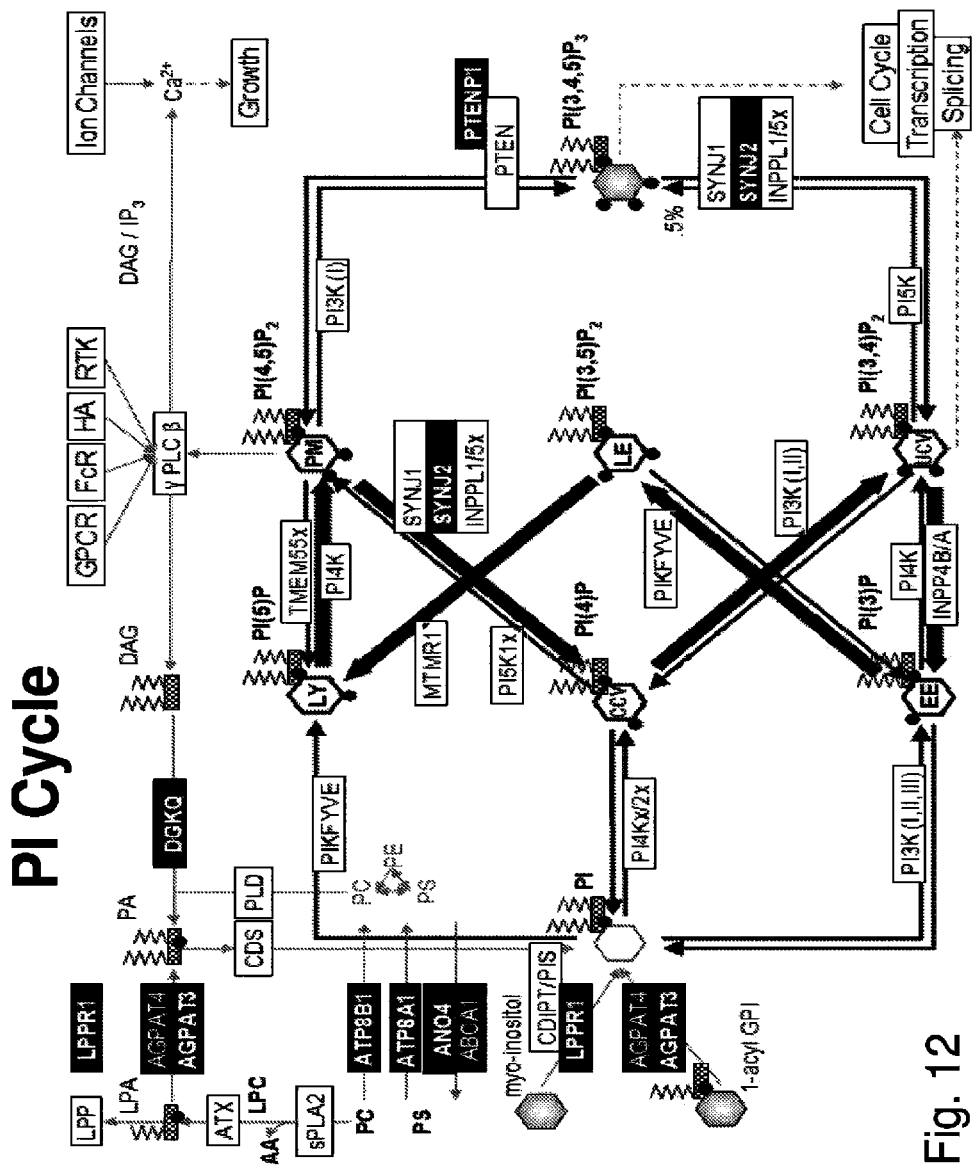
FIG. 12: Phosphatidyl-inositol (PI) cycle. Phosphatidyl-inositol (PI) is synthesized from myo-inositol (imported by HMIT) and phosphatidic acid (PA) (via CDP-DAG), which can be synthesized from lysophosphatic acid (lyso-PA (LPA), PC, or (cytosolic) phosphatidyl-serine PS), or salvaged from $IP_3$ and DAG. It can also be synthesized from 1-acyl GPI. Arrows: Within the PI cycle, phosphoinositides are phosphorylated at a 3-, 4-, or 5-position by PI-kinases (left to right) and hydrolyzed by a plethora of phosphatases (right-to-left). Genes associated with breast cancer in this GWAS are highlighted as inverted (bold: aGWS). Wide arrows in the center indicate the sequence of phosphoinositides (shown as hexagons) involved in EEC. Hexagons: PI/phosphoinositides, PM: plasma membrane, CCV: clathrin-coated vesicle, UCV: uncoated vesicle, EE: early endosome, LE: late endosome LY: lysosome. Inverted gene names indicate genes associated with phosphatidylinositol signaling and/or endocytosis. Bold arrows indicate phosphoinositides associated with endocytosis.
Figure 13A:
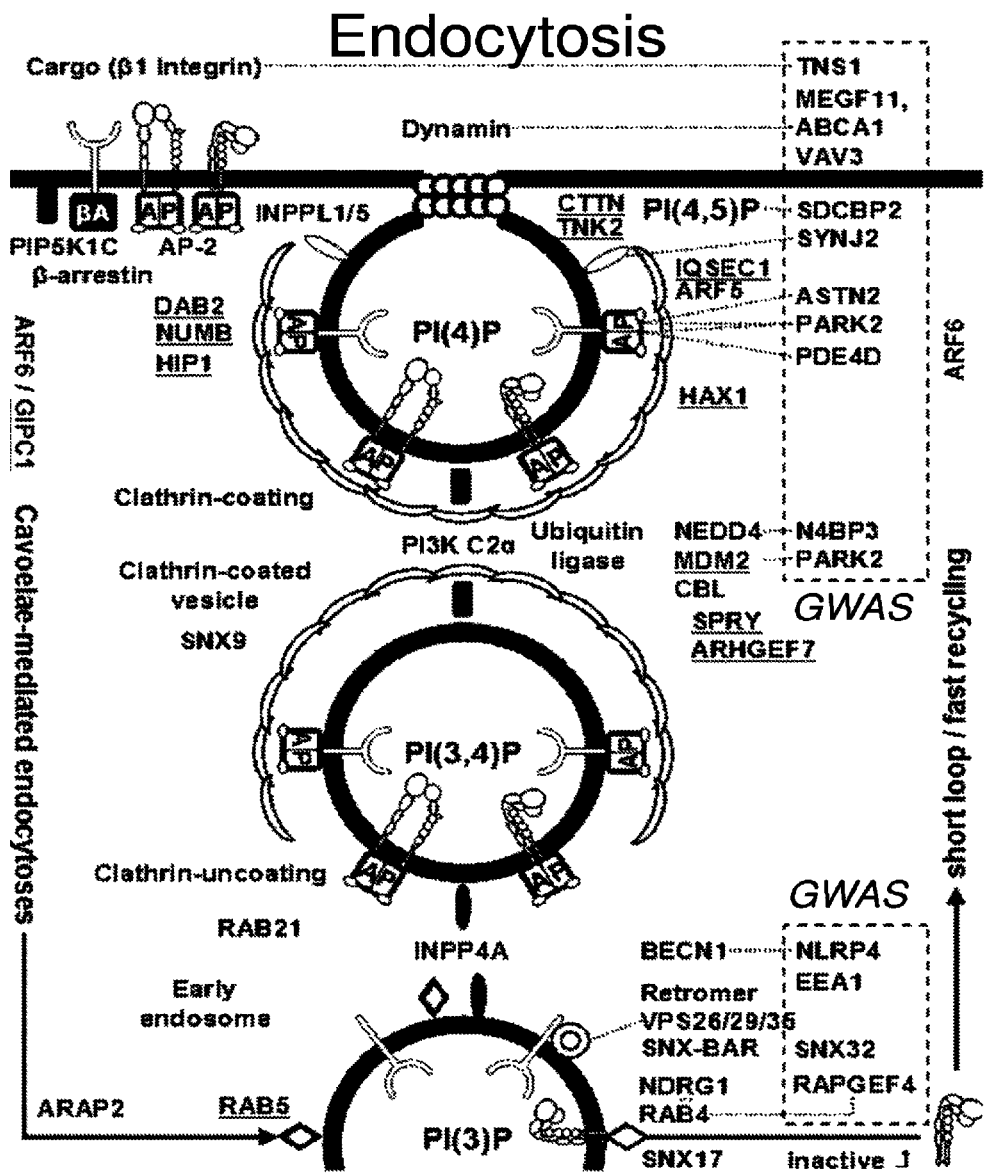
FIGS. 13A and 13B: Known relationship of genes implicated in muGWAS with stages in the process of endocytosis (13A) and exocytosis/lysosomal function (13B). Boxes: genes identified in the present disclosure by stage of endo-/exocytosis: Formation of clathrin-coated vesicles (CCVs) and E3 ubiquitination, separation of inactive integrin (fast recycling) from active integrins (slow recycling), sorting between secretory, lysosomal, and (slow) recycling pathway, and lysosomal degradation. Underlined genes are known breast cancer promoters and suppressors, respectively. Clathrin-mediated endocytosis (CME) begins with co-assembly of the heterotetrameric clathrin adaptor complex AP-2 with clathrin at $PI(4,5)P_2$-rich plasma membrane (PM) sites. AP-2 in its open conformation recruits clathrin and additional endocytic proteins, many of which also bind to $PI(4,5)P_2$. Clathrin-coated pit (CCP) maturation may be accompanied by SHIP-2-mediated dephosphorylation of $PI(4,5)P_2$ to $PI(4)P$. Synthesis of $PI(3,4)P_2$ is required for assembly of the PX-BAR domain protein SNX9 at constricting CCPs and may occur in parallel with $PI(4,5)P_2$ hydrolysis to $PI(4)P$ via synaptojanin, thereby facilitating auxilin-dependent vesicle uncoating by the clathrin-dependent recruitment and activation of $PI3KC2\alpha$, a class II PI3-kinase. $PI(3,4)P_2$ may finally be converted to $PI(3)P$ en route to endosomes by the 4-phosphatases INPP4A/B, effectors of the endosomal GTPase Rab5. Adapted from (Posor Y, Eichhorn-Grunig M, et al. (2015) Biochim Biophys Acta 1851: 794-804). In the early endosome (EE), β1 integrins are sorted. Inactive integrins undergo fast "short loop" recycling; active integrins go to the late endosome (LE)/multi-vesicular body (MVB) for slow "long group" recycling (RAB11), lysosomal degeneration (unless rescued by RAB25/CLIC3), or secretion via the trans-Golgi-network (TGN) mediated by RAB9. Fast recycling of epidermal growth factor receptor drives proliferation, so one would expect that the mutations identified in 13A increase influx of phospholipids into the PI cycle. Lysosomal and synaptic vesicle exocytosis share many similarities. Endolysosome-localized phosphoinositides may regulate lysosomal trafficking (Samie M A, Xu H (2014) J Lipid Res 55:995-1009) (derived, in part from Kegg pathways hsa04144 and hsa04721). Adapted from (Schmid S L, Mettlen M (2013) Nature 499:161-2; Bohdanowicz M, Grinstein S (2013) Physiol Rev 93:69-106; Hesketh G G, Perez-Dorado I, et al. (2014) Dev Cell 29:591-606; Mosesson Y, Mills G B, et al. (2008) Nat Rev Cancer 8:835-50)
Figure 13B:
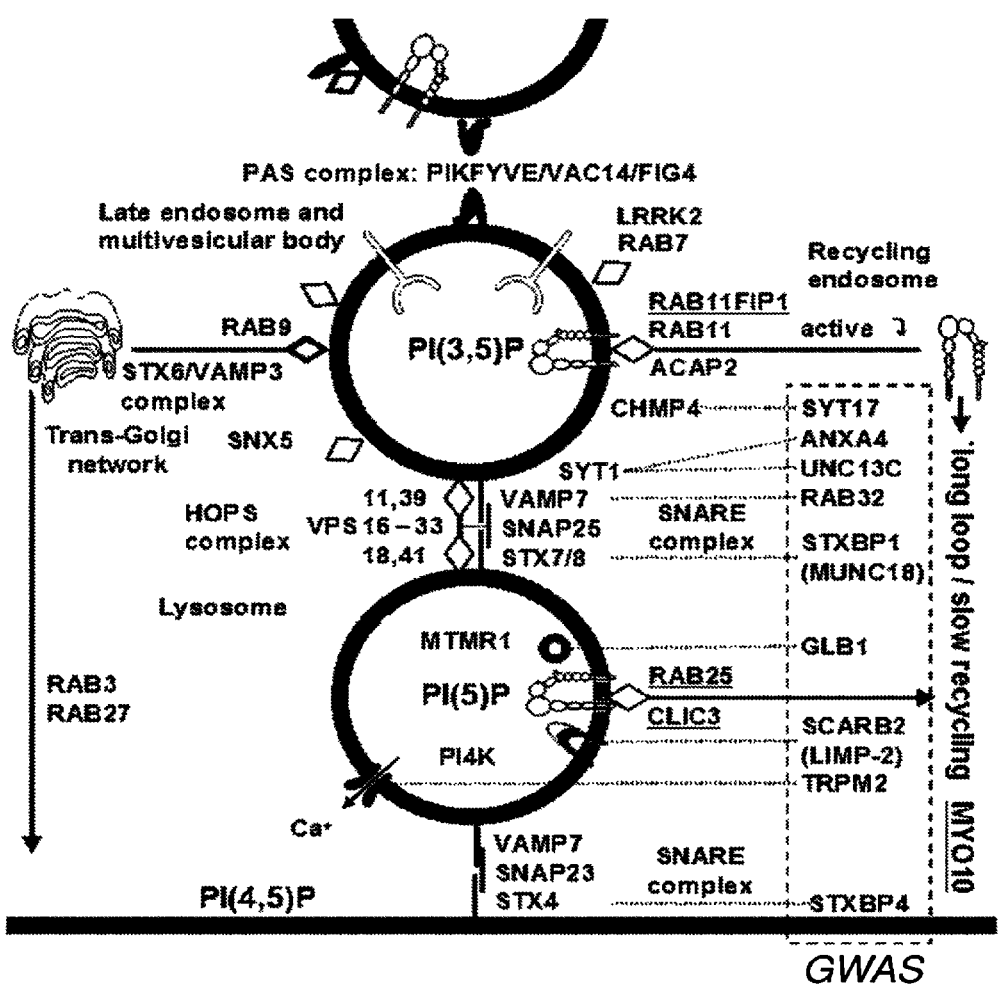

One collection of genes presented herein (FIG. 12, upper left corner) comprises eight genes (AGPAT3/4 ATP8A1/B1, ABCA1, ANO4, LPPR1, DGKQ) whose roles include providing the phosphatidyl inositol (PI) cycle with its substrate, PI. In Alzheimer's disease, "PI is one of only 10 serum lipids that can accurately predict memory loss in as much as 90% of cases, 2 years before the onset of dementia symptoms." (Waugh M G (2015) Biochim Biophys Acta 1851:1066-82) The second gene cluster comprises genes directly associated with endocytosis, a process controlled by phosphoinositides (Table 4, column PI/EC). The stages include, but are not limited to, invagination and forming of CCVs and EEs (FIG. 13). Based on this discovery, the present disclosure provides, in part, a shift in the focus for cancer treatments from controlling cell growth, a process involved in many vital functions even in older subjects, to controlling spread, migration and invasion of cells, a process of relevance primarily during pre- and early postnatal development. Based on these findings, as presented in detail herein, the present disclosure provides compositions and methods for treating malignant, neurodegenerative, vascular, metabolic, inflammatory, autoimmune, pulmonary, fibrotic, hepatic, lysosomal storage, or viral disease, disorder, or condition by modulating the PI cycle and its activity. One of the surprising results in the present disclosure is that the same intervention also reduces chronic inflammation associated with aging ("inflammaging"). Furthermore, in some embodiments, the present disclosure provides compositions and methods that may be useful for the treatment of malignant, neurodegenerative, vascular, metabolic, inflammatory, autoimmune, pulmonary, fibrotic, hepatic, lysosomal storage, or viral disease, disorder, or condition during periods, such as adulthood, where cell migration, including neuronal growth, has mostly ceased, while cell growth, such as growth of hair, skin, and the like, continues and where other cellular mechanism may decline in an age-dependent manner.

Figure 29:
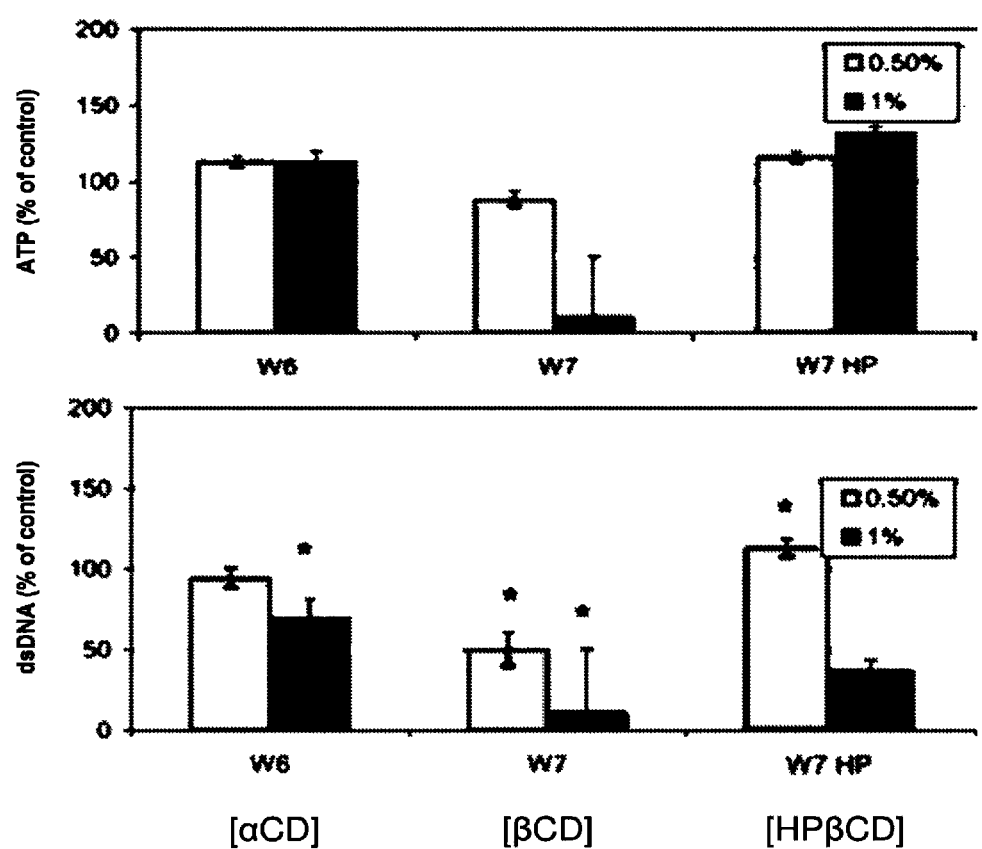
FIG. 29: HaCaT Proliferation. Influence of cyclodextrins on the proliferation of spontaneously immortalized aneuploid human (HaCaT) keratinocytes. Mean values after 48 h incubation, normalized to the control, of at least six independent measurements. Top: ATP-Assay, bottom: PicoGreen-Assay). W6: α-CD, W7: β-CD, W7 HP: HP-β-CD. Modified from (Hipler U C, Schonfelder U, et al. (2007) J Biomed Mater Res A 83:70-9)
Figure 30:
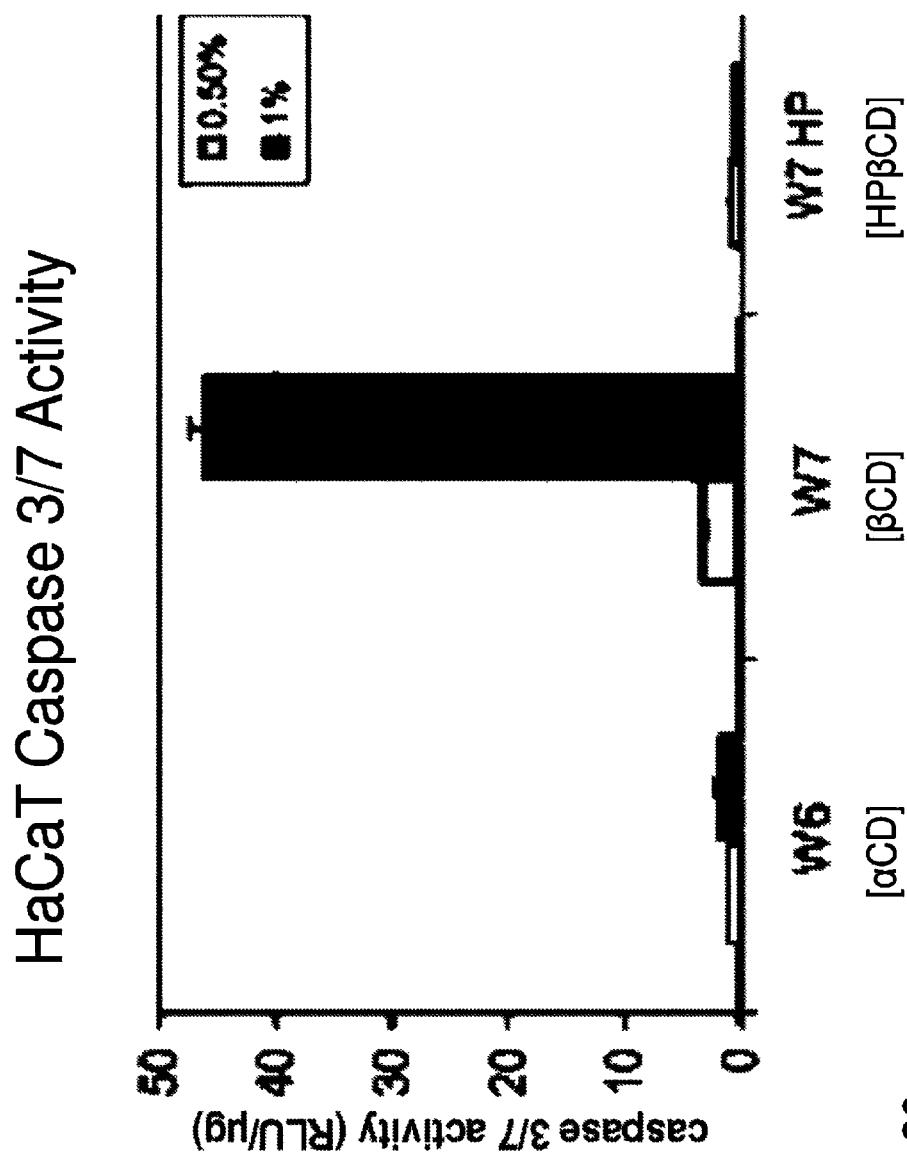
FIG. 30: HaCaT Caspase 3/7 Activity. Influence of cyclodextrins on Caspase 3/7 activity of HaCaT keratinocytes. Mean values after incubation (24 h), normalized on the control and the protein content, of at least six independent measurements. W6: α-CD, W6: β-CD, W7 HP: HP-β-CD. Modified from (Hipler U C, Schonfelder U, et al. (2007) J Biomed Mater Res A 83:70-9)
Figure 31:
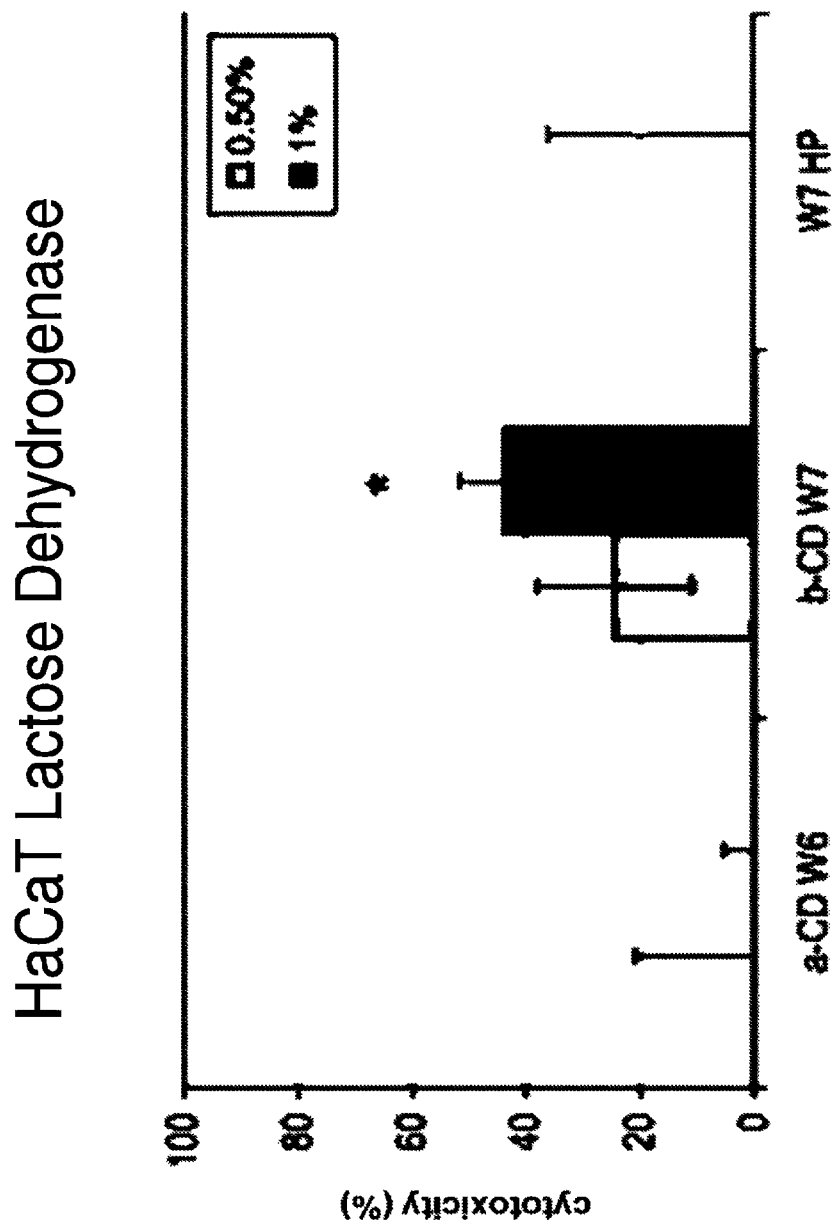
FIG. 31: HaCaT Lactose Dehydrogenase. Influence of cyclodextrins on lactose-dehydrogenase (LDH) of HaCaT keratinocytes. Mean values after incubation (48 h), normalized on the control and the protein content, of at least six independent measurements. W6: α-CD, W6: β-CD, W7 HP: HP-β-CD. Modified from (Hipler U C, Schonfelder U, et al. (2007) J Biomed Mater Res A 83:70-9)

In another part, the present disclosure is based on the re-evaluation of interpretations of published findings, which are commonly believed to assert that α-CD is as nephrotoxic as β-CD, although nephrotoxicity was primarily demonstrated for β-CD, which has substantially lower aqueous solubility than α-CD, and, thus, a higher risk of forming the long cytoplasmic crystals seen in the kidneys of rats. (Frank D W, Gray J E, et al. (1976) Am J Pathol 83:367-82) For instance, lower toxicity of α-CD v. β-CD—typically at the level of the safer HP-β-CD—was shown in HaCaT cells proliferation (FIG. 29), caspase activity (FIG. 30), and lactose dehydrogenase (FIG. 31).

In summary, "the [Joint Expert] Committee [on Food Additives (JECFA)] was reassured by the relatively low toxicity of this compound in animals and the fact that it was less toxic than beta-cyclodextrin, for which studies of human tolerance were available." (Prakash A S, Abbott P J (2001) WHO/JECFA Food Additive Series 48:1030)

In 2014, the CHMP suggested Permitted Daily Exposure (PDE) thresholds above which adverse effects may occur with parenteral administration of α-CD and HP-β-CD of 0.02 and 10 mg/kg/d. (Committee for Human Medicinal Products (CHMP) (2017) European Medicines Agency EMA/CHMP/333892/2013) On Oct. 9, 2017, these thresholds were revised to 200 mg/kg/d each (Committee for Human Medicinal Products (CHMP) (2017) European Medicines Agency EMA/CHMP/333892/2013) and cyclodextrins were included in the Guidelines on expedients (European Medicines Agency (2017) EMA/CHMP/302620/2017/EN) (Table 1).

TABLE 1

Excipients and information for the package leaflet.

| Name | Updated on | Route of Administration | Threshold | Information for the Package Leaflet | Comments |
|---|---|---|---|---|---|
| Cyclodextrins e.g.: Alfadex Betadex (E 459) γ-cyclodextrin Sulfobutyol-ether-β-cyclodextrin (SBE-β-CD) Hydroxypropyl betadex Randomly methylated β-cyclodextrin (RM-β-CD) | Sep. 10, 2017 | Oral | 200 mg/kg/day | Cyclodextrins may cause digestive problems such as diarrhea. | At high doses cyclo dextrins can cause reversible diarrhoea and cecal enlarge.ment in animals |
| Cyclodextrins e.g.: Alfadex Betadex (E 459) γ-cyclodextrin Sulfobutyol-ether-β-cyclodextrin (SBE-β-CD) Hydroxypropyl betadex Randomly methylated β-cyclodextrin (RM-β-CD) | Sep. 10, 2017 | Parenteral | 200 mg/kg/day and use for >2 weeks | If you have a kidney disease, talk to your doctor before you receive this medication | n children less I than years, the lower glomerular function may protect against renal toxicity, but can lead to higher blood levels of .cyclodextrins In patients with moderate to severe renal dysfunction accumulation of dextrins cyclo .may occur |

Source: (European Medicines Agency (2017) EMA/CHMP/302620/2017/EN)

In another embodiment, nephrotoxicity is further reduced by reducing the rate of delivery, the method comprising repeated doses per day, administering the drug over several hours via a peristaltic pump or administering the drug continuously via an implanted drug delivery system.

Some of the main embodiments of the present disclosure are described in the above Summary section of this application, as well as in the Examples, Figures, and Claims. This Detailed Description of Embodiments section provides additional description relating to the compositions and methods of the present disclosure, and is intended to be read in conjunction with all other sections of the present patent application, including the Summary, Examples, Figures, and Claims sections of the present application.

I. Abbreviations and Definitions

The abbreviations "Aβ" and "Ab" refer to amyloid beta.
The abbreviations "aCD", "aCD", and "α-CD" refer to alpha-cyclodextrin.
The abbreviation "AD" refers to Alzheimer's disease.
The abbreviation "AKT" refers to protein kinase B.
The abbreviation "ALS" refers to amyotrophic lateral sclerosis.
The abbreviation "AΦ" refers to autophagy.
The abbreviation "APP" refers to amyloid precursor protein.
The abbreviations "α-syn" and "asyn" refer to alpha-synuclein.
The abbreviation "BCa" refers to breast cancer.
The abbreviations "bCD", "βCD", and "β-CD" refers to beta-cyclodextrin.
The abbreviation "Ca" refers to calcium.
The abbreviation "CAD" refers to coronary artery disease.
The abbreviation "CD" refers to cyclodextrin.
The abbreviation "CDK" refers to cyclin-dependent kinase.
The abbreviation "CF" refers to cystic fibrosis.
The abbreviation "CGEM" refers to Cancer Genetic Markers of Susceptibility.
The abbreviation "Chr" refers to chromosome.
The abbreviation "dbGaP" refers to database of Genotypes and Phenotypes.
The abbreviation "DNA" refers to deoxyribonucleic acid
The abbreviation "EC" refers to endocytosis.
The abbreviation "EE" refers to early endosome.
The abbreviation "e.g." refers to for exempli gratia (for example).
The abbreviation "EPIC" refers to European Prospective Investigation into Cancer.
The abbreviation "ER" refers to endoplasmic reticulum
The abbreviation "FAK" refers to focal adhesion kinase.
The abbreviation "Fc" refers to fragment, crystallizable.
The abbreviation "FDA" refers to Food and Drug Administration.
The abbreviation "FSGS" refers to focal segmental glomerulosclerosis.
The abbreviations "gCD" and "γCD" refer to gamma-cyclodextrin.
The abbreviation "GPCR" refers to G-protein coupled receptor.
The abbreviation "GRAS" refers to generally recognized as safe.
The abbreviation "GWAS" refers to genome-wide association study.
The abbreviation "GRAS" refers to generally recognized as safe.
The abbreviation "HA" refers to Hyaluronic acid
The abbreviation "HER2/neu" refers to receptor tyrosine-protein kinase erbB-2.
The abbreviation "HLA" refers to human leukocyte antigen.
The abbreviation "HP" refers to hydroxypropyl.
The abbreviations "HPaCD", "HP-α-CD" and "HPαCD" refers to 2-hydroxypropyl-alpha-cyclodextrin.
The abbreviations "HPbCD", "HP-β-CD" and "HPβCD" refers to hydroxypropyl-beta-cyclodextrin.

The abbreviation "IND" refers to investigational new drug.

The abbreviation "IPV" refers to inverse p-value.

The abbreviation "i.v." refers to intravenous.

The abbreviation "LD" refers to linkage disequilibrium.

The abbreviation "LD$_{50}$" refers to median lethal dose.

The abbreviation "LE" refers to late endosome.

The abbreviation "LPC" refers to lysophosphatidylcholine.

The abbreviation "LY" refers to lysosome.

The abbreviation "LYD" refers to lysosomal dysfunction

The abbreviation "MAF" refers to minor allele frequency.

The abbreviation "MAP refers to mitogen-activated protein.

"The abbreviations "M-β-CD", "MβCD", and "MbCD" refer to methyl-β-cyclodextrin.

The abbreviation "MΦ" refers to macrophage.

The abbreviation "MS" refers to multiple sclerosis.

The abbreviation "mTOR" refers to mechanistic target of rapamycin.

The abbreviation "muGWAS" refers to multivariate u-statistics GWAS.

The abbreviation "MVB" refers to multivesicular body.

The abbreviation "No." refers to number.

The abbreviation "NIH" refers to National Institutes of Health.

The abbreviation "NPC" refers to Niemann Pick disease type C.

The abbreviation "PBCS" refers to Polish Breast Cancer Case-Control Study.

The abbreviation "PC" refers to phosphatidylcholine"

The abbreviation "PCa" refers to prostate cancer.

The abbreviation "PD" refers to Parkinson's disease.

The abbreviation "PI" refers to phosphatidylinositol.

The abbreviation "PI3R" refers to "phosphoinositide-3 kinase"

The abbreviation "PIP" refers to phosphoinositide

The abbreviation "PIP1" refers to PI(4)P.

The abbreviation "PIP2" refers to PI(4,5)P$_2$.

The abbreviation "PIP3" refers to PI(3,4,5)P$_3$.

The abbreviation "PM" refers to plasma membrane"

The abbreviation "PKB" refers to protein kinase B.

The abbreviation "PKC" refers to protein kinase C.

The abbreviation "PL" refers to phospholipid.

The abbreviation "QQ" refers to "quantile-quantile".

The abbreviation "QR" refers to "quantile-rank".

The abbreviation "RTK" refers to receptor tyrosine kinase.

The abbreviation "s.c." refers to subcutaneous.

The abbreviation "SLE" refers to systemic lupus erythematosus.

The abbreviation "SNP" refers to single nucleotide polymorphism.

The abbreviation "ssGWAS" refers to single-SNP genome-wide association study.

The abbreviation "TFEB" refers to transcription factor EB.

The abbreviation "TSC" refers to tuberous sclerosis.

The abbreviation "U.S." refers to the United States.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary, Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one 01" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, "either," "one of," "only one of," or "exactly one of" "Consisting essentially of," when used in the claims, shall have its ordinary meaning as used in the field of patent law.

The term "about" as used herein when referring to a measurable value such as an amount, a temporal duration, and the like, is meant to encompass variations of ±20%, ±10%, ±5%, ±1%, ±0.9%, ±0.8%, ±0.7%, ±0.6%, ±0.5%, ±0.4%, ±0.3%, ±0.2% or ±0.1% from the specified value, as such variations are appropriate to perform the disclosed methods.

As used herein, the term "carrier" means a diluent, adjuvant, or excipient with which a compound is administered. Pharmaceutical carriers can be liquids, such as water and oils, including those of petroleum, animal, vegetable or synthetic origin, such as peanut oil, soybean oil, mineral oil, sesame oil and the like. The pharmaceutical carriers can also be saline, gum acacia, gelatin, starch paste, talc, keratin, colloidal silica, urea, and the like. In addition, auxiliary, stabilizing, thickening, lubricating and coloring agents can be used.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, unrecited elements or method steps.

As used herein, the phrase "in need thereof" means that the animal or mammal has been identified as having a need for the particular method or treatment. In some embodiments, the identification can be by any means of diagnosis. In any of the methods and treatments described herein, the animal or mammal can be in need thereof. In some embodiments, the animal or mammal is in an environment or will be traveling to an environment in which a particular disease, disorder, or condition is prevalent.

As used herein, the terms "treat," "treating," and "treatment" encompass a variety of activities aiming at desirable changes in clinical outcomes. For example, the term "treat", as used herein, encompasses any detectable improvement in one or more clinical indicators or symptom of malignant, neurodegenerative, vascular, metabolic, inflammatory, autoimmune, pulmonary, fibrotic, hepatic, lysosomal storage, or viral disease, disorder, or condition—such as carcinomas, including, but not limited to, breast and prostate cancer or neurodegenerative diseases, including, but not limited to, Parkinson's and Alzheimer's Disease, or coronary artery disease, including, but not limited to atherosclerosis, CAD and stroke, or a digestive disorder, including, but not limited to T2DM. For example, such terms encompass alleviating, abating, ameliorating, relieving, reducing, inhibiting or slowing at least one clinical indicator or symptom, preventing additional clinical indicators or symptoms, reducing or slowing the progression of one or more clinical indicators or symptoms, causing regression of one or more clinical indicators or symptoms, relieving a condition caused by the disease or disorder, and the like. In the case of therapeutic treatments, the methods and compositions provided herein can be used in subjects that already exhibit one or more clinical indicators or symptoms of the disease or disorder, such as malignant, neurodegenerative, vascular, metabolic, inflammatory, autoimmune, pulmonary, fibrotic, hepatic, lysosomal storage, or viral disease, disorder, or condition. In the case of malignant or neurodegenerative diseases or disorders, various clinical indicators and symptoms are known to medical practitioners and those of skill in the art.

The terms "prevent" or "preventing" as used herein encompasses stopping a disease, disorder, or symptom from starting, as well as reducing or slowing the progression or worsening of a disease or disorder. For example, "preventing" breast cancer or prostate cancer includes, but is not limited to, inhibiting the formation of cancerous cells, growth of tumors, local spread of cancerous spread, or inhibiting the metastasis of malignant growths, preventing the onset of symptoms of Alzheimer's, Parkinson's, Huntington's, ALS and/or MS. In the case of prophylactic treatments, the methods and compositions provided herein can be used to prevent progression or clinical exhibiting of symptoms in subjects that do not yet exhibit any clear or detectable clinical indicators or symptoms of the disease or disorder but that are believed to be at risk of developing the disease or disorder, such as malignant, neurodegenerative, vascular, metabolic, inflammatory, autoimmune, pulmonary, fibrotic, hepatic, lysosomal storage, or viral disease, disorder, or condition.

The term "malignant, neurodegenerative, vascular, metabolic, inflammatory, autoimmune, pulmonary, fibrotic, hepatic, lysosomal storage, or viral disease, disorder, or condition" is used herein in accordance with it usual usage in the art and includes, but is not limited to malignant disorders, such as carcinomas, breast cancer, prostate cancer, malignancies of the breast, and malignancies of the prostate, as well as neurodegenerative diseases, such as Alzheimer's disease, Parkinson's disease, Huntington's disease, and "a range of disorders including brain overgrowth syndromes, [and] Charcot-Marie-Tooth neuropathies" (Waugh M G (2015) Biochim Biophys Acta 1851:1066-82).

As used herein, the term "cancer" or "hyperproliferative disease" is meant to refer to those diseases and disorders characterized by hyperproliferation of cells. Examples of hyperproliferative disease includes all forms of cancer, psoriasis, neoplasia, and hyperplasia.

The terms "subject," "individual," and "patient" are used interchangeably herein to refer to a vertebrate, preferably a mammal, more preferably a human. Mammals include, but are not limited to, murines, simians, humans, farm animals, cows, pigs, goats, sheep, horses, dogs, sport animals, and pets. Tissues, cells and their progeny obtained in vivo or cultured in vitro are also encompassed by the definition of the term subject. The term "subject" is also used throughout the specification in some embodiments to describe an animal from which a cell sample is taken or an animal to which a disclosed cell or nucleic acid sequences have been administered. In some embodiment, the animal is a human. For treatment of those conditions which are specific for a specific subject, such as a human being, the term "patient" may be interchangeably used. In some instances in the description of the present disclosure, the term "patient" will refer to human patients suffering from a particular disease or disorder. In some embodiments, the subject may be a non-human animal from which an endothelial cell sample is isolated or provided. The term "mammal" encompasses both humans and non-humans and includes but is not limited to humans, non-human primates, canines, felines, murines, bovines, equines, caprines, and porcines.

The terms "effective amount" or "therapeutically effective amount," as used herein, refer to an amount of an active agent as described herein that is sufficient to achieve, or contribute towards achieving, one or more desirable clinical outcomes, such as those described in the "treatment" description above. An appropriate "effective" amount in any individual case may be determined using standard techniques known in the art, such as a dose escalation study. In some embodiments, as used herein, the term "therapeutically effective amount" is meant to refer to an amount of an active agent or combination of agents effective to ameliorate, delay, or prevent the symptoms, shrink tumor size, prevent progression of cancer from non-metastatic to metastatic disease, or prolong the survival of the patient being treated for cancer or neurodegenerative disease. Determination of a therapeutically effective amount is well within the capabilities of those skilled in the art, especially in light of the detailed disclosure provided herein.

In some embodiments, cyclodextrin or derivatives thereof or pharmaceutically acceptable salts thereof can be co-administered with other therapeutics and/or part of a treatment regimen that includes radiation therapy.

The co-administration of therapeutics can be sequential in either order or simultaneous. In some embodiments cyclodextrin or derivatives thereof or pharmaceutically acceptable salts thereof is co-administered with more than one additional therapeutic. Examples of chemotherapeutics include common cytotoxic or cytostatic drugs such as for example: methotrexate (amethopterin), doxorubicin (adrimycin), daunorubicin, cytosinarabinoside, etoposide, 5-4 fluorouracil, melphalan, chlorambucil, and other nitrogen mustards (e.g. cyclophosphamide), cis-platin, vindesine (and other vinca alkaloids), mitomycin and bleomycin. Other chemotherapeutics include: purothionin (barley flour oligopeptide), macromomycin. 1,4-benzoquinone derivatives and trenimon. Anti-cancer antibodies, such as herceptin, and toxins are also examples of other additional therapeutics.

The therapeutic regimens can include sequential administration of cyclodextrin or derivatives thereof or pharmaceutically acceptable salts thereof and initiation of radiation therapy in either order or simultaneously. Those skilled in the art can readily formulate an appropriate radiotherapeutic regimen. Carlos A Perez & Luther W Brady: Principles and Practice of Radiation Oncology, 2nd Ed. J B Lippincott Co, Phila, 1992, which is incorporated herein by reference in its entirety describes radiation therapy protocols and parameters which can be used in the present disclosure.

When used in as part of the combination therapy the therapeutically effective amount of the inhibitor may be adjusted such that the amount is less than the dosage required to be effective if used without other therapeutic procedures.

In some embodiments, treatment with pharmaceutical compositions described herein is preceded by surgical intervention.

The disclosure also relates to methods of reducing the number of exosomes in a cancer cell by contacting said cancer cell with a therapeutically effective amount of a cyclodextrin.

The term "pharmaceutical composition" as used herein refers to a composition comprising at least one active agent as described herein (such as, for example, an ($\alpha$-CD), and one or more other components suitable for use in pharmaceutical delivery such as carriers, stabilizers, diluents, dispersing agents, suspending agents, thickening agents, excipients, and the like. The disclosure relates to a pharmaceutical composition comprising an effective amount of any alpha-cyclodextrin molecule or derivative or salt disclosed herein and a pharmaceutically acceptable carrier. In some embodiments, the pharmaceutical composition comprises any one or plurality of fatty acid molecules disclosed herein or a slat thereof. In some embodiments, the pharmaceutical composition is free of beta or gamma cyclodextrin.

The term "active agent" as used herein refers to a molecule that is intended to be used in the compositions and methods described herein and that is intended to be biologically active, for example for the purpose of treating malignant, neurodegenerative, vascular, metabolic, inflammatory, autoimmune, pulmonary, fibrotic, hepatic, lysosomal storage, or viral disease, disorder, or condition. The term "active agent" is intended to include molecules that either are, or can be converted to a form that is, biologically active. For example, the term "active agent" includes pro-drugs and/or molecules that are inactive or lack the intended biological activity but that can be converted to a form that is active or has the intended biological activity.

As used herein, the term "sample" refers generally to a limited quantity of something which is intended to be similar to and represent a larger amount of that thing. In the present disclosure, a sample is a collection, swab, brushing, scraping, biopsy, removed tissue, or surgical resection that is to be tested for clinical indicators of a disease or disorder. In some embodiments, samples are taken from a patient or subject that is believed to have malignant, neurodegenerative, vascular, metabolic, inflammatory, autoimmune, pulmonary, fibrotic, hepatic, lysosomal storage, or viral disease, disorder, or condition. In some embodiments, a sample believed to contain clinical indicators of a disease or disorder, such as malignant, neurodegenerative, vascular, metabolic, inflammatory, autoimmune, pulmonary, fibrotic, hepatic, lysosomal storage, or viral disease, disorder, or condition, is compared to a control sample that is known not to contain one or a plurality of clinical indicators of a disease or disorder, such as malignant, neurodegenerative, vascular, metabolic, inflammatory, autoimmune, pulmonary, fibrotic, hepatic, lysosomal storage, or viral disease, disorder, or condition. In some embodiments, a sample believed to contain a clinical indicator of a disease or disorder, such as malignant, neurodegenerative, vascular, metabolic, inflammatory, autoimmune, pulmonary, fibrotic, hepatic, lysosomal storage, or viral disease, disorder, or condition, is compared to a control sample that is known to not contain a clinical indicator of a disease or disorder, such as malignant, neurodegenerative, vascular, metabolic, inflammatory, autoimmune, pulmonary, fibrotic, hepatic, lysosomal storage, or viral disease, disorder, or condition. In some embodiments, a sample believed to contain a clinical indicator of a disease or disorder, such as malignant, neurodegenerative, vascular, metabolic, inflammatory, autoimmune, pulmonary, fibrotic, hepatic, lysosomal storage, or viral disease, disorder, or condition, is compared to a control sample that contains the same clinical indicators of a disease or disorder, such as malignant, neurodegenerative, vascular, metabolic, inflammatory, autoimmune, pulmonary, fibrotic, hepatic, lysosomal storage, or viral disease, disorder, or condition.

The term "scavenge" as used herein means uptake or chemically combine with and transport to including, but not limited to, the kidney for excretion.

The term "salt" refers to acidic salts formed with inorganic and/or organic acids, as well as basic salts formed with inorganic and/or organic bases. Examples of these acids and bases are well known to those of ordinary skill in the art. Such acid addition salts will normally be pharmaceutically acceptable although salts of non-pharmaceutically acceptable acids may be of utility in the preparation and purification of the compound in question. Salts of the embodiments include those formed from hydrochloric, hydrobromic, sulphuric, phosphoric, citric, tartaric, lactic, pyruvic, acetic, succinic, fumaric, maleic, methanesulphonic and benzenesulphonic acids.

In some embodiments, salts of the compositions comprising one or may be formed by reacting the free base, or a salt, enantiomer or racemate thereof, with one or more equivalents of the appropriate acid. In some embodiments, pharmaceutical acceptable salts of the present disclosure refer to amino acids having at least one basic group or at least one basic radical. In some embodiments, pharmaceutical acceptable salts of the present disclosure comprise a free amino group, a free guanidino group, a pyrazinyl radical, or a pyridyl radical that forms acid addition salts. In some embodiments, the pharmaceutical acceptable salts of the present disclosure refer to amino acids that are acid addition salts of the subject compounds with (for example) inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxybenzoic acid, 2-acetoxybenzoic acid, salicylic acid, 4-aminosalicylic acid, aromaticaliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxyethane-sulfonic acid, or aromatic sulfonic acids, for example benzene-, p-toluene- or naphthalene-sulfonic acid. When several basic groups are present mono- or poly-acid addition salts may be formed. The reaction may be carried out in a solvent or medium in which the salt is insoluble or in a solvent in which the salt is soluble, for example, water, dioxane, ethanol, tetrahydrofuran or diethyl ether, or a mixture of solvents, which may be removed in vacuo or by freeze drying. The reaction may also be a metathetical process or it may be carried out on an ion exchange resin. In some embodiments, the salts may be those that are physiologically tolerated by a patient. Salts according to the present disclosure may be found in their anhydrous form or as in hydrated crystalline form (i.e., complexed or crystallized with one or more molecules of water).

The term "soluble" or "water soluble" refers to solubility that is higher than 1/100,000 (mg/ml). The solubility of a substance, or solute, is the maximum mass of that substance that can be dissolved completely in a specified mass of the solvent, such as water. "Practically insoluble" or "insoluble," on the other hand, refers to an aqueous solubility that is 1/10,000 (mg/ml) or less. Water soluble or soluble substances include, for example, polyethylene glycol. In some embodiments, the polypeptide described herein may be bound by polyethylene glycol to better solubilize the composition comprising the peptide.

As used herein, percent "homology" or "sequence identity" is determined by using the stand-alone executable BLAST engine program for blasting two sequences (blZseq), which can be retrieved from the National Center for Biotechnology Information (NCBI) ftp site, using the default parameters (Tatusova T A, Madden T L (1999) FEMS microbiology letters 174:247-50, which is incorporated herein by reference in its entirety).

The term "derivative" as applied to a phosphate containing, monophosphate, diphosphate, or triphosphate group or moiety refers to a chemical modification of such group wherein the modification may include the addition, removal, or substitution of one or more atoms of the phosphate containing, monophosphate, diphosphate, or triphosphate group or moiety. In embodiments, such a derivative is a prodrug of the phosphate containing, monophosphate, diphosphate, or triphosphate group or moiety, which is converted to the phosphate containing, monophosphate, diphosphate, or triphosphate group or moiety from the derivative following administration to a subject, patient, cell, biological sample, or following contact with a subject, patient, cell, biological sample, or protein (e.g. enzyme). In an embodiment, a triphosphate derivative is a gamma-thio triphosphate. In an embodiment, a derivative is a phosphoramidate. In embodiments, the derivative of a phosphate containing, monophosphate, diphosphate, or triphosphate group or moiety is as described in Murakami et al. J. Med Chem., 2011, 54, 5902; Sofia et al., J. Med Chem. 2010, 53, 7202; Lam et al. ACC, 2010, 54, 3187; Chang et al., ACS Med Chem Lett., 2011, 2, 130; Furman et al., Antiviral Res., 2011, 91, 120; Vernachio et al., ACC, 2011, 55, 1843; Zhou et al, AAC, 2011, 44, 76; Reddy et al., BMCL, 2010, 20, 7376; Lam et al., J. Virol., 2011, 85, 12334; Sofia et al., J. Med. Chem., 2012, 55, 2481, Hecker et al., J. Med. Chem., 2008, 51, 2328; or Rautio et al., Nature Rev. Drug. Discov., 2008, 7, 255, all of which are incorporated herein by reference in their entirety for all purposes.

Additional definitions and abbreviations are provided elsewhere in this patent specification or are well known in the art.

Additional Description

Malignant, neurodegenerative, vascular, metabolic, inflammatory, autoimmune, virus, or age-related diseases, disorders, or other conditions are complex conditions in the sense that they involve many genes along common pathways. For instance, cardio-vascular diseases (CVDs), including, but not limited to, atherosclerosis, CAD, and stroke, and neurodegenerative diseases are known comorbidities of T2DM. Based in part on the findings that the phosphoinositides PI(3,4,5)P$_3$ and PI(3,4)P$_2$ are upregulated in malignant and neurodegenerative diseases (Waugh M G (2015) Biochim Biophys Acta 1851:1066-82) and activate Akt signaling (Ooms Lisa M, Binge Lauren C, et al. (2015) Cancer cell 28:155-69; Ma K, Cheung S M, et al. (2008) Cell Signal 20:684-94; Majerus P W, York J D (2009) Journal of Lipid Research 50:S249-S54; Bridges D, Saltiel A R (2015) Biochim Biophys Acta 1851:857-66), PI signaling is widely believed to be involved in a broad range of age-related diseases. INPP4B is known as a suppressor of some cancers, but as a risk factor for others, including, but not limited to breast or prostate cancer. (Woolley J F, Dzneladze I, et al. (2015) Trends Mol Med 21:530-2; Chew C L, Chen M, et al. (2016) Oncotarget 7:5-6) PI3K signaling has also be implied in aging, cognitive decline, and Alzheimer's disease (O'Neill C (2013) Experimental gerontology 48:647-53). Still, "clinical results with single-agent PI3K inhibitors have been modest to date," (Mayer I A, Arteaga C L (2016) Annu Rev Med 67:11-28) in part because traditional GWAS have largely failed to elucidate the precise mechanism by which PI signaling contributes to complex conditions, such as cancer and neurodegenerative disease.

From the results presented herein, all these conditions, including, but not limited to, breast and prostate cancer as well as Alzheimer's and Parkinson's disease, atherosclerosis, and type-2 diabetes are characterized by hyperactivity of the phosphatidylinositol (PI) cycle. In some aspects the present disclosure provides methods of treatment of breast and prostate cancer, cardiovascular, metabolic, and Parkinson's or Alzheimer's diseases, that comprise administering to a subject one or more therapeutically effective amounts of active agents that downregulate the PI cycle to elicit changes in endo-/exocytosis thereby causing a dampening or decrease of cellular migration and infiltration or processing of proteins, including, but not limited to, LDL, APP, tau, myelin, SOD1, HTT, and α-synuclein. Furthermore, such active agents could be, for example, drugs or compounds of drugs that are already being used safely in humans for other indications and could be repurposed for use in the treatment of malignant, neurodegenerative, vascular, metabolic, inflammatory, autoimmune, pulmonary, fibrotic, hepatic, lysosomal storage, or viral disease, disorder, or condition.

Other proposed uses are in a wide range of diseases where the same mechanisms are involved as in the above age-related diseases, including, but not limited to, neural ceroid lipofuscinoses (NCL), (Song W, Wang F, et al. (2014) J Biol Chem 289:10211-22) Parkinson's disease, Alzheimer's disease, frontotemporal dementia (FTD), and Huntington's disease (HD), stroke, (Vecsernyes M, Fenyvesi F, et al. (2014) Arch Med Res 45:711-29; Rivers J R, Maggo S D, et al. (2012) Neuroreport 23:134-8), atherosclerosis (Irie T, Fukunaga K, et al. (1992) J Pharm Sci 81:524-8; Zimmer S, Grebe A, et al. (2016) Sci Transl Med 8:333ra50), non-alcoholic fatty liver disease (NAFLD), (Walenbergh S M, Houben T, et al. (2015) Int J Mol Sci 16:21056-69) respiratory and pulmonary diseases, including, but not limited to, cystic fibrosis, asthma, chronic obstructive pulmonary disease (COPD) (Gunasekara L, Al-Saiedy M, et al. (2017) Journal of cystic fibrosis: official journal of the European Cystic Fibrosis Society; Dos Santos A G, Bayiha J C, et al. (2017) Biochim Biophys Acta 1859:1930-40; Cataldo D, Evrard B, et al. (2015) U.S. Pat. No. 9,034,846 B2), type 2 diabetes mellitus (T2DM) and insulin resistance, (Llanos P, Contreras-Ferrat A, et al. (2015) American journal of physiology Endocrinology and metabolism 308:E294-305) prion disease, (Prior M, Lehmann S, et al. (2007) Journal of virology 81:11195-207) and protection from virus, fungal, or bacterial infections. (Danthi P, Chow M (2004) Journal of virology 78:33-41; Balla T (2013) Physiological Reviews 93:1019-137; Shishido T K, Jokela J, et al. (2015) Proc Natl Acad Sci USA 112:13669-74), including, but not limited to, cellular entry of viruses (influenza, HIV-1, polio, HTLV-1, Newcastle, varicella-zoster, hepatitis B, bluetongue, and HSV.

Sphingolipids and ceramides are also involved in podocyte dysfunction (including, but not limited to Fabry's disease, Tay-Sachs disease, Alport syndrome, minimal change disease, diabetic kidney disease, focal segmental glomerulosclerosis, end-stage renal disease, kidney failure, podocytopenia, hyperhomocysteinemia, steroid-resistant nephrotic syndrome) and the pathophysiology of cancer, angiogenesis, atherosclerosis, inflammation, and insulin resistance. (Abou Daher A, El Jalkh T, et al. (2017) Int J Mol Sci 18)

Phosphoinositides, which regulate endocytosis, (Posor Y, Eichhorn-Grunig M, et al. (2015) Biochim Biophys Acta 1851:794-804) have been mentioned as drug targets in genetic diseases, including, but not limited to, muscular and corneal dystrophy or myotubular neuropathy, cancers, including, but not limited to, leukemias (ALL, AML, CML) and lymphomas (NHL), epilepsy, and thrombosis. (Viaud J, Mansour R, et al. (2016) Biochimie 125:250-8) Neurological diseases linked to phosphoinositide dysregulation include, but are not limited to, Friedreich's ataxia, Charcot-Marie-Tooth (CMT) degenerative neuropathy, renal tubulopathies (oculocerebrorenal syndrome of Lowe, Dent's disease), Andersen-Tawil syndrome, mucolipidosis, multiple sclerosis (MS), Yunis-Varon syndrome, ALS FTLD, and ciliopathies. (Waugh M G (2015) Biochim Biophys Acta 1851:1066-82) Additional diseases linked to phosphoinositide dysregulation are osteoporosis, cancers (including, but not limited to, cervical cancer, leiomyosarcoma, gastric cancer, adenocarcinoma, lung cancer), cardiac hypertrophy, and autoimmune diseases (including, but not limited to, rheumatoid arthritis (RA) and systemic lupus erythematosus), and neurological diseases including, but not limited to, bipolar disorder and schizophrenia, (Falasca M (2012) Current topics in microbiology and immunology)

Many other diseases are known to involve loss-of-function mutations affecting the lysosome, where many of the pino-/endocytosed extracellular and autophagocytosed intracellular substrates need to be degraded. (Wang C, Telpoukhovskaia M A, et al. (2017) Curr Opin Neurobiol 48:52-8) In all cases, the disease phenotype would be improved by reducing the amount of pino-/endocytosed materials that need to be degraded (MPS: muco-polysaccharidosis, MLD: metachromatic leukodystrophy):

ABCA1: renal disease; ABCA2: acoustic neuroma; ABCB9: acute myeloid leukemia (AML); ACP2: acid phosphatase deficiency, keratoconus, amyotrophic lateral sclerosis, atrichia, amebiasis; ACP5: spondyloenchondrodysplasia, bone giant cell tumor, hairy cell leucoma, tooth resorption; AGA: aspartylglucosaminuria, fucosidosis; AP3B1: Hermansky-Pudlak syndrome (HPS), oculocutaneous albinism, storage pool platelet disease; AP3B2: paraneoplastic neurologic disorders; ARSA: MLD, arylsulfatase a deficiency, multiple sulfatase deficiency, mucosulfatidosis; ARSB: MPS VI, arylsulfatase b deficiency, mucosulfatidosis; ASAH1: Farber lipogranulomatosis, (Kugelberg-Welander) spinal muscular atrophy, (Erdheim-Chester) lipogranulomatosis; ATP13A2/PARK9: NCL 12, Kufor-Rakeb syndrome, spastic paraplegia 78, juvenile onset Parkinson disease; ATP6AP2 (Perrett 2015): mental retardation, Parkinsonism with spasticity, lymphocytic choriomeningitis; ATP6V0A1: inferior myocardial infarction; ATP6V0A2: wrinkly skin syndrome, cutis laxa, myelophthisic anemia; ATP6V0A4: renal tubular acidosis, medullary sponge kidney; CD164: autosomal dominant deafness, pollen allergy, prostate cancer; CLC7: osteopetrosis; CLN1/PPT1: NCL, Batten disease, Santavuori-Haltia; CLN11/GRN: NCL, frontotemporal dementia, primary progressive aphasia; CLN3: NCL, secondary corneal edema, Spielmeyer-Vogt-Sjogren-Batten disease; CLN4/DNAJC5: NCL, CLN4 disease; CLN5: NCL; CLN5: NCL, Finnish late infantile; CLN6: NCL, Kufs disease, CLN7: NCL, macular dystrophy, neurotic disorder, depressive neurosis; CLN8: Norther epilepsy, progressive with mental retardation/Turkish late infantile; CTNS: nephropathic cystinosis, Fanconi syndrome; CTSA: galactosialidosis, glycoproteinosis, gonococcal salpingitis, triosephosphate isomerase deficiency, aspartylglucosaminuria; CTSB: occlusion of gallbladder, ileum cancer, pancreatitis, keratolytic winter erythema, breast cancer, Alzheimer's disease; CTSC: Papillon-Lefevre syndrome, Haim-Munk syndrome, periodontitis, palmoplantar keratosis, actinic keratosis; CTSD: NCL, bone chondrosarcoma, endometrial clear cell adenocarcinoma, breast diseases, Parkinson's disease (Parnetti 2017); CTSE: gastric adenocarcinoma, Rosai-Dorfman disease, histiocytosis; CTSF: NCL, Kufs disease, akinetic mutism, coma vigilans, clonorchiasis, oriental liver fluke disease; CTSG: Papillon-Lefevre syndrome, cutaneous mastocytosis, suppurative periapical periodontitis, vasculitis, Wegener granulomatosis; CTSH: thyroid crisis, intermittent explosive disorder, narcolepsy, fibrous meningioma, amyotrophic lateral sclerosis; CTSK: pycnodystostosis, hypersensitivity pneumonitis, osteosclerosis, osteomyelitis, bone giant cell tumor; CTSL: vulva basal cell carcinoma, eccrine acrospiroma, fasciolopsiasis, tracheal cancer, rectosigmoid junction neoplasm; CTSO: breast cancer; CTSS: mandibular cancer, non-suppurative otitis media, cercerial dermatitis, subepithelial mucinous corneal dystrophy, jaw cancer; CTSW: autoimmune atrophic gastritis; CTSZ: dacryoadenitis; DNASE2: calcific tendinitis, rheumatoid arthritis; FUCA1: fucosidosis, angiokeratoma, mucolipidosis III, laryngotracheitis; GAA: glycogen storage disease II (Pompe disease), acid maltase deficiency, Danon disease, α-1,4-glucosidase deficiency; GALC: Krabbe disease, leukodystrophy; GALNS: MPS IV, chondroosteodystrophy, Scheie syndrome, Kniest dysplasia; GBA: Gaucher disease (GD), pseudo Gaucher disease, GBA-associated Parkinson's disease; GLA: Fabry disease, cramp-fasciculation syndrome, angiokeratoma, MPS VII; GLB1: gm1-gangliosidosis, MPS IVb; GM2A: GM2-gangliosidosis, Tay-Sachs disease (TSD), Sandhoff-disease, mucolipidosis II α/β, I-cell disease; GNPTAB: mucolipidosis 2, mucolipidosis 3, MPS 3a; GNPTG: mucolipidosis III, pseudo-Hurler polydystrophy, articulation disorder; GNS: MPS III, multiple sulfatase deficiency, mucosulfatidosis; GUSB: MPS VII, hydrops fetalis, necrotizing ulcerative gingivitis, choledocholithiasis; GUSB: Sly disease, MSP VII, hydrops fetalis, necrotizing ulcerative gingivitis, choledocholithiasis; HEXA: Tay-Sachs disease, gm2 gangliosidosis; HEXB: Sandhoff disease, mucolipidosis IV, sphingolipidosis; HGSNAT: MPS IIIc, MPS IIIb, retinitis pigmentosa, Kluver-Bucy syndrome; HYAL1: MPS IX, bladder carcinoma, prostate cancer; IDS: MPS II, Hunter syndrome; IDUA: MPS I, Scheie syndrome, Hurler-syndrome; IGF2R: hepatocellular carcinoma, mucolipidosis II, inclusion-cell disease, colorectal cancer; LAAT1/PQLC2: cystinosis; LAMP1: Salla disease, Hermansky-Pudlak syndrome, lysosomal acid phosphatase deficiency, hemophagocytic syndrome; LAMP2: Danon disease, cardiomyopathy, atrial standstill, glycogen storage disease II, lysosomal acid phosphatase deficiency; LAMP3/CD63: Hermansky-Pudlak syndrome, melanoma, Quebec platelet disorder, mast cell disease, Schwarzman phenomenon; LAMP4/CD68/SCARD1: (breast) granular cell tumor, follicular dendritic cell sarcoma, bacterial esophagitis, axillary lipoma; LAPTM4A: pain disorder; LAPTM4B: hepatocellular carcinoma; LGMN: schistosomiasis; LIMP2/SCARB2: progressive myoclonic epilepsy, Unverricht-Lundborg disease, hand-tooth-and-mouth disease, myoclonus; LIPA: Wolman disease, cholesterol ester storage disease, splenic abscess, familial hypercholesterolemia; LITAF: Charcot-Marie-Tooth hereditary neuropathy; LMBRD1: methylmalonic aciduria and homocystinuria, cblf type, hepatitis, transcobalamin II deficiency; LYPLA3/PLA2G15; LYST: Chedliak-Higashi syndrome, exfoliation syndrome, Hermansky-Pudlak syndrome, dichromatosis symmetrica; M6PR: MPS IIIa, mucolipidosis II, NCL, Niemann-Pick disease; MANB: mannosidosis ($\alpha/\beta$); MCOLN1: mucolipidosis IV, ataxic cerebral palsy, sphingolipidosis, strabismus, mucolipin-1 deficiency; NAGA: Kanzaki disease, Schindler disease, neuroaxonal dystrophy, agiokeratoma; NAGLU: MPS III, Charcot-Marie-Tooth disease, acute pyelonephritis; NAGPA: familial persistent stuttering, articulation disorder, MPS IIIb, speech disorder, diabetic nephropathy; NAPSA: ovarian clear cell adenofibroma, Krukenberg/lung adeno/pulmonary adeno (Bishop D V (2010) PLoS One 5:e15112)/ovarian clear cell/carcinoma, malignant fibrous mesothelioma; NEU1: sialidosis, hydrops fetalis, parainfluenza virus type 3; NPC1/2: Niemann-Pick disease C1/2; PSAP: atypical Gaucher disease, combined saposin deficiency, MLD, Krabbe disease; PSEN1 (Lee 2015, Sato 2017): frontotemporal dementia, Alzheimer's disease 3, familial acne inversa, dilated cardiomyopathy; RAB27A: Griscelli syndrome, hemophagocytic lymphohistiocytosis, Chedliak-Higashi syndrome; RAB7 (Perrett 2015): Charcot-Marie-Tooth disease 2b, choroideremia, tabes dorsalis, NCL; SGSH: MPS III, Klver-Bucy syndrome, Sanfillipo syndrome; SLC11A: Buruli ulcer, tuberculosis, typhoid fever; SLC11A2: microcytic anemia, hemosiderosis, anemia; SLC17A5/SIALIN: Salla disease, sialic acid storage disorder, sialuria, fascioliasis; SMPD1: Niemann-Pick disease, acid sphingomyelinase deficiency, narcissistic personality disorder; SORT1: inclusion-cell disease, I-cell disease, myocardial infarction; SQSTM1: ALS; SUMF1: multiple sulfatase deficiency, MLD, spinocerebellar ataxia, MPS VI; TMEM106B: amyotrophic lateral sclerosis (ALS)/Frontotemporal lobar degeneration (FTLD). (Sullivan P M, Zhou X, et al. (2017) Lysosomes—Associated Diseases and Methods to Study Their Function 63-91) TPP1: NCL, spinocerebellar ataxia, Bielschowsky-Jansky disease.

Other conditions where age-related insufficient lysosomal function is involved are cardio- and cerebrovascular diseases including, but not limited to, arteriosclerosis, coronary heart disease, arrhythmia, heart failure, hypertension, orthostatic hypotension, myocardial infarction. angina pectoris. heart failure, atherosclerosis, stroke, renal artery disease or stenosis, peripheral vascular disease, chronic obstructive pulmonary disease, ("COPD"), chronic renal diseases with renal failure, and heart disease. Exemplary inflammatory diseases and conditions include arthritis, such as rheumatoid arthritis. Additional exemplary age-associated diseases and disorders ulcers. osteopetrosis. progeria. weakness, hearing loss, and type-2 diabetes. It is to be understood that "age-related" refers to diseases frequently associated with aging, however, a given patient need not be of advance age, but rather the subject methods and compositions may be used regardless of the patient's age.

A) Active Agents

As further described in the Examples and other sections of the present application, agents that can be used in the methods of the invention may reduce the concentration of phospholipids available to cells, including, but not limited to, neurons, macrophages, microglia, and tumor cells. In some embodiments, the agent is a cyclic oligosaccharide. In some embodiments, the cyclic oligosaccharide is an $\alpha$-CD optionally modified by an alkyl group from about 1 to about 20 or more carbons in length. In some embodiments, the cyclodextrin is $\alpha$-CD optionally modified by a hydroxylalkyl group from about 1 to about 20 or more carbons in length. In yet another embodiment, the agent is hydroxypropyl-(HP-)$\alpha$-CD. In some embodiments, the agent is a clathrate of an $\alpha$-CD. In some embodiments the agent is a clathrate of an $\alpha$-CD with a fatty acid. A "fatty acid" as used herein means a carboxylic acid with a long aliphatic chain, which is either saturated or unsaturated. In some embodiments, the aliphatic chain is from about 3 to about 70 carbons long. In some embodiments, the aliphatic chain is from 8 to about 30 carbons long. In some embodiments the fatty acid has one or more aliphatic chains branched or unbranched with one or more substituents. In some embodiments, the fatty acid comprises from about 6 to about 22 carbon atoms in its aliphatic chain. In some embodiments, any one of the bonds between each carbon atom may be in the cis or trans configuration.

Cyclodextrins are natural compounds formed during bacterial digestion of cellulose. They are not hydrolyzed by common mammalian amylases, but can be fermented by the intestinal microflora. They are poorly resorbed in typical situations and do not interact with cells or tissues. On Dec. 22, 2004, $\alpha$-CD was declared GRAS by the FDA for "use in selected foods, except meat and poultry, for fiber supplementation, as a carrier or stabilizer for flavors (flavor adjuvant), as a carrier or stabilizer for colors, vitamins and fatty acids and to improve mouthfeel in beverages (GRN No. 155, updated November 2016 as GRN 678 to reflect an expected $90^{th}$ percentile for intake of 420 mg/kg, or ~30 g/d at 70 kg). An $\alpha$-CD monograph is included in the U.S. Pharmacopeia/National Formulary (USP/NF25), the European Pharmacopoeia (EP 6.0), and the Handbook of Pharmaceutical Excipients. cyclodextrins are exempted from the requirement of a tolerance under 40 CFR 180.950 when used in or on various food commodities. (FR 70 128 28780 2005 Jul. 6). On Oct. 9, 2017, cyclodextrins were included in the Annex to the European Commission guideline on 'Expedients in the labelling and package leaflet of medical products for human use'.

Figure 1:
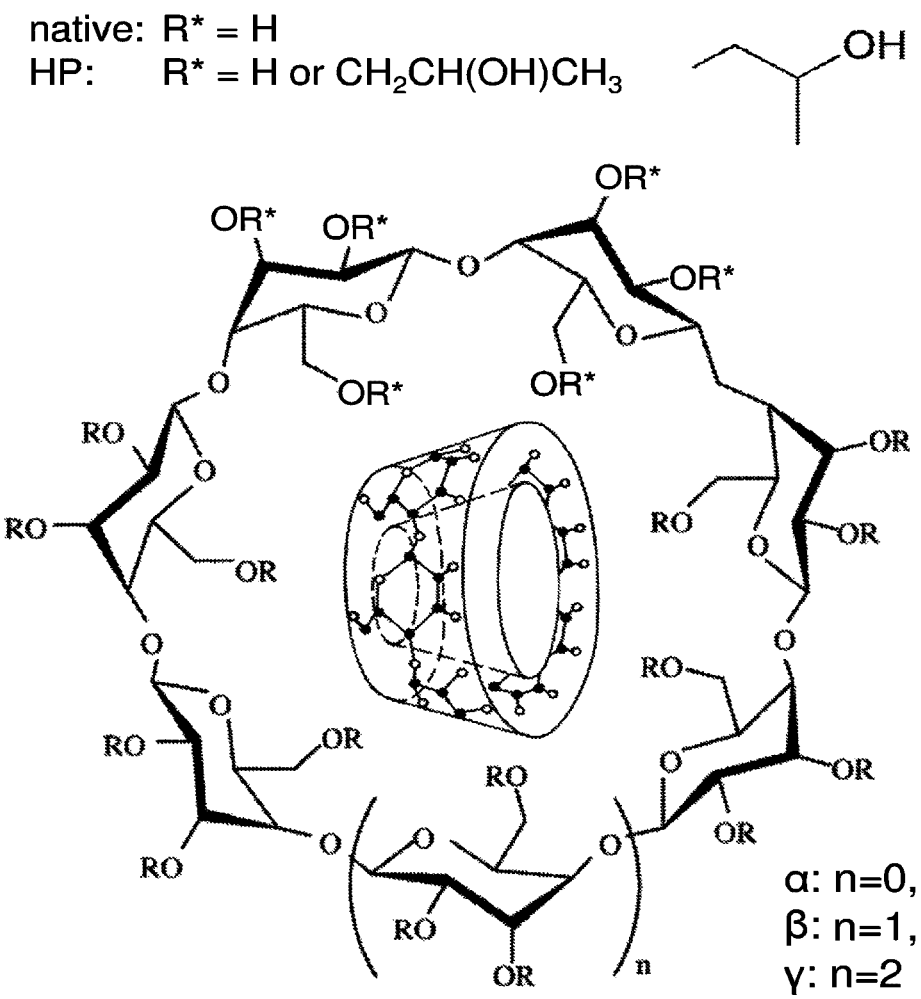
FIG. 1: Cyclodextrins, Including Hydroxypropyl Cyclodextrins. Up to n×3 degrees of substitution may be realized, with numerous positional and regio-isomers possible. Substitutions for R include, but are not limited to, H (parent), methyl (including randomly methylated), butyl, 2-hydroxypropyl (HP) (shown), acetyl, succinyl, glucosyl, maltoseyl, carboxymethyl ether, phosphate ester, simple polymers, or carboxymethyl. Typical cyclodextrins contain 6 (α-CD), 7 (β-CD) or 8 (γ-CD) D-glucose monomers in a ring, creating a cone shape that can accommodate guest molecules into their hydrophobic cavity.

The common cyclodextrins are made up of six ($\alpha$-CD), seven ($\beta$-CD), or eight ($\gamma$-CD) D-glucose molecules bound together in a toroid (truncated cone) with a lipophilic inner and a hydrophilic outer surface (FIG. 1). This combination of features makes them suitable as an expedient to solubilize lipophilic drugs. "Chemical modifications have been made to [cyclodextrins] to increase their hydrophilic activity with the hope that the improved solubility would eliminate the renal toxicity [in rats]." (Irie T, Uekama K (1997) J Pharm Sci 86:147-62) Substitution of any of the hydroxyl groups, even by hydrophobic moieties, will result in a dramatic increase in water solubility. The main reason for the solubility enhancement is that chemical manipulation frequently transforms the crystalline cyclodextrins into amorphous mixtures of isomeric derivatives. For example, the aqueous solubility of $\beta$-cyclodextrin increases with increasing degree of methylation. The highest solubility is obtained when about two-thirds of the hydroxyl groups (i.e., 14 of 21) are methylated. HP-$\beta$-CD substantially improves water solubility over $\beta$-CD (Table 2, see also Table 8).

TABLE 2

Physicochemical characteristics of selected cyclodextrins

|  | α-CD | HP-α-CD | β-CD | HP-β-CD |
|---|---|---|---|---|
| Number of glucose units | 6 | 6 | 7 | 7 |
| Internal diameter | 4.5-5.2 | 4.7-5.3 | 6.0-6.5 | 6.0-6.5 |
| Solubility in water [g/l] | 145 | >500 | 18.5 | >600 |

Common cyclodextrins obtained by the substitution of the R groups on the edge (rim) of the toroid (FIG. 1, (Brewster M E, Loftsson T (2007) Advanced Drug Delivery Reviews 59:645-66)) include, but are not limited to, methyl (including randomly methylated) $CH_3$, 2-hydroxypropyl (HP): $CH_2CHOHCH_3$, sulfobutylether $(CH_2)_4SO_3Na^+$, acetyl, succinyl, glucosyl, maltosyl, carboxymethyl ether, phosphate ester, simple polymers, or carboxymethyl. Since both the number of substitutes and their location will affect the physicochemical properties of the cyclodextrin molecules, such as their aqueous solubility and complexing abilities, each derivative listed should be regarded as a group of closely related cyclodextrin derivatives.

Low solubility in water, as with β-CD, in particular, often results in precipitation of solid cyclodextrin complexes. β-CDs, for instance, form intramolecular hydrogen bonds between secondary OH groups, which detracts from hydrogen bond formation with surrounding water molecules, resulting in low aqueous solubilities. (Loftsson T, Brewster M E (1996) J Pharm Sci 85:1017-25)

B) Cytotoxicity/Hemolysis

With parenteral delivery, "the steady-state volume of distribution for β-CD . . . in rats, rabbits, dogs, and humans corresponds well with the extracellular fluid volume of each species, suggesting that no deep compartments or storage in pools are involved. [ . . . ] α- and β-[cyclodextrin] are excreted almost completely in an intact form into the urine" (Irie T, Uekama K (1997) J Pharm Sci 86:147-62) Still cyclodextrins may cause two types of adverse events with parenteral delivery. First, they can accumulate in kidney cells, causing nephrotoxicity. Second, after the lipophilic drug is delivered, they form "a new lipid-containing compartment (or pool) in the aqueous phase into which [cellular lipid] compounds [are] extracted," (Irie T, Uekama K (1997) J Pharm Sci 86:147-62) which could cause hemolysis.

Phospholipids and cholesterol, the major building blocks of plasma membranes, are all lipids. Hence, when cyclodextrins are given parenterally without having their lipophilic cavity filled (or after the lipophilic drug has been delivered), they can potentially extract lipids (phospholipids and cholesterol, depending on the type of cyclodextrin) from plasma membranes. "Several cyclodextrins have been demonstrated to cause cell lysis in different types of cells, indicating that the effect is not cell-type specific [(Irie T, Uekama K (1997) J Pharm Sci 86:147-62)]" (Stella V J, He Q (2008) Toxicol Pathol 36:30-42) In particular, cyclodextrins are known to induce shape changes of plasma membrane invagination on erythrocytes and, at higher concentrations, induce hemolysis of erythrocytes in the order of β-CD>α-CD>γ-cyclodextrin. (Irie T, Otagiri M, et al. (1982) J Pharmacobiodyn 5:741-4), i.e., the hemolytic activity of α-CD is lower than that of both β-CD and HP-β-CD (Irie T, Uekama K (1997) J Pharm Sci 86:147-62, FIG. 6). In addition, β-CD, but not α-CD and HP-β-CD, induces caspase-dependent apoptotic cell death in keratinocytes by depleting plasma membrane cholesterol. (Stella V J, He Q (2008) Toxicol Pathol 36:30-42) HP-α-CD was found to be less cytotoxic than α-CD on heterogeneous human epithelial colorectal adenocarcinoma (Caco-2) cells. (Roka E, Ujhelyi Z, et al. (2015) Molecules 20:20269-85; Ono N, Arima H, et al. (2001) Biol Pharm Bull 24:395-402) From these observations, HP-cyclodextrins are have not only less nephrotoxicity, but also less cyto- and hemolytic toxicity.

HP-β-CD is used as an expedient/solvent for many lipophilic drugs, including the neurosteroid allopregnanolol. α-CD has been approved and is used as an expedient of alprostadil (a prostaglandin) for intracavernosal injection in the treatment of erectile dysfunction.

Still, less cytotoxicity overall does not mean safe for human use. A 2010 study showed that HP-β-CD causes permanent hearing loss in cats at doses of 4-8 g/kg, (Ward S, O'Donnell P, et al. (2010) Pediatr Res 68:52-6) In a recent study of 14 NPC1 patients, mid-frequency to high-frequency hearing-loss requiring hearing aids for management. (Ory D S, Ottinger E A, et al. (2017) Lancet 390:1758-68) These results raised concerns for the use of β-cyclodextrin as an active ingredient (larger dose), rather than an excipient (smaller dose).

In 2014, it was observed that the reported benefit of the neurosteroid allopregnanolol in Niemann-Pick C (NPC) disease was, in fact, due to the excipient, HP-β-CD. (Vance J E, Karten B (2014) Journal of Lipid Research 55:1609-21; Liu B, Turley S D, et al. (2009) Proc Natl Acad Sci USA 106:2377-82) It was demonstrated the β-cyclodextrin at therapeutic doses reduces cholesterol in cellular components, rather than extracting cholesterol from cell membranes as previously believed. In September 2015, a phase 2b/3 study of HP-β-CD started in patients with neurologic manifestations of NPC1 disease. (NIH (2015) ClinicalTrialsgov NCT02534844) The question was whether one could retain the benefit for treating NPC while avoiding risk of ototoxicity ("dead or deaf?").

There is a positive correlation between the hemolytic activity of several cyclodextrins and their capacity to solubilize cholesterol," (Irie T, Uekama K (1997) J Pharm Sci 86:147-62) suggesting that ototoxicity might be directly related to the extraction of cholesterol from outer hair cells.

The results of the genetic study reported herein show that progression in breast cancer, including metastases, are caused, in part, by excessive conversion of serum glycerophospholipids (LPC, PC) into PI, the substrate of the PI cycle, which regulates endocytosis through phosphoinositides. Of note, LPC is also involved in surfactant inhibition in cystic fibrosis, where "LPC or FFA mediated surfactant inhibition was reversed by M-β-CD, even in the relative absence of cholesterol [likely reflecting] the capacity of M-β-CD to sequester non-steroidal lipids in addition to cholesterol.". (Gunasekara L, Al-Saiedy M, et al. (2017) Journal of cystic fibrosis: official journal of the European Cystic Fibrosis Society)

Figure 2:
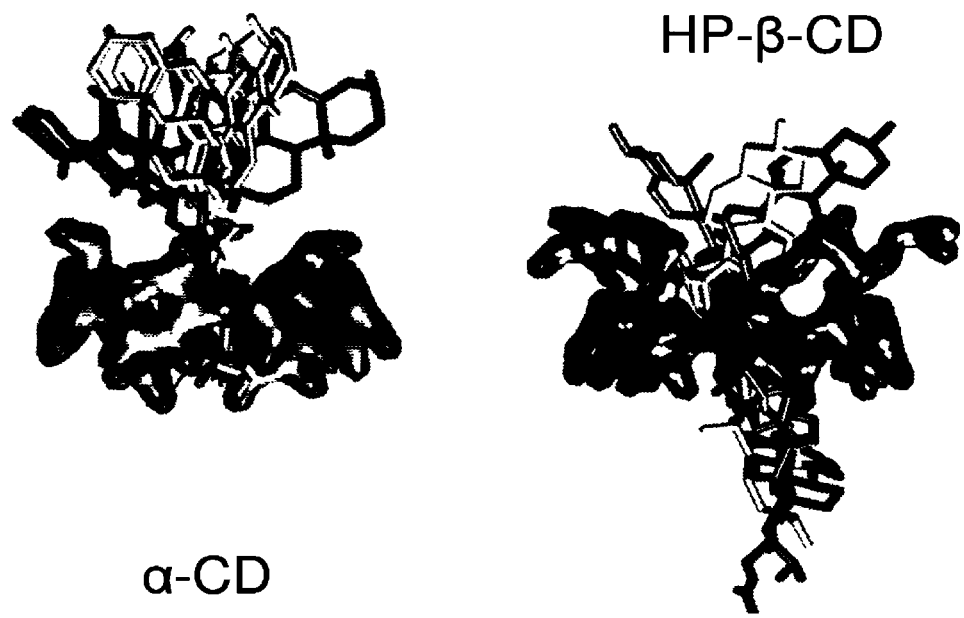
FIG. 2: Clustering analysis of cholesterol interaction with α-CD and HP-β-CD. Displayed are the last 25 ns of the trajectories. CD molecules are depicted using the solid surface representation method with a probe radius of 0.4 Å, density isovalue of 0.7 and grid spacing of 0.5 to visualize the binding cavity. Hydrogen atoms are omitted to enhance clarity. Modified from (Shityakov S, Salmas R E, et al. (2016) J Toxicol Sci 41:175-84)
Figure 3:
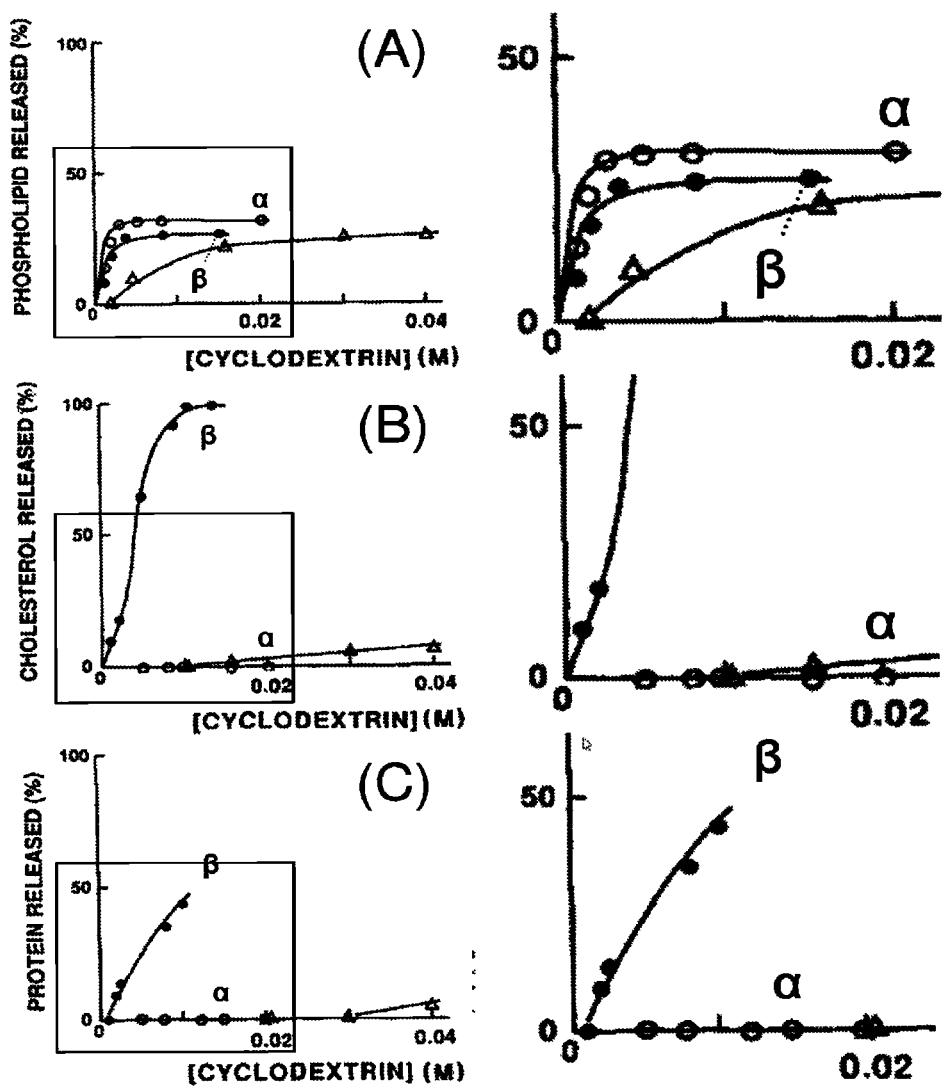
FIG. 3A through FIG. 3C: Specificity of Lipid Release I. Release of phospholipids (3A) cholesterol, (3B), and proteins (3C) from intact (3B) or ghost (3A and 3C) erythrocytes treated with cyclodextrins. ○: α-CD; ●: β-CD; Δ: γ-CD. Modified from: (Ohtani Y, Irie T, et al. (1989) European Journal of Biochemistry 186:17-22)
Figure 4A:
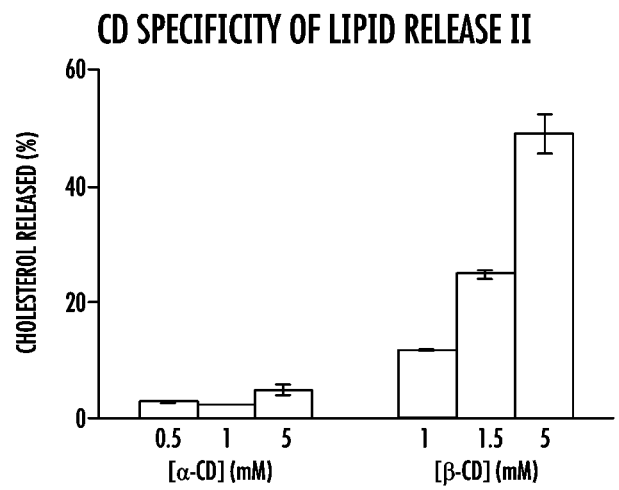
FIG. 4A-FIG. 4B: Specificity of Lipid Release II. 4A) Cholesterol released from brain capillary endothelial cell (BCECs) after 2 h of incubation in the presence of various concentrations of α- and β-CDs. Results are expressed as a percentage of cholesterol released from BCECs compared with the control. Each percentage is the mean of three different filters and representative of two series of independent experiments. (4B) Phosphatidylcholine (PC) (light columns) and sphingomyelin (SM, dark columns) released from BCECs after 2 h of incubation in the presence of α- and β-CDs at 0.5, 5, and 50 mM, respectively. Results are expressed as a percentage of phospholipids released from BCECs compared with the control. Each percentage is the mean of three different filters and representative of two series of independent experiments. Modified from: (Monnaert V, Tilloy S, et al. (2004) Journal of Pharmacology and Experimental Therapeutics 310:745-51)
Figure 4B:
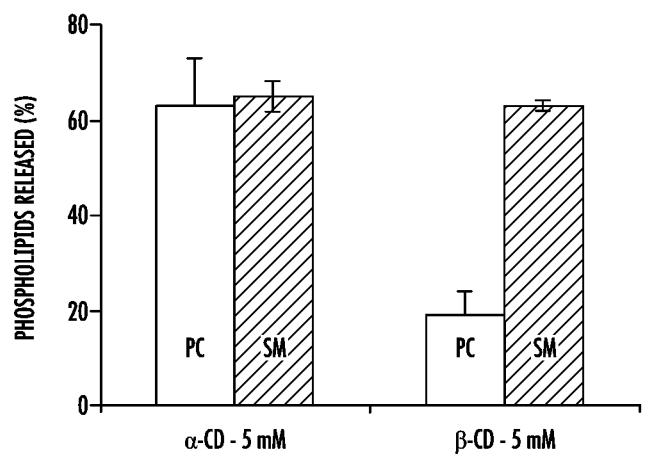

All cyclodextrins have the ability to scavenge phospholipids. β-CDs (seven sugars) have often been chosen over α-CDs (six sugars, FIG. 1) because they can be used as expedients for more (larger) drugs. The smaller α-CD is known to have higher specificity for the smaller phospholipids (Ohtani Y, Irie T, et al. (1989) European Journal of Biochemistry 186:17-22; Vance J E, Karten B (2014) Journal of Lipid Research 55:1609-21). because steroids and sterols, including, but not limited to, cholesterol, (Zarzycki P K, Ohta H, et al. (2008) Anal Bioanal Chem 391:2793-801) do not fit its smaller cavity (FIG. 2). The specificity of extraction of phospholipids, cholesterol, and proteins are shown in FIG. 3 (Ohtani Y, Irie T, et al. (1989) European Journal of Biochemistry 186:17-22). Among the phospholipids, α-CD is known to scavenge glycerolipids, such as PC, and sphingolipids more specifically than β-CDs (FIG. 4). In particular, α-CD is known to form complexes both around both the inositol head or the sn-2 chain of PI. (Fauvelle F, Debouzy J C, et al. (1997) J Pharm Sci 86:935-43), Hence, α-CDs are expected to downregulate the substrates for the PI cycle and, thereby, downregulate endocytosis with higher specificity than β-CD. (Cai W, Du A, et al. (2013) J Immunol 191:6093-100) HP-α-CD retains the preference of α-CD for phospholipids over cholesterol. (Huang Z, London E (2013) Langmuir 29:14631-8) One of the surprising result in this disclosure (see Example 16) is that HP-α-CD in serum is even more specific than expected, scavenging PC, but neither lyso-phospholipids nor PS.

Ototoxicity of β-cyclodextrin has been shown to be caused by β-cyclodextrin depriving prestin of the cholesterol it needs to function in outer hair cells (Takahashi S, Homma K, et al. (2016) Sci Rep 6:21973; Kamar R I, Organ-Darling L E, et al. (2012) Biophysical Journal 103:1627-36). The fact that the cavity of α-CDs is too small for cholesterol explains that α-CD and its derivates, including, but not limited to, HP-α-CD, are not ototoxic.

Long-term parenteral administration of HP-β-CD (200 mg/kg) was reported to decrease bone mineral density (BMD), which was associated with increased bone resorption, (Kantner I, Erben R G (2012) Toxicol Pathol 40:742-50) while a CD-bisphosphonate conjugate, alendronate-β-CD (ALN-β-CD) was shown to be bone-anabolic. (Liu X-M, Wiswall A T, et al. (2008) Biomaterials 29:1686-92)

C) Cyclodextrin Specific Activity

Only in part related to the different physicochemical characteristics Table 2, α-CDs, β-CDs, and γ-CD cyclodextrins have dramatically different biochemical function and, thus, different uses.

- Only γ-CDs can be hydrolyzed by pancreatic amylases and saliva and are rapidly metabolized and absorbed in the small intestine.
- β-CDs and γ-CDs can bind fats at most at a 1:1 molar ratio, but α-CD can bind fat 9-times its weight.
- Size of the cavity v. the molecule is a major determinant for the use of cyclodextrins. β-CDs (and γ-CDs, to a lesser extent), but not α-CDs can bind sterols (including cholesterol) and steroids), because these molecules are too large to fit into the smaller cavity of α-CDs.
- Methylated β-CDs have a high affinity to common constituents of cell membranes and, thus, an extreme hemolytic effect, while α-CDs have very low effect on human erythrocytes.
- The effect of the neuromuscular blocking drug rocuronium is reversed by the specifically designed γ-CD derivative sugammadex (octakis-(6-deoxy-6-S-mercaptopropionyl-γ-cyclodextrin sodium salt) to prevent residual paralysis. (Booij L H (2009) Anaesthesia 64 Suppl 1:31-7)
- For cyclosporin A, a mixture of α-CD and γ-CD is used to enhance the drug solubility without causing ocular irritation.
- For intranasal insulin, DMβCD and α-CD are potent enhancers, but γ-CD, β-CD, and HPβCD are not. (Merkus F W, Verhoef J C, et al. (1991) Pharm Res 8:588-92; Shao Z, Krishnamoorthy R, et al. (1992) Pharmaceutical Research 9:1157-63)
- α-CD but not β-CD supplementation decreased atherosclerotic lesions in aorta in apoE-KO mice, although β-CD but not α-CD supplementation decreases intestinal lipid absorption. (Sakurai T, Sakurai A, et al. (2017) Mol Nutr Food Res 61)
- Only α-CD can be used for gold extraction through environmentally friendly co-precipitation. (Liu Z C, Samanta A, et al. (2016) Journal of the American Chemical Society 138:11643-53)

Figure 5:
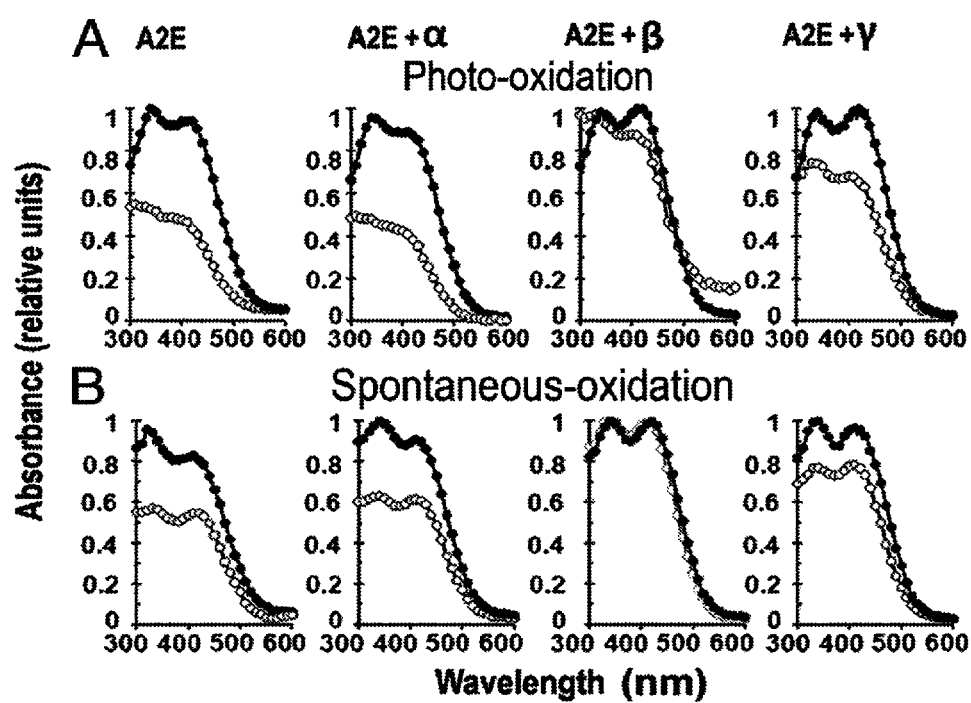
FIG. 5: MβCD, but not αCD protect A2E against oxidation. The bisretinoid A2E was the first compound identified in extracts of ocular lipofuscin. Protection of A2E against oxidation was monitored by changes in the UV-visible absorption spectra of 5 µM A2E solutions. (5A) A2E oxidative status before (•) and after (o) blue-light irradiation in the presence of indicated cyclodextrins (12 mM). (5B) A2E oxidative status at time 0 (•) and 1 d (○) after incubation at room temperature in the dark in the presence of cyclodextrins. Modified from (Nociari M M, Lehmann G L, et al. (2014) Proceedings of the National Academy of Sciences 111:E1402-E8)

This "in-complete" list of differences between cyclodextrin demonstrates that effects seen by one cyclodextrin cannot be extrapolated to other cyclodextrins. In fact, there are only few examples, where more than one of the cyclodextrins is used for the same application:

- HP-β-CD is used, for instance,
  - As the active ingredient of Febreze®; the smaller α-CDs would trap too few malodourous molecules.
  - To remove cholesterol from whole egg, milk, the smaller α-CDs do not fit cholesterol
- α-CDs are used
  - In foods based on vegan coconut milk powder (UK) as a replacement for sodium caseinate
  - In powdered alcohol
  - In Coenzyme Q10/L-Carnitine supplements to form complexes with the essential alpha linoleic acid Therapeutic uses also are highly specific. In one age related application (Nociari M M, Lehmann G L, et al. (2014) Proceedings of the National Academy of Sciences 111:E1402-E8), demonstrated that HP-β-CD could bind A2E, a lipofuscin component, while α-CD could not (FIG. 5)

Rarely, if ever are several cyclodextrins used with the same type of substrates, attesting to the fact that their function is highly specific despite them comprising rings of sugars. One of the most important differences is the number of these sugars: "Cyclodextrin-Lipid Complexes: Size Matters". (Szente L, Fenyvesi E (2017) Structural Chemistry 28:479-92) In some embodiments, the α-CD is a hydroxypropyl, hydroxyethyl, hydroxymethyl, hydroxybutyl, hydroxypentyl-α-CD or salt or derivative thereof. In some embodiments, the pharmaceutical composition of the disclosure comprises hydroxypropyl, hydroxyethyl, hydroxymethyl, hydroxybutyl, hydroxypentyl-α-CD or salt or derivative thereof but is free of alpha-cycoldextrin or beta-cyclodextrin. In some embodiments, the pharmaceutical composition is free of beta or gamma cyclodextrin and or derivatives of salts thereof.

D) Treatment of Cancer Patients with α-CD or Derivatives or Salts Thereof

Several embodiments of the disclosure include the use of α-CD and/or derivatives or pharmaceutically acceptable salt thereof.

Embodiments of the present disclosure are particularly useful to treat individuals who have cancer identified as having one or a plurality of cells with an abnormally high rate of endocytosis or exocytosis, or, in some embodiments, a dysfunctional PI cycle or lysosome. In some embodiments, methods for treating a subject who has cancer comprise the steps of first identifying cancer as having a high rate of endocytosis or exocytosis, or, in some embodiments, a dysregulated PI cycle, and then administering to such a subject a therapeutically effective amount of an α-CD. In some preferred embodiments, the identification of cancer as having a high rate of endocytosis or exocytosis, or, in some embodiments, a dysfunctional PI cycle, is done by PET imaging, preferably using a fluorescent tag, antibody, or other agent that identifies mutations in the amino acid sequence of Table 5b or an amino acid sequence at least about 70%, 80%, 90%, 95% 96%, 97%, 98%, or 99% homology to the amino acid sequences of Table 5b, In some embodiments, the α-CD or derivative or salt thereof is effective to scavenge phospholipid in greater than about 50% of cells in an in vitro migration assay at a concentration of less than 4 mM, 3 mM, 2 mM, or 1 mM. In some embodiments, the α-CD or derivative or salt thereof is effective to inhibit migration of cells in greater than about 50% of cells in an in vitro cell migration assay at a concentration of about 1 mM. In some embodiments, the α-CD or derivative or salt or clathrate thereof is effective to reduce cell migration in greater than 50% of cells in an in vitro cell migration assay at a concentration from about 0.5 to about 1.5 mM.

In some embodiments of the present disclosure, methods for treating an individual who has been identified as having cancer comprise administering to such an individual a therapeutically effective amount of the α-CD or derivative or salt thereof which is known to be effective to inhibit cell migration in greater than 50% of cells in an in vitro migration assay at a concentration of less than 1 mM. In some preferred embodiments, the α-CD or derivative or salt thereof is effective to inhibit cell migration in greater than 50% of cells in an in vitro cell migration assay at a concentration of less than about 1.5 mM. In some preferred embodiments, the α-CD or derivative or salt thereof is effective to inhibit cell migration in greater than about 50%, 60%, 70%, 80%, or 90% of cells in an in vitro cell migration assay at a concentration of about 1 mM, In some preferred embodiments, prior to administration of the α-CD or derivative or salt thereof, the cancer is confirmed as being a cancer comprising one or a plurality of cells characterized by an abnormally high rate of endo- or exocytosis, or, in some embodiments, a dysfunctional PI cycle or lysosome. The preferred method of doing so is be PET imaging, polymerase chain reaction (PCR) of a sample such as a biopsy.

Methods are provided for inhibiting, even partially, metastasis of a cancer cell. The methods comprise delivering to the cancer cell an amount of α-CD or derivative or salt thereof effective to inhibit cell migration of the cell. The α-CD or derivative or salt thereof used is effective to slow migration of a cancer cell in greater than 50% of cells in an in vitro cell migration assay at a concentration of less than about 2 mM or about 1.5 mM. In some embodiments, the α-CD or derivative or salt thereof is effective to inhibit cell migration in greater than 50% of cells in an in vitro cell migration assay at a concentration of less than 1.5 mM. In some preferred embodiments, the cyclodextrin or derivative or salt thereof is effective to inhibit cell migration in greater than 50% of cells in an in vitro cell migration assay at a concentration of at or about less than 1.0 mM. In some embodiments, the treatment simultaneously reduces the ototoxicity of the treatment.

Embodiments of the present disclosure are particularly useful to treat patients who have cancer with cancer cells that have abnormally high rate of endo- or exocytosis, or, in some embodiments, a dysfunctional PI cycle. Such cancers include most cancers and generally exclude those cancers arising from tissues associated with lipid production such as liver cancer, and cancer involving fat cells. Cancer cells that have abnormally high rate of endocytosis or exocytosis, or, in some embodiments, a dysfunctional PI cycle, are generally limited to epithelial cell derived cancers. In some embodiments, cancer is from epithelial cells of the breast, colon, lung, or prostate. Thus, some methods of the invention relate to methods of treating a cancer patient who has cancer that have abnormally high rate of endo- or exocytosis, or, in some embodiments, a dysfunctional PI cycle, wherein such methods comprise the step of administering to such patient or subject a therapeutically effective amount of cyclodextrin. In preferred embodiments, the α-CD or derivative or salt thereof is known to be effective to slow cell migration in greater than 50% of cells in an in vitro cell migration assay at a concentration of less than 2 mM. In some preferred embodiments, the α-CD or derivative or salt thereof is effective to induce apoptosis in greater than about 50%, 60%, 70%, 80%, or 90% of cells in an in vitro cell migration at a concentration of less than 1.5 mM. Cancer cells that have abnormally high rate of endo- or exocytosis, or, in some embodiments, a dysfunctional PI cycle, generally have dysfunction of enzymes of Table 5b and/or metabolize and/or uptake high levels of phospholipids around their microenvironment. In some preferred embodiments, prior to administration of an α-CD or derivative or pharmaceutically acceptable salt thereof, the cancer is confirmed as being a cancer characterized by an abnormally high rate of endocytosis or exocytosis, or, in some embodiments, a dysfunctional PI cycle. The preferred method of doing so is be PET imaging, PCR or immunohistochemistry of a sample.

Methods are provided for preventing or inhibiting the rate of metastases of a cancer cell characterized by an abnormally high rate of endo- or exocytosis, or, in some embodiments, a dysfunctional PI cycle, The methods comprise delivering to the cancer cell an amount of an α-CD or derivative or pharmaceutically acceptable salt thereof effective to reduce cell migration of the cell. The α-CD or derivative or pharmaceutically acceptable salt thereof used is effective to inhibit or reduce the rate of cell migration in greater than about 50%, 60%, 70%, 80%, or 90% of cells in an in who cell migration assay at a concentration of less than 1.5 mM. In some preferred embodiments, the disclosed treatment herein is effective to inhibit or reduce the rate of cell migration in greater than about 50%, 60%, 70%, 80%, or 90% of cells in an in vitro cell migration assay at a concentration of less than 1.1 mM. In some preferred embodiments, the disclosed treatment herein is effective to inhibit or reduce the rate of cell migration in greater than about 50%, 60%, 70%, 80%, or 90% of cells in an in vitro cell migration assay at a concentration of less than about 1.0 mM.

In some embodiments, any of the methods disclosed herein are free of administration of a cyclodextrin that scavenges cholesterol upon administration to a subject. In some embodiments, any of the methods disclosed herein are free of administration of a beta-cyclodextrin (β-CD, (βCD) or hydroxy-alkyl beta cyclodextrin.

The production of α-CDs is relatively simple and involves treatment of ordinary starch with a set of easily available enzymes. Commonly, cyclodextrin glycosyltransferase (CGTase) is employed along with α-amylase. First starch is liquefied either by heat treatment or using α-amylase, then CGTase is added for the enzymatic conversion. CGTases can synthesize all forms of cyclodextrins, thus the product of the conversion results in a mixture of the three main types of cyclic molecules, in ratios that are strictly dependent on the enzyme used: each CGTase has its own characteristic α:β:γ synthesis ratio. Purification of the three types of cyclodextrins takes advantage of the different water solubility of the molecules: β-CD, which is very poorly water-soluble (18.5 g/l or 16.3 mM) (at 25° C.) can be easily retrieved through crystallization while the more soluble α- and γ-CDs (145 and 232 g/l respectively) are usually purified by means of chromatography techniques. As an alternative a "complexing agent" can be added during the enzymatic conversion step: such agents (usually organic solvents like toluene, acetone or ethanol) form a complex with the desired cyclodextrin which subsequently precipitates. The complex formation drives the conversion of starch towards the synthesis of the precipitated cyclodextrin, thus enriching its content in the final mixture of products. Wacker Chemie AG uses dedicated enzymes, that can produce α-, β- or γ-cyclodextrin specifically. This is very valuable especially for the food industry, as only α- and γ-cyclodextrin can be consumed without a daily intake limit.

E) Pharmaceutical Compositions and Routes of Administration

In some embodiments, the present disclosure provides compositions comprising any one or more of the active agents described herein, either alone or in combination, for example for use in treating malignant, neurodegenerative, vascular, metabolic, inflammatory, autoimmune, pulmonary, fibrotic, hepatic, lysosomal storage, or viral disease, disorder, or condition. For example, in some embodiments, the present disclosure provides compositions comprising an α-CD, or an analogue or derivative thereof, for example for use in treating breast or prostate cancer. In some embodiments, the present disclosure provides compositions comprising an α-CD, or an analogue or derivative thereof, for example for use in treating breast or prostate cancer.

Pharmaceutical compositions provided by the present disclosure include compositions wherein the active ingredient (e.g., compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule (e.g., PIP1, PIP2, PIP3), and/or reducing, eliminating, or slowing the progression of disease symptoms (e.g. symptoms of malignant, neurodegenerative, vascular, metabolic, inflammatory, autoimmune, pulmonary, fibrotic, hepatic, lysosomal storage, or viral disease, disorder, or condition such as symptoms of Alzheimer's or Parkinson's disease). Determination of a therapeutically effective amount of a compound of the disclosure is well within the capabilities of those skilled in the art, especially in light of the detailed disclosure herein.

The pharmaceutical composition may be formulated by one having ordinary skill in the art with compositions selected depending upon the chosen mode of administration. Suitable pharmaceutical carriers are described in the most recent edition of Remington's Pharmaceutical Sciences, A. 0501, a standard reference text in this field.

Administering the pharmaceutical composition can be effected or performed using any of the various methods known to those skilled in the art. Systemic formulations include those designed for administration by injection, e. g. subcutaneous, intravenous, intramuscular, intrathecal or intraperitoneal injection, as well as those designed for transdermal, transmucosal, oral or pulmonary administration. In some embodiments, administration of the effective amount of pharmaceutical composition disclosed herein is not limited to any particular delivery system and includes, without limitation, parenteral (including subcutaneous, intravenous (via injection or infusion), intramedullary, intraarticular, intramuscular, or intraperitoneal injection), rectal, topical, transdermal, mucosal or oral (for example, in capsules, suspensions, or tablets) administration. In some embodiments, administration to a subject in need thereof occurs in a single dose or in repeat administrations, and in any of a variety of physiologically acceptable salt forms, or with an acceptable pharmaceutical carrier or additive as part of a pharmaceutical composition. In some embodiments, any suitable and physiological acceptable salt forms or standard pharmaceutical formulation techniques, dosages, and excipients are utilized. In some embodiments, the step of administering comprises administering the composition or pharmaceutical composition intravenously, intramuscularly, topically, intradermally, intramucosally, subcutaneously, sublingually, orally, intravaginally, intracavernously, intraocularly, intranasally, intrarectally, gastrointestinally, intraductally, intrathecally, subdurally, extradurally, intraventricular, intrapulmonary, into an abscess, intraarticularly, into a bursa, subpericardially, into an axilla, intrauterine, into the pleural space, intraperitoneally, transmucosally, or transdermally.

Pharmaceutical compositions of the invention may be administered by a variety of routes including oral, buccal, sublingual, rectal, transdermal, subcutaneous, intravenous injection, intravenous infusion, intramuscular, intrathecal, intraperitoneal and intranasal. Depending on whether intended route of delivery is oral or parenteral, the active agents can be formulated as compositions that are, for example, either injectable, topical or oral compositions. Liquid forms of compositions may include a suitable aqueous or nonaqueous vehicle with buffers, suspending and dispensing agents, colorants, flavors and other suitable ingredients known in the art. Solid forms of compositions may include, for example, binders, excipients, lubricants, coloring agents, flavoring agents and other suitable ingredients known in the art. The active agents and pharmaceutical compositions described herein may also be administered in sustained release forms or from sustained release drug delivery systems known in the art.

The pharmaceutical composition may depend on the disease or condition and on whether the administration is to prevent or to treat the disease or condition. For instance, administration for prevention of several diseases or conditions, including, but not limited to cancer, may be orally, without penetration enhancers, and at a lower dose. Administration for a subject showing symptoms of cancer, such as triple-negative node-positive breast cancer, the administration may be parenteral, regioselective, and at higher dose. Methods for targeting may include, but are not limited to combination with folate or antifolates (methotrexate, pemetrexed). Combination includes, but is not limited to esterification with or without linkers. In a preferred embodiment, the linker would be a disulfide linker (including, but not limited linkers comprising cystein, 3-mercaptopropionic acid, or 2-mercaptoethanol), linking to both the α-CD and pemetrexed via an ester. In another preferred embodiment, the α-CD/pemetrexed compound would be co-administered with folate. Administration to a subject showing symptoms of a neurodegenerative disease may be intrathecally without penetration enhancers and modifications for targeting.

In some embodiments the compositions of the present disclosure are pharmaceutical compositions comprising one or more active agents, as described herein, together with one or more conventionally employed components suitable for use in pharmaceutical delivery such as carriers, stabilizers, diluents, dispersing agents, suspending agents, thickening agents, excipients, and the like, may be placed into the form of pharmaceutical formulations. Nonlimiting examples of such formulations include solutions, creams, gels, gel emulsions, jellies, pastes, lotions, salves, sprays, ointments, powders, solid admixtures, aerosols, emulsions (e.g., water in oil or oil in water), gel aqueous solutions, aqueous solutions, suspensions, liniments, tinctures, and patches suitable for topical administration. The pharmaceutical compositions and formulations described herein may, where appropriate, be conveniently presented in discrete unit dosage forms and may be prepared by any of the methods well known in the art of pharmacy. Such methods include the step of bringing into association an active agent with liquid carriers, solid matrices, semi-solid carriers, finely divided solid carriers or combinations thereof, and then, if necessary, shaping the product into the desired delivery system. Unit dosage forms of a pharmaceutical composition or formulation preferably contain a predetermined quantity of active agent and other ingredients calculated to produce a desired therapeutic effect, such as an effective amount of a therapeutically effective amount. Typical unit dosage forms include, for example, prefilled, premeasured ampules or syringes of liquid compositions, or pills, tablets, capsules or the like for solid compositions.

For parenteral administration, the cyclodextrin or derivative thereof can be, for example, formulated as a solution, suspension, emulsion or lyophilized powder in association with a pharmaceutically acceptable parenteral vehicle or pharmaceutically acceptable carrier. Examples of such vehicles or carriers are water, saline, Ringer's solution, dextrose solution, 5% human serum albumin, Ringers dextrose, dextrose and sodium chloride, lactated Ringers and fixed oils, polyethylene glycol, polyvinyl pyrrolidone, lecithin (glycerophospholipids), arachis oil or sesame oil. Liposomes and nonaqueous vehicles such as fixed oils may also be used. The vehicle or lyophilized powder may contain additives that maintain isotonicity (e. g, sodium chloride, mannitol) and chemical stability (e.g., buffers and preservatives). The formulation is sterilized by commonly used techniques. Parenteral dosage forms may be prepared using water or another sterile carrier. For example, a parenteral composition suitable for administration by injection is prepared by dissolving 1.5% by weight of active ingredient in 0.9% sodium chloride solution. Alternatively, the solution can be lyophilized and then reconstituted with a suitable solvent just prior to administration.

Pharmaceutically acceptable carriers are well known to those skilled in the art and include, but are not limited to, from about 0.01 to about 0.1 M or about 0.05 M phosphate buffer or about 0.8% saline. Intravenous carriers include fluid and nutrient replenishers, electrolyte replenishers such as those based on Ringer's dextrose, and the like. Additionally, such pharmaceutically acceptable carriers can be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, ethanol, alcoholic/aqueous solutions, glycerol, emulsions or suspensions, including saline and buffered media.

The pharmaceutical compositions can be prepared using conventional pharmaceutical excipients and compounding techniques. Oral dosage forms may be elixirs, syrups, tablets, pills, dragees, capsules, liquids, gels, syrups, slurries, suspensions and the like, for oral ingestion by a patient to be treated. The typical solid carrier may be an inert substance such as lactose, starch, glucose, cellulose preparations such as maize starch, wheat starch, rice starch, potato starch, gelatin, gum tragacanth, methyl cellulose, hydroxypropyl-methyl-cellulose, sodium carboxymethylcellulose, and/or polyvinylpyrrolidone (PVP); granulating agents; binding agents, magnesium stearate, dicalcium phosphate, mannitol and the like. A composition in the form of a capsule can be prepared using routine encapsulation procedures. For example, pellets containing the active ingredient can be prepared using standard carrier and then filled into a hard gelatin capsule; alternatively, a dispersion or suspension can be prepared using any suitable pharmaceutical carrier(s), for example, aqueous gums, celluloses, silicates or oils and the dispersion or suspension then filled into a soft gelatin capsule. Typical liquid oral excipients include ethanol, glycerol, glycerin, non-aqueous solvent, for example, polyethylene glycol, oils, or water with a suspending agent, preservative, flavoring or coloring agent and the like. All excipients may be mixed as needed with disintegrants, diluents, lubricants, and the like using conventional techniques known to those skilled in the art of preparing dosage forms. If desired, disintegrating agents may be added, such as the crosslinked polyvinylpyrrolidone, agar, or alginic acid or a salt thereof such as sodium alginate. If desired, solid dosage forms may be sugarcoated or coated using standard techniques, including, but not limited to the use of chitosan, to target specific regions of the gastrointestinal tract. For oral liquid preparations such as, for example, suspensions, elixirs and solutions, suitable carriers, excipients or diluents include water, glycols, oils, alcohols, etc. Additionally, flavoring agents, preservatives, coloring agents and the like may be added.

For buccal administration, the compositions of the disclosure may take the form of tablets, lozenges, and the like formulated in conventional manner. The compounds may also be formulated in rectal or vaginal compositions such as suppositories or enemas. A typical suppository formulation comprises a binding and/or lubricating agent such as polymeric glycols, glycerides, gelatins or cocoa butter or other low melting vegetable or synthetic waxes or fats. For administration by inhalation, the compounds for use according to the present disclosure are conveniently delivered in the form of an aerosol spray from pressurized packs or a nebulizer, with the use of a suitable propellant, e. g., di- or trichlorofluoromethane, dichlorotetrafluoroethane, carbon dioxide or other suitable gases. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. Even the larger (3CD was seen to be suitable for inhalation. (Vecsernyes M, Fenyvesi F, et al. (2014) Arch Med Res 45:711-29)

The formulations may also be a depot preparation which can be administered by implantation (for example subcutaneously or intramuscularly) or by intramuscular injection. In such embodiments, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems may be employed. Liposomes and emulsions are well known examples of delivery vehicles that may be used. Certain organic solvents such as dimethylsulfoxide also may be employed, although usually at the cost of greater toxicity. Additionally, the compounds may be delivered using a sustained release system, such as semipermeable matrices of solid polymers containing the therapeutic agent. Various of sustained-release materials have been established and are well known by those skilled in the art. Sustained release capsules may, depending on their chemical nature, release the compounds for a few weeks up to over 100 days. Depending on the chemical nature and the biological stability of the therapeutic reagent, additional strategies for protein stabilization may be employed.

The compounds described herein may also be formulated for parenteral administration by bolus injection or continuous infusion and may be presented in unit dose form, for instance as ampoules, vials, small volume infusions or prefilled syringes, or in multi-dose containers with an added preservative.

Preservatives and other additives can also be present, such as, for example, antimicrobials, antioxidants, chelating agents, inert gases and the like. All carriers can be mixed as needed with disintegrants, diluents, granulating agents, lubricants, binders and the like using conventional techniques known in the art.

F) Dosages

The dose of an active agent described herein may be calculated based on studies in humans or other mammals carried out to determine efficacy and/or effective amounts of the active agent (see section E, Clinical Outcomes, below). The dose amount and frequency or timing of administration may be determined by methods known in the art and may depend on factors such as pharmaceutical form of the active agent and route of administration, and patient characteristics including age, body weight or the presence of any medical conditions affecting drug metabolism.

In one embodiment, a dose may be administered as a single dose. In another embodiment, a dose may be administered as multiple doses over a period of time, for example, at specified intervals, such as, daily, bi-weekly, weekly, monthly, and the like. In another embodiment, the dose will be 700 mg/kg/d (Table 3, 2010 April 15). In another embodiment, the dose will be increased over time until early signs of renal or cytotoxicity are observed, in which case the dose level will be decreased to the previous, well-tolerated level.

In some embodiments, the dose of active agent is about at least 10 mg, at least 20 mg, at least 30 mg, at least 40 mg, at least 50 mg, at least 75 mg, at least 100 mg, at least 125 mg, at least 150 mg, at least 175 mg, at least 200 mg, at least 225 mg, at least 250 mg, at least 275 mg, at least 300 mg, at least 325 mg, at least 350 mg, at least 375 mg, at least 400 mg, at least 425 mg, at least 450 mg, at least 475 mg, at least 500 mg, at least 550 mg, at least 600 mg, at least 650 mg, at least 700 mg, at least 750 mg, at least 800 mg, at least 850 mg, at least 900 mg, at least 950 mg, at least 1000 mg, at least 1200 mg, at least 1500 mg, at least 2000 mg, at least 2500 mg, at least 3000 mg, at least 4000 mg, at least 5000 mg, at least 7500 mg, at least 10,000 mg, at least 15,000 mg, at least 20,000 mg, or at least 25,000 mg. In some such embodiments the above dosages are mg/day or mg/kg/day.

In another embodiment, the dose of active agent is in the range of 1 to 10000 mg, 1 to 7500 mg, 1 to 5000 mg, 1 to 2500 mg, 1 to 1000 mg, 1 to 500 mg, 1 to 250 mg, 250 to 10000 mg, 250 to 5000 mg, 250 to 1000 mg, 250 to 500 mg, 500 to 10000 mg, 500 to 5000 mg, 500 to 1000 mg. In some embodiments, the above dosages are mg/day or mg/kg/day. In some embodiments, the dose of clathrate or α-cyclodextrin, derivative or salt thereof is from about 1 to about 20 grams per day. In some embodiments, the dose of clathrate or α-cyclodextrin, derivative or salt thereof is from about 10 to about 20 grams per day. In some embodiments, the dose of clathrate of or α-cyclodextrin, derivative or salt thereof is about 15 grams per day. In some embodiments, the dose of clathrate of or α-cyclodextrin, derivative or salt thereof is about 15 grams per day. In some embodiments, the dose of clathrate of or α-cyclodextrin, derivative or salt thereof is about 20 grams per day. In some embodiments, the dose of clathrate of or α-cyclodextrin, derivative or salt thereof is about 25 grams per day. In some embodiments, the dose of clathrate of or α-cyclodextrin, derivative or salt thereof is about 30 grams per day. In some embodiments, the dose of clathrate of or α-cyclodextrin, derivative or salt thereof is about 35 grams per day. In some embodiments, the dose of clathrate of or α-cyclodextrin, derivative or salt thereof is about 40 grams per day. In some embodiments, the dose of clathrate of or α-cyclodextrin, derivative or salt thereof is about 45 grams per day. In some embodiments, the dose of clathrate of or α-cyclodextrin, derivative or salt thereof is about 50 grams per day. In some embodiments, the dose of clathrate of or α-cyclodextrin, derivative or salt thereof is about 55 grams per day. In some embodiments, the dose of clathrate of or α-cyclodextrin, derivative or salt thereof is about 10 grams per day. In some embodiments, the dose of clathrate of or α-cyclodextrin, derivative or salt thereof is about 15 grams per day. In some embodiments, the dose of clathrate or α-cyclodextrin, derivative or salt thereof is about 60 grams per day. In some embodiments, the dose is about 5 grams three times per day.

In some embodiments, a single dose may be administered. In another embodiment, multiple doses may be administered over a period of time, for example, at specified intervals, such as, four times per day, three times a day, twice per day, once a day, weekly, monthly, 4 times over 14 days, 2 times over 21 days, twice per month, 4 times over 21 days, 4 times per month, or 5, 6, 7, 8, 9, 10, 11, 12 or more times per month, per 21 days, per 14 days, or per week, and the like.

In one embodiment, the doses administered intravenously or intrathecally may be 5600 mg/kg per week or 400 mg per week (Table 3).

TABLE 3

Hempel twins dose adjustment

| Date | Description |
|---|---|
| 2004 Januray | Birth |
| 2008 Aug. 14 | confirmed diagnosis of NPC |
| 2009 Feb. 22 | HP-β-CD treatment plan |
| | Initial infusion: 4 d continuous i.v. of 80 mg/kg/d at a rate of 20 ml/h |
| | Next: Weekly 8 h infusions starting at 160 mg/kg/d + add'l weekly infusions |
| | Next: 320 mg/kg/d |
| | Next: 400 mg/kg/d |
| 2009 Apr. 13 | Approval of i.v. infusion (INDs 104,114 and 104,116) |
| 2009 Jul. 7 | Protocol extension |
| | 400 mg/kg/d administered as a weekly 8 h infusion |
| 2009 Jul. 16 | Increased dosing frequency (twice/week) and rate of dose titration (100 mg/kg/infusion) |
| | Week 1: 500 mg/kg/d; 8 h x1 + 3-4 d 600 mg/kg/d; 8 h x1 |
| | Week 2: 700 mg/kg/d; 8 h x1 + 3-4 d 800 mg/kg/d; 8 h x1 |

TABLE 3-continued

Hempel twins dose adjustment

| Date | Description |
|---|---|
| | Week 3: 900 mg/kg/d; 8 h x1 + 3-4 d 1000 mg/kg/d; 8 h x1 |
| | Initial infusion: 500 mg/kg/d over 8 h at a rate of 20 ml/h |
| 2009 Oct. 8 | Pulmonary clinic visit |
| | 2800 mg/kg twice weekly over 8 h (800 mg/kg/d) |
| 2010 Mar. 7 | "HPβCD Raises Hearing Threshold in . . . Cats." (Ward S, O'Donnell P, et al. (2010) Pediatr Res 68: 52-6) |
| 2010 Apr. 15 | Hearing unaffected despite receiving steady state IV doses of 2.5 g/kg bi-weekly for >1 yr (5 g/kg/wk ≈ 700 mg/kg/d) |
| 2010 May 17 | Orphan-drug designation granted |
| 2010 Aug. 13 | Request for intrathecal delivery filed |
| | 200 mg HP-β-CD intrathecal biweekly (≈60 mg/kg/d) |
| | (Maarup T J, Chen A H, et al. (2015) Mol Genet Metab 116: 75-9) |

From Hastings C (2009 Feb. 22) Addi and Cassi Hydroxy-Propyl-Beta-Cyclodextrin Plan. Compassionate Use Clinical Study. Treatment Plan Version #2, http://addiandcassi.com/wordpress/wp-content/uploads/2009/09/FDA-Submission-for-Addi-and-Cassi-Cyclodextrin-Treatment-Plan.pdf
NPC: http://www.nnpdf.org/cyclodextrin.html G) Subjects The methods and compositions described herein may be used to treat or prevent malignant, neurodegenerative, vascular, metabolic, inflammatory, autoimmune, pulmonary, fibrotic, hepatic, lysosomal storage, or viral disease, disorder, or condition, in any subject in need of such treatment. In one embodiment, the subject is a human. It should be noted that, while in some embodiments the subjects to be treated are post-menopausal women, in other embodiments the methods of treatment described herein are not intended to be limited to such subjects. Rather, in some embodiments the subjects can be of any age, ranging from newborns to older adults. In some embodiments it may be desirable to treat young subjects, for example young infants, particularly where family history or genetic testing indicates that the subject is at risk for developing malignant, neurodegenerative, vascular, metabolic, inflammatory, autoimmune, pulmonary, fibrotic, hepatic, lysosomal storage, or viral disease, disorder, or condition. Similarly, in some embodiments it may be desirable to treat much older subjects, particularly where such subjects begin to exhibit indicators or symptoms of malignant, neurodegenerative, vascular, metabolic, inflammatory, autoimmune, pulmonary, fibrotic, hepatic, lysosomal storage, or viral disease, disorder, or condition.

The methods and compositions described herein may be employed as prophylactic treatments or therapeutic treatments. For prophylactic treatments, the methods and compositions provided herein can be used preventatively in subjects that do not yet exhibit any clear or detectable clinical indicators or symptoms of malignant, neurodegenerative, vascular, metabolic, inflammatory, autoimmune, pulmonary, fibrotic, hepatic, lysosomal storage, or viral disease, disorder, or condition but that are believed to be at risk of developing malignant, neurodegenerative, vascular, metabolic, inflammatory, autoimmune, pulmonary, fibrotic, hepatic, lysosomal storage, or viral disease, disorder, or condition, such as MS, prostate cancer or breast cancer, or diseases that are characterized by dysfunctional lysosomes. A subject receiving prophylactic treatment for t-CD, for example, may not exhibit any clinical indicators or symptoms of MS, prostate cancer or breast cancer, or diseases that are characterized by dysfunctional lysosomes. In the case of therapeutic treatments, the methods and compositions provided herein can be used in subjects that already exhibit one or more clinical indicators or symptoms of the disease or disorder, such as MS, prostate cancer or breast cancer, or diseases that are characterized by dysfunctional lysosomes. A subject receiving therapeutic treatment for MS, prostate cancer or breast cancer, or diseases that are characterized by dysfunctional lysosomes, for example, may have been clinically diagnosed with MS, prostate cancer or breast cancer, or diseases that are characterized by dysfunctional lysosomes or may otherwise exhibit one or more clinical indicators or symptoms of MS, prostate cancer or breast cancer, or diseases that are characterized by dysfunctional lysosomes. In some embodiments, the disclosure relates to methods of treating cancers comprising cells that are deficient or substantially deficient in any of the genes identified in the Figures or specification, such that the limited expression or lack of expression of those genes results in lysosomal dysfunction.

In one embodiment, a subject may have been identified as being at risk of developing malignant, neurodegenerative, vascular, metabolic, inflammatory, autoimmune, pulmonary, fibrotic, hepatic, lysosomal storage, or viral disease, disorder, or condition. In one embodiment, the subject has a family history of malignant, neurodegenerative, vascular, metabolic, inflammatory, autoimmune, pulmonary, fibrotic, hepatic, lysosomal storage, or viral disease, disorder, or condition. In one embodiment, the subject has one or more genetic risk factors associated with malignant, neurodegenerative, vascular, metabolic, inflammatory, autoimmune, pulmonary, fibrotic, hepatic, lysosomal storage, or viral disease, disorder, or condition, for example, a genetic mutation in a gene associated with PI cycle function.

H) Clinical Outcomes

In some embodiments the methods of treatment provided herein (which comprise, for example, administering to a subject an effective amount of a composition according to the present disclosure) result in, or are aimed to achieve, a detectable improvement in one or more clinical indicators or symptoms of the age-related diseases.

In the context of cancer, for instance, the clinical indicators or symptoms include, but not limited to, changes growth, migration, or invasion. In some embodiment of the present disclosure a symptom or indicator of improvement is selected from the group comprising survival, disease-free survival, distant metastasis-free survival, results of a blood test (including, but not limited to circulating tumor DNA, prostate-specific antigen, β-galactosidase/β-hexosaminidase (Tiribuzi R, Orlacchio A, et al. (2011) J Alzheimers Dis 24:785-97), and lysozyme and/or cathepsin S (Haldar K, Alam S (2017))), an x-ray evaluation, the result of a physical examination (including, but not limited to a palpable tumor), or a tissue biopsy for histological evaluation.

To determine the highest tolerated dose in an individual complete blood count and serum chemistry will be collected and analyzed. The serum chemistries may include, but will not be limited to evaluation of electrolytes, bicarbonate, glucose, BUN, creatinine, magnesium, phosphate, hepatic enzymes (AST and ALT), total protein, albumin, bilirubin, and alkaline phosphatase. In addition, a complete lipid panel may be obtained and shape of erythrocytes may be evaluated microscopically. Bone density may be measured to identify early signs of osteoporosis.

The compositions and methods described herein are illustrative only and not intended to be limiting. Those of skill in the art will appreciate that various combinations or modifications of the specific compositions and methods described above can be made, and all such combinations and modifications of the compositions and methods described herein may be used in carrying out the present disclosure. Furthermore, certain embodiments of the present disclosure are further described in the following non-limiting Examples, and also in the following Claims.

All publications, including patent applications and journal articles are incorporated by reference in their entireties.

EXAMPLES

Example 1: The PI-Cycle is a Drug Target Against Metastases in Breast Cancer

The methods used to obtain the results presented in Example 1 are further described in (Wittkowski K M (2014) US 2016/0206581 A1), which is hereby incorporated by reference in its entirety.

Almost a decade after the completion of the Human Genome Project, the scientific and medical advances hoped for from genome-wide association studies (GWAS) have not yet been realized. Enlarging the sample size to tens of thousands of subjects greatly increases the duration and cost of data collection and, in a nonrandomized study, may somewhat paradoxically increase the risk of false positives. This Example describes combining a novel computational biostatistics approach with decision strategies fine-tuned to the exploratory nature of GWAS. With these methodological advances, disease-relevant functional gene clusters can now be suggested from studies of a few hundred narrowly defined cases only.

Although a history of familial breast cancer being a known risk factor of either breast and prostate cancer attests to a high degree of heritability, the genetic risk factors for breast and prostate cancer in the general population are still poorly understood. A single-SNP GWAS (ssGWAS) of breast cancer including data from 250,000 women did not result in a testable hypothesis. (Michailidou K, Lindstrom S, et al. (2017) Nature 551:92-4) As described herein, data from three independent sub-populations of this study (available from NIH's dbGaP) were analyzed using u-statistics for genetically structured wide-locus data (muGWAS) to explore epistasis. To account for systematic, but disease-unrelated differences in (non-randomized) GWAS and for conducting multiple tests in overlapping genetic regions, a novel study-specific criterion for 'adaptive genome-wide significance' (aGWS) was applied (Wittkowski K M, Sonakya V, et al. (2014) Transl Psychiatry 4:e354). Enrichment of the results in all three studies with genes associated with influx of phospholipids into the PI cycle and lysosome function confirms the hypothesis that an imbalance between high levels of endocytoses and age-dependent decline of lysosome function is involved in driving metastases in breast cancer.

Subjects

The study was approved as appropriate. No human participants were involved in the research. The results described herein are based on three studies of breast cancer in the US and Europe. These studies included data from the Cancer Genetic Markers of Susceptibility (CGEM) breast cancer GWAS which included 1145 cases/1142 controls (Hunter D J, Kraft P, et al. (2007) Nature Genet 39:870-4) (dbGaP: phs000147.v3.p1), and from two sub-studies of the nested case-control and one case-control study of estrogen receptor negative (ER$^-$) breast cancer within the Breast and Prostate Cancer Cohort Consortium, both included in (Garcia-Closas M, Couch F J, et al. (2013) Nat Genet 45:392-8, 8e1-2): the European Prospective Investigation into Cancer (EPIC) of 511 ER$^-$ cases and 500 controls, and the Polish Breast Cancer Case-Control Study (PBCS) of 543 ER$^-$ cases (229 triple-negative) and 511 controls. (dbGaP: phs000812.v1.p1)

Methods ssGWAS: After eliminating non-informative or low-quality SNPs, a traditional ssGWAS was performed, using u-statistics for univariate data (also known as the Mann-Whitney test (Mann H B, Whitney D R (1947) Ann Math Stat 18:50-60) which is equivalent to the Wilcoxon rank-sum test (Wilcoxon F (1954) Biometrics 1:80-3)). By construction, the results of this analysis are very close to those obtained with the traditional Cochran-Armitage trend test. (Armitage P (1955) Biometrics 11:375-86)

Annotation: The annotation files available have proven to be inadequate to appropriately distinguish between genes (or splice variants of genes) that are too far away or close enough to be likely related to a SNP or region being implicated. On the other hand, diplotypes may span linkage-disequilibrium (LD) blocks outside of genes or their regulatory regions, in which case it is unlikely that the functional implication of the variation can be identified. Also, there may not be sufficient information avail-able to determine the function of a gene, in which case the funding would not be useful for identifying collections of functionally related genes. Hence, the results returned from the grid/cloud infrastructure, still need to be manually reviewed to resolve ambiguities regarding the annotation.

Wide-locus approach. To overcome several of the shortcomings seen in previous applications of ssGWAS when applied to common diseases, several strategies were combined at different stages of the analysis process. Wide-loci of up-to six neighboring SNPs were aimed at as a primary outcome and the same non-parametric GWAS approach was applied based on u-statistics for structured multivariate data (Hoeffding W (1948) Ann Math Stat 19:293-325) with genotypic structures (muGWAS) as in the previous childhood absence epilepsy (Wittkowski K M, Sonakya V, et al. (2013) Pharmacogenomics 14:391-401) and autism (Wittkowski K M, Sonakya V, et al. (2014) Transl Psychiatry 4:e354) studies. To avoid spurious findings, loci outside of LD blocks containing genes with known function or adjacent to their 5'-end were excluded. Loci highly influenced by a single SNP only were also excluded, unless this SNP was implicated in more than one of the studiers or had been implicated in previous studies.

Information Content: In contrast to traditional regression methods, muGWAS provides an intrinsic measure of "information content", which can be used to highlight regions with high significance, but low information content as likely artifacts. In the Manhattan plot, below, highly significant results with low information content are highlighted in red and excluded (crossed out in white), unless there is other supportive evidence, such as a nearby SNP that had previously been reported as associated with breast cancer or another cancer. Some regions with low information content are dominated by a single SNP or involve diplotypes spanning LD blocks without being within a gene or its regulatory region. Diplotypes may also be excluded if moving the window by one SNPs results in a large (more than 100-fold) change in significance. Of note, these manual interventions cannot cause false positive results and current research aims at formalizing more of these rules to facilitate interpretation and avoid false negative results.

MAF-significance correlation: With any finite sample size, the significance of a u- or rank test is limited. Hence, more significant results can only be obtained for SNPs with sufficiently high MAF. ssGWAS simulations were performed with 2,500,000 permuted phenotypes, comparing two groups of equal size for various MAFs. The $1\text{-}10^{-5}$ quantile of the permutation distribution drops from the expected $s=-\log_{10} p=5.26$ cut-off, which is routinely met for MAF>0.33, to 4.9 (n=1000 subjects), 4.7 (n=500), and 4.5 (n=300) for a MAF of 0.05. For the 7.5 level, the bias is projected to be even larger. Due to this MAF-significance correlation, the expected diagonal in a ssGWAS QQ plot under the null hypothesis that "no SNP is associated with the trait" (Pearson T A, Manolio T A (2008) JAMA 299:1335-44) turns into an expected curve dropping below the diagonal towards the end. (Wittkowski K M, Sonakya V, et al. (2014) Transl Psychiatry 4:e354)

Estimating the expected s-value ($-\log_{10}(p)$) distribution from $>10^8$ permutations to obtain stable estimates of the $1\text{-}10^{-7.5}$ quantile is neither practical, nor sufficient to avoid a biased selection of SNPs for limited tests. Due to the MAF-significance correlation, any SNP 'significant' when comparing observed phenotypes, is also more likely to be 'significant' with random phenotype permutations. (Wittkowski K M, Sonakya V, et al. (2014) Transl Psychiatry 4:e354)

Non-randomization bias: The reason for this curvature often not being recognized is that GWAS subjects are deterministically categorized based on their outcome (e.g., non-verbal v. verbal), rather than randomly assigned to interventions (as in clinical trials). Any deterministically categorized populations, however, are expected to differ systematically in aspects related to neither the condition of interest nor common ancestry factors (which could potentially be accounted for through stratification). When the downward trend from using a limited test and the upward bias from deterministic selection are similar, the s-values may still appear to follow the diagonal, except for loci suggesting 'true association' (Pearson T A, Manolio T A (2008) JAMA 299:1335-44)

Multiplicity adjustments for diplotype length: For multivariate tests of overlapping diplotypes, the estimated quantile-rank (QR) curve needs to be elevated above the diagonal throughout to account for multiple tests conducted around the same SNP. Because most of these tests are highly dependent, the elevation of the estimated QR curve compared to the estimated QQ curve (FIG. 6-FIG. 11) is limited, but the distance is likely to vary across diseases and populations. (Wittkowski K M, Sonakya V, et al. (2014) Transl Psychiatry 4:e354)

Projected QR curves: The diagonal of the traditional QQ-plot does not depend on any data, including the most 'significant' data. The s-values are expected to fit the diagonal for the most part (except for the most significant results), (Pearson T A, Manolio T A (2008) JAMA 299:1335-44) as the vast majority of SNPs are expected not to be associated with the disease. In direct analogy, the QR curve for a multivariate test should be 'smooth', with upward deviations indicating 'true association', which could be disease-related or not. Based on the above rationale and the simulation results mentioned above, the highest point of the projected QR curve (apex) for each chromosome can be estimated from a smooth projection of the s-values after truncating as many of the highest values as needed for the projection to have a monotone increase and, conservatively for a limited test, a non-positive second derivative. Fitting against the data also reduces the effect of population stratification (Pearson T A, Manolio T A (2008) JAMA 299:1335-44). (For computational convenience, locally weighted polynomial regression (Cleveland W S, Devlin S J (1988) J Am Statist Assoc 83:596-610) was selected, as implemented in S+(TIBCO Software Inc.) as 'loess. smooth( . . . degree=2, family="gaussian"))

Estimated whole genome QR apex: While chromosomes may differ with respect to their content of related and unrelated risk factors (see, e.g., the HLA region in autoimmune diseases), random errors are expected to have the same distribution across all chromosomes. Hence, the expected WG apex can be estimated as the (winsorized) median projected apex among chromosomes with the smallest deviation of s-values from the projection. (Here, ten chromosomes were selected based on the maximum norm, and the median for robustness, but the strategy to determine the optimal number, including the criteria for 'optimality', remains to be determined.) (Wittkowski K M, Sonakya V, et al. (2014) Transl Psychiatry 4:e354)

Estimated QR curves: The estimated curve for each chromosome is then calculated as the loess projection (Cleveland W S, Devlin S J (1988) J Am Statist Assoc 83:596-610) of this chromosome's s-values with as many of the highest values replaced with the estimated WG apex until the curve's apex is at or below that level. Applied to the WG projection (QR plots, bottom right), this procedure yields the estimated WG curve. Simulation results demonstrate the low variance of the estimates from phenotype permutations and the similarity of their median apex with the winsorized median apex estimated from the observed s-values. (Wittkowski K M, Sonakya V, et al. (2014) Transl Psychiatry 4:e354)

Study-specific genome-wide significance: For studies aiming to confirm individual SNPs as associated with a phenotype, the 'confirmatory' paradigm (Tukey J W (1980) American Statistician 34:23-5) requires adjustment for multiplicity. When applied to GWAS, these adjustments are typically based on a 'customary' fixed 0.05 level, irrespective of study size or relative risk of type I over type II errors (see (Fisher R A (1956), p. 358) and (Gigerenzer G (2004) Psychol Sci 15:286-7) for a discussion), and the assumption of 1,000,000 independent SNPs, irrespective of chip density (Pearson T A, Manolio T A (2008) JAMA 299:1335-44). Moving from individual SNPs to overlapping diplotypes increases the dependency of any formal multiplicity adjustment on assumptions with questionable biological validity. (Wittkowski K M, Sonakya V, et al. (2014) Transl Psychiatry 4:e354)

As in most GWAS, however, the studies described in this Example do not aim to confirm hypotheses regarding specific SNPs. Instead, the studies described here aim at picking likely candidates from >40,000 (pseudo-) genes, whose relative importance and epistatic interactions are unknown.

Since graphical procedures are particularly useful for such 'exploratory' studies (Tukey J W (1977)), QR plots were chosen to guide with interpretation. Exact cut-offs for deviation of s-values from the estimated curve are unknown. When "the knowledge [is] at best approximate[,] an approximate answer to the right question, which is often vague, [is far better] than an exact answer to the wrong question, which can always be made precise" (Tukey J W (1962) Ann Math Stat 33:1-67). Hence, a heuristic approach is presented that relies on fewer unrealistic assumptions than typical attempts to quantify a particular error rate. (Wittkowski K M, Sonakya V, et al. (2014) Transl Psychiatry 4:e354)

The expected WG curve needs to be estimated, the s-values have a complex dependency structure, and the appropriate level of significance ($\alpha$) for the given sample size is unknown. Hence, a heuristic decision rule is proposed based on weak assumptions only. In the long run one would expect most s-values above the apex to be significant at any $\alpha>0$ (consistency) and regions with the strongest association to have the highest odds at being included (unbiasedness). For a particular $\alpha$, one could lower the cut-off, but to account for variance in estimating the apex, one would need to raise it. As a compromise, the estimated WG apex is proposed as a cut-off for study-specific GWS. (Wittkowski K M, Sonakya V, et al. (2014) Transl Psychiatry 4:e354)

Figure 6:
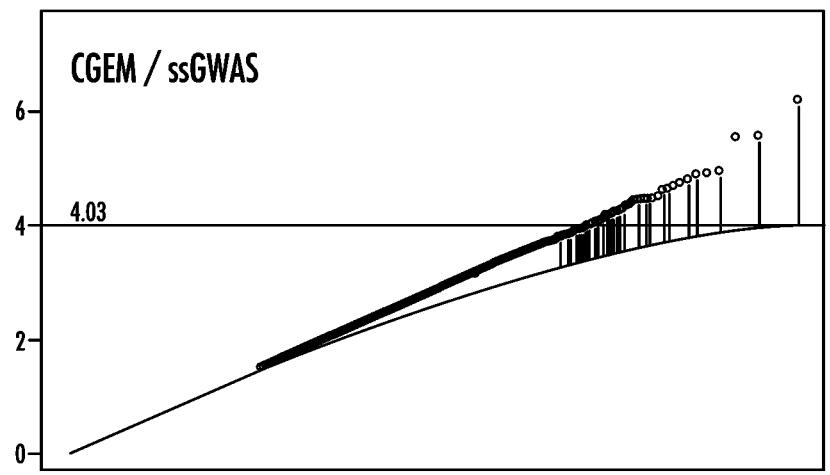
FIG. 6: QR-Plot of ssGWAS results for CGEM. The "null" projection (horizontal) ends at the median among the endpoints of the convex projections for individual chromosomes. Genes to the right of the vertical line are above the cut-off for study-specific genome-wide significance. Regions below (to the left) of the cut-off are given for descriptive purposes only.
Figure 7:
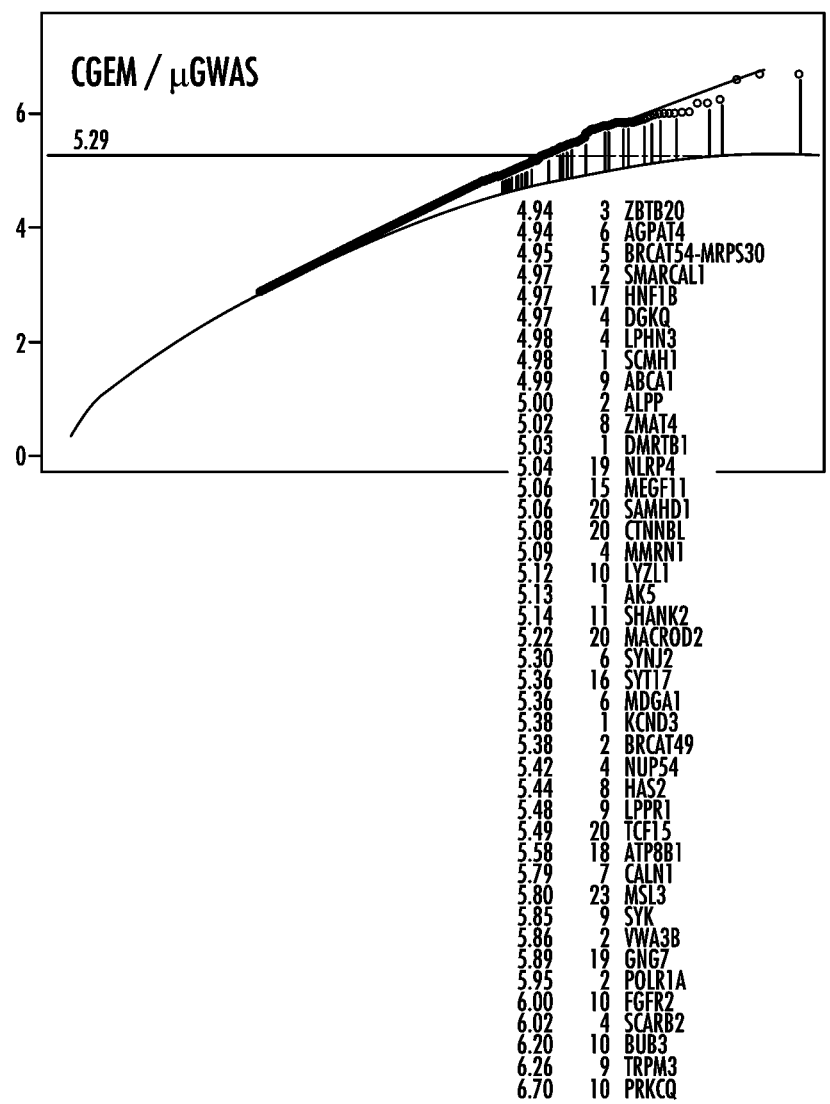
FIG. 7 QR-Plot of muGWAS results for CGEM. (see FIG. 6 for legend)
Figure 8:
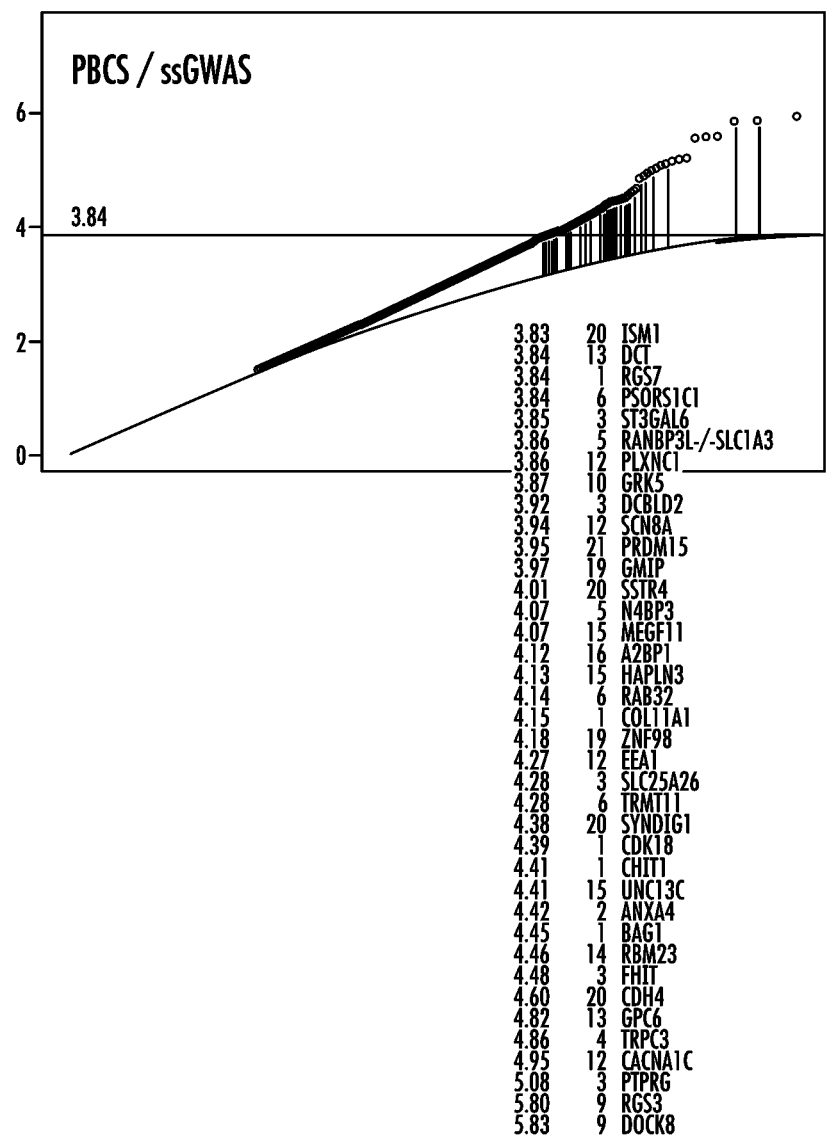
FIG. 8 QR-Plot of ssGWAS results for EPIC. (see FIG. 6 for legend)
Figure 9:
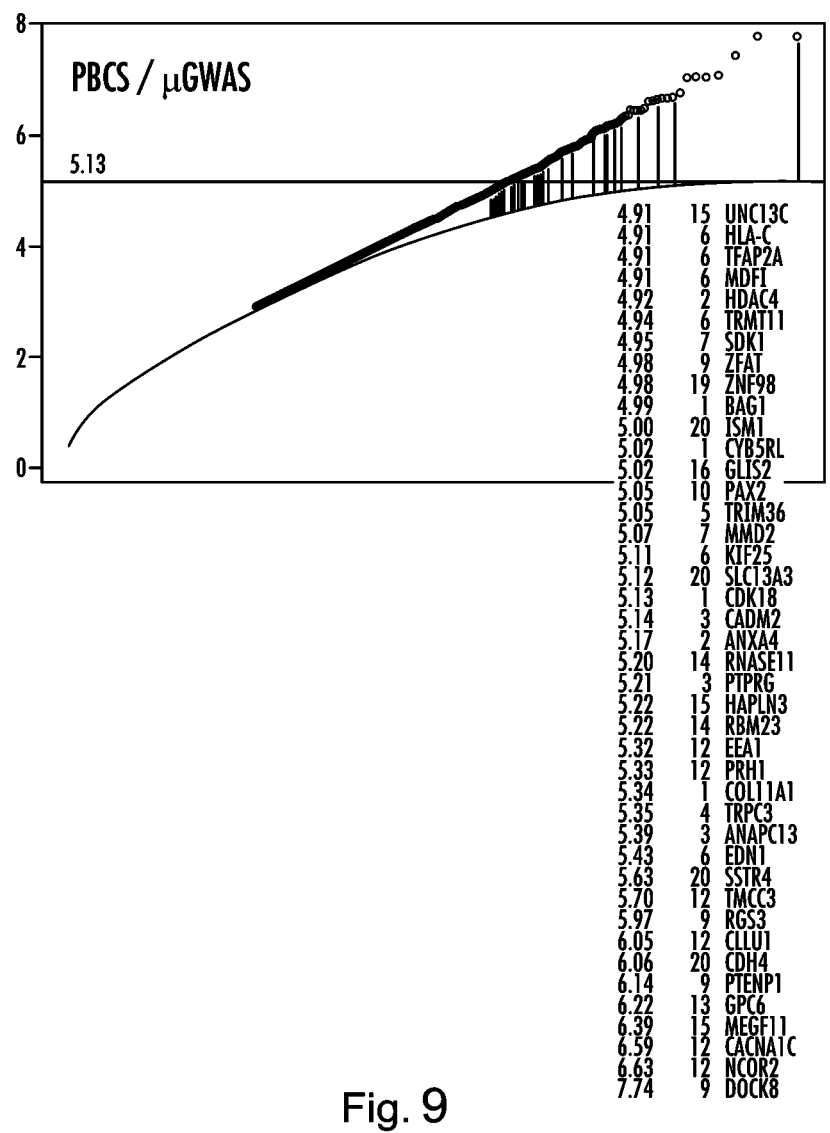
FIG. 9 QR-Plot of muGWAS results for EPIC. (see FIG. 6 for legend)
Figure 10:
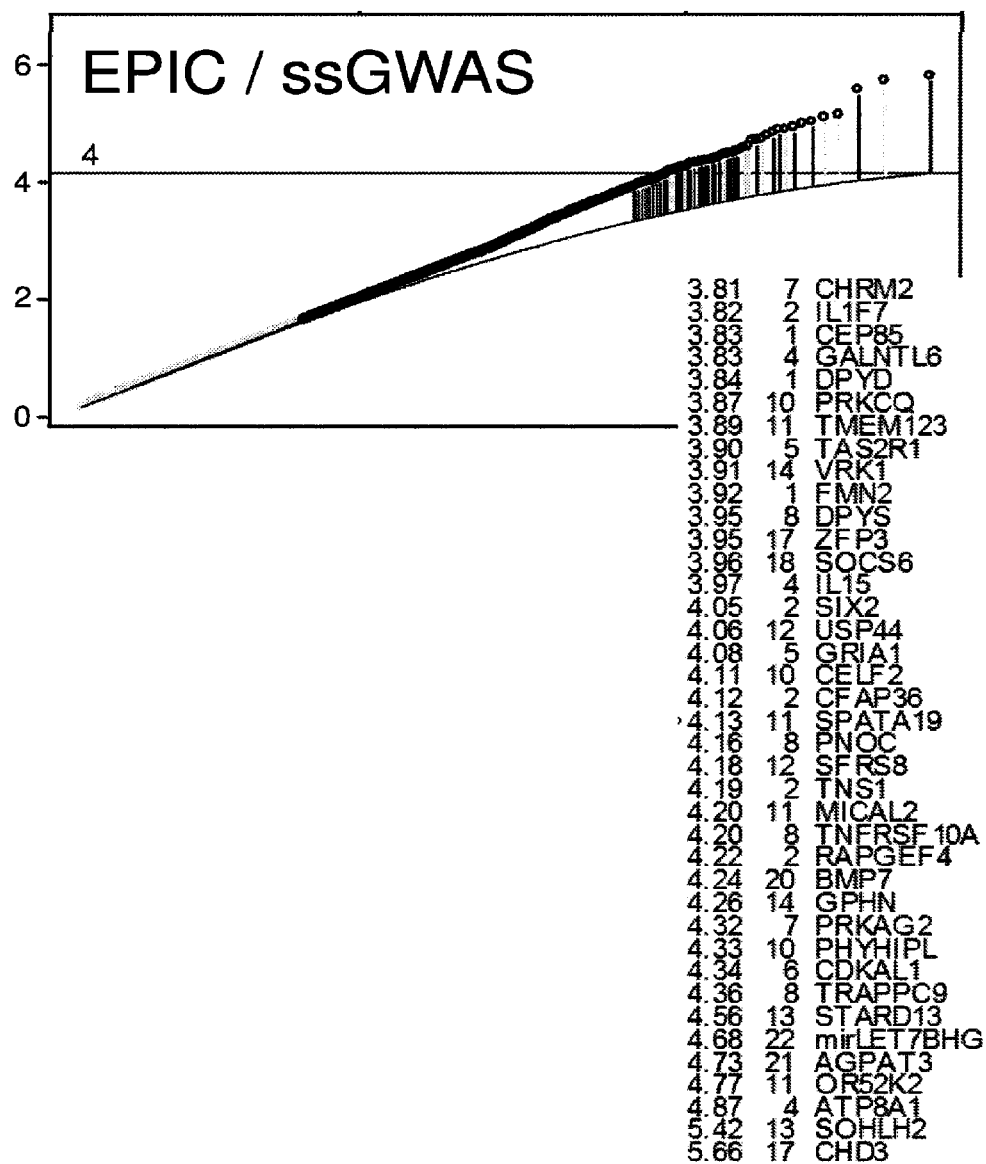
FIG. 10 QR-Plot of ssGWAS results for PBCS. (see FIG. 6 for legend)
Figure 11:
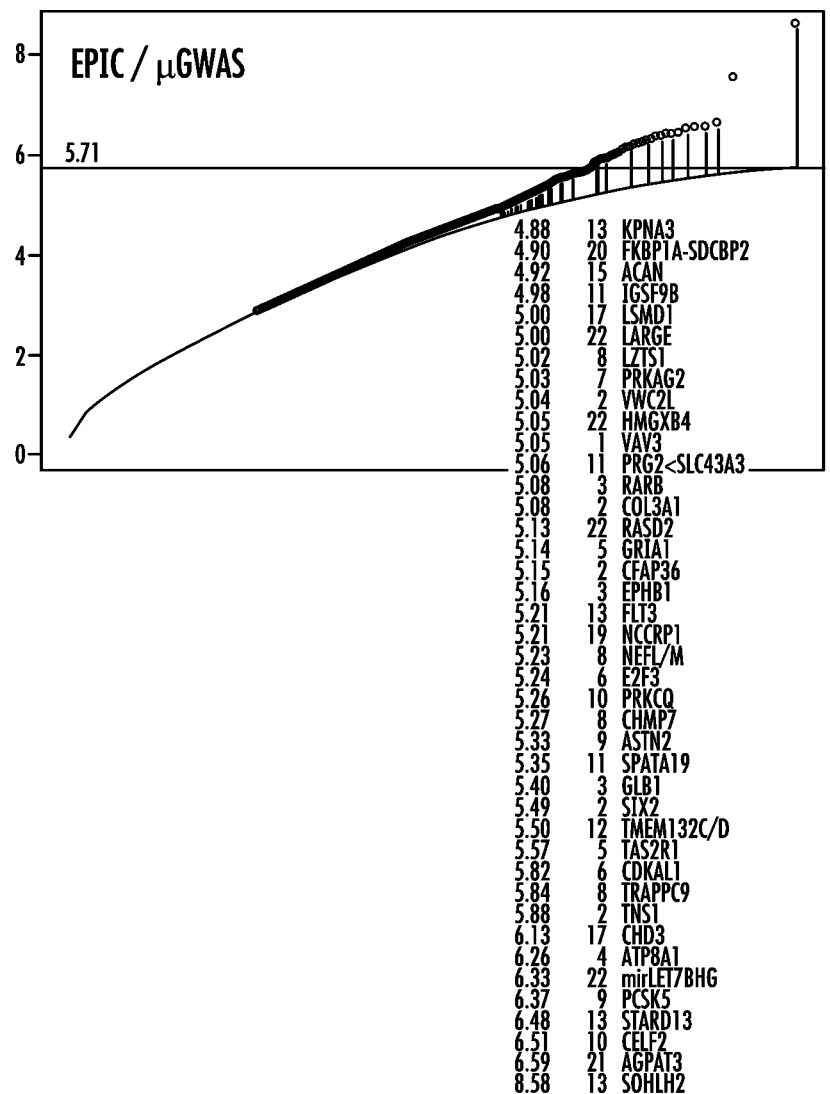
FIG. 11 QR-Plot of muGWAS results for PBCS. (see FIG. 6 for legend)

Quantile-rank (QR) plots: As is customary with selection procedures, p-values were used mainly for the purpose of ranking loci. As no particular hypotheses regarding specific loci were to be confirmed, the traditional approach of exploring characteristics of the 'QQ plot' as decision criteria was modified and formalized. For multivariate tests of overlapping diplotypes, the straight line expected in the traditional 'QQ plot' under the univariate WG permutation hypothesis turns into a curve because many tests are performed per SNP. Even though the number of tests performed increases substantially, the increase in s-values shown in the QR curve compared to the QQ line (FIG. 7 v. FIG. 6, FIG. 9 v. FIG. 8, FIG. 11 v. FIG. 10) is limited, because most tests are highly dependent. (Wittkowski K M, Sonakya V, et al. (2014) Transl Psychiatry 4:e354)

Whole-genome permutation bias: To estimate the expected distribution of s-values, one could average the results of repeated runs with random phenotype permutations. As each GWAS analysis may require >100,000 hours on a grid/cloud with GPU enabled nodes, however, simulations requiring >108 replications to estimates the $1-10^{-7.5}$ quantile may not be feasible. The estimate from WG permutations (including computationally efficient approximations) is affected by biases due to subjects being categorized based on their outcome (e.g., non-verbal v. verbal), rather than randomly assigned to interventions (as in clinical trials), so that the groups are expected to differ systematically in aspects related to neither the condition of interest nor common ancestry factors. With binary outcomes, significant results can also not be caused by a few 'outliers' only, so that significance is correlated with high MAF (ssGWAS) or low skewness of the scores (µGWAS). Hence, regions with significant allelotype differences between observed phenotypes have also a larger chance to be significant among random phenotype permutations. (Wittkowski K M, Sonakya V, et al. (2014) Transl Psychiatry 4:e354)

Selective chromosome permutation: The proposed use of a selected chromosome permutation approach reduces this bias. While chromosomes may differ with respect to their content of disease related and unrelated risk factors, random errors are expected to have the same distribution across all chromosomes. Hence, the above biases are reduced by excluding chromosomes containing regions of high significance when determining the permutation distribution. In particular, the endpoint of the expected distribution for each chromosome can be estimated from the loess projection to the p-values after truncation to ensure a monotone increase and a non-positive second derivative. Similarly, the endpoint of the expected distribution is estimated from the median of the limited set of, e.g., ten, chromosomes with the lowest maximum deviation of the distribution of s-values from the loess projection. (Wittkowski K M, Sonakya V, et al. (2014) Transl Psychiatry 4:e354)

Formal QR cut-off for deviation: The estimate of the expected distribution for each chromosome is then calculated as the loess fit of the individual chromosomes' data with a sufficient number of results at the high end replaced with the expected endpoint until the curve is curtailed to that level, unless the initial loess fit already remains below this target level. The same procedure, when applied to the WG data, yields the estimation of the WG distribution. Simulation results demonstrate the low variance of the estimates based on random permutations of the phenotypes and that their median is closely resembled by the estimate of the distribution obtained from the observed data. (Wittkowski K M, Sonakya V, et al. (2014) Transl Psychiatry 4:e354)

Results

Previously known results from CGEM: Traditionally, GWAS have often identified only a small number of SNPs per study. A previous ssGWAS analysis of the CGEMS data (Hunter D J, Kraft P, et al. (2007) Nature Genet 39:870-4) had implicated two loci in trend analysis:

| | | | | | |
|---|---|---|---|---|---|
| chr10: | 124,992,475 | rs10510126: | 6.15 | BUB3, | (long EST not5 identified) |
| chr10: | 123336180 | rs1219648: | 5.49 | FGFR2 | |
| | 123341314 | rs2420946 | 5.46 | FGFR2 | | ssGWAS results: Single-SNP GWAS confirmed these findings at essentially equivalent levels of 6.20 and 5.57, respectively. Many other results had been dismissed in previous published analyses because p-values did not reach the traditional level of "fixed genome-wide significance" (typically, 7.5). From the ssGWAS QR plots (CGEM: FIG. 6, EPIC: FIG. 8, and PBCS: FIG. 10) many of the genes above the cut-off for study-specific genome-wide significance fit the paradigm of being involved in signaling at the membrane (GPCRs, Fc receptors, growth factor receptors, ion channels) or processes in the nucleus (cell cycle control, transcription, splicing) (see Table 4, columns Mbrn and Ncls).

muGWAS results: In muGWAS (CGEM: FIG. 7, EPIC: FIG. 9, and PBCS: FIG. 11), the proportion of genes related to membrane signaling and nuclear processes is even higher than in ssGWAS. In addition, a group of genes known to play a role in either in the PI cycle (FIG. 12) or in endocytosis (FIG. 8A) stands out.

Table 4: Genes identified by Study. Study; IPV6/IPV1: −log 10(p-value) in muGWAS/ssGWAS; Mbrn: membrane-associated genes (GPCR, Fc-Receptor, HA, RTK, Ion channels), PI/EC: PI signaling/endocytosis, MPK: MAP kinases, Ncls: nucleus (cell cycle control, transcription, splicing). Top block of rows within each study: genes with diplotypes above aGWS in muGWAS (CGEM: 5.29, FIG. 7; EPIC: 5.71, FIG. 9; PBCS: 5.13, FIG. 11); center block of rows within each study: other genes with diplotypes among the top 41 in muGWAS; bottom block of rows within each study: genes with SNPs above the study-specific level of genome-wide significance in ssGWAS (CGEM: 4.03, FIG. 6; EPIC: 4.00, FIG. 8; PBCS: 3.84, FIG. 10); ssGWAS results for genes also implicated in muGWAS are shown next to the muGWAS results); black squares: known breast cancer genes (from http://www.genecards.org); Boxed gene names indicate replication of the same gene (bold, PRKCQ, MEGF11) or replication of a closely related gene belonging to the same family (ATP8A1/ATP8B1, AGPAT3/AGPAT4, BMP7/BMPR1B). (See FIG. 49A through 49C).

Validation (same intragenic region): PRKCQ (chr 10), was significant by muGWAS in CGEM (mu: 6.70, ss: 3.47, "indicating study-specific genome-wide significance) and by ssGWAS in EPIC (mu: 5.26, ss: 3.87*). The same region (chr10:6,540,724-6,573,883) was implicated in both populations. In PBCS, in contrast, there was no association in this region (<2.00), consistent with the notion of different risk factors for breast cancer in different populations.

Validation (same gene): MEGF11 was implicated in both CGEM and PBCS. MEGF11 was even elevated (3.31) in EPIC. A single SNP was highly influential in either population, but it was not the same SNP (CGEM: rs189155, PBCS: rs12903880, EPIC: rs333554). All three SNPs are located in the coding region, but they are not in LD. One other SNP in MEGF11 (rs1477798) has been implicated in colorectal cancer. (Cicek M S, Cunningham J M, et al. (2012) PLoS One 7:e38175)

Validation (similar function): In a complex disease, populations may differ with respect to the risk factors that are present in each population. In particular, the proportion of risk conferred by different genes with similar function may differ and, even if the same gene is involved, risk may be associated with different SNPs.

In ssGWAS, only one pair of functionally related genes stands out (Table 4):
BMPR1B (CGEM)—BMP7 (EPIC)

Among muGWAS results (Table 4), there are three more pairs of functionally related genes:
ATP8B1 (CGEM)—ATP8A1 (EPIC)
MEGF11 (CGEM, PBCS)
AGPAT4 (CGEM)—AGPAT3 (EPIC)

Mutations in PI3K, PTEN, and SYNJ2 are known to be associated with breast cancer.

The mechanism commonly believed to be involved is the dysregulation of the AKT/TSC/mTOR growth pathway downstream of $PI(3,4,5)P_3$ and $PI(3,4)P_2$. The results of this analysis point to three additional points where the PI cycle is involved (FIG. 12):
1. PI(4,5)P2 (SCARB2, UNC13C, STXBP1, SDCBP2, MEGF11, SYT17, N4BP3, VAV3) and
2. PI(3)P (NLRP4, EEA1, RAB32), as well as
3. overall activation of PI (ATP8A1, ATP8B1, SLC5A3, AGPAT3, AGPAT4, ANXA4)

With the exception of CHMP7, RAPGEF4, and EEA1, all these genes have previously been shown to be associated with breast cancer (http://www.genecards.org).

The novel finding is that breast cancer risk is conferred not only by a variety of variations in
genes involved in nuclear processes causing susceptibility for cancer and
genes involved in membrane processes providing growth signals,
as well as a few specific variations connecting the two by increasing
$PI(3,4,5)P_3$(loss-of-function in PTEN, gain-of-function in PI3K),
$PI(3,4)P_2$(gain-of-function in SYNJ1/2 or INPPL1), or
PI(3)P(gain-of-function in INPP4B),
but by a global dysregulation of the PI cycle, including
entry of phosphatidylinositol (PI) (involving AGPAT3, AGPAT4, and SLC5A3), and
entry of phosphatidylserine/phosphatidylcholine (PS/PC) (involving ATP8A1, ATP8B1, and ANXA4),
and endocytosis as a critical component of migration and invasion. Endocytosis is known to be controlled by PI signaling, which is consistent with the genes identified in the results presented:
at the plasma membrane stage (PM, eight genes),
at the early endosome stage (EE, four genes), and
at the late endosome stage (LE, two genes).

In some embodiments, the subject has a disease or disorder that is characterized by a dysfunctional lysosomal pathway by deficient expression of any one or combination of genes disclosed above.

DISCUSSION

The approach used here differs from traditional GWAS in both the statistical method being used and the decision strategy. To address the statistical method challenges specific to GWAS, the novel approach (a) avoids making assumptions about a particular degree of dominance, (b) draws for the fact that both SNPs neighboring a disease locus should be in LD, unless they are separated by a recombination hotspot, (c) can distinguish between SNPs belonging to the same tag sets, but differ in their order along the chromosome, (d) accounts for different disease loci within the same region having similar effects and for compound heterozygosity within the statistical method (rather than through visual inspection looking for several SNPs within a region having high significance), and (e) provides additional information ("information content") that can be used to prioritize results.

The use of a decision rule that accounts for (a) GWAS being non-randomized, (b) the aim being selecting sets of genes, knowing that some must have an effect, rather than testing the hypothesis that no gene has an effect, at all, (c) accounting for differences in MAF in estimating the expected distribution of p-values, and (d) adjusts for tests in overlapping diplotypes being related.

The validation of GWAS in childhood absence epilepsy (Wittkowski K M, Sonakya V, et al. (2013) Pharmacogenomics 14:391-401) demonstrated the ability of GWAS to identify genes modulating a known disease pathway, where traditional ssGWAS had identified a single SNP (in a pseudo-gene) only. The subsequent application to mutism in autism (Wittkowski K M, Sonakya V, et al. (2014) Transl Psychiatry 4:e354) confirmed the ability of GWAS to identify clusters of genes related to the same biological function in two independent populations.

By using this novel decision rule alone with traditional single-SNP GWAS, the number of "significant" genes rises from none to >20 in each of the three studies considered here. The set of genes seen in ssGWAS using the novel decision rules includes half of the genes associated with the novel PIP cycling pathway. The novel non-parametric wide-locus approach then adds the other half of the genes involved in regulation and function of the PI cycle.

The PI cycle is critical for many cellular functions in eukaryotic cells, including developmental functions such as oocyte maturation, fertilization, embryogenesis, but also cell growth, cytoskeleton dynamics, membrane trafficking, and nuclear events. (Shulga Y V, Myers D S, et al. (2010) Biochemistry 49:312-7; Busa W B (1988) Philos Trans R Soc Lond B Biol Sci 320:415-26) Hence, it is not surprising that the PI cycle is tightly controlled. In particular, PI(4.5) P2, PI(4)P, PI(3,4)P2, and PI(3)P are tightly regulated by both three kinases and three groups of phosphatases. (Waugh M G (2015) Biochim Biophys Acta 1851:1066-82) Different subsets of phosphatases (FIG. 12, boxes) are counteracting the effects of the kinases, further reducing the impact any variation in a particular phosphatase might have on the system as a whole. Hence, a specific intervention modifying the state of this tightly regulated system might not suffice to achieve a sustained effect.

That "both PtdIns(3,4,5)$P_3$ and PtdIns(3,4)$P_2$ are likely required for a cell to achieve and sustain a malignant state", has been formulated as the "two PIP hypothesis" (Kerr W G (2011) Ann N Y Acad Sci 1217:1-17) The results presented here suggest not only that PI(3)P is required, but shift in focus further toward to the PI cycle as a whole. This new focus has direct implications for the development of drugs.

The model of a linear (PI-PIP1-PIP2-PIP3) PI system suggested inhibition of PI3K as a strategy to reduce activity along the AKT/TSC/mTOR growth pathway. Only a small proportion of patients, however, benefit from interrupting this linear pathway by blocking PI3K. (Bosch A, Li Z, et al. (2015) Sci Transl Med 7:283ra51-ra51) The limited success of wortmannin and other inhibitors of PI3K is consistent with the ability of the PI cycle to compensate not only for natural, but also for pharmaceutical disturbance at a particular point.

High levels of PI(3,4,5)P3, PI(3,4)P2, and PI(3)P all are known to correlate with a negative outcome of cancers. "Altered abundance of phosphatidylinositides (PIPs) is a feature of cancer. Various PIPs mark the identity of diverse membranes in normal and malignant cells." (Sengelaub C A, Navrazhina K, et al. (2015) The EMBO Journal) The model of a PI cycle tightly regulated around the PI(4,5)P2-PI(4)P-PI(3,4)$P_2$-PI(3)P pathway suggests overall downregulation of PI cycle activity as a more successful strategy to correct for excessive activation involving the PI cycle than blocking individual or pairs of kinases or phosphatases.

Neither breast nor prostate cancer per se are lethal; it is metastases spreading to other organs that cause cancer-related death. As seen in treatments involving cytotoxic drugs, reducing cell growth, in general, often causes side-effects (nausea, loss-of-hair, . . . ), without necessarily reducing the risk of metastases, because growth and metastasis may be regulated by different pathways.

Figure 14:
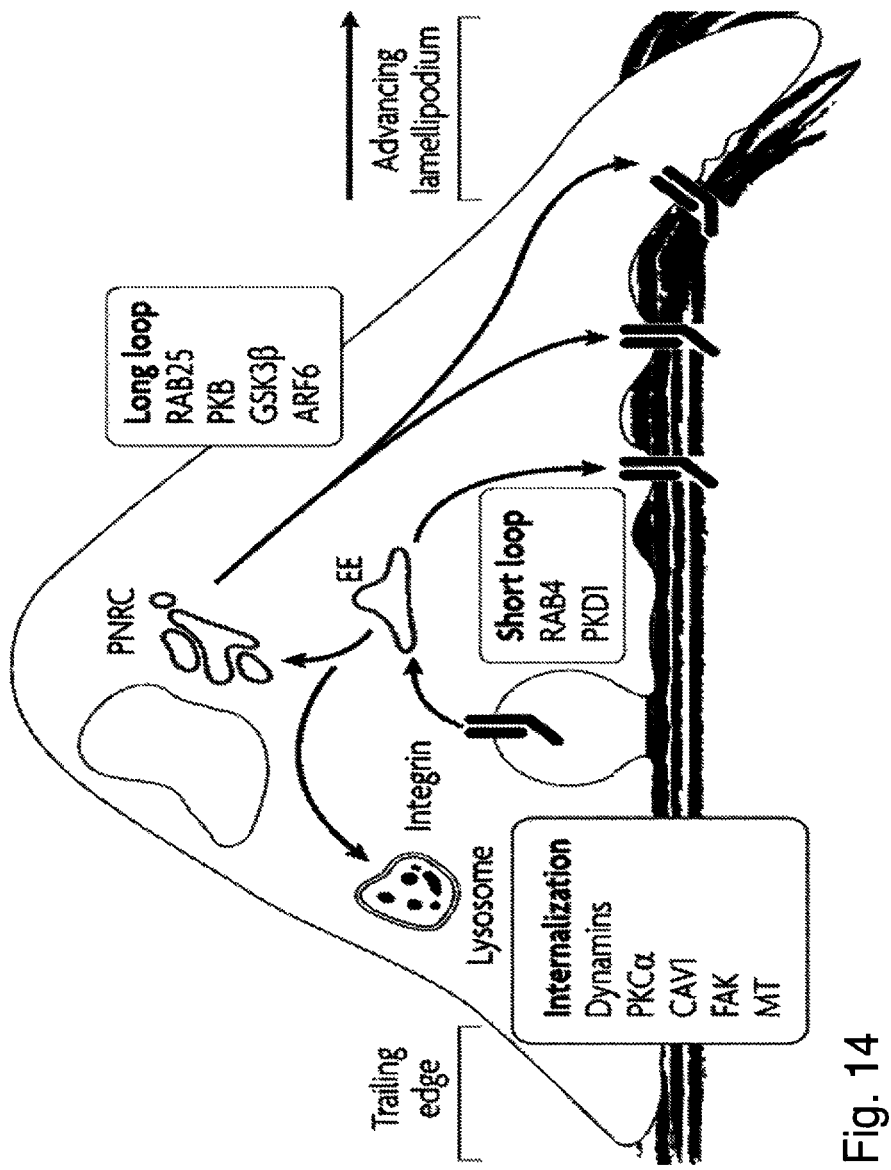
FIG. 14: Endocytic mechanisms underlying tumor cell migration and invasion through tissue barriers. The diagram presents a motile cell, the advancing lamellipodium of which moves directionally (arrow). Focal adhesions (FAs) are schematically shown, and integrin heterodimers are present at these. Cell migration necessitates polarized endocytosis and trafficking of FA complexes. Integrin internalization is controlled by dynamin, which is activated by microtubules (not shown), and protein kinases, such as FAK and protein kinase Cα (PKCα). Both clathrin- and caveolin 1 (CAV1)-coated domains of the plasma membrane are involved in internalization of integrin. Once in early endosome (EE), integrins are sorted for degradation in lysosomes (LYs), recycled to the plasma membrane through a RAB4-dependent route, or transported to the perinuclear recycling compartment (PNRC). Recycling from the PNRC requires Rab11 family members, such as RAB25, and for some integrin heterodimers, also the protein kinase B (PKB)—GSK3β (glycogen synthase kinase-β) axis, ARF6 or certain isoforms of PKC. Human tumors often aberrantly express RAB25, display a specific repertoire of growth factor-induced integrin heterodimers or present abnormally stabilized microtubules, which promote trafficking of integrins. FAK, Integrin, RAB25, and PKB have functions associated with oncogenesis and/or display aberrant expression in human tumors (modified from Mosesson Y, Mills G B, et al. (2008) Nat Rev Cancer 8:835-50).

To metastasize, tumor cells "must develop motile and invasive phenotypes", which is known to required endocytosis for cell migration. (Mellman I, Yarden Y (2013) Cold Spring Harbor Perspectives in Biology 5) As "defective vesicular trafficking of growth factor receptors, as well as unbalanced recycling of integrin- and cadherin-based adhesion complexes, has emerged in the past 5 years as a multifaceted hallmark" of cancer, correcting for "derailed endocytosis" has been suggested as a strategy to prevent cancer metastases. (Mosesson Y, Mills G B, et al. (2008) Nat Rev Cancer 8:835-50) "Activation of signal transduction pathways associated with endocytic trafficking (FIG. 14) is critical for tumor cell migration. Hence, selectively targeting endocytic trafficking and signaling could potentially allow for the development of novel cancer therapeutics to prevent metastasis." (Chew C L, Chen M, et al. (2016) Oncotarget 7:5-6).

Example 2: The Genetic Risk Factors in the PI Cycle and Along the Endocytosis Pathway are Known as Shared Risk Factors for "Derailed Endocytosis" in Breast Cancer and "Defective/Deranged Endocytosis" Parkinson's Disease/Alzheimer's Disease Alzheimer's disease and Parkinson's disease are known to share risk factors: Aβ and α-synuclein have been hypothesized to interact, (Crews L, Tsigelny I, et al. (2009) Neurotox Res 16:306-17; Tsigelny I F, Crews L, et al. (2008) PLoS One 3:e3135) and "moderate association" of AD with PD was found in a meta analysis of 14 studies conducted 1986-2010, (Feldman A L, Johansson A L, et al. (2014) Neuroepidemiology 42:69-80) but a meta-analysis of single-SNP summary statistics from two sets of AD and PD GWAS, each imputed to 7,815K SNPs, "resulted in no significant evidence [for SNP] loci that increase the risk of both PD and AD". (Moskvina V, Harold D, et al. (2013) JAMA Neurology 70:1268-76) Recently, having disease with Lewy bodies (DLB) diagnosed as either Parkinson's disease or Alzheimer's disease was identified as a potential confounder in these studies (Guerreiro R, Escott-Price V, et al. (2016) Neurobiol Aging 38:214 e7-10; Bras J, Guerreiro R, et al. (2014a) Hum Mol Genet 23:6139-46) and the above results suggest that lack of "significant evidence" above may have been because of ssGWAS having lower power than muGWAS for cis-epistatic effects.

Overlapping epidemiology and etiology of breast cancer and Alzheimer's disease/Parkinson's disease: breast cancer has high co-occurrence with Parkinson's disease. (Disse M, Reich H, et al. (2016) Dermatol Surg 42:141-6) Earlier reports that cancers reduce Alzheimer's disease risk were linked to statistical models not accounting for competing risks (Hanson H A, Horn K P, et al. (2016) J Gerontol B Psychol Sci Soc Sci) and/or treatment effects of cancer drugs. (Malkki H (2016) Nat Rev Neurol 12:126-) Another reason for limited association between breast cancer and Alzheimer's disease may be that mutations may have opposite effects, such as gain-of-function in breast cancer (and Parkinson's disease) and loss-of-function in Alzheimer's disease. Overlapping genetic risk factor have already been reported. Mutations in the Parkinson's disease gene PSEN2 were also found in breast cancer and Parkinson's disease. (Cai R, Hao Z, et al. (2015) Bioinformatics 31:1701-7) Mutations in MAPT, which encodes the Parkinson's disease microtubule-associated protein tau, were found in breast cancer (Rouzier R, Rajan R, et al. (2005) Proc Natl Acad Sci USA 102:8315-20) and Parkinson's disease; (Lopez Gonzalez I, Garcia-Esparcia P, et al. (2016) Int J Mol Sci 17:206) DJ-1 was seen as elevated, (Kawate T, Iwaya K, et al. (2015) Cancer Sci 106:938-43) and the $G_{2019}S$ mutation in endosomal LRRK2 (Rivero-Rios P, Gomez-Suaga P, et al. (2015) Biochem Soc Trans 43:390-5) increases risk. (Agalliu I, San Luciano M, et al. (2015) JAMA Neurol 72:58-65) Still, "the etiology of this link continues to be elusive". (Disse M, Reich H, et al. (2016) Dermatol Surg 42:141-6)

Overlap of genetic risk factors for breast cancer (above and published results) and Alzheimer's disease/Parkinson's disease (published results): The vast majority of genes related to the PI cycle and EEC genes identified in muGWAS of breast cancer (Table 4, column PI/EC) had already been identified in previous functional studies and gene expression studies of both breast cancer and Alzheimer's disease/Parkinson's disease (Table 5 and Table 6).

TABLE 5

PI-Cycle overlap between Breast Cancer, PD, and AD. Gene: Genes identified in breast cancer GWAS. EEC function: Known function in PI-cycle and/or EEC. KEGG: KEGG pathway (http://www.genome.jp/kegg/pathway.html), EC: epithelial cancer (carinoma). ND: Neurodegenerative disease.

| Gene | PI-Cycle | KEGG | EC | ND | References |
|---|---|---|---|---|---|
| ATP8A1 ATP8B1 | Decreasing extracellular PE and PS enhances endocytosis, LY, migration | | | | (Farge E, Ojcius DM, et al. (1999) Am J Physiol 276: C725-33; Levano K, Sobocki T, et al. (2009) Glycoconj J 26: 739-48; Levano K, Punia V, et al. (2012) J Neurochem 120: 302-13; Andersen JP, Vestergaard AL, et al. (2016) Front Physiol 7: 275) |
| | | | BC | | (da Costa A, Lenze D, et al. (2012) J Comp Pathol 146: 143-51; Sjöblom T, Jones S, et al. (2006) Science 314: 268-74) |
| | | | PC | | (Lee BH, Taylor MG, et al. (2013) Cancer Res 73: 1211-8; Sekine Y, Demosky SJ, et al. (2010) Mol Cancer Res 8: 1284-94; Transion SE, Kim YS, et al. (2009) Mol Cancer Ther 8: 1934-45) |
| | | | | PD | (Levano K, Punia V, et al. (2012) J Neurochem 120: 302-13) ATP8A2: (Zhu X, Libby RT, et al. (2012) PLOS Genetics 8: e1002853) |
| | | | | AD | (Soderberg M, Edlund C, et al. (1992) J Neurochem 59: 1646-53) ATP8B4: (Li H, Wetten S, et al. (2008) Arch Neurol 65: 45-53) (Picollo A, Malvezzi M, et al. (2015) J Mol Biol 427: 94-105) |
| ANO4 | Ca + dep. PL scramblase | | SC | | (Weber GF (2015) Sarcoma 2015: 839182) |
| | | | | AD | (Sherva R, Tripodis Y, et al. (2014) Alzheimers Demenet 10: 45-52) |
| ABCA1 | Regulates cellular lipid efflux; interacts with MEGF10 | hsa02010 | | | (Hamon Y, Trompier D, et al. (2006) PLoS One 1: e120) |
| | | | BC | | (Zhao W, Prijic S, et al. (2016) Cancer Res 76: 2037-49; Schimanski S, Wild PJ, et al. (2010) Horm Metab Res 42: 102-9) |
| | | | PC | | (Lee BH, Taylor MG, et al. (2013) Cancer Res 73: 1211-8; Sekine Y, Demosky SJ, et al. (2010) Mol Cancer Res 8: 1284-94) |
| | | | | PD | (Dong Y, Gou Y, et al. (2015) Elife 4; Pinho R, Guedes LC, et al. (2016) PLoS One 11: e0157852; Dong X, Liu T, et al. (2016) Genes & Genomics 38: 243-50; Loane DJ, Washington PM, et al. (2011) J Neurotrauma 28: 225-36) |
| | | | | AD | (Koldamova R, Fitz NF, et al. (2014) Neurobiol Dis 72 Pt A: 13-21; Pahnke J, Langer O, et al. (2014) Neurobiol Dis 72 Pt A: 54-60; Boehm-Cagan A, Bar R, et al. (2016) PLoS One 11: e0166195; Nordestgaard LT, Tybjaerg-Hansen A, et al. (2015) Alzheimers & Dementia 11: 1430-8) |
| | | | | HD | (Valenza M, Marullo M, et al. (2015) Cell Death Differ 22: 690-702) |
| AGPAT3 AGPAT4 | converts lyso-PI (LPI) into phosphatidylinositol (PI) | hsa00564 | | | (Bradley RM, Marvyn PM, et al. (2015) Biochimica et Biophysica Acta (BBA) - Molecular and Cell Biology of Lipids 1851: 1566-76) |
| | | | BC | | (Sahay D, Leblanc R, et al. (2015) Oncotarget 6: 20604-20; Hopkins MM, Zhang Z, et al. (2016) J Clin Med 5) |
| | | | PC | | AGPAT6: (Gatto F, Miess H, et al. (2015) Sci Rep 5: 10738) |
| | | | | PD | (Chenge D, Jenner AM, et al. (2011) PLoS One 6: e17299) |
| | | | | AD | (Sherva R, Baldwin CT, et al. (2011) J Alzheimers Dis 23: 349-59) |
| DGKQ | Regenerates PA from diacylglycerol (DAG) | hsa00564, hsa04070 | | | (Sakane F, Kanoh H (1997) Int J Biochem Cell Biol 29: 1139-43) |
| | | | BC | | (Filigheddu N, Cutrupi S, et al. (2007) Anticancer Res 27: 1489-92) |
| | | | PC | | AGK: (Bektas M, Payne SG, et al. (2005) J Cell Biol 169: 801-11) |
| | | | | PD | (Lill CM, Roehr JT, et al. (2012) PLoS Genet 8: e1002548; Nalls MA, Pankratz N, et al. (2014) Nat Genet 46: 989-93) |
| | | | | AD | (Zhu XC, Cao L, et al. (2016) Mol Neurobiol) |
| LPPR1 | complexes with LPPR3/4/5, regulates PIS (CDIPT) | | | | LPPR4: (Yu P, Agbaegbu C, et al. (2015) Journal of Cell Science 128: 3210-22) |
| | | | | PD | (Moran LB, Duke DC, et al. (2006) Neurogenetics 7: 1-11) |

TABLE 5-continued

| | | | | |
|---|---|---|---|---|
| SYNJ2 | is recruited to the nascent clathrin coated pit | hsa04070 | BC<br>PC<br>PD<br>AD | (Schmid SL, Mettlen M (2013) Nature 499: 161-2)<br>(Ben-Chetrit N, Chetrit D, et al. (2015) Sci Signal 8: ra7)<br>(Rossi MR, Hawthorn L, et al. (2005) Cancer Genet Cytogenet 161: 97-103)<br>SYNJ1 = PARK20<br>SYNJ1: (Cao J, Gaamouch FE, et al. (2017) Sci Rep 7: 11372)<br>(Koran ME, Hohman TJ, et al. (2014) J Alzheimers Dis 38: 145-54) |
| PTENP1 | PI3K/PTEN and PI(3, 4, 5)P3 are involved in endocytosis/cancer | hsa04070 | BC<br>PC<br>PD<br>AD<br>HD | PTEN: (Erneux C, Ghosh S, et al. (2016) Curr Pharm Des 22: 2309-14)<br>(Zhang H-Y, Liang F, et al. (2013) Oncology Letters 6: 161-8)<br>(Pourmand G, Ziaee AA, et al. (2007) Urology journal 4: 95-100)<br>PINK1: (Choubey V, Cagalinec M, et al. (2014) Autophagy 10: 1105-19)<br>(Frere S, Slutsky I (2016) Nat Neurosci 19: 416-8)<br>PINK1: (Khalil B, El Fissi N, et al. (2015) Cell Death Dis 6: e1617) |

Sequences for Table 5a Genes.

| Name | Entrez | Acession | | |
|---|---|---|---|---|
| ATP8A1 | 10396 | AF067820 | | (SEQ ID NO: 1) |

```
  1 mptmrrtvse irsraegyek tddvsektsl adqeevrtif inqpqltkfc nnhvstakyn
 61 iitflprfly sqfrraansf flfiallqqi pdvsptgryt tlvpllfila vaaikeiied
121 ikrhkadnav nkkqtqvlrn gaweivhwek vavgeivkvt ngehlpadli slsssepqam
181 cyietsnldg etnlkirqgl patsdikdvd slmrisgrie cespnrhlyd fvgnirldgh
241 gtvplgadqi llrgaqlrnt qwvhgivvyt ghdtklmqns tspplklsnv eritnvqili
301 lfciliamsl vcsvgsaiwn rrhsgkdwyl nlnyggasnf glnfltfiil fnnlipisll
361 vtlevvkftq ayfinwdldm hyeptdtaam artsnlneel gqvkyifsdk tgtltcnvmq
421 fkkctiagva vghvpepedy gcspdewqns qfgdektfsd ssllenlqnn hptapiicef
481 ltmmavchta vperegdkii yqaaspdega lvraakqlnf vftgrtpdsv iidslgqeer
541 yellnvleft sarkrmsviv rtpsgklrly ckgadtviyd rlaetskyke itlkhleqfa
601 teglrtlcfa vaeisesdfq ewravyqras tsvqnrllkl eesyeliekn lqllgataie
661 dklqdqvpet ietlmkadik iwiltgdkqe tainighsck llkknmgmiv inegsldgtr
721 etlsrhcttl gdalrkendf aliidgktlk yaltfgvrqy fldlalscka viccrvsplq
781 ksevvemvkk qvkvvtlaig dgandvsmiq tahvgvgisg neglqaanss dysiaqfkyl
841 knllmihgaw nynrvskcil ycfyknivly iieiwfafvn gfsgqilfer wciglynvmf
901 tamppltlgi ferscrkenm lkypelykts qnaldfntkv fwvhclnglf hsvilfwfpl
961 kalqygtafg ngktsdylll gnfvytfvvi tvclkaglet sywtwfshia iwgsialwvv
1021 ffgiysslwp aipmapdmsg eaamlfssgv fwmgllfipv asllldvvyk vikrtafktl
1081 vdevqeleak sqdpgavvlg kslteraqll knvfkknhvn lyrseslqqn llhgyafsqd
1141 engivsqsev iraydttkqr pdew
```

| ATP8B1 | 5205 | AF038007 | | (SEQ ID NO: 2) |
|---|---|---|---|---|

```
  1 msterdsett fdedsqpnde vvpysddete delddqgsav epeqnrvnre aeenrepfrk
 61 ectwqvkand rkyheqphfm ntkflcikes kyannaikty kynaftfipm nlfeqfkraa
121 nlyflallil qavpqistla wyttlvpllv vlgvtaikdl vddvarhkmd keinnrtcev
181 ikdgrfkvak wkeiqvgdvi rlkkndfvpa dilllsssep nslcyvetae ldgetnlkfk
241 msleitdqyl qredtlatfd gfieceepnn rldkftgtlf wrntsfplda dkillrgcvi
301 rntdfchglv ifagadtkim knsgktrfkr tkidylmnym vytifvvlil lsaglaigha
```

TABLE 5-continued

```
 361 yweaqvgnss wylydgeddt psyrgflifw gyiivlntmv pislyvsvev irlgqshfin
 421 wdlqmyyaek dtpakarttt lneqlgqihy ifsdktgtlt qnimtfkkcc ingqiygdhr
 481 dasqhnhnki eqvdfswnty adgklafydh ylieqiqsgk epevrqfffl lavchtvmvd
 541 rtdgqlnyqa aspdegalvn aarnfgfafl artqntitis elgtertynv laildfnsdr
 601 krmsiivrtp egniklyckg adtviyerlh rmnptkqetq daldifanet lrtlclcyke
 661 ieekeftewn kkfmaasvas tnrdealdkv yeeiekdlil lgataiedkl qdgvpetisk
 721 lakadikiwv ltgdkketae nigfacellt edtticyged insllharme nqrnrggvya
 781 kfappvqesf fppggnrali itgswlneil lekktkrnki lklkfprtee errmrtqskr
 841 rleakkeqrq knfvdlacec saviccrvtp kqkamvvdlv krykkaitla igdgandvnm
 901 iktahigvgi sgqegmqavm ssdysfaqfr ylqrlllvhg rwsyirmckf lryffyknfa
 961 ftlvhfwysf fngysaqtay edwfitlynv lytslpvllm glldqdvsdk lslrfpglyi
1021 vgqrdllfny krffvsllhg vltsmilffi plgaylqtvg qdgeapsdyq sfavtiasal
1081 vitvnfqigl dtsywtfvna fsifgsialy fgimfdfhsa gihvlfpsaf qftgtasnal
1141 rqpyiwltii lavavcllpv vairflsmti wpsesdkiqk hrkrlkaeeq wqrrqqvfrr
1201 gvstrrsaya fshqrgyadl issgrsirkk rspldaivad gtaeyrrtgd s
```

ANO4      121601          AK091540                                                  (SEQ ID NO: 3)

```
    1 aaaaactcca ttcgaaccca tggagcagaa aaccaccgac atctactcta tgagtgctgg
   61 gcctcctggg gcgtgtggta taaataccaa cctttggatc ttgtaaggcg gtactttgga
  121 gagaagattg ggttatattt tgcctggttg ggctggtaca ccggcatgct cttcccagct
  181 gccttcattg gattgtttgt cttttttgtat ggcgtcacca ctctggatca cagccaagtc
  241 agtaaagaag tctgccaagc tacagatatc atcatgtgtc ctgtgtgtga taaatactgt
  301 ccattcatga ggctgtcaga cagctgtgta tatgccaagg taacccacct ttttgacaat
  361 ggagccactg tcttctttgc tgttttcatg gcagtctggg caacagtttt cctggagttt
  421 tggaaaagac ggcgagcagt aattgcttat gactgggatt tgatagactg ggaagaagag
  481 gaggaagaaa tacgacccca gtttgaagcc aagtattcca agaaagagcg gatgaatcca
  541 atttctggaa agccagaacc ttatcaagca tttacagata aatgcagcag acttatcgtt
  601 tctgcatctg gaatattttt tatgatctgc gtggtgattg ctgccgtgtt cgggatcgtc
  661 atttaccggg tggtgactgt cagcactttc gctgcccttta agtgggcgtt aatcaggaat
  721 aactctcagg ttgcaaccac agggactgct gtgtgcatca acttctgtat cattatgttg
  781 ctgaatgtgc tctatgaaaa agttgccctg cttctgacga atttagaaca gcctcgcaca
  841 gagtctgagt gggagaacag cttcaccctg aaaatgtttc ttttttcagtt tgtcaatctg
  901 aacagctcca cattttacat cgcattcttc ctcggaagat ttacaggaca cccaggtgcc
  961 tacttgaggc tgataaacag gtggagacta gaagagtgcc accctagtgg atgccttatt
 1021 gatctgtgta tgcaaatggg tattataatg gtgctaaagc agacctggaa taatttcatg
 1081 gaacttggct acccgttaat tcagaattgg tggactagaa gaaagtacg acaagaacat
 1141 ggacctgaaa ggaaaataag tttcccacaa tgggaaaagg actataacct tcagccgatg
 1201 aatgcctatg gactcttcga tgaatactta gaaatgattc ttcagtttgg attcacaact
 1261 atctttgtgg cagcttttcc cctagcacca cttctggcct tactgaataa cataattgaa
 1321 aatcgacttg atgcttacaa atttgtcaca cagtggagga gaccttttagc ttcaagggcc
 1381 aaagacatag gaatttggta tggaattctt gaaggcattg gaattctctc tgttatcaca
 1441 aatgcatttg tcatagcgat aacatctgac tttatccctc gcttggtgta tgcttataag
```

TABLE 5-continued

```
1501 tatggacctt gtgcaggcca aggagaagct gggcaaaagt gcatggttgg ctatgtgaat 1561 gccagcttgt ctgtatttcg aatttctgac tttgagaacc gatctgagcc tgaatctgat 1621 ggcagtgagt tctcggggac tcctcttaag tactgcagat accgggacta ccgtgacccg 1681 cctcattcac tggtgcccta tggctacaca ctgcagtttt ggcatgtcct agctgctcga 1741 ttagctttta tcattgtctt tgagcacctc gtgttttgta taaagcacct catttcgtat 1801 ctgatcccag acctcccaaa agacctaagg gatcgaatga agagagaa gtacttgatt 1861 caggagatga tgtatgaagc agaactgaa cgtctccaga aggaacgaaa ggagaggaag 1921 aagaatggaa aagcacacca caacgagtgg ccgtgaccat aaaatagtcc ctttccaggc 1981 caaggacctg aattctgttt acttcttctg gctgtgcaaa agcacactca agtgaatgac 2041 taaaaatgca accacagtgc atgttgcaga taccggcggc cgcaggaggg gcagcatcca 2101 gtagaggact ggcgttggag tcacactgct gtgaaatcac gttgcagtcc agcgcacaat 2161 tgctatctat ccatagacca ttcttgacca agcaagcatg cacattatgg gcagttacat 2221 tctcaagttt ttaaaatcaa ggggaacttg tatactgggc ctgtttttca gcctgtttgc 2281 tacctttttt gcattctatc ccatgtgaat tttacagaca ctgggctaaa aagggtattc 2341 agacacatgg acacacattc ctagaatgtc atcatatggt cctaattcca tgtcaccaag 2401 aacacagaca agaccctgtt tacaactttt tctttccttt ttttttaattt tagacctttc 2461 tgagaagatt attatatatg acatatctat agctatgtgt atggccatag atgtatttct 2521 gtgtgtacat atgtatagtc atgtattcct gcatatgtac atacaaatac agagatatat 2581 aaagtacata gaaattcctt acttgtaaat agccaaaaag tactgacatg agtgaatttt 2641 cacatttaaa tagtcatcaa tatgaagcca tgattaatgc ttgtataatg tgatgcaata 2701 aaatttaaaa taaatttctg cacatggaat attttc
```

```
ABCA1        19                    AAF86276                                (SEQ ID NO: 4)
   1 macwpqlrll lwknltfrrr qtcqlllleva wplfiflili svrlsyppye qhechfpnka 61 mpsagtlpwv qgiicnannp cfryptpgea pgvvgnfnks ivarlfsdar rllllysqkdt 121 smkdmrkvlr tlqqikkssss nlklqdflvd netfsgflyh nlslpkstvd kmlradvilh 181 kvflqgyqlh ltslcngsks eemiqlgdqe vselcglpre klaaaervlr snmdilkpil 241 rtlnstspfp skelaeatkt llhslgtlaq elfsmrswsd mrqevmfltn vnsssssstqi 301 yqavsrivcg hpeggglkik slnwyednny kalfggngte edaetfydns ttpycndlmk 361 nlessplsri iwkalkpllv gkilytpdtp atrqvmaevn ktfqelavfh dlegmweels 421 pkiwtfmens qemdlvrmll dsrdndhfwe qqldgldwta qdivaflakh pedvqssngs 481 vytwreafne tnqairtisr fmecvnlnkl epiatevwli nksmellder kfwagivftg 541 itpgsielph hvkykirmdi dnvertnkik dgywdpgpra dpfedmryvw ggfaylqdvv 601 eqaiirvltg tekktgvymq qmpypcyvdd iflrvmsrsm plfmtlawiy svaviikgiv 661 yekearlket mrimgldnsi lwfswfissl ipllvsagll vvilklgnll pysdpsvvfv 721 flsvfavvti lqcflistlf sranlaaacg giiyftlylp yvlcvawqdy vgftlkifax 781 llspvafgfg ceyfalfeeq gigvqwdnlf espveedgfn lttsvsmmlf dtflygvmtw 841 yieavfpgqy giprpwyfpc tksywfgees dekshpgsnq kriseicmee epthlklgvs 901 iqnlvkvyrd gmkvavdgla lnfyegqits flghngagkt ttmsiltglf pptsgtayil 961 gkdirsemst irqnlgvcpq hnvlfdmltv eehiwfyarl kglsekhvka emeqmaldvg 1021 lpssklkskt sqlsggmqrk lsvalafvgg skvvildept agvkpysrrg iwelllkyrq
```

TABLE 5-continued

```
1081 grtiilsthh mdeadvlgdr iaiishgklc cvgsslflkn qlgtgyyltl vkkdvessls
1141 scrnssstvs ylkkedsvsq sssdaglgsd hesdtltidv saisnlirkh vsearlvedi
1201 gheltyvlpy eaakegafve lfheiddrls dlgissygis ettleeiflk vaeesgvdae
1261 tsdgtlparr nrrafgdkqs clrpftedda adpndsdidp esretdllsg mdgkgsyqvk
1321 gwkltqqqfv allwkrllia rrsrkgffaq ivlpavfvci alvfslivpp fgkypslelq
1381 pwmyneqytf vsndapedtg tlellnaltk dpgfgtrcme gnpipdtpcq ageeewttap
1441 vpqtimdlfq ngnwtmqnps pacqcssdki kkmlpvcppg agglpppqrk qntadilqdl
1501 tgrnisdylv ktyvqiiaks lknkiwvnef ryggfslgvs ntqalppsqe vndaxkqmkk
1561 hlklakdssa drflnslgrf mtgldtrnnv kvwfnnkgwh aissflnvin nailranlqk
1621 genpshygit afnhplnltk qqlsevaxmt tsvdvlvsic vifamsfvpa sfvvfliqer
1681 vskakhlqfi sgvkpviywl snfvwdmcny vvpatlviii ficfqqksyv sstnlpvlal
1741 llllygwsit plmypasfvf kipstayvvl tsvnlfigin gsvatfvlel ftdnklnnin
1801 dilksvflif phfclgrgli dmvknqamad alerfgenrf vsplswdlvg rnlfamaveg
1861 vvfflitvli qyrffirprp vnaklsplnd ededvrrerq rildgggqnd ileikeltki
1921 yrrkrkpavd ricvgippge cfgllgvnga gksstfkmlt gdttvtrgda flnxnsilsn
1981 ihevhqnmgy cpqfdaitel ltgrehveff allrgvpeke vgkvgewair klglvkygek
2041 yagnysggnk rklstamali ggppvvflde pttgmdpkar rflwncalsv vkegrsvvlt
2101 shsmeeceal ctrmaimvng rfrclgsvqh lknrfgdgyt ivvriagsnp dlkpvqdffg
2161 lafpgsvxke khrnmlqyql psslsslari fsilsqskkr lhiedysvsq ttldqvfvnf
2221 akdqsdddhl kdlslhknqt vvdvavltsf lqdekvkesy v
```

AGPAT3    56894           AF156774                                      (SEQ ID NO: 5)

```
   1 tctatgaaac caacatacat ggcgtttgca tcacagttgg agtcagatgt gagcccggag
  61 ggcaggtgtc tggcttgtcc acccggaagc cctgagggca gctgttccca ctggctctgc
 121 tgaccttgtg ccttggacgg ctgtcctcag cgaggggccg tgcacccgct cctgagcagc
 181 gccatgggcc tgctggcctt cctgaagacc cagttcgtgc tgcacctgct ggtcggcttt
 241 gtcttcgtgg tgagtggtct ggtcatcaac ttcgtccagc tgtgcacgct ggcgctctgg
 301 ccggtcagca agcagctcta ccgccgcctc aactgccgcc tcgcatactc actctggagc
 361 caactggtca tgctgctgga gtggtggtcc tgcacggagt gtacactgtt cacggaccag
 421 gccacggtag agcgctttgg gaaggagcac gcagtcatca tcctcaacca caacttcgag
 481 atcgacttcc tctgtgggtg gaccatgtgt gagcgcttcg gagtgctggg gagctccaag
 541 gtcctcgcta agaaggagct gctctacgtg cccctcatcg gctggacgtg gtactttctg
 601 gagattgtgt tctgcaagcg gaagtgggag gaggaccggg acaccgtggt cgaagggctg
 661 aggcgcctgt cggactaccc cgagtacatg tggtttctcc tgtactgcga ggggacgcgc
 721 ttcacggaga ccaagcaccg cgttagcatg gaggtggcgg ctgctaaggg gcttcctgtc
 781 ctcaagtacc acctgctgcc gcggaccaag ggcttcacca ccgcagtcaa gtgcctccgg
 841 gggacagtcg cagctgtcta tgatgtaacc ctgaacttca gggaaacaa gaacccgtcc
 901 ctgctgggga tcctctacgg gaagaagtac gaggcggaca tgtgcgtgag gagatttcct
 961 ctggaagaca tcccgctgga tgaaaaggaa gcagctcagt ggcttcataa actgtaccag
1021 gagaaggacg cgctccagga gatatataat cagaagggca tgtttccagg ggagcagttt
1081 aagcctgccc ggaggccgtg gaccctcctg aacttcctgt cctgggccac cattctcctg
1141 tctcccctct tcagttttgt cttgggcgtc tttgccagcg gatcacctct cctgatcctg
```

TABLE 5-continued

```
1201 actttcttgg ggtttgtggg agcagcttcc tttggagttc gcagactgat aggagtaact
1261 gagatagaaa aaggctccag ctacggaaac caagagttta agaaaaagga ataattaatg
1321 gctgtgactg aacacacgcg gccctgacgg tggtatccag ttaactcaaa ccaacacac
1381 agagtgcagg aaaagacaat tagaaactat ttttcttatt aactggtgac taatattaac
1441 aaaacttgag ccaagagtaa agaattcaga aggcctgtca ggtgaagtct tcagcctccc
1501 acagcgcagg gtcccagcat ctccacgcgc gcccgtggga ggtgggtccg gccggagagg
1561 cctcccgcgg acgccgtctc tccagaactc cgcttccaag agggacctt ggctgctttc
1621 tctccttaaa cttagatcaa atttaaaaaaaaaaaaaa
```

AGPAT4   56895          AF156776                                           (SEQ ID NO: 6)

```
   1 tgaacccagc cggctccatc tcagcttctg gtttctaagt ccatgtgcca aaggctgcca
  61 ggaaggagac gccttcctga gtcctggatc tttcttcctt ctggaaatct tgactgtgg
 121 gtagttattt atttctgaat aagagcgtcc acgcatcatg acctcgcgg gactgctgaa
 181 gtctcagttc ctgtgccacc tggtcttctg ctacgtcttt attgcctcag ggctaatcat
 241 caacaccatt cagctcttca ctctcctcct ctggcccatt aacaagcagc tcttccggaa
 301 gatcaactgc agactgtcct attgcatctc aagccagctg gtgatgctgc tggagtggtg
 361 gtcgggcacg gaatgcacca tcttcacgga cccgcgcgcc tacctcaagt atgggaagga
 421 aaatgccatc gtggttctca accacaagtt tgaaattgac tttctgtgtg ctggagcct
 481 gtccgaacgc tttgggctgt taggggctc caaggtcctg gccaagaaag agctggccta
 541 tgtcccaatt atcggctgga tgtggtactc caccgagatg gtcttctgtt cgcgcaagtg
 601 ggagcaggat cgcaagacgg ttgccaccag tttgcagcac ctccgggact ccccgagaa
 661 gtatttttc ctgattcact gtgagggcac acggttcacg gagaagaagc atgagatcag
 721 catgcaggtg gcccgggcca agggctgcc tcgcctcaag catcacctgt gccacgaac
 781 caagggcttc gccatcaccg tgaggagctt gagaaatgta gtttcagctg tatatgactg
 841 tacactcaat ttcagaaata tgaaaatcc aacactgctg ggagtcctaa acggaaagaa
 901 ataccatgca gatttgtatg ttaggaggat cccactggaa gacatccctg aagacgatga
 961 cgagtgctcg gcctggctgc acaagctcta ccaggagaag gatgcctttc aggaggagta
1021 ctacaggacg ggcaccttcc cagagacgcc catggtgccc ccccggcggc cctggaccct
1081 cgtgaactgg ctgttttggg cctcgctggt gctctaccct ttcttccagt tcctggtcag
1141 catgatcagg agcgggtctt ccctgacgct ggccagcttc atcctcgtct tctttgtggc
1201 ctccgtggga gttcgatgga tgattggtgt gacggaaatt gacaagggct ctgcctacgg
1261 caactctgac agcaagcaga actgaatga ctgactcagg gaggtgtcac catccgaagg
1321 gaaccttggg gaactggtgg cctctgcata tcctccttag tgggacacgg tgacaaaggc
1381 tgggtgagcc cctgctgggc acggcggaag tcacgacctc tccagccagg gagtctggtc
1441 tcaaggccgg atggggagga agatgttttg taatcttttt ttccccatgt gctttagtgg
1501 gctttggttt tcttttgtg cgagtgtgtg tgagaatggc tgtgtggtga gtgtgaactt
1561 tgttctgtga tcatagaaag ggtattttag gctgcagggg agggcagggc tggggaccga
1621 agggacaag ttccccttc atcctttggt gctgagtttt ctgtaaccct tggttgccag
1681 agataaagtg aaaagtgctt taggtgagat gactaaatta tgcctccaag aaaaaaaaat
1741 taaagtgctt ttctgggtca aaaaaaaaaa aaaa
```

TABLE 5-continued

| DGKQ | 1609 | L38707 | (SEQ ID NO: 7) |

```
   1 gggcggacct aaagggctc gggccgctcg ggcggggaat ggcggcggcg gccgagcccg
  61 gggcccgcgc ctggctgggc ggcggctccc cgcgccccgg cagcccggcc tgcagccccg
 121 tgctgggctc aggaggccgc gcgcgcccgg ggccggggcc ggggcgggga cgngaccgag
 181 cgggcggcgt cagagcccgg gcccgtgccg cgccgggaca cagcttccgg aaggtgacgc
 241 tcaccaagcc caccttctgc cacctctgct ccgacttcat ctgggggctg gccggcttcc
 301 tgtgcgacgt ctgcaatttc atgtctcatg agaagtgcct gaagcacgtg aggatcccgt
 361 gcacgagtgt ggcacccagc ctggtccggg ttcctgtagc ccactgcttc ggcccccggg
 421 ggctccacaa gcgcaagttc tgtgctgtct gccgcaaggt cctggaggca ccggcgctcc
 481 actgcgaagt gtgtgagctg cacctccacc cagactgtgt gcccttcgcc tgcagtgact
 541 gccgccagtg ccaccaggat gggcaccagg atcacgacac ccatcaccac cactggcggg
 601 agggaacct gccctcggga gcgcgctgcg aggtctgcag aagacgtgc ggctcctctg
 661 acgtgctggc cggcgtgcgc tgcgagtggt gcggggtcca ggcgcactcc ctctgctccg
 721 cggcactggc tcccgagtgt ggcttcgggc gtctgcgctc cctggtcctg cctcccgcgt
 781 gcgtgcgcct tctgcccggc ggcttcagca agacgcagag cttccgcatc gtggaggccg
 841 cggagccggg cgaggggggc gacggcgccg acggagcgc tgccgtgggt ccaggcagag
 901 agacacaggc aactccggag tccgggaagc aaacgctgaa gatctttgat ggcgacgacg
 961 cggtgagaag aagccagttc cgcctcgtca cggtgtcccg cctggccggt gccgaggagg
1021 tgctggaggc cgcactgcgg gcccaccaca tccccgagga ccctggccac ctggagctgt
1081 gccggctgcc cccttcctct caggcctgtg acgcctgggc tggggcaag gctgggagtg
1141 ctgtgatctc ggaggagggc agaagcccg ggtccggcga ggccacgcca gaggcctggg
1201 tcatccgggc tctgccgcgg gcccaggagg tcctgaagat ctaccctggc tggctcaagg
1261 tgggcgtggc ctacgtgtcc gtgcgagtga ccctaagag cacggctcgc tctgtggtgc
1321 tggaggtcct gccgctgctc ggccgccagg ccgagagtcc cgagagcttc agctggtgg
1381 aggtggcgat gggctgcagg cacgtccagc ggacgatgct gatggacgaa cagccctgc
1441 tggaccggct acaggacatc cggcagatgt ctgtgcggca ggtgagccag acgcggttct
1501 acgtggcaga gagcagggat gtagccccgc acgtctccct gtttgttggc ggcctgcctc
1561 ccggcctgtc tcccgaggag tacagcagcc tgctgcatga ggccggggct accaaagcca
1621 ccgtggtgtc cgtgagtcac atctactcct cccaaggcgc ggtagtgttg gacgttgcct
1681 gctttgcgga ggccgagcgg ctgtacatgc tgctgaagga catggctgtg cggggccggc
1741 tgctcactgc cctggtgctc cccgacctgc tgcacgcgaa gctgccccca gacagctgtc
1801 ccctccttgt gttcgtgaac cccaagagtg gaggcctcaa gggccgagac ctgctctgca
1861 gcttccggaa gctactgaac cctcatcagg tcttcgacct gaccaacgga ggtcctcttc
1921 ccgggctcca cctgttctcc caggtgccct gcttccgggt gctggtgtgt ggtggcgatg
1981 gcactgtggg ctgggtgctt ggcgcccgg aggagacacg gtaccgactg gcctgcccgg
2041 agccttctgt ggccatcctg cccctgggca cagggaatga ccttggtcga gtcctccgct
2101 gggggcggc ctacagcggc gaggaccgt tctccgtact gctgtctgtg gacgaggccg
2161 acgccgtgct catggaccgc tggaccatcc tgctggatgc ccacgaagct ggcagtgcag
2221 agaacgacac ggcagacgca gagccccca agatcgtgca gatgagtaac tactgtggca
2281 ttggcatcga cgcggagctg agcctggact tccaccaggc acgggaagag gagcctggca
```

TABLE 5-continued

```
2341 agttcacaag caggctgcac aacaagggtg tgtacgtgcg ggtggggctg cagaagatca
2401 gtcactctcg gagcctgcac aagcagatcc ggctgcaggt ggagcggcag gaggtggagc
2461 tgcccagtat tgaaggcctc atcttcatca acatccccag ctggggctcg ggggccgacc
2521 tgtggggctc cgacagcgac accaggtttg agaagccacg catggacgac gggctgctgg
2581 aggttgtggg cgtgacgggc gtcgtgcaca tgggccaggt ccagggtggg ctgcgctccg
2641 gaatccggat tgcccaggt tcctacttcc gagtcacgct cctcaaggcc accccgtgc
2701 aggtggacgg ggagccctgg gtccaggccc cggggcacat gatcatctca gctgctggcc
2761 ctaaggtgca catgctgagg aaggccaagc agaagccgag gagggccggg accaccaggg
2821 atgcccgggc ggatcgtgcg cctgcccctg agagcgatcc taggtagggg tggctggggc
2881 agcccaaggg ctcgagccat ctctgctccc gccagccttg ttttcaggtg gtctggaggc
2941 agctccacgt cacacagtgg ctgtcatata ttgaagttac cttcccactg gaaaaaaaat
LPPR1    54886           AY304515         (SEQ ID NO: 8)
   1 gtggctcgga ccgccgcctg aatgtacctc gctcccggga gccggacggc ccagtagggc
  61 gcactggagg acgctccgct gcgggagcct ggacagtttt tgacggtgca gtcttgctat
 121 atggtgtgag aaatggctgt aggaaacaac actcaacgaa gttattccat catcccgtgt
 181 tttatatttg ttgagcttgt catcatggct gggacagtgc tgcttgccta ctacttcgaa
 241 tgcactgaca cttttcaggt gcatatccaa ggattcttct gtcaggacgg agacttaatg
 301 aagccttacc cagggacaga ggaagaaagc ttcatcaccc ctctggtgct ctattgtgtg
 361 ctggctgcca ccccaactgc tattattttt attggtgaga tatccatgta tttcataaaa
 421 tcaacaagag aatccctgat tgctcaggag aaaacaattc tgaccggaga atgctgttac
 481 ctgaacccct tacttcgaag gatcataaga ttcacagggg tgtttgcatt tggacttttt
 541 gctactgaca ttttttgtaaa cgccggacaa gtggtcactg gtggtcactg gcacttaac
 601 ctgactgtgt gcaagccaaa ctacaccagt gcagactgcc aagcgcacca ccagtttata
 661 aacaatggga acatttgtac tggggacctg gaagtgatag aaaaggctcg gagatccttt
 721 ccctccaaac acgctgctct gagcatttac tccgccttat atgccacgat gtatattaca
 781 agcacaatca agacgaagag cagtcgactg gccaagccgg tgctgtgcct cggaactctc
 841 tgcacagcct cctgacaggg cctcaaccgg gtctctgagt atcggaacca ctgctcggac
 901 gtgattgctg gtttcatcct gggcactgca gtggccctgt ttctgggaat gtgtgtggtt
 961 cataacttta aggaacgca aggatctcct tccaaaccca agcctgagga tccccgtgga
1021 gtaccctaa tggctttccc aaggatagaa agccctctgg aaccttaag tgcacagaat
1081 cactctgcgt ccatgaccga agttacctga gacgactgat gtgtcacaag ctgtttttta
1141 aaatcatctt ccaattctat acttcaaaac acacagttgc tcaatgtcaa actgtgatga
1201 caaatattac gtttatctag ttagaagcta atgttttgta catttttgt atgaggaagt
1261 gatgtagctt gccctgattt tttttttttt ttttggtcag ctttaatata tttatgccag
1321 aattttaaaa ccaacaaaat tttcttgttc aagcgtgcat tgaagaacca catttattca
1381 atggttgacg ttgttttgtg atatttgtac acaaattttc ttttctcagt tttataaaca
1441 cagaagtaaa tataacaatt cacttttaaac ttttattacc acagttgctg cctcctccag
1501 aatttttgaa tttttaataaa aggcaaactt ttgagctgca ggaaggacaa tgttggttaa
1561 taataaatct caaagtcaat tgtagaaaaa aaattgtctt caaaagaat gttgcactct
1621 gatctcttaa caaattgtta cgttcaaagt ttaaagtgat atattaacaa agtcacctag
1681 ttatacaaac aattgtcaga gaattctgga tttggagggt attggggtta tatgattctt
```

TABLE 5-continued

```
1741 tcttagataa tggcctctac taaataactc aagatctttc tggaatgtct tctggcaggc 1801 aggtgccact gtcagctttt ctccaaaaag cagccaacat cagcctcccc tgtcaactca 1861 acagttttgt atctcatatt atatggactt tatatgaaaa tgaatatttt acagtttgca 1921 cagtattatt ttacagaaaa ggaatcagag aatctacaac atagggcccc agaacaacag 1981 tttcactttg tggcttttaa ttattctaga attttaactg catctcattt ttctagcatg 2041 gtgagaacta atatgtaact cctttgattg aaggagctct tttgtccgta cctatcagaa 2101 tgttttcttg acacttccat gttggctctt ctcagctttt tttgtacata ttttttttt 2161 ctaaagagaa gaaaagtta tcacaaaatg taaaaaaga aaaaaaaaa aaaaa
```

TABLE 6

EEC overlap between breast cancer and PD/AD. (see Table 5 for legend)

| Gene | EEC Function | KEGG | EC | ND | References |
| --- | --- | --- | --- | --- | --- |
| ASTN2 | regulates trafficking of ASTN1, during early clathrin-dependent endocytosis; | hsa04144 | | | (Wilson P M, Fryer R H, et al. (2010) The Journal of Neuroscience 30: 8529-40; Solecki D J (2012) Curr Opin Neurobiol 22: 791-8) |
| | binds AP-2z | | BC | | (Kawauchi T (2012) Int J Mol Sci 13: 4564-90) |
| | | | | AD | (Wang K S, Tonarelli S, et al. (2015) J Neural Transm (Vienna) 122: 701-8) |
| | | | | ID | ASTN1: (Anazi S, Maddirevula S, et al. (2016) Mol Psychiatry) |
| TNS1 | controls cell polarization, migration, and invasion binds a5b1 integrin during endocytosis | | | | (Rainero E, Howe J D, et al. (2015) Cell Rep 10: 398-413; McCleverty C J, Lin D C, et al. (2007) Protein Science: A Publication of the Protein Society 16: 1223-9; Burghel G J, Lin W-Y, et al. (2013) PLoS One 8: e83859) |
| | | | BC | | (Hall E H, Daugherty A E, et al. (2009) J Biol Chem 284: 34713-22) |
| MEGF11 | In *C. elegans*, DYN-1 (DNM1) depends on the function of CED-1 (MEGF10/11) | hsa04144 hsa04721 | | | CED-1: (Shen Q, He B, et al. (2013) Development 140: 3230-43) |
| | | | | AD | MEGF10: (Sherva R, Tripodis Y, et al. (2014) Alzheimers Dement 10: 45-52; Singh T D, Park S Y, et al. (2010) FEBS Lett 584: 3936-42) |
| SDCBP2 | Syndecans bind PI(4,5)P2 and are involved in both endo- and exocytosis. | | | | (Baietti M F, Zhang Z, et al. (2012) Nat Cell Biol 14: 677-85; Hurley J H, Odorizzi G (2012) Nat Cell Biol 14: 654-5) |
| | | | BC | | (Yang Y, Hong Q, et al. (2013) Breast Cancer Res 15: R50) |
| | | | | PD | (Tomlinson P R, Zheng Y, et al. (2015) Ann Clin Transl Neurol 2: 353-61) |
| | | | | AD | (Leonova E I, Galzitskaya O V (2015) Adv Exp Med Biol 855: 241-58) |
| N4BP3 | NEDD4 controls growth factor receptor endocytosis (NEDD9 expression is assoc. with BC metastasis) | hsa04144 | | | (Persaud A, Alberts P, et al. (2011) EMBO J 30: 3259-73; Jung S, Li C, et al. (2013) Int J Oncol 43: 1587-95) |
| | | | BC | | (Jung S, Li C, et al. (2013) Int J Oncol 43: 1587-95; Minn A J, Gupta G P, et al. (2005) Nature 436: 518-24; Liao C J, Chi H C, et al. (2015) Oncotarget 6: 9341-54) |
| | | | | PD | (Perrett R M, Alexopoulou Z, et al. (2015) Mol Cell Neurosci 66: 21-8) |
| | | | | AD | (Rodrigues E M, Scudder S L, et al. (2016) J Neurosci 36: 1590-5; Salminen A, Kaarniranta K, et al. (2013) Prog Neurobiol 106-107: 33-54) |
| SYNJ2 | is recruited to the nascent clathrin coated pit | hsa04070 | BC | PD | see (Table 5) |
| NLRP4 | and NLRP3 associate with BECN1, a component of the PI3K complex that mediates vesicle trafficking | | | | (Jounai N, Kobiyama K, et al. (2011) J Immunol 186: 1646-55; Zhang Y, Sauler M, et al. (2014) The Journal of Immunology 192: 5296-304; Rohatgi R A, Shaw L M (2016) Mol Cell Oncol 3) |
| | | | BC | | (Zhiyu W, Wang N, et al. (2016) Oncotarget 7: 50766) |

TABLE 6-continued

EEC overlap between breast cancer and PD/AD. (see Table 5 for legend)

| Gene | EEC Function | KEGG | EC | ND | References |
|---|---|---|---|---|---|
| | | | | PD | (Choubey V, Cagalinec M, et al. (2014) Autophagy 10: 1105-19; Wang J D, Cao Y L, et al. (2015) Autophagy 11: 2057-73) |
| | | | | AD | (Antonell A, Llado A, et al. (2015) Mol Neurobiol; Swaminathan G, Zhu W, et al. (2016) Autophagy 12: 2404-19) |
| PTENP1 | PI3K/PTEN and PI(3,4,5)P3 are involved in endocytosis and cancer | hsa04070 | | | see (Table 5) |
| VAV3 | VAV . . . promote BCR endocytosis | hsa04666 | | | (Inabe K, Ishiai M, et al. (2002) J Exp Med 195: 189-200; Malhotra S, Kovats S, et al. (2009) The Journal of Biological Chemistry 284: 36202-12) |
| | | | BC | | (Chen XIN, Chen S I, et al. (2015) Oncology Letters 9: 2143-8) |
| | | | | PD | (Moran L B, Duke D C, et al. (2006) Neurogenetics 7: 1-11) |
| | | | | AD | (Wilkinson B L, Cramer P E, et al. (2012) Neurobiology of Aging 33: 197.e21-.e32) |
| PDE4D* | Binds ARRB2 (fast recycling) | hsa04144 | | | (Haddad S A, Ruiz-Narvaez E A, et al. (2016) Carcinogenesis) |
| | | | BC | | (Lin D-C, Xu L, et al. (2013) Proc Natl Acad Sci USA 110: 6109-14) |
| | | | | PD | (Yang L, Calingasan N Y, et al. (2008) Exp Neurol 211: 311-4) |
| | | | | AD | (Gurney M E, D'Amato E C, et al. (2015) Neurotherapeutics 12: 49-56) |
| EEA1 | binds to early endosomes in a Rab5 and PI(3)P dependent manner. | hsa04144 | | | (Pfeffer S R (1999) Nat Cell Biol 1: E145-E7) |
| | | | | PD | (Walter J, Fluhrer R, et al. (2001) J Biol Chem 276: 14634-41) |
| | | | | AD | (Armstrong A, Mattsson N, et al. (2014) Neuromolecular Med 16: 150-60) |
| RAB32 | RAB32/RAB38 interact AP-3 and with LRRK2 (PSRK8) | hsa05012 | | | (Hesketh G G, Perez-Dorado I, et al. (2014) Dev Cell 29: 591-606; Waschbusch D, Michels H, et al. (2014) PLoS One 9: e111632; Bultema J J, Ambrosio A L, et al. (2012) J Biol Chem 287: 19550-63) |
| | | | BC | | (Agalliu I, San Luciano M, et al. (2015) JAMA Neurol 72: 58-65) |
| | | | | PD | (Fukuda M (2016) Traffic 17: 709-19) |
| | | | | AD | (Fukuda M (2016) Traffic 17: 709-19) |
| SNX32* | Sorting Nexin (late endosome), SNX-BAR retromer with other Vps17 orthologs SNX5/SNX6 interacts with VPS35 | hsa04144 | | | (Wang X, Huang T, et al. (2014) Molecular Neurodegeneration 9: 1-9; van Weering J R, Verkade P, et al. (2012) Traffic 13: 94-107; Zhang Q Y, Tan M S, et al. (2015) Mol Neurobiol) |
| | | | BC | | (Rivera J, Megias D, et al. (2010) J Cell Biochem 111: 1464-72) |
| | | | | PD | (Small S A, Petsko G A (2015) Nat Rev Neurosci 16: 126-32) |
| | | | | AD | (Reitz C (2012) Future Neurol 7: 423-31) |
| SCARB2 | required for maintenance of endo- and lysosomes, located in limiting membranes | hsa04142 | | | (Gonzalez A, Valeiras M, et al. (2014) Mol Genet Metab 111: 84-91) |
| | | | BC | | (Nishimura Y, Yoshioka K, et al. (2006) Histochem Cell Biol 126: 627-38; Nishimura Y, Itoh K, et al. (2003) Pathol Oncol Res 9: 83-95) |
| | | | | PD | (Alcalay R N, Levy O A, et al. (2016) NPJ Parkinsons Dis 2) |
| | | | | AD | (Shimizu E, Kawahara K, et al. (2008) J Immunol 181: 6503-13; Bras J, Guerreiro R, et al. (2014b) Hum Mol Genet 23: 6139-46) |
| GLB1 | Galactosidase Beta, related to Galectin 3 (LGALS3) | | | | (Ahmed H, AlSadek D M (2015) Clin Med Insights Oncol 9: 113-21) |
| | | | BC | | (O'Reilly E A, Gubbins L, et al. (2015) BBA Clin 3: 257-75) |
| | | | | PD | (van Dijk K D, Persichetti E, et al. (2013) Mov Disord 28: 747-54) |
| | | | | AD | (Tiribuzi R, Orlacchio A, et al. (2011) J Alzheimers Dis 24: 785-97) |
| RAPGEF4 | GEF for RAB1A/1B/2A; involved in excocytosis through RIMS2 | | | | (Parnell E, Palmer T M, et al. (2015) Trends Pharmacol Sci 36: 203-14; Almahariq M, Tsalkova T, et al. (2013) Mol Pharmacol 83: 122-8) |
| | | | BC | | (Jiang H L, Sun H F, et al. (2015) Oncotarget 6: 16352-65) |

TABLE 6-continued

EEC overlap between breast cancer and PD/AD. (see Table 5 for legend)

| Gene | EEC Function | KEGG | EC | ND | References |
|---|---|---|---|---|---|
| UNC13C STXBP1 (MUNC18) | Interacting with each other and with PI(4,5)P2. Involved in docking/priming in exocytosis | hsa04721 | BC | PD | (Winslow A R, Chen C W, et al. (2010) J Cell Biol 190: 1023-37) |
| | | | | AD | (Puthiyedth N, Riveros C, et al. (2016) PLoS One 11: e0152342; Bereczki E, Francis P T, et al. (2016) Alzheimers Dement) |
| | | | | | (Betz A, Okamoto M, et al. (1997) J Biol Chem 272: 2520-6; Martin T F (2015) Biochim Biophys Acta 1851: 785-93) |
| | | | | | (Fernandez-Nogueira P, Bragado P, et al. (2016) Oncotarget 7: 5313-26) |
| | | | | PD | (Keogh M J, Daud D, et al. (2015) Neurogenetics 16: 65-7; Campbell I M, Yatsenko S A, et al. (2012) Genet Med 14: 868-76) |
| | | | | AD | (Leonova E I, Galzitskaya O V (2015) Adv Exp Med Biol 855: 241-58; Miller J A, Woltjer R L, et al. (2013) Genome Med 5: 48; Takahashi M, Iseki E, et al. (2000) J Neurol Sci 172: 63-9; Law C, Schaan Profes M, et al. (2016) J Neurosci 36: 561-76) |
| STXBP4* | Prevents interaction between STX4 and VAMP2, | hsa04130, hsa04721 | BC | | (Zhang QY, Tan MS, et al. (2015) Mol Neurobiol) |
| | | | | | (Antoniou A C, Beesley J, et al. (2010) Cancer Res 70: 9742-54; Day P, Riggs K A, et al. (2011) Int J Oncol 39: 863-71) |
| | | | | PD | (Diao J, Burre J, et al. (2013) Elife 2: e00592) |
| | | | | AD | (Russell C L, Semerdjieva S, et al. (2012) PLoS One 7: e43201) |
| ANXA4 | Forms exocytotic complexes with SYT1 and the RAB3A effector RPH3A. | hsa04721 | BC | | (Lizarbe M A, Barrasa J I, et al. (2013) Int J Mol Sci 14: 2652-83; Willshaw A, Grant K, et al. (2004) FEBS Lett 559: 13-21) |
| | | | | | (Wei B, Guo C, et al. (2015) Clin Chim Acta 447: 72-8; Yao H, Sun C, et al. (2016) Front Biosci (Landmark Ed) 21: 949-57) |
| | | | | PD | (Matigian N, Abrahamsen G, et al. (2010) Disease Models & Mechanisms 3: 785-98) |
| | | | | AD | (Kuzuya A, Zoltowska K M, et al. (2016) BMC Biol 14: 25; Tan M G, Lee C, et al. (2014) Neurochem Int 64: 29-36) |
| | | | | HD | SYT1: (Valencia A, Sapp E, et al. (2013) Journal of Huntington's disease 2: 459-75) |
| SYT17 | "B/K protein may play a role in exocytosis" | | | | (Chin H, Choi S H, et al. (2006) Exp Mol Med 38: 144-52; Fukuda M (2013) Madame Curie Regulated Database [Internet]) |
| | | | BC | | (Weng L, Ziliak D, et al. (2013) Annals of Oncology) |
| | | | | AD | (Gautam V, D'Avanzo C, et al. (2015) Mol Neurodegener 10: 31) |
| PARK2 | "Loss of parkin promotes . . . endocytosis by accumulating CAV1"; PARK2 binds AP-2 via arrestin | hsa04141 | BC | | (Cha S H, Choi Y R, et al. (2015) Mol Neurodegener 10: 63; Ahmed M R, Zhan X, et al. (2011) Biochemistry 50: 3749-63) |
| | | | | | (Wang H, Liu B, et al. (2009) J Pathol 218: 76-85) |
| | | | | PD | (Feng D D, Cai W, et al. (2015) Transl Neurodegener 4: 20; Kitada T, Asakawa S, et al. (1998) Nature 392: 605-8) |
| | | | | AD | (Martin-Maestro P, Gargini R, et al. (2016) Hum Mol Genet 25: 792-806) |
| DNAJC1* | ER membrane protein. DNAJC (Hsp40) controls release of proteins via HSPA5 (BiP, GRP78); DNAJC13 interacts with SNX-BAR | hsa04141 | BC | | (Michailidou K, Hall P, et al. (2013) Nat Genet 45: 353-61, 61e1-2; Chen C-L, Hou W-H, et al. (2009) Journal of Cell Science 122: 1863-71) |
| | | | | PD | DNAJC6/13: (Seaman M, Freeman CL (2014) Commun Integr Biol 7: e29483; Vilarino-Guell C, Rajput A, et al. (2014) Hum Mol Genet 23: 1794-801) |
| | | | | AD | (Hsu W C, Wang H K, et al. (2008) J Neural Transm (Vienna) 115: 1537-43) |

*from previous GWAS.
Underlined: functionally related genes identified in the literature.

Example 3: Elevated Endocytosis Combined with Age-Related Decline in Lysosomal Function is a Common Epistatic Risk Factor in Age-Related Diseases endocytosis is a known component of the etiology of many age-related diseases. In cancers (Mosesson Y, Mills G B, et al. (2008) Nat Rev Cancer 8:835-50), Alzheimer's disease (Schreij A M, Fon E A, et al. (2015) Cell Mol Life Sci; Wang X, Huang T, et al. (2014) Molecular Neurodegeneration 9:1-9; Kim S, Sato Y, et al. (2016) Mol Psychiatry 21:707-16), and PD (Rivero-Rios P, Gomez-Suaga P, et al. (2015) Biochem Soc Trans 43:390-5), endocytosis of β1-integrin (FIG. 14), APP (FIG. 15), and α-synuclein (SNCA, FIG. 16), respectively, are known to be critical early steps in the etiology leading to formation of plaques. The terms "derailed endocytosis" and "deranged endocytosis" have been used to characterize an important component of the etiology of cancers (Mosesson Y, Mills G B, et al. (2008) Nat Rev Cancer 8:835-50), Alzheimer's disease (Van Dooren T, Princen K, et al. (2014) Biomed Res Int 2014: 167024), and other "pathological conditions". (Di Fiore P P, von Zastrow M (2014) Cold Spring Harbor Perspectives in Biology 6) "[G]enes that influence endocytosis are overrepresented as Alzheimer's disease risk factors [and] endocytosis-related genes are the earliest known disease-specific neuronal response in Alzheimer's disease. They develop early in Down syndrome, a cause of early-onset Alzheimer's disease linked to an extra copy of APP." (Kim S, Sato Y, et al. (2016) Mol Psychiatry 21:707-16)

Figure 15:
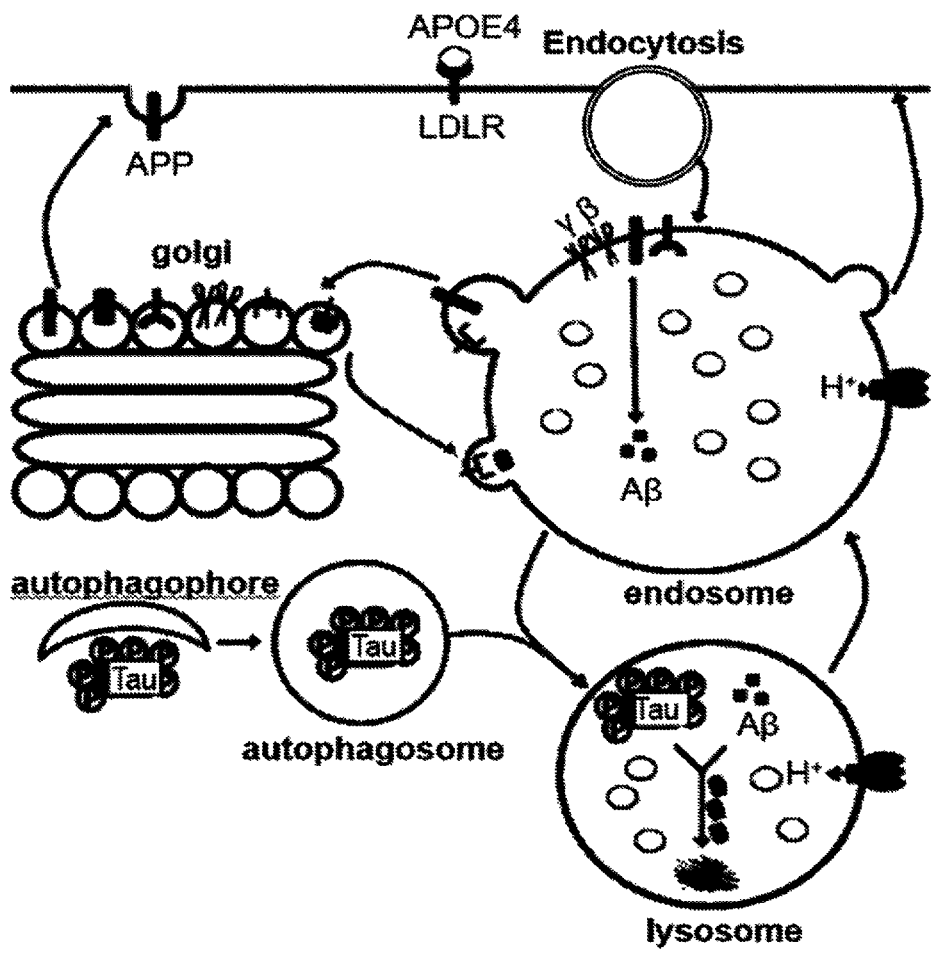
FIG. 15: EEC in Alzheimer's disease (AD). APP is synthesized in the endoplasmic reticulum (ER), transported to the TGN, and inserted into the plasma membrane via secretory vesicles. Cell-surface APP can be internalized to endosomes from which it can either be recycled back to the cell surface or delivered to lysosomes for degradation. Within the EE, the acidic environment favors production of amyloid-beta, which can be degraded in lysosomes by cathepsins, accumulated in EEs, or released to extracellular spaces via exocytosis (modified from Chen X, Hui L, et al. (2014) J Parkinsons Dis Alzheimers Dis 1).
Figure 16:
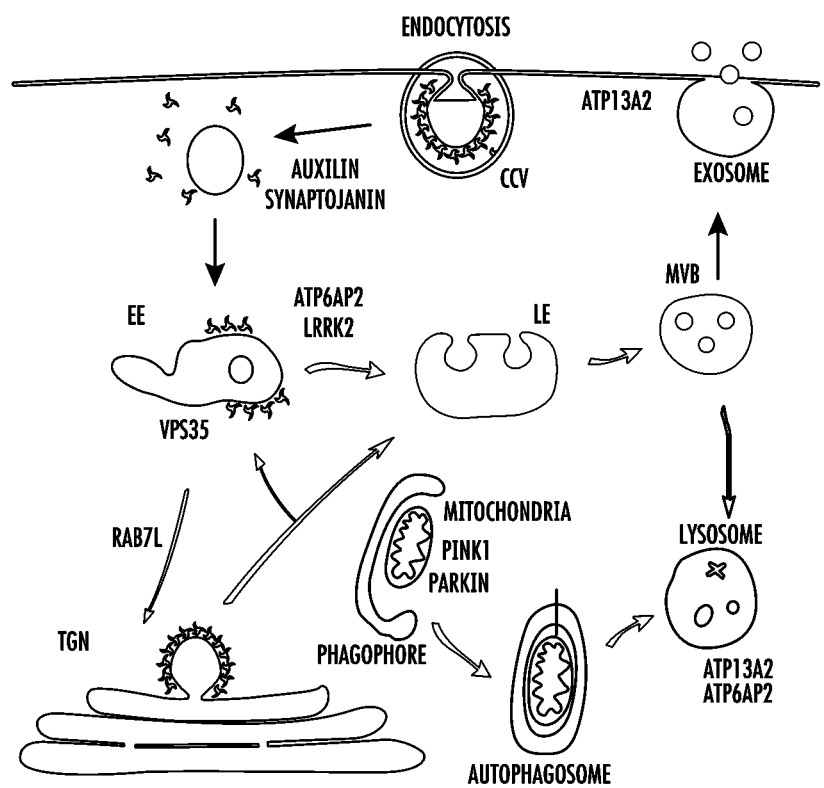
FIG. 16: EEC in Parkinson's disease (PD). Following endocytic entry, cargo is transported to early endosomes. From there, cargo can recycle back to the plasma membrane, either directly or via recycling endosomes. Alternatively, cargo can be retained in the EEs, which will form LEs/MVBs, and fuse with lysosomes for degradation. In parallel, cargo are transported between EEs and the trans-Golgi network (TGN). Alterations in these processes lead to lysosomal dysfunction and accumulation of undegraded macromolecules, toxic to the cell. (adopted from (Schreij A M, Fon E A, et al. (2015) Cell Mol Life Sci))
Figure 17:
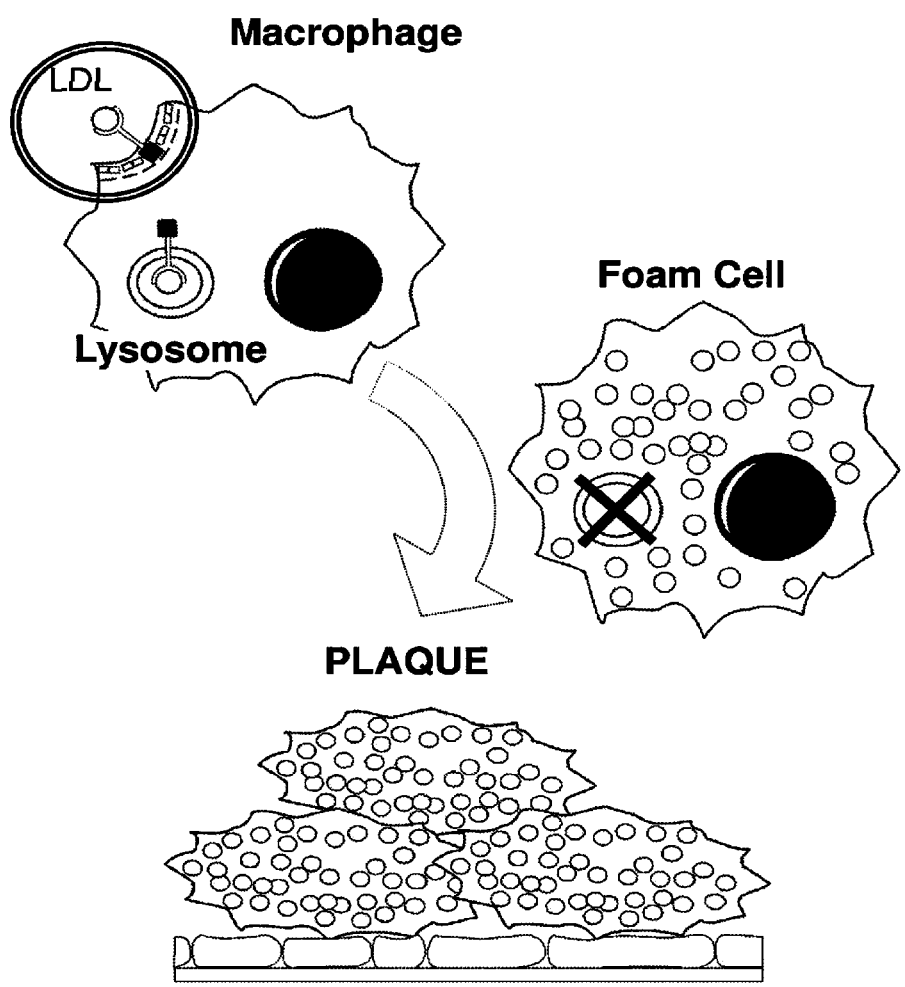
FIG. 17: Macropinocytosis in Atherosclerosis (CAD) Following endocytic entry, low-density lipoprotein (LDL) is transported to the lysosome for degradation. Deficiencies in the lysosomal process lead to accumulation of LDL and. macrophages turn into foam cells, which accumulate to form atherosclerotic plaques.
Figure 18A:
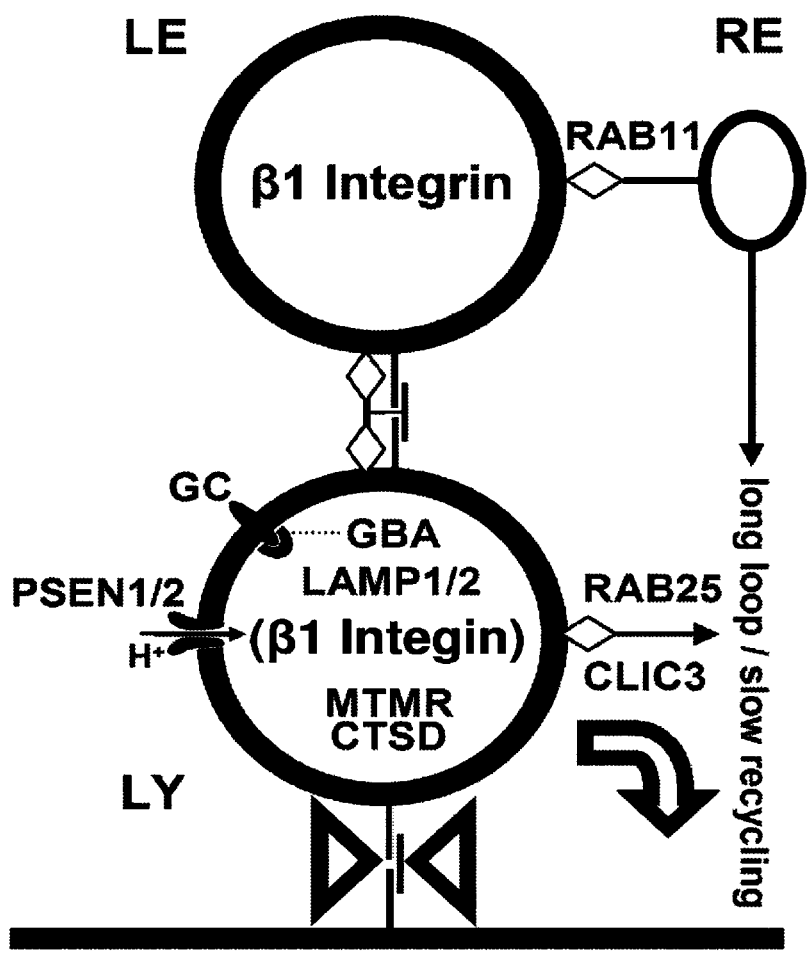
FIG. 18A-C: Lysosomal Dysfunction in Cancer (18A), AD/PD (18B, and CAD (18C). Published results show overlapping genetic risk factors for lysosomal dysfunction across diseases, leading to reduced lysosomal clearance (▶◀) and, in cancer, increases in recovery of integrins from the lysosome (⌐)
Figure 18B:
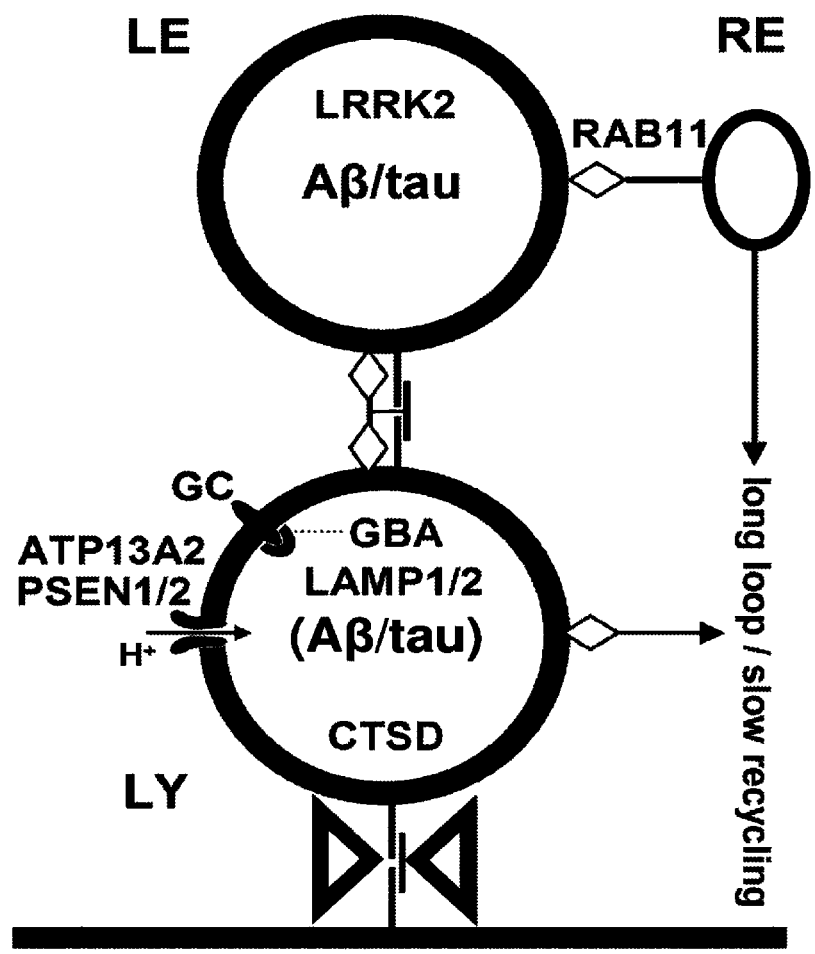
Figure 18C:
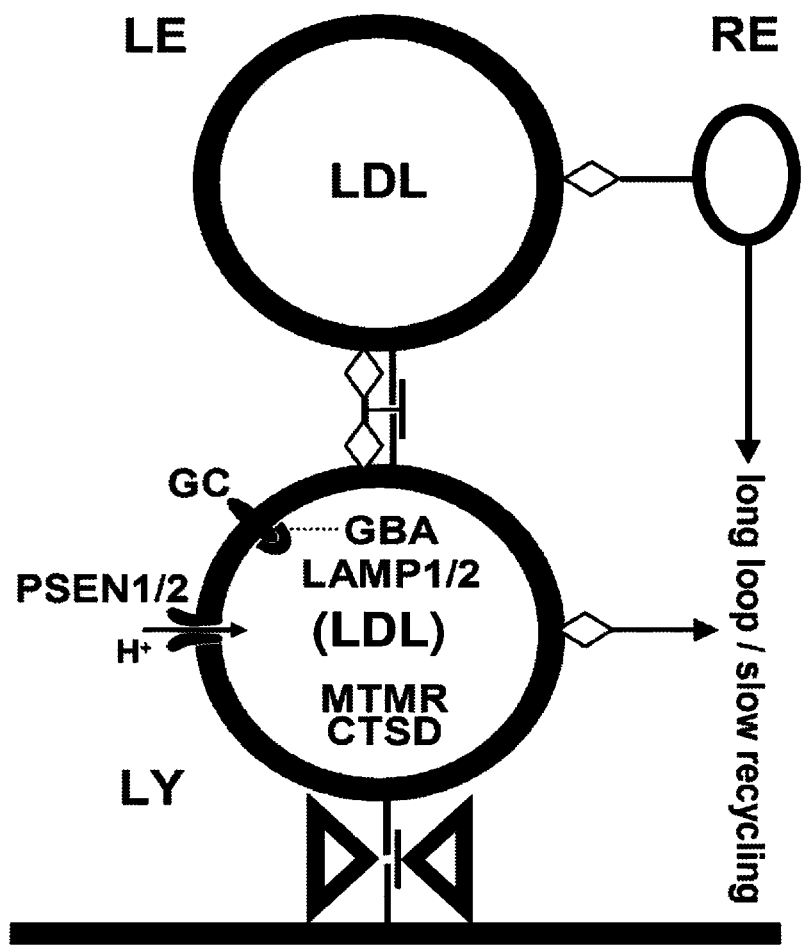

"New reports implicate altered [vacuolar H⁺]-ATPase activity and lysosomal pH dysregulation in cellular aging, longevity, and adult-onset neurodegenerative diseases, including forms of [Parkinson's disease] and [Alzheimer's disease]," (Colacurcio D J, Nixon R A (2016) Ageing Res Rev) but also atherosclerosis, see also FIG. 15, FIG. 16, and FIG. 17. In Parkinson's disease, "an age-related pathological depletion of functional endosomes may increase the susceptibility to stochastic molecular defects in this same pathway, which in some individuals may trigger [a] vicious circle. [ . . . ] Disease causing mutations cluster within [the endosomal] pathway and alter receptor recycling and/or α-synuclein degradation. In turn, α-synuclein accumulation [ . . . ] exacerbates defective endosomal processing by impairing the machinery involved in the sorting or fusion of endosomes". (Perrett R M, Alexopoulou Z, et al. (2015) Mol Cell Neurosci 66:21-8) In Alzheimer's disease, "accelerated endocytosis causes endocytic cargos to accumulate within enlarged [LEs] and impairs lysosomal functions. [ . . . ] Pathogenic endocytosis [ . . . ] could be modulated therapeutically at multiple possible targets." (Kim S, Sato Y, et al. (2016) Mol Psychiatry 21:707-16) "The underlying molecular mechanisms [in Alzheimer's disease and Parkinson's disease] remain poorly understood, yet dysfunction in endocytic membrane trafficking is a recurrent theme, which may explain the neurodegenerative process." (Schreij A M, Fon E A, et al. (2015) Cell Mol Life Sci), Given the failure of previous GWAS to identify functionally related collections of genes and novel insights into the etiology of common diseases, the surprising results based on the novel GWAS approach (Example 1) were consistent with previous results not only in breast cancer, but also in Alzheimer's disease and Parkinson's disease (Example 2), in general, and with genes involving lysosomal function, in particular (FIG. 18A and FIG. 18B for overlap in lysosomal genetic risk factors).

Figure 19:
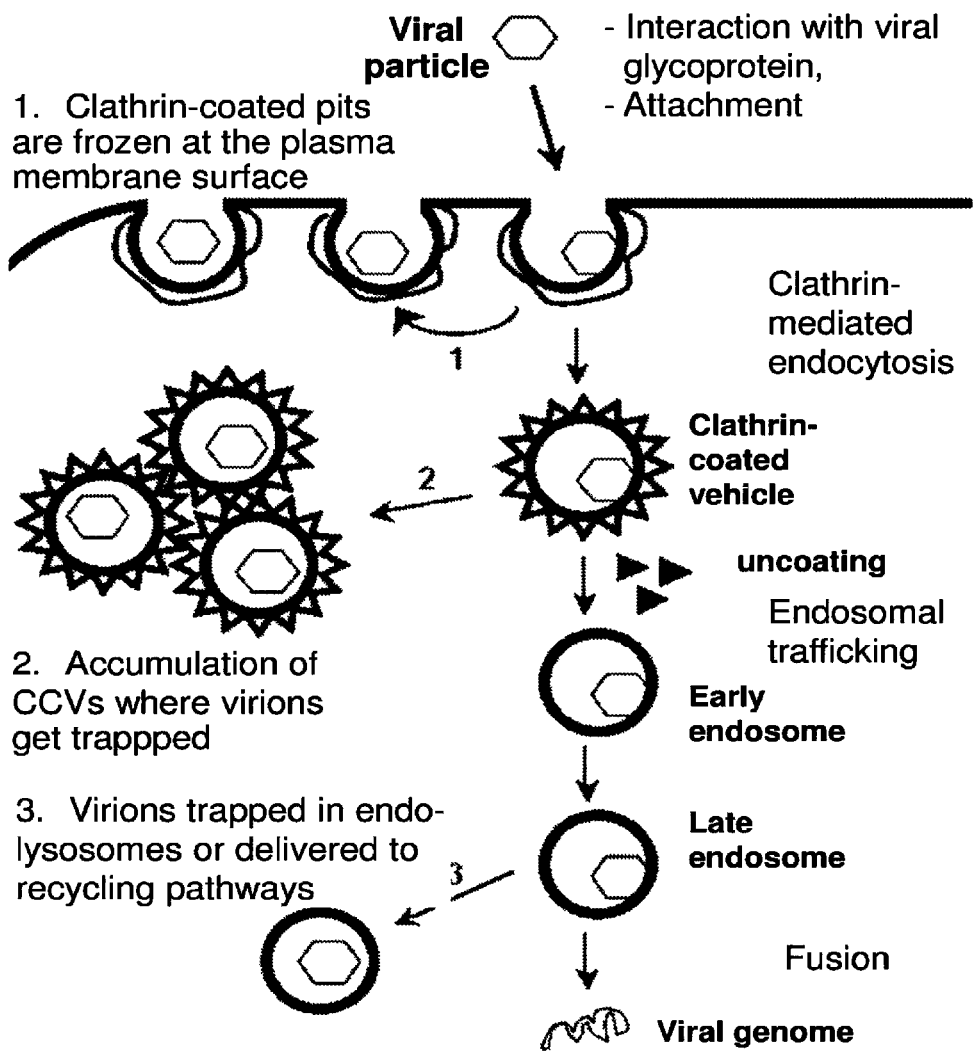
FIG. 19: Viruses "Hijacking" Endocytosis. Viral particles depend on clathrin-mediated endocytosis for entry into cells. CCV: clathrin-coated vesicle. Modified from FIG. 2 in (Blaising J, Polyak S J, et al. (2014) Antiviral research 107:84-94)

Endocytosis has also been implicated as playing an important role in virus infections. For instance, hepatitis B virus (HBV) has been shown to "hijacks cellular processes, in particular the endocytic machinery" (Schroeder B, McNiven M A (2014) Compr Physiol 4:1403-17) and "HBV capsid-like core particles are internalized through clathrin-mediated endocytosis." (Cooper A, Shaul Y (2006) J Biol Chem 281:16563-9) In fact, umifenovir (Arbidol), which impairs clathrin-mediated endocytosis, (Pecheur E I, Borisevich V, et al. (2016) Journal of virology 90:3086-92) has broad antiviral activity, including activity against hepatitis viruses (Blaising J, Polyak S J, et al. (2014) Antiviral research 107:84-94) (FIG. 19).

Example 4: βCDs Exert their Effects on "Derailed", "Deranged", or "Defective" Endocytosis not Through a Mechanism Independent of Cholesterol The present disclosure provides α-CD or HP-α-CD and analogues and derivatives thereof as non-limiting examples of compounds that may be useful for treating age-related conditions including but not limited to conditions involving "derailed endocytosis," a "hallmark of cancer" (Mitra S, Cheng K W, et al. (2012) Biochem Soc Trans 40:1404-8) also seen in neurodevelopmental diseases. (Rivero-Rios P, Gomez-Suaga P, et al. (2015) Biochem Soc Trans 43:390-5; Van Dooren T, Princen K, et al. (2014) Biomed Res Int 2014:167024). In some embodiment of the present disclosure α-CDs are used for treating age-related conditions, such as cancers (including, but not limited to, prostate and breast cancer) and neurodegenerative diseases (including, but not limited to, PD or AD). CDs lower the amount of PIPs available without directly interfering with their distribution.

In Cancer, AD, and PD, a plethora of studies have investigated the effect of βCDs in vitro Cancer: M-β-CD suppressed invasion activity in three H7 Lewis lung cancer cell lines and highly metastatic cell lines had more β1 integrin (Zhang Q, Furukawa K, et al. (2006) J Biol Chem 281:18145-55) and breast cancer and prostate cancer cell lines were more sensitive to M-β-CD-induced cell death than their normal counterparts. (Li Y C, Park M J, et al. (2006) Am J Pathol 168:1107-18; quiz 404-5) In particular, M-β-CD treatment induced a substantial decrease (40%) in activity of breast cancer resistance protein (BCRP), (Storch C H, Ehehalt R, et al. (2007) J Pharmacol Exp Ther 323:257-64) which transports PS ("eat me signal") and PC analogues. (Daleke D L (2007) J Biol Chem 282:821-5) In subsequent functional studies, M-β-CD inhibited spheroid migration and invasion of MDA-MB-241 and ZR751 breast cancer cells (Raghu H, Sodadasu P K, et al. (2010) BMC Cancer 10:647) and also endocytosis (Palaniyandi K, Pockaj B A, et al. (2012) Journal of cancer science & therapy 4:214-22) and migration (Guerra F S, Sampaio LdS, et al. (2016) Translational Medicine Communications 1:3) of MCF7 breast cancer cells. M-β-CD was more toxic for invasive than for non-invasive urothelial cancer cells, (Resnik N, Repnik U, et al. (2015) PLoS One 10:e0137878) interfered with RTK-[PIP2]-PI3K-[PIP3]-AKT signaling in HeLa cells, (Yamaguchi R, Perkins G, et al. (2015) FEBS Lett 589:4097-105) and inhibited the growth of leukemia cell lines. (Yokoo M, Kubota Y, et al. (2015) PLoS One 10:e0141946)

Figure 20:
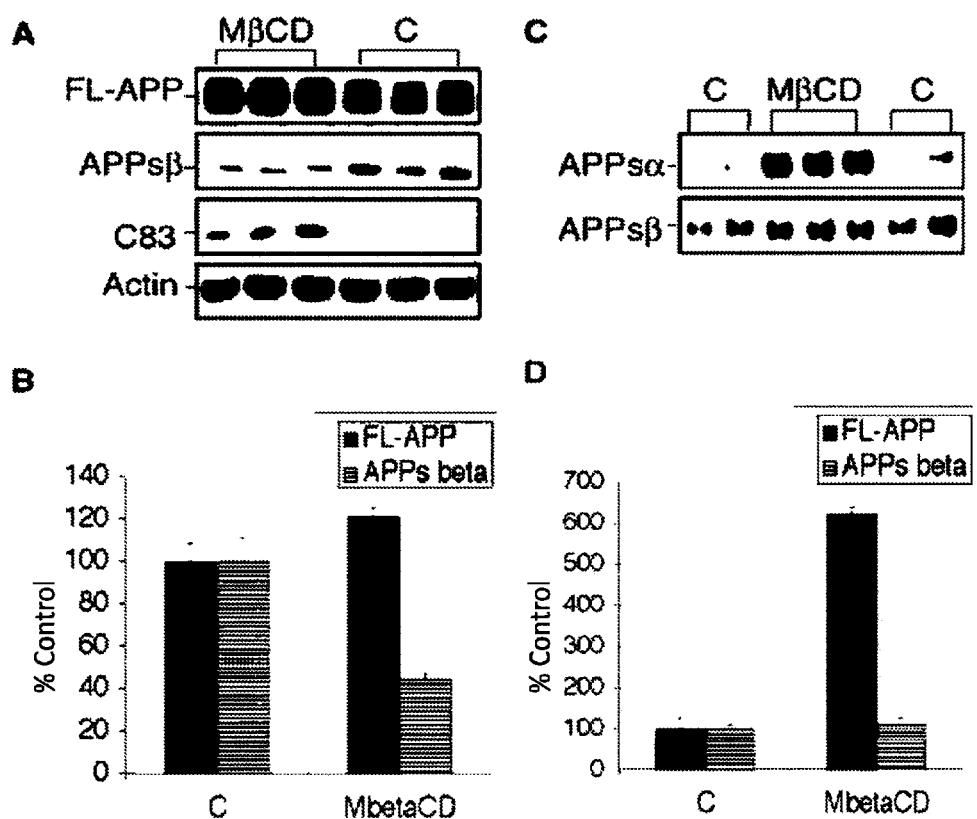
FIG. 20: MβCD in AD Mouse Cells. MβCD (M-β-CD) caused an increase in the levels of a secretase cleavage products C83 (A) and a decrease in the levels of intracellular APPsβ (A and B). APPsα levels were increased in the medium from M-β-CD-treated cells, while APPsβ levels did not change (C and D). (adapted from (Cole S L, Grudzien A, et al. (2005) J Biol Chem 280:18755-70))

AD: M-β-CD inhibits secretion of amyloid-beta from hippocampal neurons of rats infected with recombinant Semliki Forest virus (SFV) carrying APP, (Simons M, Keller P, et al. (1998) Proc Natl Acad Sci USA 95:6460-4) promotes the non-amylogenic α-secretase pathway, (Kojro E, Gimpl G, et al. (2001) Proc Natl Acad Sci USA 98:5815-20) and increased activity of α-secretase while decreasing activity of β-secretase, reducing the level of cell-associated APPsβ (FIG. 20) "[I]mpaired internalization of APP [ . . . ] is responsible for increased α-secretase cleavage after acute cholesterol depletion by MβCD". (Cole S L, Grudzien A, et al. (2005) J Biol Chem 280:18755-70) Cell membrane cholesterol accumulation was detected in N2a cells overexpressing Swedish mutant APP (SwN2a), and the level of membrane cholesterol was reduced by HP-α-CD treatment, which dramatically lowered the levels of Aβ42 in SwN2a cells, and the effects were persistent for 24 h after withdrawal. (Yao J, Ho D, et al. (2012) J Exp Med 209:2501-13)

PD: In HeLa cells transfected with α-synuclein, α-synuclein was shown to colocalize with the lipid raft. Incubation with 20 mM M-β-CD for 1 hr dramatically reduced this co-location of α-synuclein with the cell membrane. (Fortin D L, Troyer M D, et al. (2004) J Neurosci 24:6715-23)

The relevance of the above in vitro findings was confirmed by several in vivo studies.

Ca: M-β-CD had higher concentration in tumor than in other cells (except kidney and liver) and was effective in a mouse model of breast cancer, (Grosse P Y, Bressolle F, et al. (1998) Br J Cancer 78:1165-9) reduced the number of lung metastases in mice implanted with H7-O Lewis lung cancer cells, (Zhang Q, Furukawa K, et al. (2006) J Biol Chem 281:18145-55) and inhibited growth of primary effusion lymphoma (PEL) in mice. (Gotoh K, Kariya R, et al. (2014) Biochem Biophys Res Commun 455:285-9) (M-)β-CDs have found to increase the effectiveness of anti-tumor drugs, such as curcumin in a lung cancer mouse model (Rocks N, Bekaert S, et al. (2012) Br J Cancer 107:1083-92) and of raloxifen in a chemically induced tumor mouse model (Agardan N B, Degim Z, et al. (2015) AAPS PharmSciTech). HP-β-CD was necessary in triple combination treatment for tumor regression in mice implanted with renal cancer cells. (Yamaguchi R, Perkins G, et al. (2015) FEBS Lett 589:4097-105) and prolonged survival in leukemia mouse models. (Yokoo M, Kubota Y, et al. (2015) PLoS One 10:e0141946)

AD: Scavenging of cholesterol and/or binding directly to amyloid-beta or a-synuclein was also believed to be the mode of action for β-CD in Alzheimer's disease and Parkinson's disease: "HPβCD, which diminishes the pool of both cholesterol and PLs, had "neuroprotective effects [ . . . ] in a transgenic mouse model of AD [by] enhancing clearance mechanisms". Four months of subcutaneous HPβCD administration significantly improved spatial learning and memory deficits in Tg19959 mice, diminished amyloid-beta plaque deposition, and reduced tau immunoreactive dystrophic neurites (DN). Tg19959 mice are transgenic mice with 2 mutations in the amyloid precursor protein (APP) gene which have been associated with human Alzheimer's disease and beneficial effects were attributed to a reduction in cholesterol. (Yao J, Ho D, et al. (2012) J Exp Med 209:2501-13) "Toxicity of Aβ1-40/42 was reduced in rats via stereotactical injection [of β-CD] into the hippocampus," (Jameson L P, Smith N W, et al. (2012) ACS Chem Neurosci 3:807-19).

PD: "Treatment of mice with MβCD resulted in [ . . . ] reduced accumulation of α-synuclein in neuronal cell body and synapses" (Bar-On P, Rockenstein E, et al. (2006) J Neurochem 98:1032-45) This "possibly transcriptional effect of MβCD" (Bar-On P, Rockenstein E, et al. (2006) J Neurochem 98:1032-45) was seen as related to β-CD preventing aggregation of α-synuclein ex vivo (Gautam S, Karmakar S, et al. (2014) Biochemistry 53:4081-3) via direct interaction. The results of the present invention, instead, suggest that cyclodextrins act by regulating endocytosis as a common component in the etiology, the same age-related mechanism controlled by cyclodextrins in cancer.

Clinical/Epidemiological

Although Atherosclerosis and AD are comorbid, (Song Y, Stampfer M J, et al. (2004) Ann Intern Med 141:137-47) An analysis of the Framingham cohort also did not find an association between cholesterol levels and AD. (Tan Z S, Seshadri S, et al. (2003) Archives of internal medicine 163:1053-7) While HP-β-CD was effective against tumors in animal models and well tolerated in most peripheral and central organ systems, (Cronin S, Lin A, et al. (2015) J Assoc Res Otolaryngol 16:599-611) it was shown to carry the risk of causing permanent hearing loss in mice, (Crumling M A, Liu L, et al. (2012) PLoS One 7:e53280) cats, (Ward S, O'Donnell P, et al. (2010) Pediatr Res 68:52-6; Vite C H, Bagel J H, et al. (2015) Sci Transl Med 7:276ra26) and one human. (Maarup T J, Chen A H, et al. (2015) Mol Genet Metab 116:75-9) This ototoxicity is believed to be due to depriving prestin (SLC26A5) in outer hair cells of cholesterol. (Takahashi S, Homma K, et al. (2016) Sci Rep 6:21973; Kamar R I, Organ-Darling L E, et al. (2012) Biophysical Journal 103:1627-36; Yamashita T, Hakizimana P, et al. (2015) PLoS Genet 11:e1005500)

The Mechanism of HP-β-CD is Independent of Cholesterol

The direct action of cyclodextrins consists in extracting lipids (cholesterol and phospholipids) from membranes and serum. After parenteral application, the lipids are excreted into urine. From the mechanism of β-CD in NPC and elevated cholesterol levels seen in several cancers, including breast cancer, (Yokoo M, Kubota Y, et al. (2015) PLoS One 10:e0141946) β-CDs are thought to reduce cancer growth by lowering cholesterol levels. In Alzheimer's disease, HP-β-CD is believed to act on hydrophobic residues of another large lipid, amyloid-beta.

Early evidence that HP-β-CD might not exert its action by directly binding top large lipids emerged from the study of exosomes, which play a key role in development of breast cancer (Lowry M C, Gallagher W M, et al. (2015) Clin Chem 61:1457-65; Peinado H, Lavotshkin S, et al. (2011) Semin Cancer Biol 21:139-46). Treatment of MDA-MB-231 breast cancer cells with M-β-CD inhibited the internalization of exosomes containing integrins, (Hoshino A, Costa-Silva B, et al. (2015) Nature 527:329-35) but did so independently of cholesterol. (Koumangoye R B, Sakwe A M, et al. (2011) PLoS One 6:e24234)

Figure 21:
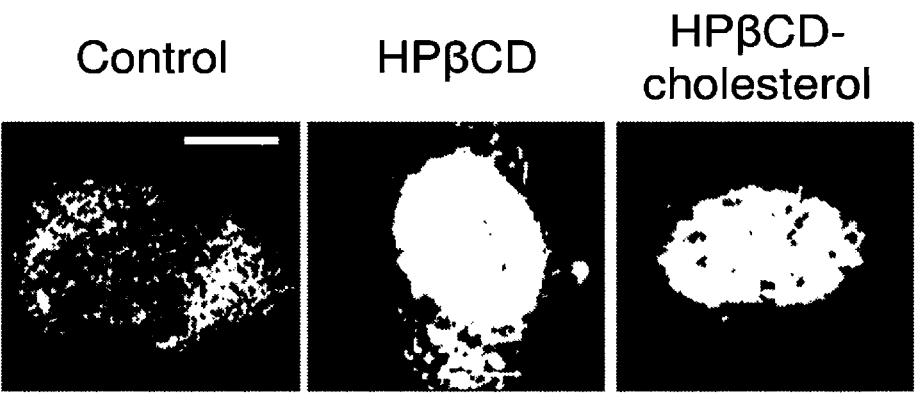
FIG. 21: HP-β-CD Clearance of a-Syn. HP-β-CD-mediated clearance of a-syn aggregates does not depend on the ability of HP-β-CD to alter cholesterol levels. H4/a-syn-GFP cells untreated or treated with HP-β-CD (1 mM) or HP-β-CD-cholesterol complex (1 mM) for 24 h. Representative images are reported. 21A) Immunofluorescence microscopy analyses of TFEB subcellular localization using a FLAG-specific anti-body. Scale bar represents 10 µm. 21B) a-syn-GFP fluorescense microscopy analyses. Scale bar represents 20 µm. Modified from FIG. 6 in (Kilpatrick K, Zeng Y, et al. (2015) PLoS One 10:e0120819).
Figure 21:
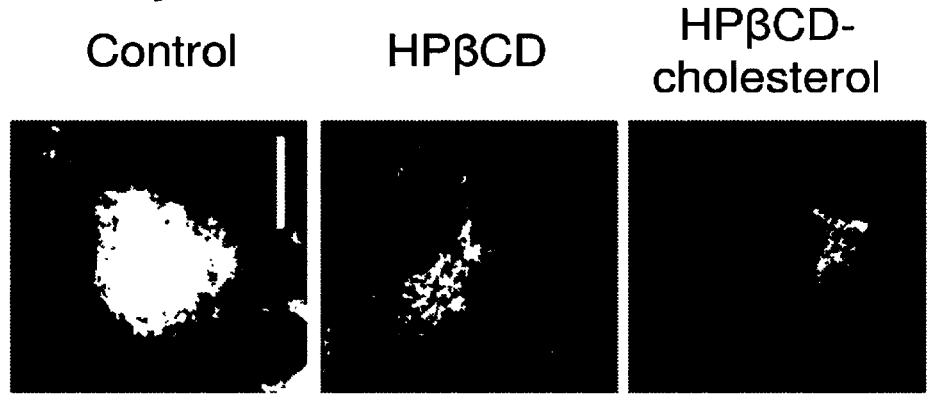

In fact, broad evidence suggests that cholesterol is not involved. Although CAD and Alzheimer's disease are comorbid, (Song Y, Stampfer M J, et al. (2004) Ann Intern Med 141:137-47) an analysis of the Framingham cohort did not find an association between cholesterol levels and Alzheimer's disease. (Tan Z S, Seshadri S, et al. (2003) Archives of internal medicine 163:1053-7) In Parkinson's disease, the effect of HP-β-CD on clearance of a-syn is independent on cholesterol (Kilpatrick K, Zeng Y, et al. (2015) PLoS One 10:e0120819) (FIG. 21).

Figure 28:
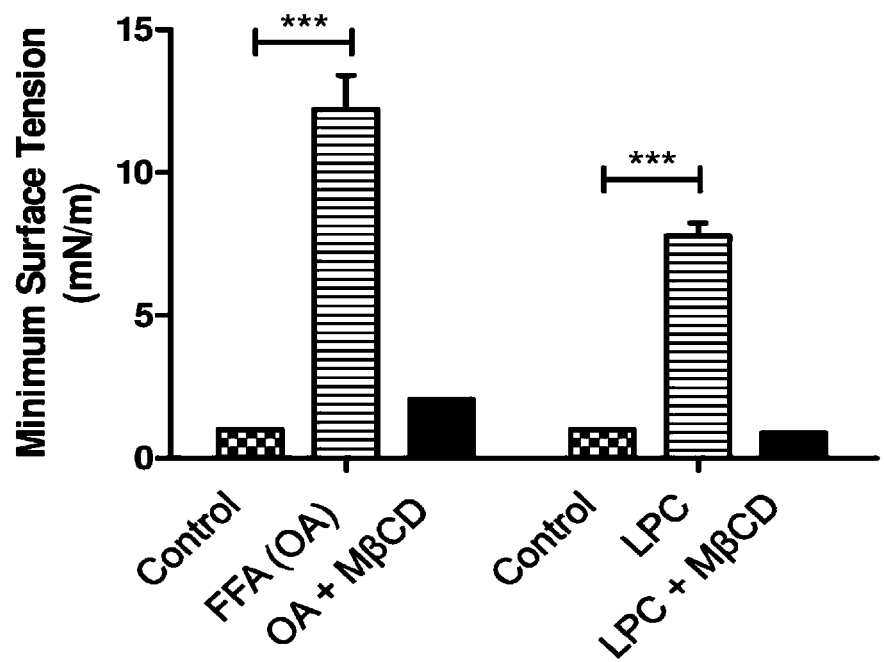
FIG. 28: MβCD Restores Surface Tension. "Minimum surface tension during dynamic cycle 20 with [Bovine Lipid Extract Surfactant] BLES containing 27 mg/ml BLES in control CBS buffer (checkers bars), 50% w/w FFA (oleic acid [, OA]) or LPC in control CBS buffer (horizontal bars) or buffer containing 40 mg/ml M-β-CD (solid black bars). (\*\* p≤0.01, \*\*\* p≤0.001). BLES with FFA or LPC shows marked impairment, which is repaired to normal functionality in the presence of M-β-CD. Cholesterol was present at very low concentrations (~2.1%) in these experiments." Modified from Supplementary Figure S6 in (Gunasekara L, Al-Saiedy M, et al. (2017) Journal of cystic fibrosis: official journal of the European Cystic Fibrosis Society)

A recent study compared surface activity of surfactant in bronchial lavage fluid (BLF) from 16 cystic fibrosis patients treated with M-β-CD and 9 healthy controls. Alveolar macrophages were enlarged as a result of lysosomal lipid overload. Since release of FFAs, such as arachidonic acid, oleic acid, LPC, and lysophosphatic acid (LPA). It was concluded that hydrolysis products of PC, LPC and FFAs, inhibited surfactant function. This dysfunction was reversed by MβCD even in the relative absence of cholesterol (FIG. 28), and M-β-CD also reduce the inflammatory effects of these products. (Gunasekara L, Al-Saiedy M, et al. (2017) Journal of cystic fibrosis: official journal of the European Cystic Fibrosis Society; Strandvik B (2010) Prostaglandins, leukotrienes, and essential fatty acids 83:121-9) The common involvement of AA and LPC is consistent with the known comorbidity between fibroses and CAD (Skolnik K, Levy R D, et al. (2016) Journal of cystic fibrosis: official journal of the European Cystic Fibrosis Society 15:e70-e1)

Figure 22:
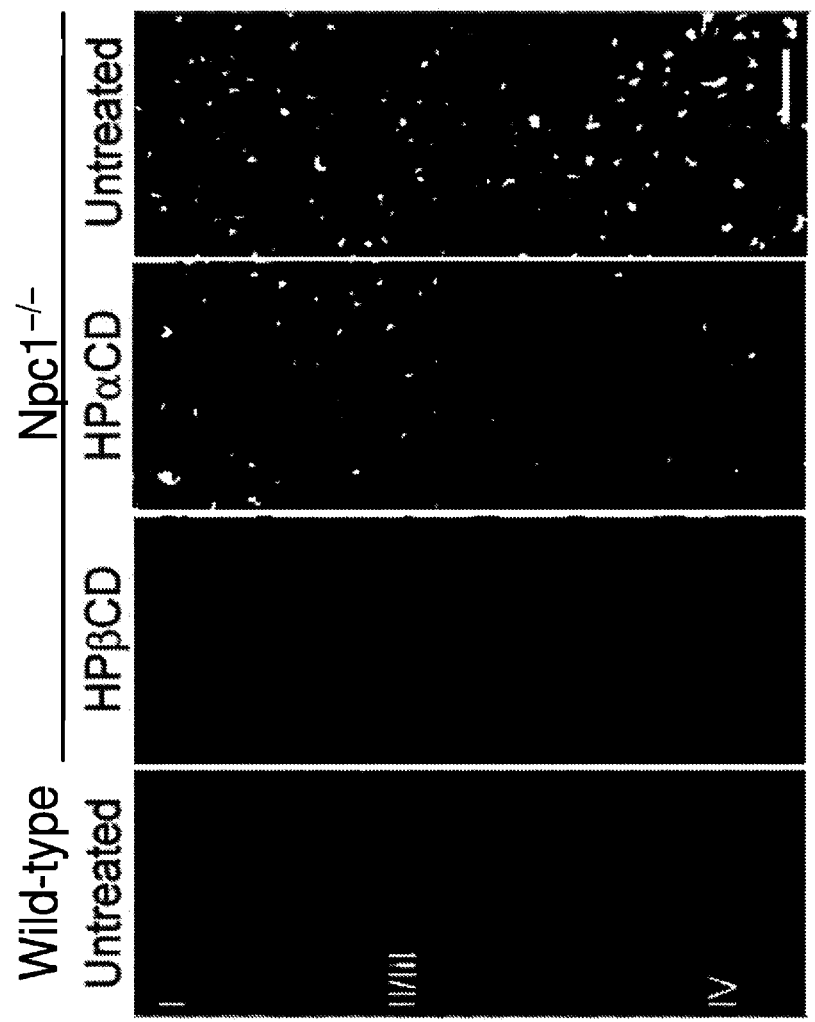
FIG. 22: Cholesterol Accumulation in Mouse Brain. Unesterified cholesterol (UC) accumulation in the brain cells of 3-week-old mice treated with different CDs. Sample fluorescence photomicrographs of dorsal neocortex from untreated stained with filipin to detect UC. Cortical layers are marked by roman numerals. Virtually, all neurons in untreated Npc1$^{-/-}$ mice show positive cytoplasmic staining of UC (white spots), where as those in Wt mice are negative. HP-β-CD shows highly effective reduction in UC storage. HP-α-CD UC storage, albeit clearly reduced, was reported by the authors as "grossly equivalent to untreated mice". Modified from FIG. 1 in (Davidson C D, Fishman Y I, et al. (2016) Ann Clin Transl Neurol 3:366-80).

Even in NPC, where cholesterol is seen to accumulate in late endosomes and lysosomes, the mechanism of action is uncertain and its molecular target is unknown, (Dai S, Dulcey A E, et al. (2017) Autophagy 13:1435-51) except that HP-β-CD was shown to work in a manner that is independent of the functions of the actions of NPC1 and NPC2 on cholesterol. (Liu B, Li H, et al. (2008) J Lipid Res 49:663-9) Moreover, mechanistic studies have shown that some of the effects of β-CDs are also seen with α-CDs, which is too small to fit cholesterol. (Shvartsman D E, Gutman O, et al. (2006) Traffic 7:917-26) In Npc1a mice, for instance, HP-α-CD reduces cholesterol accumulation, albeit not as effectively as HP-β-CD (FIG. 22).

In US 2015/0216895 A1 (McKew J, Zheng W E I, et al. (2014)), M-β-CD was the most effective cyclodextrin against various LYD diseases (FIG. 23) and the proposed combination with 10 μM delta-toxopherol (vitamin E) reduced the concentrations needed and, thus, reduced (but not eliminated) the risk of oto- and nephrotoxicity. While α-CD (and HP-β-CD) were less effective than M-β-CD, it was not appreciated that the fact that α-CD (which cannot fit cholesterol) was similarly effective as HP-β-CD (which can fit cholesterol) implies that the effects cannot be due to scavenging of cholesterol.

Our surprising genetics results show that the effect of β-CDs seen in age-related diseases is not mediated by cholesterol, as but by phospholipids and, thus, suggest for the first time that the less toxic α-CDs is preferable over the more toxic HP-β-CD and M-β-CD for the treatment and prevention of age-related diseases, disorders, and conditions, and even for the treatment of LYD diseases.

Example 5: HPβCD Activates Formation of Autophagolysosomes Through a Mechanism Involving Reduction of Serum Phospholipids "Genetic variation in lysosomal genes modifies the disease course of sporadic AD". (Whyte L S, Lau A A, et al. (2017) J Neurochem 140:703-17). Autophagy has been linked to human oral diseases, including but not limited to "periapical lesions, periodontal diseases, and oral candidiasis". (Tan Y Q, Zhang J, et al. (2017) Autophagy 13:225-36) "Crosstalk between [autophagy] and other cellular stresses [have been] implicated in ALS pathogenesis [with] therapeutic implications of regulating [autophagy] in ALS." ATG16L1, a regulator of autophagy is consistently associated with inflammatory bowel disease (including, but not limited to, Crohn's disease and ulcerative colitis). (Pugazhendhi S, Baskaran K, et al. (2017) PLoS One 12:e0178291). Autophagy "is emerging as a core regulator of Central Nervous System (CNS) aging and neurodegeneration, [affecting diseases] including ischemia/stroke, Alzheimer's, Parkinson's, and Huntington's, and multiple sclerosis, [ . . . ] involving microglial phagocytosis of apoptotic cells, amyloid-beta (Aβ), synaptic material, and myelin debris, and regulate the progression of age-associated neurodegenerative diseases." (Plaza-Zabala A, Sierra-Torre V, et al. (2017) Int J Mol Sci 18)

Figure 24:
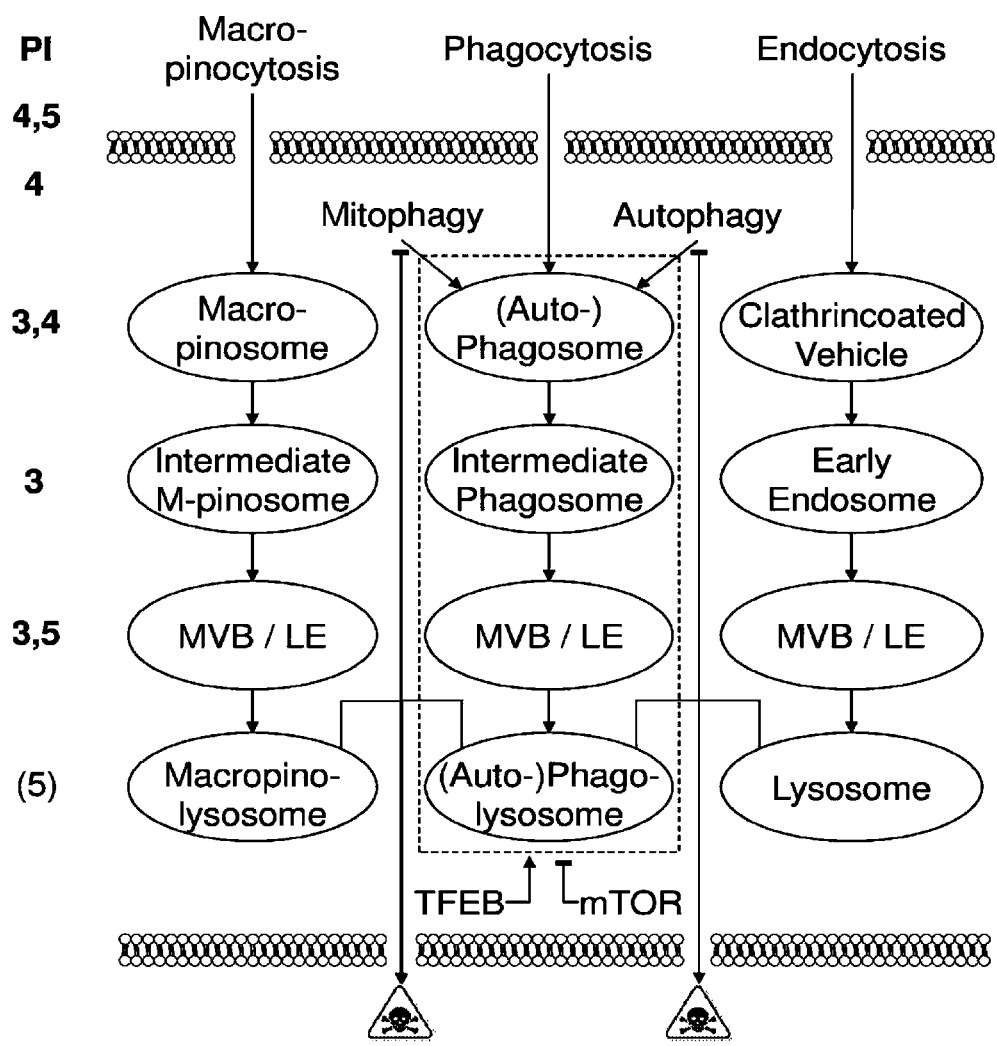
FIG. 24: Pino-/Phago-/Endocytosis: Macropinocytosis, phagocytosis, and endocytosis are regulated in the same fashion by the PI cycle and lysosomal dysfunction in all three processing pathways causes substrates with unwanted function to be excreted (modified from FIG. 1 in (Sole-Domenech S, Cruz D L, et al. (2016) Ageing Res Rev 32:89-103)).

Activation of autophagy has been deemed desirable in Parkinson's disease (Moors T E, Hoozemans J J, et al. (2017) Mol Neurodegener 12:11), Alzheimer's disease, Huntington's disease, and ALS (Moloudizargari M, Asghari M H, et al. (2017) Ageing Res Rev 40:64-74), yet no effective drugs are available. "mTOR has been shown to be [a] key regulator but the detailed mechanisms are not satisfactorily solved." (Chen Y, Yu L (2017) Traffic 18:358-61) (FIG. 24)

The transcription factor EB (TFEB) regulates the expression of genes belonging to the Coordinated Lysosomal Expression and Regulation (CLEAR) network and of genes involved in autophagy. Overexpression of TFEB was found to decrease the accumulation of huntingtin aggregates in a rat cell model of Huntington's disease (Settembre C, Di Malta C, et al. (2011) Science 332:1429-33) and also to reduce neurodegeneration in in vitro and in vivo models of Parkinson's disease by restoring lysosome levels and increasing autophagic clearance (Decressac M, Mattsson B, et al. (2013) Proc Natl Acad Sci USA 110:E1817-26; Dehay B, Bove J, et al. (2010) J Neurosci 30)." (Kilpatrick K, Zeng Y, et al. (2015) PLoS One 10:e0120819)

Figure 25:
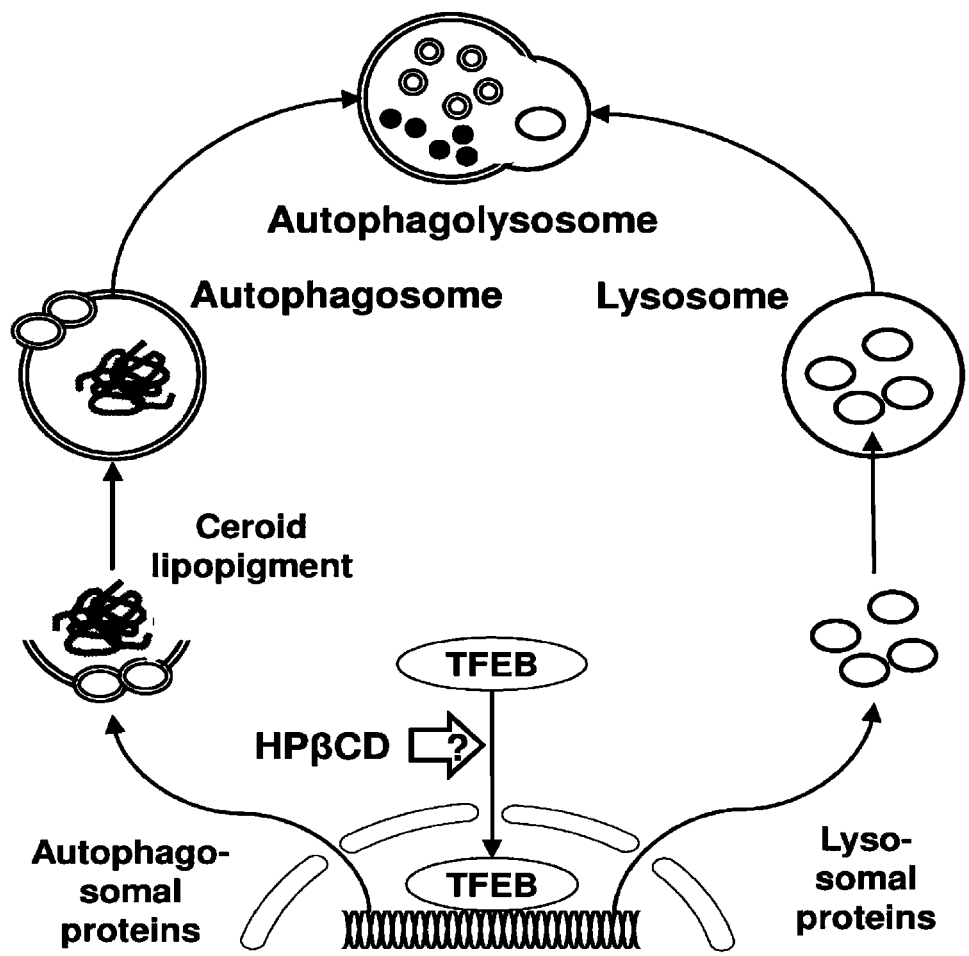
FIG. 25: HPβCD activates autophagy. Administration of HP-β-CD results in activation of transcription factor EB TFEB. Upon translocation from the cytoplasm to the nucleus, TFEB regulates the expression of genes involved in biogenesis and fusion of lyso- and autophago-somes. As a result, HP-β-CD administration results in enhanced clearance of the autophagy substrate ceroid lipo-pigment. The mechanism by which HP-β-CD improves TFEB activation, however, was not understood (adapted from (Song W, Wang F, et al. (2014) J Biol Chem 289:10211-22))

Treatment of HeLa/TFEB cells with HP-β-CD up-regulated Microtubule-associated protein 1A/1B-light chain 3 (LC3), which is essential for the formation of autophagy vesicles, SQSTM1/p62 which is essential for cargo recognition, and BECN1, which is required for the formation of autophagosomes. In late infantile neuronal ceroid lipofuscinosis (LINCL) fibroblasts, which lack TPP1, HP-β-CD treatment resulted in clearance of ceroid lipopigment in a dose- and time-dependent fashion. HP-β-CD treatment resulted in transcriptional up-regulation of all autosomal (LC3, SQSTM1, BECN1) lysosomal genes tested (GBA, HEXA, LAMP1) through activation of TFEB. HP-β-CD treatment results in coordinated up-regulation of lysosome biogenesis and autophagy and enhanced autophagic clearance through TFEB-induced activation of the autophagy system, but blockage of downstream steps of the autophagy flux (e.g. blockage of ATG7 expression) prevents clearance of ceroid lipopigment. HP-β-CD activates the pro-survival autophagy pathway, but not apoptosis. Impairment or deregulation of autophagy is linked to the development and progression of a number of human diseases ranging from neurodegenerative diseases to cancer. The use of HP-β-CD was suggested for the treatment of diseases characterized by inefficient autophagic clearance and accumulation of storage material, although the mechanism of HP-β-CD's action remained unknown (FIG. 25) (Song W, Wang F, et al. (2014) J Biol Chem 289:10211-22).

"HPbCD was shown to induce nuclear translocation of TFEB, upregulation of the CLEAR network, and increase in autophagic clearance (Song W, Wang F, et al. (2014) J Biol Chem 289:10211-22). In particular, activation of TFEB in neuroglioma cells with HP-β-CD promoted clearance of a-syn aggregates (Parkinson's disease) via autophagy. (Kilpatrick K, Zeng Y, et al. (2015) PLoS One 10:e0120819) M-β-CD also reduces α-syn aggregation [in vitro and in vivo] (Bar-On P, Rockenstein E, et al. (2006) J Neurochem 98:1032-45);

However, the molecular mechanism underlying M-β-CD's and HP-β-CD's action on autophagy "are unclear." (Kilpatrick K, Zeng Y, et al. (2015) PLoS One 10:e0120819) or "still needs to be clarified", (Sardiello M (2016) Ann N Y Acad Sci 1371:3-14) respectively, although it is known that it is not mediated via cholesterol. "[W]e tested TFEB activation and accumulation of α-syn aggregates in cells treated with HPbCD-cholesterol inclusion complexes . . . .

Confocal microscopy . . . revealed that [both] the extent of nuclear translocation . . . of TFEB . . . (FIG. 21A) [and] clearance of a-syn aggregates (FIG. 21B) [are] independent of HPbCD [sic] ability to deplete . . . cholesterol." (Kilpatrick K, Zeng Y, et al. (2015) PLoS One 10:e0120819)

Figure 26:
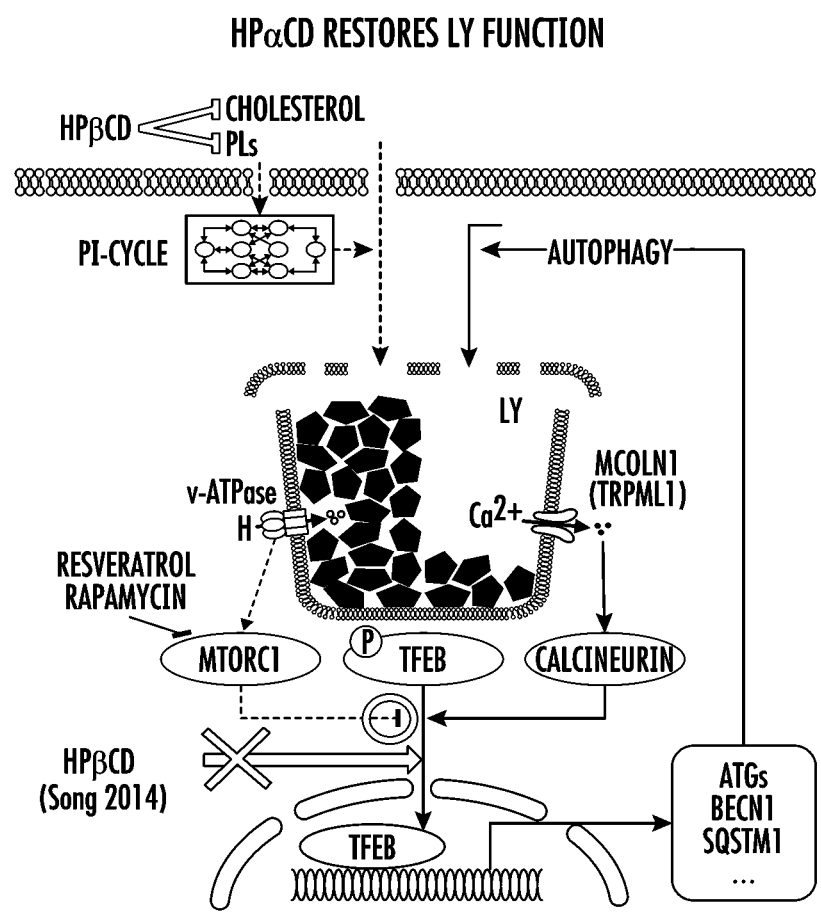
FIG. 26: Activation of TFEB by HPbCD: HP-β-CD has been shown to activate transcription factor EB (TFEB), yet the mechanism of action is unknown (FIG. 25). The unexpected genetics results (Example 2) confirmed by the urinalysis results (Example 16) showed that the mechanism of action of HP-β-CD is (a) reduction of serum phospholipids, (b) reduction of PI-cycle activity, (c) reduction of endocytosis, (d) prevention of lysosomal stress, (e) prevention of MTORC1 activation, (f) continued dephosphorylation and translocation of TFEB, (g) continued activation of autophagy. Adapted from (Kim S, Choi K J, et al. (2016) Sci Rep 6:24933; Medina D L, Ballabio A (2015) Autophagy 11:970-1)

The surprising genetic results of Example 1 provide the answer. It is already known that PI3K inhibitors, which interfere with the function of the PI cycle (FIG. 12) promote TFEB nuclear translocation. (Cheng J, Ohsaki Y, et al. (2006) Biochem Biophys Res Commun 351:246-52) HP-β-CD reduces activity of the entire PI cycle by scavenging phospholipids, thus, promotes TFEB nuclear translation in a more consistent fashion than PI3K inhibitors (which act primarily via the PI3K/mTOR/TFEB pathway), but without causing imbalances within the PI cycle (FIG. 26).

This novel finding is supported by other evidence. Paeoniflorin is known to act by reducing serum lipids, (Yang H O, Ko W K, et al. (2004) Fitoterapia 75:45-9) the common mechanism of action of cyclodextrins. Paeoniflorin mitigates the disease phenotype of mice with spinobulbar muscular atrophy (SBMA), where autophagy in the spinal cord is diminished. Paeoniflorin has been successfully tested in animal models of LPC induced inflammation (Li J Z, Wu J H, et al. (2013) Int J Mol Med 31:493-7) and, like cyclodextrins of NAFLD, (Ma Z, Chu L, et al. (2017) Sci Rep 7:44819) insulin resistance, (Ma Z, Liu H, et al. (2017) Biomed Pharmacother 90:361-7) and atherosclerosis. (Li H, Jiao Y, et al. (2017) Inflammation 40:2042-51)

Example 6: Elevated Phagocytosis Combined with Lysosomal Dysfunction is a Known Component in the Etiology of Multiple Sclerosis (MS)

Early studies of MS in the 1970s reported "myelin-like material in lysosomes" and "synthesis of abnormal myelin by diseased glial cells" in spite of "increased lysosomal reaction", including increased β-glycoronidase activity (Cuzner M L, Davison A N (1973) J Neurol Sci 19:29-36) and "suggest[ed] early changes of glial cells as a basic mechanism of the disease." It was hypothesized "that some acquired exogenous factor like virus infection is the basic cause which will trigger off the disease and the immunopathology." (Riekkinen P J, Rinne U K, et al. (1972) Zeitschrift fur Neurologie 203:91-104)

In 1977, three lysosomal enzymes, N-acetyl-β-d-glucosaminidase (MGEA4, also known as HEXC), β-galactosidase (GLB1), and cathepsin D (CTSD) were found up-regulated, the highest activity in plaque areas." (McKeown S R, Allen I V (1977) Biochem Soc Trans 5:1416-8; (1979) Neuropathol Appl Neurobiol 5:405-15) Enzyme levels in serum and CSF, in general, were not elevated in MS. (Hultberg B, Olsson J E (1978) Acta Neurol Scand 57:201-15; (1979) Acta Neurol Scand 59:23-30)

In 1980, it was suggested that "[macrophage]s were stimulated to increase lysosomal enzyme activity, initiated by stimulation of T-lymphocytes caused by MS-specific antigen", (Rastogi S C, Clausen J (1980) Clin Exp Immunol 42:50-6) yet no such antigens were identified, except that "a microglial component" is likely involved (Allen I V (1981) Neuropathol Appl Neurobiol 7:169-82)

In 1983, a "2-step demyelination" hypothesis was proposed: (1) a toxin penetrates into myelin, and its degradation creates antigen. (2) Antigen-activated macrophages settle in and digest myelin. (Schwyzer R U, Henzi H (1983) Med Hypotheses 12:129-42) yet the toxin remained elusive. (Tulpule K, Dringen R (2013) Journal of Neurochemistry 127:7-21)

In 1996, still, "little is known about the source of [activated] macrophages in the early stages of plaque evolution . . . . A key issue in understanding the pathogenesis of MS is the reliable identification of phagocytes capable of degrading myelin and presenting autoantigen to T cells at the onset of demyelination, [although] results indicate that microglia are the main population of phagocytes in the early staged of demyelination." (Li H, Cuzner M L, et al. (1996) Neuropathol Appl Neurobiol 22:207-15)

Aside from confirming HLA-DRB 1*15:01 as a risk factor, a recent "metaanalysis" of 7125 cases (George M F, Briggs F B, et al. (2016) Neurology Genetics 2:e87) did not provide any actionable insights.

Microglia have "similar transcriptome pattern" to macrophages; the function of microglia is to "scan the entire volume of the brain over the course of a few hours". Hence, it has been proposed that dysregulation of microglial function contributes to CNS disorders, and that "targeting the mechanisms that are dysregulated may arrest or reverse neurodevelopmental and neurodegenerative disorders in which microglia play a role." (Salter M W, Stevens B (2017) Nat Med 23:1018-27) During the process of scanning the brain, microglia either targets the substrates for degradation by the lysosome or, in the case of pathogens, processes it for antigen presentation. "endocytosis, sorting, transport, compartment acidification, and degradation . . . may be altered during aging". (Sole-Domenech S, Cruz D L, et al. (2016) Ageing Res Rev 32:89-103)

Figure 27:
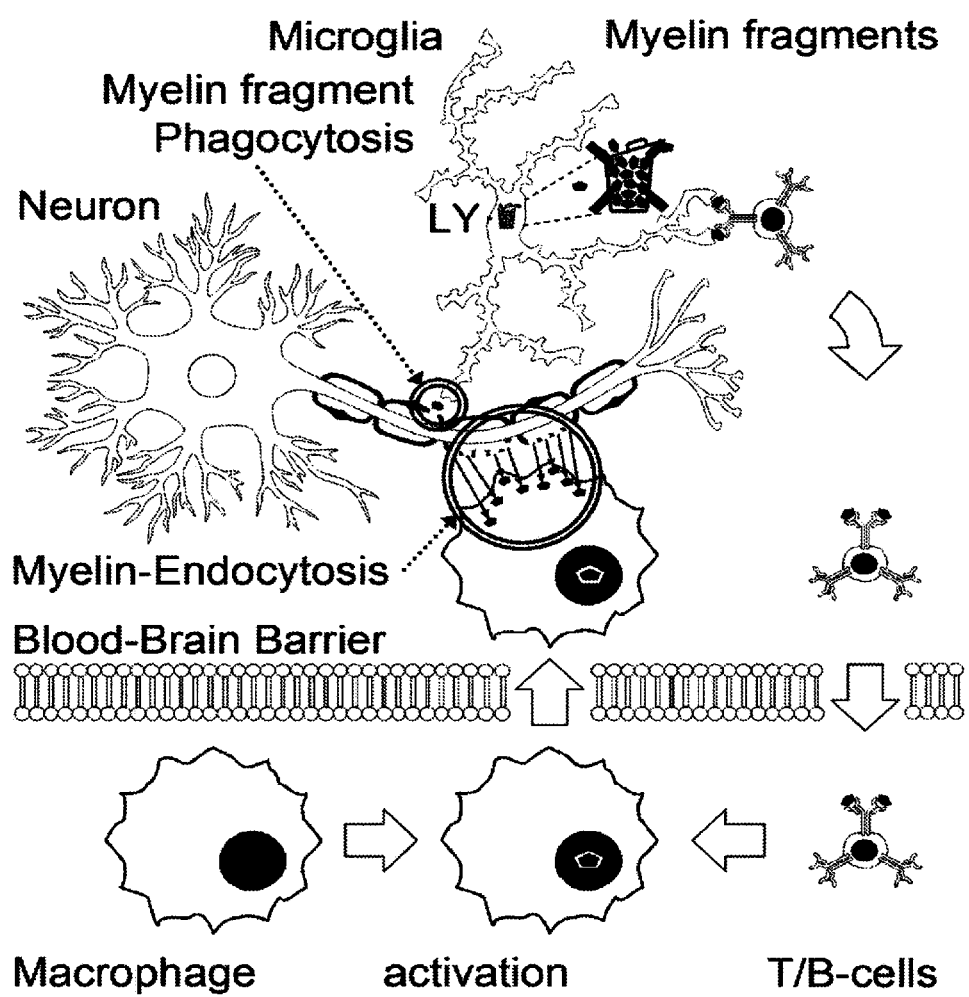
FIG. 27: Phago-/Endocytosis in Multiple Sclerosis (MS). The vicious cycle in the etiology of MS starts with microglia phagocytosing a probes of myelin from the healthy myelin sheath. If the lysosome (LY) is losing its ability to discard all of these probes, some of them are presented as antigens to T- and B-cells, which then cross the blood-brain barrier (BBB) to activate peripheral macrophages. These macrophages then infiltrate the CNS and endocytose myelin for destruction. (Modified from (Salter M W, Stevens B (2017) Nat Med 23:1018-27; Luo C, Jian C, et al. (2017) Neuropsychiatr Dis Treat 13:1661-7)) Equivalent mechanisms are involved in Alzheimer's disease and Rett syndrome. (Prinz M, Priller J (2014) Nat Rev Neurosci 15:300-12)

The current invention links two recent findings in atherosclerosis and Fabry disease to the etiology of MS. Foamy macrophages, containing myelin degradation products, are abundantly found in active MS lesions. (Bogie J F, Jorissen W, et al. (2013) Acta Neuropathol Commun 1:43) Fabry disease, a deficiency of lysosomal alpha-galactosidase A (GLA) is often mis-diagnosed as MS (Germain D P (2010) Orphanet journal of rare diseases 5:30; Bottcher T, Rolfs A, et al. (2013) PLoS One 8:e71894) and both diseases show familial comorbidity. (Cammarata G, Fatuzzo P, et al. (2015) Biomed Res Int 2015:504784) From the better understanding of the mechanism causing foamy macrophages in atherosclerosis (intake of more LDL than lysosomes can handle, FIG. 17) and Fabry disease (lack of lysosomal galactosidase activity), the nature of the "toxin" becomes evident. The process starts, in fact, with the microglia. (Riekkinen P J, Rinne U K, et al. (1972) Zeitschrift fur Neurologie 203:91-104) When the microglial lysosomes cannot degrade all the myelin that is phagocytosed during scanning of the entire brain, the undegraded myelin is accidentally presented to the T-cells waiting for antigens from the microglia as "MS-specific antigen" (Rastogi S C, Clausen J (1980) Clin Exp Immunol 42:50-6) and the T-cells then move to the circulation to activate macrophages against myelin. The activated macrophages return to the CNS where they begin to—mistakenly—endocytose myelin (FIG. 27).

As the process is the same as in Alzheimer's disease, Parkinson's disease, and CAD, the solution is the same: Slowing down phagocytosis of myelin by aging microglia prevents the lysosomes from "overflowing" and, thus, myelin from being presented to macrophages as "MS-specific antigen". Slowing down endocytosis of myelin by macrophages further reduces demyelination in case that not all "MS-specific antigens" can be prevented.

In support of shared risk factors, MS and vascular diseases are comorbid. "[H]aving type-2-diabetes, hypertension, dyslipidemia or peripheral vascular disease at any point in the disease course may be associated with a greater progression in disability . . . . The results of published clinical trials of statins as an intervention in MS were however conflicting." (Tettey P, Simpson S, Jr., et al. (2014) J Neurol Sci 347:23-33)

M-β-CD enhancing CD30 shedding has been suggested in Th1-mediated diseases, such as MS and RA. (von Tresckow B, Kallen K J, et al. (2004) Journal of Immunology 172: 4324-31)

Example 7: Phospholipids as a Drug Target

The invention provides the phospholipids entering the PI cycle as the drug target (Example 1) and α-CDs as a safer version of a class of drugs (β-CDs) that have been demonstrated to be effective in models of Alzheimer's disease, Parkinson's disease, and CAD and in humans with other lysosomal function diseases (including, but not limited to, NPC).

The results presented here show that the number of combinations of genes involved in endocytosis across different patients is too large for the goal of "targeting endocytosis" to be likely achieved by targeting selected phosphatases or kinases (Table 5) or genes regulated by the PI cycle (Table 6). As discussed above, the PI cycle is designed to compensate for dysregulation of individual kinases or phosphatases. "Decreasing levels of PA" by siRNA directed toward DGKQ or PLD and use of several inhibitors (including Wortmannin) and activators aiming at "increasing intracellular levels of PIP1 and/or PIP2" were proposed based on the linear PI-PIP1-PIP2-PIP3 model and the effect of amyloid-beta on PA and phosphoinositides. (Kim T W, Di Paolo G, et al. (2012) U.S. Pat. No. 8,288,378) (U.S. Pat. No. 8,288,378)

Downregulating the entire PI cycle, however, could achieve the goal of reducing endocytosis. The breadth of genes involved in entry of PI and PC into the PI cycle suggests a different strategy as more effective. Reduction of serum phospholipids reduces the intracellular concentration of phosphoinositides, which are known to regulate endocytosis during ligand binding (PI(4,5)P2), pit-formation (PI(4)P), vesicle formation (PI(3,4)P2), fusion to early endosomes (PI(3)P), and sorting into cell organelles, including lysosomes (PI(3,5)P2). "Activation of signal transduction pathways associated with endocytic trafficking is critical for tumor cell migration [and disease progression in Parkinson's disease/Alzheimer's disease]. As a consequence, [ . . . ] targeting endocytic trafficking and signaling could potentially allow for the development of novel cancer therapeutics to prevent metastasis [and anti-aging therapeutics to prevent Parkinson's disease and Alzheimer's disease]." (Chew C L, Chen M, et al. (2016) Oncotarget 7:5-6)

For instance, FAK (integrin-mediated focal adhesion kinase) is overexpressed and activated in tumors, but rarely mutated. (Alanko J, Ivaska J (2016) Trends Cell Biol 26:391-8) FAK inhibitors have been shown to decrease tumor growth, metastasis, and angiogenesis in mice, and are in early clinical trials for non-hematologic cancers, including, but not limited to, pancreatic cancer, lung cancer, mesothelioma, and ovarian cancer, with mixed results (clinicaltrials.gov). Regulating endocytosis of integrins provides an alternative strategy for reducing the activity of FAK, either alone or in combination with immunotherapy. (Symeonides S N, Anderton S M, et al. (2017) Journal for immunotherapy of cancer 5:17)

Example 8: α-CD is More Efficient than β-CD in Solubilizing Phospholipids

In some embodiment of the present disclosure α-CDs are used for treating age-related conditions, such as cancers (including, but not limited to, breast and prostate cancer) and neurodegenerative diseases (including, but not limited to, Parkinson's disease or Alzheimer's disease). Cyclodextrins lower the amount of phosphoinositides available without directly interfering with their distribution.

Scavenging phospholipids, which regulate endocytosis more specifically (by α-CD, six sugar molecules), rather than also scavenging larger cholesterol molecules (by the larger β-CD, seven sugar molecules) avoids cholesterol-mediated side effects, including ototoxicity. (Cronin S, Lin A, et al. (2015) J Assoc Res Otolaryngol 16:599-611). "The acryl chain of phospholipids fits tightly into the hydrophobic cavity of the smallest α-CD and more loosely into the larger inner space of β- and γ-CDs, whereas the side chain of cholesterol is preferably included in the β-CD cavity." (Irie T, Uekama K (1997) J Pharm Sci 86:147-62) "Cyclodextrins partially removed phospholipids . . . with a potency of α>β>>γ. Cholesterol . . . was extracted . . . most effectively by [β-CD] . . . , while [the effect] of [α-CD] was negligible even at hemolytic concentrations." (Ohtani Y, Irie T, et al. (1989) European Journal of Biochemistry 186:17-22) "β-CD also remove proteins from erythrocyte membranes" (Irie T, Uekama K (1997) J Pharm Sci 86:147-62) (FIG. 3).

At 10 mM, α- and β-cyclodextrin reduce transferrin endocytosis by 20% and 80%, respectively. The reduction by 20% has been interpreted as α-cyclodextrin not having "any significant effect" (Rodal S K, Skretting G, et al. (1999) Molecular Biology of the Cell 10:961-74). The results presented here, however, show that these results are consistent with a more physiologic 30% reduction of phospholipids, rather than an extreme 95% reduction of cholesterol (FIG. 3) (Ohtani Y, Irie T, et al. (1989) European Journal of Biochemistry 186:17-22). Moreover, even increasing the concentration of α-cyclodextrin above 10 mM does not increase release of phospholipids, which might disrupt vital functions, while increasing the concentration of β-cyclodextrin results in a massive increase of protein release (FIG. 3). Hence, at the same level where β-cyclodextrin interferes with vital cell function by limiting available cholesterol, α-cyclodextrin merely reduces endocytosis to normal ranges by reducing regulatory phospholipids. (Ohtani Y, Irie T, et al. (1989) European Journal of Biochemistry 186:17-22)

"PIPs are [also] involved in . . . common [neurodegenerative diseases] such as [Alzheimer's disease] that are becoming more widespread as life expectancy increases". (Waugh M G (2015) Biochim Biophys Acta 1851:1066-82)] Membrane anchored inhibitors of β-secretase have been postulated as a strategy to prevent endocytosis of APP. (Rajendran L, Knolker H-J, et al. (2010) Nat Rev Drug Discov 9:29-42) The results presented herein provide reduction of overall endocytosis by attenuation of PI levels via α-CD as an alternative to inhibiting β-secretase (FIG. 4), which has higher affinity for neuregulin than for APP. (Ben Halima S, Mishra S, et al. (2016) Cell Rep 14:2127-41)

Since cyclodextrins have been successfully applied both intravenously and intrathecally, different routes of administrations can be used to prevent bone and lung metastases v. glioblastoma and neurodegenerative diseases.

Materials: The degree of substitution for α-, β-, and γ-HP-CDs was 5.3, 5.1, and 5.4, respectively. In preparations of samples, 5% (w/w) NaOH was used as a solvent and catalyst in the condensation reaction of epoxide with cyclodextrin. Radioactive lipids were purchased from NEN Research Products, Boston, Mass., and nonradioactive lipids were purchased from Sigma Chemical Company, St. Louis, Mo. (Irie T, Fukunaga K, et al. (1992) J Pharm Sci 81:524-8)

Methods: Measurement of lipids was accomplished with clinical diagnostic kits (Sigma and Wako Chemicals, Dallas, Tex.). Solubilities of lipids were measured after brief sonication of the suspension of an excess of radioactive sample (in phosphate-buffered isotonic saline, pH 7.4; in a closed vessel under argon atmosphere) and equilibration by shaking (for cholesterol, the period of shaking was 1 week; for cholesterol oleate, L-α-dipalmitoylphosphatidylcholine, and triolein, the period of shaking was 3 days). Thereafter, the suspension was filtered through a membrane filter (Millex; SLGS, 0.25; OS, 0.22 µm), and the radioactivity in the filtrate was measured by liquid scintillation counting. The same process was used for sphingomyelin, except that 1 day of shaking and a clinical kit for measurement of phospholipids were used. These methods are prone to yield somewhat higher values for the solubilities of surface-active compounds in buffer, because the filtrate is enriched by the mono-layers of the surface-active compound that form at the air-buffer interface. However, these methods are suited for measurement of solubilities of lipids in HP-CD solutions. This fact was established by comparing results obtained with the filtration methods described above and those from a method that used titration of a lipid sample with a solution of HP-CD, with the end point of dissolution being determined visually. The same titration method was used to establish that cholesterol and cholesteryl methyl ether dissolve in the solutions of HP-β-CD to about the same extent. (Irie T, Fukunaga K, et al. (1992) J Pharm Sci 81:524-8)

Figure 32:
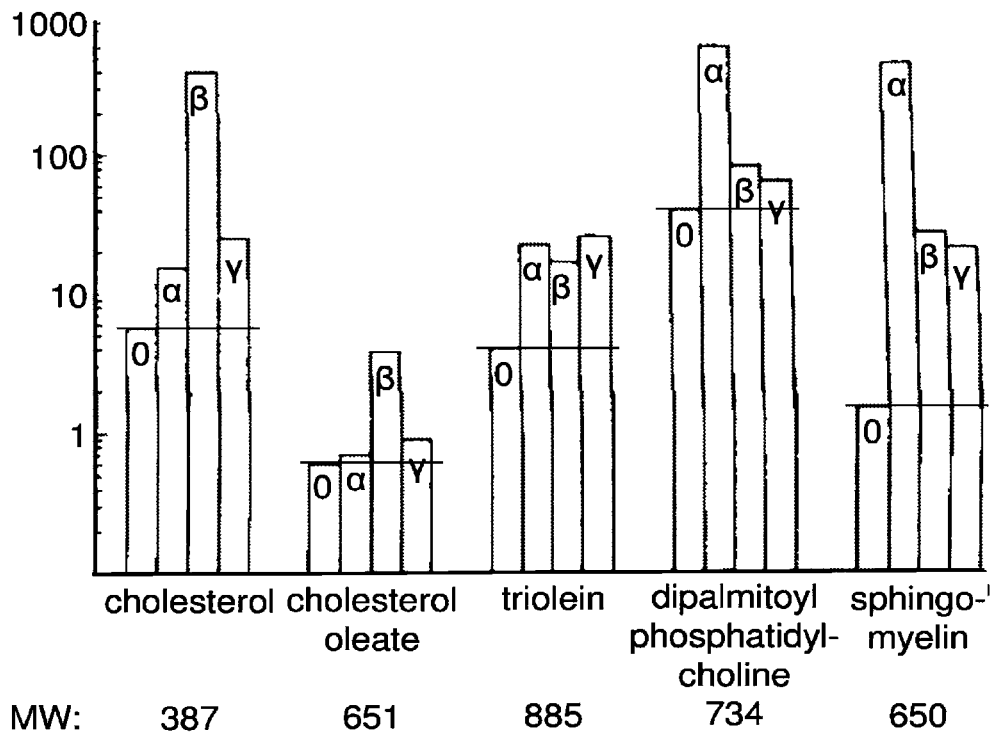
FIG. 32: Solubility Enhancements by Hydroxypropyl-cyclodextrins (HP-CD). Enhancement of apparent solubilities of lipids by HP-cyclodextrins. Bar denoted "0" represents apparent solubilities in isotonic phosphate-buffered saline; those denoted by α, β, and γ represent the solubilities in the same saline but supplemented with the respective HP-cyclodextrins at 5% (w/w) concentration. MW: molecular weight. Modified from: (Irie T, Fukunaga K, et al. (1992) J Pharm Sci 81:524-8), FIG. 1.
Figure 33:
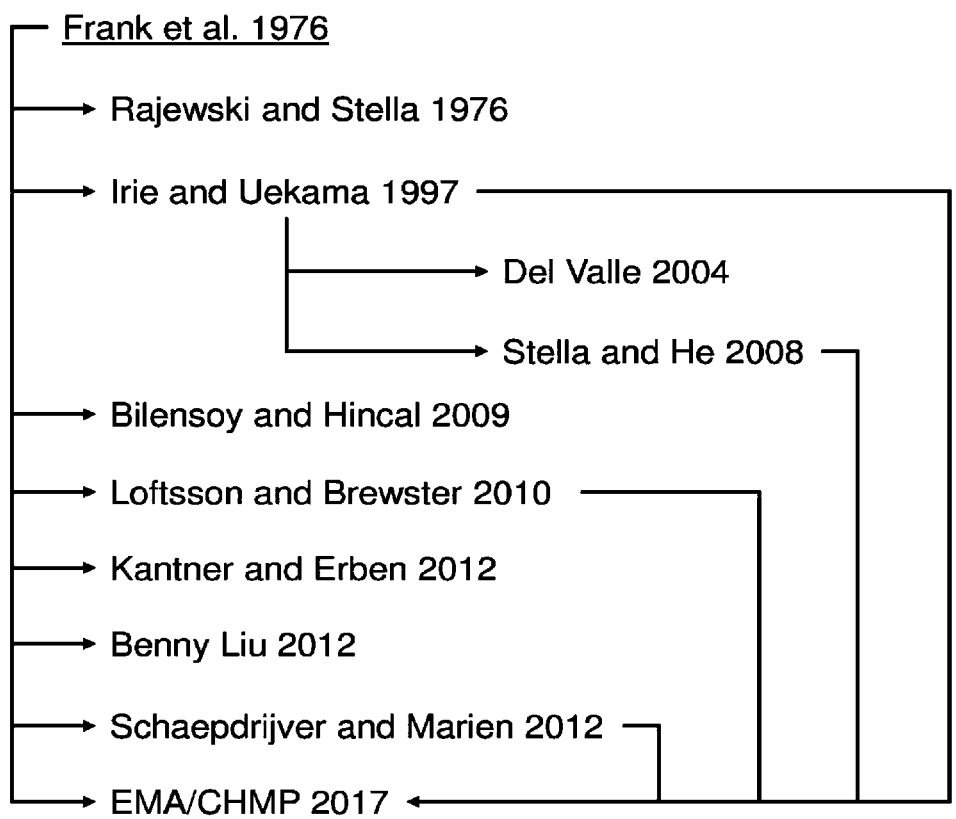
FIG. 33: Nephrotoxicity of α-CD and β-CD. The 2017 assessment by the EMA (and several other authors) of similar risks associated with parenteral administration of α-CD and β-CD in rats is based on a single study (Frank D W, Gray J E, et al. (1976) Am J Pathol 83:367-82).

Results: The differential effects of α-, β-, and γ-HP-cyclodextrins on five representative pure lipids are shown in FIG. 32. HP-β-CD preferentially solubilized cholesterol, whereas phospholipids were best solubilized with HP-α-CD.

Example 9: α-CD is at Least as Effective as HP-β-CD in Preventing Lysosomal Dysfunction in Cell-Lines of Various Lysosomal Storage Diseases The results of Example 9 are consistent with findings in US 2015/0216895 A1, FIG. 5, (McKew J, Zheng W E I, et al. (2014)) which found that "[αCD, βCD, and γCD] can reduce cholesterol accumulation, and MBCD [MβCD] was most potent." In particular, the authors noted that all three CDs "can reduce cholesterol accumulation in NPC cells [and] that these CDs increased intracellular Ca2+ and enhanced exocytosis."

Figure 23:
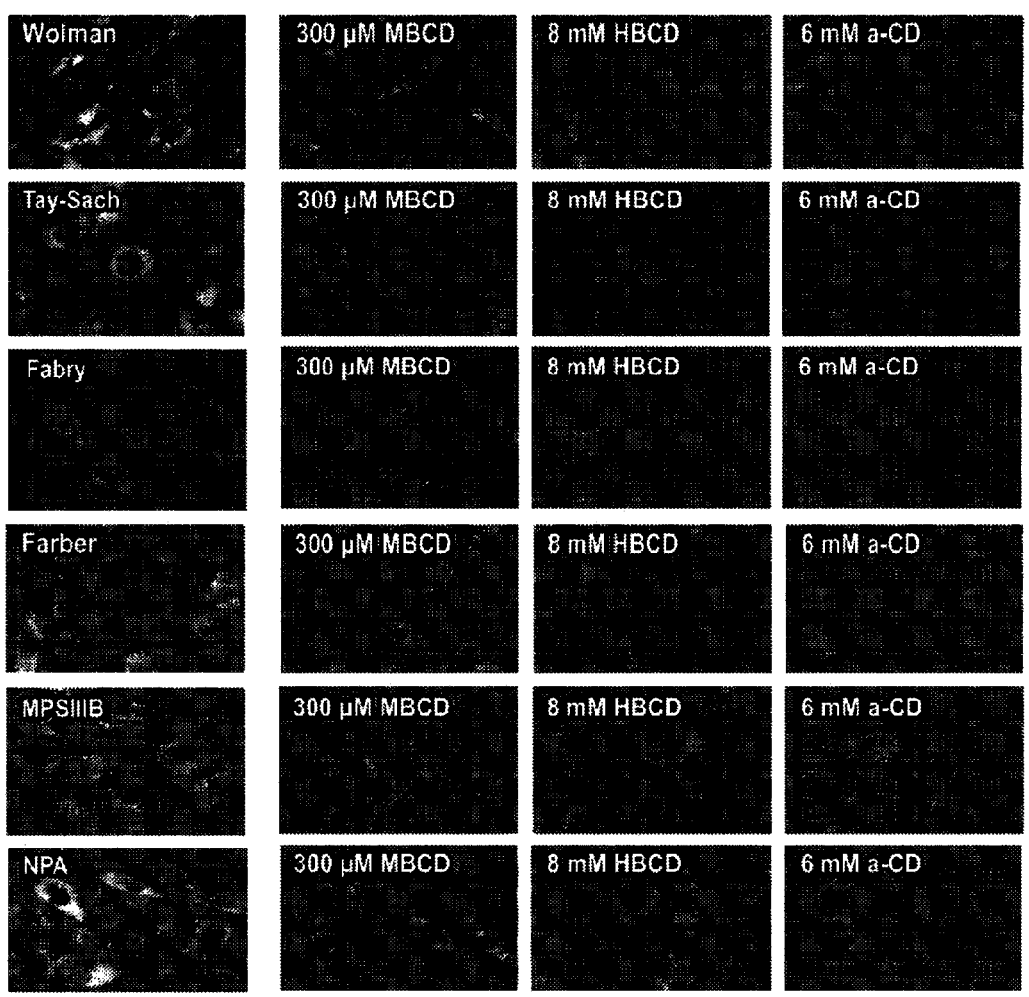
FIG. 23: CDs in Lysosomal Storage Diseases. Effect of cyclodextrins using lysotracker red staining to indicate enlarged lysosomes in ML111 fibroblasts. Wolman (LAL), TSD, Fabry (GLA), Farber (AC), MPSIIIB: mucopolysaccharidose II type B (NAGLU), NPA: Niemann-Pick type A (ASM), HBCD: HP-β-CD (Kleptose) According to the inventors, "the other cyclodextrins did not have that profound an effect", (McKew J, Zheng W E I, et al. (2014)) It was overlooked, however, that, the effect of 6 mM α-CD (⅓ of the M-β-CD dose) was more profound than the effect of 8 mM HP-β-CD. Modified from (McKew J, Zheng W E I, et al. (2014)).

What has not been appreciated is that efficacy of α-CD against cholesterol storage disease implies that the effect cannot be due to scavenging of cholesterol, because α-CD cannot fit cholesterol. Our novel genetics results show that the effect is instead mediated by phospholipids and, thus, explain for the first time why about 6 mM α-CD actually was more effective in reducing lysosomal storage than about 8 mM HP-β-CD (FIG. 23).

The results also provide an explanation why intravenous HP-β-CD is effective in NPC, even though neither cyclodextrins nor cholesterol can cross the blood brain barrier (BBB). The surprising findings also may end the current "battle" over intravenous v. intrathecal use of HP-β-CD. (Wadman M (2016) Science 354:18-9) As phospholipids cross the BBB more easily, an oral (absorbed from the intestine) version of HP-α-CD may prevent the need for either implanting an intrathecal pump or administering HP-β-CD as an intravenous infusion over several hours to prevent cytoplasmic crystals from forming in the tubules of the kidney. (Frank D W, Gray J E, et al. (1976) Am J Pathol 83:367-82)

Example 10: α-CD is Less Nephrotoxic than β-CD in Delayed Release Applications

Despite the differences in phospholipid profiles in vitro (Example 8), in vivo results are commonly interpreted as showing that α-CD is at least as nephrotoxic as β-CD:
1. "Cyclodextrins were found rather toxic and the high doses applied parenterally are definitely kidney damaging (Frank D W, Gray J E, et al. (1976) Am J Pathol 83:367-82)." (Pitha J (1981) Life Sci 29:307-11)
2. "The work of Frank et al. [(Frank D W, Gray J E, et al. (1976) Am J Pathol 83:367-82)] and others [(Perrin J H, Field F P, et al. (1978) Research communications in chemical pathology and pharmacology 19:373-6)] showing nephrotoxicity of the unmodified cyclodextrins limited further studies on the parent cyclodextrins to . . . nonparenteral routes." (Rajewski R A, Stella V J (1996) J Pharm Sci 85:1142-69)
3. "Early studies showing the nephrotoxicity of the parent cyclodextrins [(Frank D W, Gray J E, et al. (1976) Am J Pathol 83:367-82)] limited administration routes . . . to . . . non-parenteral routes", see p. 147 (Irie T, Uekama K (1997) J Pharm Sci 86:147-62)
4. "[T]oxicological studies have also shown that the parent α- and β-[cyclodextrin] . . . are not suitable for parenteral administration, . . . [(Irie T, Uekama K (1997) J Pharm Sci 86:147-62)]" (Del Valle E M M (2004) Process Biochemistry 39:1033-46)
5. "The renal toxicity of α-CD and β-CD after parenteral administration [(Frank D W, Gray J E, et al. (1976) Am J Pathol 83:367-82)] . . . have been well documented [(Irie T, Uekama K (1997) J Pharm Sci 86:147-62); Thompson 1997 (review only); Gould and Scott 2005 (β-CD only)]." See p. 31 of (Stella V J, He Q (2008) Toxicol Pathol 36:30-42)
6. "Two of the natural cyclodextrins [α- and β-cyclodextrin] are known to be parenterally unsafe owing to nephrotoxic effects [(Frank D W, Gray J E, et al. (1976) Am J Pathol 83:367-82)]" (Bilensoy E, Hincal A A (2009) Expert Opin Drug Deliv 6:1161-73)
7. "One of the hallmarks of the toxicity of CDs after parenteral administration is nephrotxocity . . . [(Frank D W, Gray J E, et al. (1976) Am J Pathol 83:367-82)]" (Kantner I, Erben R G (2012) Toxicol Pathol 40:742-50)
8. "When administered parenterally, [natural cyclodextrins] caused nephrotoxicity . . . [(Frank D W, Gray J E, et al. (1976) Am J Pathol 83:367-82)]" (Liu B (2012) Clinical lipidology 7:289-301)
9. "Following administration of poorly soluble parent α- and β-CD[,] prominent microcrystals are observed in lysosomes. [(Frank D W, Gray J E, et al. (1976) Am J Pathol 83:367-82)]" (De Schaepdrijver L, Marien D, et al. (2015) Reproductive toxicology (Elmsford, N.Y.) 56:87-96)

These findings are summarized in a 2017 European Medicines Agency report (Committee for Human Medicinal Products (CHMP) (2017) European Medicines Agency EMA/CHMP/333892/2013):
"Both α-CD and β-CD showed renal toxicity after parenteral administration . . . . Above 200 mg/kg/day cyclodextrin may theoretically . . . cause mild renal toxicity when given parenteral[ly]."

The surprising result of a literature review regarding nephrotoxicity of cyclodextrins is that, as outlined in FIG.

33, the above statements, including the 2017 summary about the clinical safety of about the toxicity of α-CD v. β-CD, are all based on the data of the same 1976 publication (Frank D W, Gray J E, et al. (1976) Am J Pathol 83:367-82) where the Abstract noted that "renal toxicity of . . . α and β-[cyclodextrin] is manifested" and the Discussion stated: "Repeated administration of large doses of the [cyclodextrin]s resulted in numerous giant [proximal tubule] lysosomes distorted by enclosed microcrystals [in a dose-dependent manner] . . . [cyclodextrin] nephrosis apparently represents irreversible injury . . . [cyclodextrin] . . . concentration within the lysosomes results in the toxic injury to the cell." Of note, neither the Abstract nor the Discussion mentioned the differences between cyclodextrins reported in the results.

Drugs can be administered parenterally to reach systemic concentration as a bolus (within seconds or minutes), e.g., intravenously (single injection), or spread out over hours, e.g., intravenously (repeated injections ir infusion), subcutaneously, or intraperitoneally. The former type of parenteral application results in high peak levels, while the latter applications achieve lower and longer lasting levels. The effect of increasing the frequency of administration has been noted: "One way to avoid . . . overloading [of the kidney] would be to lower the spikes of cyclodextrin concentration in blood [as r]epeated doses of cyclodextrins applied parenterally were less toxic than a single cumulative dose (Frank D W, Gray J E, et al. (1976) Am J Pathol 83:367-82) . . . . [A] peristaltic pump was used to inject slowly the solution and thus a "spike" was spread to 6-8 hours. Using this technique . . . [d]oses of 1 g/kg not only did not result in animal deaths, but did not even influence the growth of the young animals compared to controls." (Pitha J, Szente L (1981) Proceedings of the First International Symposium on Cyclodextrins 457-66). In the treatment of Niemann-Pick disease (Hastings C (2010) FDA-Filing 2010)

Consistent with the latter results, "there are no cases of kidney injury caused by cyclodextrins in humans," (Committee for Human Medicinal Products (CHMP) (2017) European Medicines Agency EMA/CHMP/333892/2013) see also Table 3.

The surprising results of this re-evaluation of published data (Frank D W, Gray J E, et al. (1976) Am J Pathol 83:367-82) is that while α-CD and β-CD had a similar $LD_{50}$ of 1 g/kg only with bolus i.v. injections, α-CD was less nephrotoxic than β-CD with daily s.c. injections. Only one rat died (after 2 days) among the groups given up to 7 daily doses of 1 g/kg α-CD, while all rats died within 4 days among the groups given a lower dose of 0.900 g/kg/d β-CD (see Table 7, p=0.0285)."

TABLE 7

Toxicity of cyclodextrins in rats (compiled from Frank D W, Gray J E, et al. (1976) Am J Pathol 83: 367-82)

| | α-CD [g/kg] | β-CD [g/kg] |
|---|---|---|
| i.v. single dose ($LD_{50}$) s.c. Single dose | 0.788/1.008 * | 0.788/1.008 * |
| Nephrosis (light microscopy), s.c. 1,2, 3, 4, or 7 daily doses | 0.100 no changes — — — 1.000 changes seen | — 0.225 no changes 0.450 no changes duration-dependent alterations in EM 0.670 changes seen 1.000 changes seen |
| Nephrosis/Death | 0.100 no nephrosis — 1.000 all had severe nephrosis, one died (after 2 days) | — 0.225 one nephrosis after 4 days 0.450 severe nephrosis 0.900 all died within 4 davs |

Legend:
"—" not reported,
* the paper is ambiguous about which drug caused either $LD_{50}$.

Adding HP groups is known to reduce toxicity of native CDs (Table 8). In humans, HP-β-CD is approved (as an excipient for itraconazole) for bolus i.v. injection up to 16 g (100 mg/kg). No side effects were observed after parenteral administration of 12 g twice daily for 15 days. The pharmacokinetics of SBEβ-CD (Vfend, Pfizer, 14 g i.v.) is very similar to that of HP-β-CD (Stella V J, He Q (2008) Toxicol Pathol 36:30-42)

TABLE 8

Pharmacologic and toxicologic characteristics of selected cyclodextrins

| | α-CD | HP-α-CD | β-CD | HP-β-CD |
|---|---|---|---|---|
| Solubility in water [g/l] | 145 [1] | >500 [2] | 18.5 | >600 [2] |
| oral absorption in rats [1] | 2-3% | | 1-2% | ≤3% |
| half-life ($t_{1/2}$) after i.v. in rats [min] [1] | 25 | | 20 | 20 |
| excreted after i.v. unchanged in urine | ~90% | | ~90% | ~90% |

TABLE 8-continued

Pharmacologic and toxicologic characteristics of selected cyclodextrins

|  | α-CD | HP-α-CD | β-CD | HP-β-CD |
|---|---|---|---|---|
| hemolytic IC$_{50}$ [mM] [8] | 16 | >100 |  |  |
| whole blood TD$_{50}$ [mM/L] [9] | 11 | 360 | 3.6 | 9 |
| i.v. toxicity, 1 g/kg daily [4] | 1 died @ 2 d |  | all died ≤ 4 d | no signs [6] |
| i.v. toxicity, 500 mg/kg |  |  | kidney damage | no damage |
| LD$_{50}$ i.v./i.p. in mice/rats [g/kg] [7] | 0.5-1.0 |  | 0.8/1.0 [4] | 10 |
| BBB breakdown [mM] [5] | 1 | 2.5 | 2.5 | 2.5 |
| Transport across BBB [%, 2 h] [5] | 21.5 (0.5 mM) | 16.5 (1 mM) | 26.7 (1 mM) | 6.6 (1 mM) |

From
[1] (Brewster M E, Loftsson T (2007) Advanced Drug Delivery Reviews 59: 645-66)
[2] (Loftsson T, Brewster ME (2010) J Pharm Pharmacol 62: 1607-21)
[3] (Loftsson T, Moya-Ortega M D, et al. (2016) J Pharm Pharmacol 68: 544-55)
[4] (Frank D W, Gray J E, et al. (1976) Am J Pathol 83: 367-82)
[5] (Monnaert V, Tilloy S, et al. (2004) Journal of Pharmacology and Experimental Therapeutics 310: 745-51)
[6] (Gould S, Scott RC (2005) Food Chem Toxicol 43: 1451-9)
[7] (Riebeek W M (1990a) TNO-CIV Institute V90; (1990b) TNO-CIV Institute V90; Prinsen M K (1991) TNO-CIV Institute V91)
[8] (Roka E, Ujhelyi Z, et al. (2015) Molecules 20: 20269-85)
[9] (Leroy-Lechat F, Wouessidjewe D, et al. (1994) International Journal of Pharmaceutics 101: 97-103)
[10] (Frijlink H W, Eissens A C, et al. (1991) Pharm Res 8: 9-16)

In four studies of outbred rodents (Riebeck 1990a/b/c, Prinsen 1991a, as quoted in WHO http://www.inchem.org/documents/jecfa/jecmono/v48je10.htm) macroscopic examination of dead and surviving animals either "did not reveal treatment-related alterations" (Riebeck 1990a/b/c) or merely "a pale renal cortex" (Prinsen 1991a).

Example 11: α-CDs are More Efficient in Crossing the Blood-Brain Barrier (BBB) than β-CDs As phospholipids can easily cross the BBB, α-CDs would not need to cross the BBB to be effective, but it would increase their effectiveness. Published data show that α-CDs are consistently twice as efficient as β-CDs in crossing the BBB in vitro. After 2 h of incubation, 16.5-43.0% (vs 6.6-26.7%) were transported through the BBB (compared to 96% for caffeine or nicotine). See Journal of Pharmacology and Experimental Therapeutics, 310 (2), 745-51. These results were confirmed in an independent study of βCDs. (Binkowski-Machut C, Hapiot F, et al. (2006) Bioorganic & Medicinal Chemistry Letters 16:1784-7)

While α-CD was more toxic, HP-α-CD, β-CD, β-CD, and HP-β-CD were similarly safe (Table 8: Pharmacologic and toxicologic characteristics of selected cyclodextrins). (Monnaert V, Tilloy S, et al. (2004) Journal of Pharmacology and Experimental Therapeutics 310:745-51)

Example 12: α-CD is Safer than β-CD and More Effective in Preventing Migration of Human Tumor Cells In Vitro Introduction
Published results have shown that β-CD inhibits human MDA-MB 231 cell migration (Guerra F S, Sampaio LdS, et al. (2016) Translational Medicine Communications 1:3). This inhibition was attributed to the ability of β-CD to "deplete cholesterol". β-CD, however, depletes also phospholipids. To determine whether inhibition of migration is caused by β-CD depleting cholesterol, as commonly assumed, or by β-CD depleting phospholipids, as implicated by the results of the present disclosure, the wound healing experiment was replicated, comparing both HP-β-CD (Sigma, 389145-5G) and HP-α-CD (Sigma, 390690-5G) v. control in both MDA-MB 231 (CRM-HTB-26, ER−) and MCF-7 (ATCC HTB-2, ER+) human breast epithelial cell lines.

Method
Cells were cultured in 24-well culture plates (Cytoselect CBA-120, 0.9 mm wound healing/gap closure migration assay) for 24 h with wound healing insert in place. Cells were then treated for 2 h with HP-β-CD, HP-α-CD, or control.

Protocol: Warm up the 24-well plate (CBA-120, Cell BioLabs Inc.) with 0.9 mm CytoSelect Wound Healing Inserts at room temperature for 10 min. Using sterile forceps, orient the desired number of inserts in the plate wells with their "wound field" aligned in the same direction. Create a cell suspension containing 0.5-1.0×10$^6$ cells/ml in media containing 10% fetal bovine serum (FBS). Add 500 µL of cell suspension to each well by carefully inserting the pipette tip through the open end at the top of the insert. For optimal cell dispersion, add 250 µL of cell suspension to either side of the open ends at the top of the insert. Incubate cells in a cell culture incubator for 12-24 hours. Carefully remove the insert from the well to begin the wound healing assay. Use sterile forceps to grab and lift the insert slowly from the plate well. Slowly aspirate and discard the media from the wells. Wash wells with media to remove dead cells and debris. Finally, add media to wells to keep cells hydrated. Repeat wash if wells still have debris or unattached cells. When washing is complete, add media with FBS and/or compounds to continue cell culture and wound healing process. Agents that inhibit or stimulate cell migration can be added directly to the wells. Incubate cells in a cell culture incubator (2 hours) and then wash cells with PBS and then add fresh media without compounds. Incubate 12-24 hours before wash and fixing. Remove the fixation solution and add 400 µL of Cell Stain Solution to each well. Allow the stain to incubate with the cells for 15 minutes at room temperature. Aspirate and discard the solution. Carefully wash each stained well 3× with deionized water. Discard washes and allow cells to dry at room temperature. Cells that migrated into the wounded area or protruded from the border of the wound were visualized and photographed under an inverted microscope. Determine the surface area of the defined wound area: Total Surface Area=0.9 mm×length. Determine the surface area of the migrated cells into the wound area: Migrated Cell Surface Area=length of cell migration (mm)×2× length. Percent Closure (%)=Migrated Cell Surface Area/Total Surface Area×100 (see FIG. 36)

Cell-based scratch assay. Cells were cultured in 24-well culture plates for 24 h up to 90%-100% confluence. Scratched wound lines on the upside of cultured cells were created by 200 µl yellow micropipette tip. The scratched cells were washed with PBS after removal of culture media. The cells were cultured for 2 h with 2 mM MβCD and after the removal of culture media cells were cultured for the next 2, 8, 12 or 24 h. All cell-based scratch assays were performed in the presence of the anti-mitotic reagent cytosine arabinoside (Sigma) at a final concentration of $10^5$ M in order to inhibit cell proliferation and analyze only cell migration. The wound area was measured from the image taken with an Axiovert 100 microscope (Carl Zeiss, Germany) by Image J program (NIH, USA) at 3 different sites from each wound area of gaps. Three independent experiments were performed.

Other methods used are described in (Guerra F S, Sampaio LdS, et al. (2016) Translational Medicine Communications 1:3; Okada S S, Kuo A, et al. (1995) J Pharmacol Exp Ther 273:948-54), each of which are incorporated herein by reference in their entireties.

Results

Figure 35:
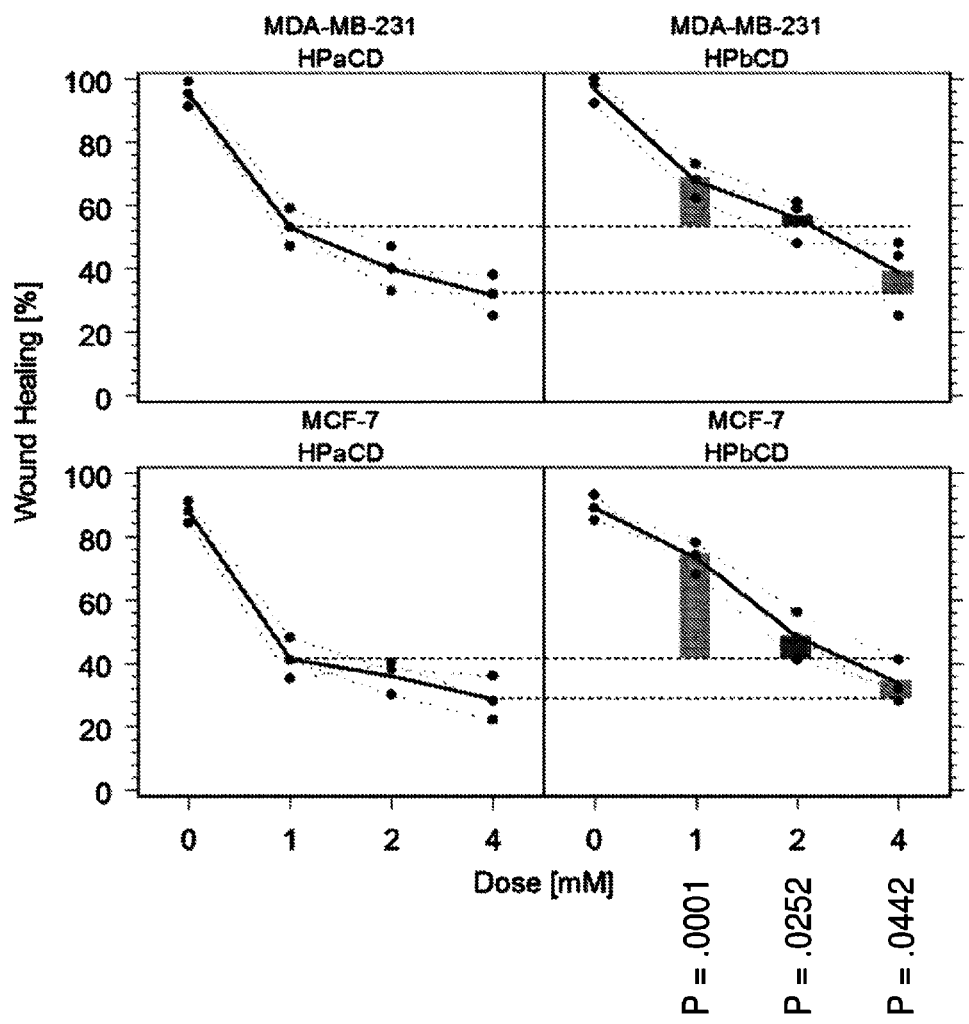
FIG. 35: Wound healing by cyclodextrins in breast cancer cell lines. Dashed horizontal line indicates inhibition of wound healing in HPαCD at 1 and 4 mM respectively. ANOVA P values are shown for HPαCD v. HPβCD with MCF-7 and MDA-MB-231 as (fixed) blocks.

Results are shown in FIG. 35. In the absence of cyclodextrins, >80% of the wound are is closed. With cyclodextrins, wound closure is inhibited in a phospholipid-dependent manner. Extraction of cholesterol does not seem to inhibit wound closure, but has been shown to cause side-effects (ototoxicity). The results are highly consistent: In all cases, migration decreased with higher concentration of either HP-α-CD or HP-β-CD and HP-α-CD had a stronger effect on migration than HP-β-CD (Inhibition at 1 mM HP-α-CD was superior to inhibition at 2 mM HP-β-CD.)

Discussion

The results in human two human tumor cancer cell lines confirm the hypothesis that the primary effect of β-CDs on cell migration is not by scavenging cholesterol, but by scavenging phospholipids. The present disclosure has demonstrated that "derailed", "deranged", and "defective" endocytosis in cancers, neurodegenerative diseases, and other age-related conditions is caused by genetic risk factors causing excessive influx of glycophospholipids, including PC, into the PI cycle (FIG. 12). Previous studies with β-CDs did not proceed to clinical trials because of risk of cholesterol-related ototoxicity; they can now be resumed after the elimination of cholesterol is avoided, while the phospholipid-related efficacy seen in β-CD is increased.

Figure 34:
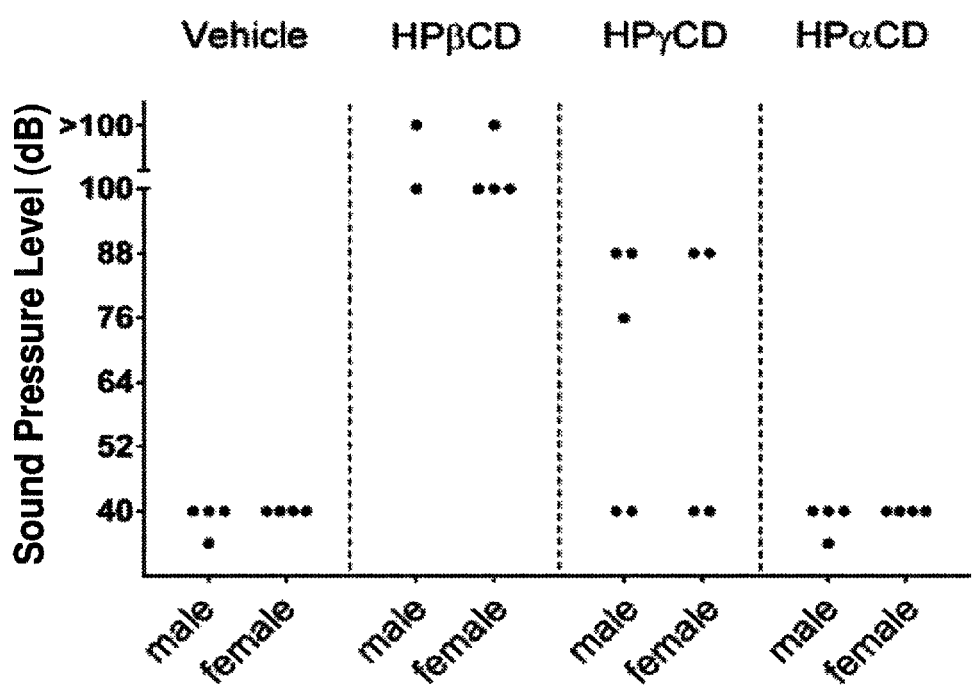
FIG. 34: Ototoxicity of CDs. Ototoxicity of different CDs as assessed by auditory brainstem response (ABR) recordings at 12 weeks of age. Plot of hearing thresholds for individual mice reveals minute variability across mice treated with a particular CD with the exception of HPγCD, in which hearing thresholds were more variable. Modified from FIG. 5B in (Davidson C D, Fishman Y I, et al. (2016) Ann Clin Transl Neurol 3:366-80)

In addition to not carrying HP-β-CD's risk of ototoxicity (FIG. 34), HP-α-CD has lower toxicity than HP-β-CD (Example 10) but is about twice as effective in scavenging phospholipids, in general, and even more effective in scavenging PC (Monnaert V, Tilloy S, et al. (2004) Journal of Pharmacology and Experimental Therapeutics 310:745-51) In children with NPC (Table 3), doses of up to 1000 mg/kg/d HP-β-CD were well tolerated. With 700 mg/kg/d HP-β-CD having been proven as safe in parenteral treatment of NPC, doses up to 700 mg/kg/d HP-β-CD could now be used to continue with the human experiments that were stopped when β-CDs were shown to have cholesterol-related ototoxicity.

Example 13. HP-α-CD is More Effective than HP-β-CD in Reducing Tumor Growth, Metastases, and Inflammation in NSG Mice Infected with Human MDA-MB-231 Breast Cancer Cells Introduction:

HP-β-CD has been shown to be effective in several animal models of breast cancer (see Example 4), but further result on HP-β-CD was halted when it was seen to cause permanent hearing loss by depriving outer hair cells in the ears of the cholesterol they need. The genetics results in Example 1 led to the novel hypothesis that HP-β-CD is acting via scavenging phospholipids, rather than cholesterol and, thus, that HP-α-CD, which also scavenges phospholipids, but is too small to fit cholesterol, is a safer alternative and the in vitro results in Example 12 have shown HP-α-CD to be more effective in vitro than HP-β-CD.

Methods:

NSG mice (NOD.Cg-Prkdcscid Il2rgtm1Wjl/SzJ, strain #005557 (10 wk old) were obtained from Jackson Laboratories (Bar Harbor, Me.), housed in isolated quarters, and fed with autoclaved water and food.

An MDA-MB-231 cell line was obtained (ATCC) and kept frozen in liquid nitrogen. Upon start of culture, cells were thawed (1.5 min in 37° C. water) and transferred to DMEM/F-12 supplemented with 5% FBS, 2 mM L-glutamine, 1 mM sodium pyruvate, and 0.02 mM non-essential amino acids. Cells were grown to several millions in 60 mm dishes at 70-80% confluence. Before injection, cells were briefly rinsed twice in PBS followed by Versene (EDTA, Invitrogen) and placed on ice with excess phosphate-buffered saline and phenol red-free matrigel basement membrane extract to a concentration of about 15 mg/mL matrigel. 100 µL cell mixture (20,000 cells or saline only) were injected into the lactiferous duct of the $3^{rd}$ or $4^{th}$ mammary glands under brief isofluorane anesthesia. Groups of 15 mice each were injected IP with 800 mg/kg of HP-α-CD, HP-β-CD per week (over four days, Mon, Tue, Thu, Fri), or saline (control) for six weeks. Size of the primary tumor was measured weekly.

Breast tissue were palpated and measured twice a week with a micro-metric analytical device scaled to 1 mm precision. Mice were weighed weekly on a digital scale (0.1 g precision).

At the end of the study period, mice were anaesthetized with isofluorane with 1× phosphate-buffered saline (PBS) and subsequently with 4% formaldehyde in PBS. Tissue from lung and liver were removed and fixated in formalin for microscopic examination. Metastases were visualized and counted by tissue embedding in paraffin and sectioning with immunohistochemistry and histological stain (H&E) and immunostained with anti-HLA antibody. After blocking for 1 h with BSA (5%, frac V), the anti-HLA was incubated at 4° C. overnight, washed for 1 h in PBS, then incubated with biotinylated anti-mouse IgG for 1 h at room temperature. After washing with PBS, metastases were detected on the slide using Envision (Dako).

After blood collection, whole blood samples were centrifuged (at 10,000 m/s² for 15 min and then at 100,000 m/s² for 10 min), and plasma was isolated. The samples were stored at −80° C. until analysis.

Prior to analysis (30 min), samples and assay reagents were equilibrated to room temperature. The samples were run at a 1:4 dilution and quantified in duplicate using a multi-plex mouse panel for quantification of IL-1β, IL-18, IL-6, IL-8, IL-17A, and GM-CSF (Bio-Plex Pro assays, Bio-Rad Laboratories) on a Luminex Bio-Plex 200 System (Bio-Rad Laboratories).

Results: The mice grew at a typical rate (FIG. 38A) and appeared healthy, except for the two mice in the Vehicle and HP-β-CD groups each and one in the HP-α-CD group, who died ('†' at the bottom, '+' at the end of the growth curve). More growth in the Vehicle group could be due to either more tumor growth (FIG. 38B) or to the known effect of cyclodextrins to reduce the amount of fat being absorbed from the intestine and, thus, less growth. Tumors grew faster in the Vehicle group (to a median of 525 mm$^3$) than in the cyclodextrin groups (FIG. 38B). The effect was larger for HP-α-CD (356 mm3) than for HP-β-CD (378 mm3, p=0.0258).

All mice developed lung and/or liver metastases (FIG. 39), but one mouse in the Vehicle group, 3 mice in the HP-β-CD group, and 5 mice in the HP-α-CD group did not develop lung metastases. By u-statistics for multivariate data (Wittkowski K M, Lee E, et al. (2004) Stat Med 23:1579-92), both cyclodextrins are effective in reducing metastases overall (P<0.001), and the data are consistent with HP-α-CD being more effective (P=0.098).

All plasma cytokines showed reduced levels under both cyclodextrins, with the exception of IL17-A under HP-β-CD (FIG. 40). At the conventional 0.05 level, HP-β-CD was significant in four other markers (not in IL-8), while HP-α-CD was not significant only in IL-6. A comprehensive analysis of all six markers via u-statistics for multivariate data (Wittkowski K M, Lee E, et al. (2004) Stat Med 23:1579-92) shows HP-α-CD be more effective than HP-β-CD (p(a:b)=0.0417).

Conclusion:

The in vivo results confirm the in vitro results (Example 12) that HP-α-CD is more effective than HP-β-CD in preventing breast cancer tumor growth (FIG. 38, P=0258) and metastases (FIG. 39, P=0.098). Inflammation is also known as a component in the etiology of cancer. The surprising results in FIG. 40 (P<0.02 for each of GM-CSF, IL-18, IL17-A, IL-4, and IL1-b) confirm the hypothesis that α-CDs also reduce inflammation by reducing the activity of sPLA2 to produce arachidonic acid, the precursor of inflammatory COX-1, COX-2, and LOX, and that HP-α-CD, by not spending part of its lipid-carrying capacity on cholesterol, is also more effective than HP-β-CD.

Example 14. HP-α-CD Reduces Disease Phenotypes in Mouse Models of ALS and HD

Introduction:

Many neurodegenerative diseases, including Alzheimer's disease and Parkinson's disease affect higher cognitive functions and involve largely unknown, complex genetic risk factors. Hence there are few animal models that are known to represent the more relevant aspects of the disease etiology. Aggregation of amyloid-beta, tau, and alpha-synuclein are associated with Alzheimer's disease and Parkinson's disease, yet it is not known whether the aggregates are causal or merely an effect. In Alzheimer's disease, for instance, most drugs aiming at reducing the aggregation of amyloid-beta have failed. Current treatments confer symptomatic relief, but there are no treatments available to halt or slow disease progression.

The genetics result presented in Example 2 have let to novel insights on the common genetic risk factors underlying "derailed", "deranged", and "defective" endocytosis in metastatic and neurodegenerative diseases, which now explain the underlying mechanism for the previously observed impaired autophagy in Alzheimer's disease, Parkinson's disease, ALS, and Huntington's disease. (Guo F, Liu X, et al. (2018) Brain Pathol 28:3-13)

In contrast to Alzheimer's disease and Parkinson's disease, where the most prevalent disease forms are "idiopathic" (of unknown genetic cause), and, thus, relevant animal models are difficult to identify, the genetic risk factors for ALS, and Huntington's disease are well understood.

Huntington's disease is caused by an expansion of exon 1 of the HTT gene to >40 CGA repeats (mutant HTT, mHTT). Transgenic mice with approximately 120 CAG repeat develop neuronal inclusions containing the both mHTT and ubiquitin proteins. They display a progressive neurological phenotype that, typical for a mono-genic disease closely mimics human Huntington's disease, including movement disorders and loss of body weight.

As SOD1 mutations account for 10-20% of familial ALS and 1-2% of sporadic ALS, SOD1 aggregates are routinely found in these patients, and SOD1-ALS patients have low levels of the autophagy transcription factor TFEB, mice with sod1 mutations are a highly plausible mouse model for human ALS. SOD1 is also associated with Parkinson's disease, Alzheimer's disease, and Down syndrome. FUS (fused in sarcoma), a major protein aggreate in affected neurons in Huntington's disease, is also associated with ALS.

Given the comorbidities, autophagy-related pathology, and genetic overlap between neurodegenerative diseases, mouse models for Huntington's disease and ALS to evaluate the activity of HP-α-CD against neurodegenerative (and other autophagy-related) diseases.

Methods:

ALS mice SOD1 G93A strain (B6SJL-Tg(SOD1*G93A) 1Gur/J strain #002726, 10 wk old, and HTT mice (B6CBA-Tg(HDexon1)62Gpb/33; strain #006494 HTT: R6/2, 8 wk old), were obtained from Jackson Laboratories (Bar Harbor, Me.), housed in standard housing with controlled ambient conditions and provided with water and food at libitum.

Results:

Among 8 wk old HTT mice, treatment with HP-α-CD reduced decline in bodyweight over 5 wk (starting from day 7 at 9 wk of age, P(T*D)<0.0001). The effect was more striking in male (P(T*DIM)<0.0001) than in female mice (P(T*DIM)=0.0394).

Untreated SOD1 mice began to lose bodyweight after 21 days of observation (at age 11 wk), while mice treated with HP-α-CD continued to grow for at least two more weeks; similar effects were seen in both sexes (FIG. 42, p<0.0001).

Conclusion:

Consistent with the known comorbidity of metastatic, neurodegenerative, and other age-related diseases and conditions, these results provide evidence that HP-α-CD is effective not only in carcinomas (Example 13), where it was shown to be more effective than HP-β-CD, but also in neurodegenerative diseases, including, but not limited to, Huntington's disease and ALS and, by extension, Parkinson's disease and Alzheimer's disease, and in other diseases, where HP-β-CD has been shown to be effective in animal models.

Example 15: A Clathrate of HPαCD and Sodium Caprate (C-10) as an Oral Drug Extracts Phospholipids into Urine and does so More Efficiently than a Mixture of the Components Oral β-CD is rarely absorbed in mammals (~1%); of the smaller α-CD, 1.6% (Van Ommen B, De Bie A T, et al.

(2004) Regul Toxicol Pharmacol 39 Suppl 1:57-66) and 2.0% (Irie T, Uekama K (1997) J Pharm Sci 86:147-62) were found in urine within 6-8 h post oral administration. In rats, instead of 1% for β-CD alone administered orally, up to 5% of β-CD were absorbed rectally when administered rectally in suppositories containing triglycerides (Witepsol H5). Rectal absorption increased from 5% to 26% when β-CD was replaced by the more water soluble HP-β-CD. (Duchene D, Wouessidjewe D (1990) Drug Dev Ind Pharm 16:2487-99). Absorption of oral HP-α-CD has not been studied.

Background:

Published results in LDL-receptor knockout mice who were fed a "Western diet (21% milk fat)" showed that adding "2.1% of "nonabsorbable" α-CD (10% of dietary fat content)" decreased plasma phospholipids by 17.5%, (Wagner E M, Jen K L, et al. (2008) Metabolism 57:1046-51) yet no mechanism of action was identified. From the above genetic and in vitro results, the reduction in plasma phospholipids seen was not (or not only) due to "saturated fat absorption" in the intestine and "excretion into the feces", as speculated by the authors, but (also) through scavenging of phospholipids by α-CD absorbed from the intestine in the presence of milk fatty acids. A role of milk fatty acids is consistent with higher absorption of HP-β-CD in rats prior to weaning. (De Schaepdrijver L, Marien D, et al. (2015) Reproductive toxicology (Elmsford, N.Y.) 56:87-96)

While cyclodextrins are widely used as absorption enhancer, (Shaikh I, Derle N D, et al. (2012) J Appl Pharmacol Sci 2:34-9) the present disclosure utilized a cyclodextrin as an active ingredient and sodium caprate as an absorption enhancer for the cyclodextrin. In particular, it utilizes the smaller α-CD, applies the HP derivatization previously shown to enhance absorption of β-CD, uses a sodium salt of a fatty acid component of triglycerides as an effective absorption enhancer for delivery in the intestine (Yoshitomi H, Nishihata T, et al. (1987) J Pharm Pharmacol 39:887-91) The novel hypothesis was tested in a human PK/PD study.

Study Design:

A randomized n-of-1 dose escalation study was conducted to assess the activity of a clathrate of HP-α-CD and sodium caprate (C-10 fatty acid, capric acid, decanoic acid) in extracting phospholipids from serum into urine. Capric acid was chosen because it is known to regulates the paracellular permeability of the tight junctions in Caco-2 monolayers and in rat and human intestinal segments is more efficiently than either lauric acid (C12) or caprylic acid (C8).

Methods:

Urine samples (5-10 mL) were pipetted into culture tubes and then frozen for 30 min and samples were then lyophilized for 48-72 h, sealed and stored at −80° C. Phospholipids were extracted from urine samples after reconstitution, with chloroform (CHCl3) and methanol (3:1), and filtered through glass wool. The eluent was washed with 1 M KCl with 0.01% sodium azide. The wash was centrifuged at 3000 g for 30 min and CHCl3 layer transferred to fresh tube and evaporated at 60° C. under nitrogen. Phospholipid extracts and standards were digested in 10 M $H_2SO_4$ with 0.16 $Ca(NO_3)_2$ and 30% $H_2O_2$ and heated for 25 min at 180° C. Samples were cooled and equilibrated with $H2O/(NH_4)_6Mo_7O_{24}$ and 0.65% $(N_2H_5)HSO_4$. These were vortexed and heated at 35° C. for 30 min. All samples were analyzed in triplicate.

Phosphate content was measured at lambda-820 using a Molecular Dynamics Lambda5 analyzer. a Waters (Milford, Mass.) high performance chromatography system with tandem UV-vis wavelength detector (203 nM) was employed for urinalysis and separation enhancement of interested molecules. This was coupled to a Beckman Ultra SI column using an isocratic elution profile along a mobile phase of acetonitrile-methanol-phosphoric acid solvent (100:10:1.8) at a flow rate of 1.0 mL/min at RT. The lyophilized samples were resuspended in a hexane-propanol-phenolphthalene mix (3:1:0.1) before injection.

Technical controls were formulated and injected at a final amount of 0.125 mg phosphatidylcholine (PC) and 0.6 g HP-α-CD in same resuspension buffer. The standard curves (FIG. 43) were generated using DiPalmitoyl-PC in the range of 0.65-32 μM phosphate equivalence. Percentage efficiency of isolation was determined through a comparison of the extraction recovery of total phosphate from normal urine spiked with known amount of synthetic PL with a parallel PL sample digested and assayed without extraction.

The present disclosure reports the surprising results of absorption and activity of different strategies of absorption enhancement of orally administered HP-α-CD. The results shown in FIG. 44 confirm that the novel and non-obvious pharmacologic complex, a HP-α-CD/sodium-caprate clathrate to reduce endocytosis in malignant, neurodegenerative, vascular, metabolic, inflammatory, autoimmune, pulmonary, fibrotic, hepatic, lysosomal storage, or viral disease, disorder, or condition yields an intervention that is capable of reducing serum phosphatidylcholine by a clinically relevant amount. In particular, the results presented in FIG. 44 show the following findings. First, they confirm that previous observations with α-CD also apply to HP-α-CD:

In human adults, oral HP-α-CD is not absorbed (in a therapeutically effective amount). Among the mixtures and/or clathrates tested, HP-α-CD was the only formulation where the median value in the HP-α-CD fraction 2 (labeled "aCD") was lower than in fraction 1.

After confirming that native HP-α-CD is not absorbed and, thus not active, the results presented in FIG. 44 show several unexpected and surprising findings:

The proposed oral HP-α-CD/capric acid clathrate is the first oral cyclodextrin that is absorbed in human adults. In contrast to native HP-α-CD (HPaCD), after oral application of the clathrate (HPaCD/FA, HPaCD/FA&PE), a substantial amount of HP-α-CD is found in urine after 8 h (an increase to (about 2 on the scale of arbitrary absorption units) at the fraction expected for a molecule of molecular weight of 1180 for HP-α-CD (Sigma-Aldrich 390690) (HPaCD: HPaCD/FA, fraction 2: $P_{u-test}=0.0079$)

An increase in HP-α-CD absorption correlates with an increase in excretion of PC. The increase in excretion of PC into urine over native HP-α-CD (P=0.0367) is independent of the formulation (P=0.4523) but, as the formulations differ in HP-α-CD absorption, is low for the formulations with low absorption (HPaCD&FA, HPaCD&PE) and high for formulations with high absorption (HPaCD/FA, HPaCD/FA&PE).

The clathrate is more effective than a mixture. Substantially more PC is extracted with the clathrate (HPaCD/FA) than with the mixture (HPaCD&FA) (min(fraction 5|HPaCD/FA)=5.78, max(fraction 5|HPaCD&FA)=5.75, $P_{u-test}=0.0079$) to extract a therapeutically effective amount of monomeric phospholipids present at an extremely low concentration in serum.

A previously proposed oily suspension containing FA is not more effective than FA alone. A comparison between the clathrate v. intake of an oily suspension comprising the same amount of HP-α-CD and C-10 and additional permeation enhancers (Tuvia S, Pelled D, et al. (2014) Pharmaceutical Research 31:2010-21) (HPaCD&PE) showed no advantage over the mixture of HP-α-CD with the fatty acid (HPaCD&FA). A suspension of the clathrate (HPaCD/FA&PE) showed no advantage over the clathrate alone (HPαCD/FA)

The clathrate does not extract lysophospholipids. It is commonly believed that alpha-cyclodextrins scavenge a wide range of lipids, including lyso-phospholipids. The average median value of fractions 9 and 10 (labeled LPC) in HPaCD is higher than in all other groups. This unexpected surprising result has broad implications (see the following Example 16).

Example 16: Selectivity of HPαCD/Sodium-Caprate Clathrate for Selected PC Over PA and LPLs Exerts Effects Similar to Anti-Inflammatory Drugs (NSAIDs sPLA2 inflammatory activity is ongoing in the majority of MS patients, active or stable, regardless of treatment. In rats, EAE symptoms were attenuated by inhibition of sPLA2. (Cunningham T J, Yao L, et al. (2006) J Neuroinflammation 3:26) Increased sPLA2 activity is observed in the cerebrospinal fluid of Alzheimer's disease patients (Chalbot S, Zetterberg H, et al. (2011) J Alzheimers Dis 25:505-15), and may serve as a marker of increases in permeability of the BBB (Chalbot S, Zetterberg H, et al. (2011) J Alzheimers Dis 25:505-15). Patients with Alzheimer's disease AD and mild cognitive impairment had aberrant PLA2 activity. (Klavins K, Koal T, et al. (2015) Alzheimer's & dementia (Amsterdam, Netherlands) 1:295-302)

(FIGS. 43A and 43B:) Excretion of the serum phospholipid PC (mW≈780 Da) is substantially increased by the clathrate, as expected. Unexpectedly, however, PA (675) and SM (650) are not reduced and neither are lyso-phospholipids (460-550).

The unexpected high specificity of the clathrate for PC implies that the clathrate does not only reduce activity of the PI cycle, but also reduces inflammation, because PC is split by sPLA2 into LPC (which is transformed by ATX into LPA) and proinflammatory arachidonic acid (AA) FIG. 37. It is well known that "lysoPCs act as uncompetitive product inhibitors of plasma secreted PLA2 enzymes (sPLA2s)". (Cunningham T J, Yao L, et al. (2008) Journal of inflammation (London, England) 5:17) Hence, scavenging primarily lysophospholipids (LPC, LPA), rather than PC could activate sPLA2 and, thus, increase inflammation (FIG. 47). Scavenging PC only, instead, reduces sPLA2 activity by increasing the LPC/PC ratio and, thus, maintaining inhibition of sPLA2 while reducing availability of its substrate.

sPLA2-IIa activates HER2 and HER3, is overexpressed in lung, breast, pancreatic, skin, liver, and prostate cancer. (Dong Z, Meller J, et al. (2014) Int J Oncol 45:978-84) activates EGFR in MCF7 human BC cancer cells (Hernandez M, Martin R, et al. (2010) Neuro-oncology 12:1014-23), and is a marker of metastases.

"Researchers have been considering PLA2s could be a better therapeutic target than the downstream enzymes cyclooxygenase and lipoxygenase [yet]" (Yarla N S, Bishayee A, et al. (2016) Curr Drug Targets 17:1940-62) Human PLA2s are involved in eicosanoic synthesis, phagocytosis by macrophages, airway hypersensitivity, inflammation, tumorigenesis (V) and allergen-induces asthma, myocardial ischemia/reperfusion injury, AA metabolism, inflammation tumorigenesis, atherosclerosis (X). (Yarla N S, Bishayee A, et al. (2016) Curr Drug Targets 17:1940-62)

The unexpected reduction of inflammatory arachidonic acid exerts effects similar to corticosteroids (sPLA2 inhibition), NSAIDs (COX inhibition), and asthma drugs (LOX and leukotriene inhibition), see FIG. 6. Hence, α-CDs could become the next "baby-aspirin."

The best known function of PLA2s is the hydrolysis of phospholipids including PC, PE, and PS. (Mallat Z, Lambeau G, et al. (2010) Circulation 122:2183-200) sPLA2 acts not only on phospholipids, but also activates integrins (avb3, a4b1, and a5b1) (Saegusa J, Akakura N, et al. (2008) J Biol Chem 283:26107-15; Fujita M, Zhu K, et al. (2015) J Biol Chem 290:259-71) inhibits angiogenesis. Hence the termination of the first phase 3 trial (NCT01130246) of varespladib, a pan-sPLA2 inhibitor, for lack of efficacy and possible harm (Nicholls S J, Kastelein J J, et al. (2014) JAMA 311:252-62) could have been caused by the disruption of other pathways involving some sPLA2 or by unknown effects of varespladib on other pathways. Thus, one of the advantages of α-CDs as "starvation mimics" lies in the fact that humans have evolved to tolerate paucity of nutrients, including phosphatidylcholine (egg yolk or soy bean lecithin).

Example 17: Treatment with Phosphatidylcholine (PC, Lecithin) May Worsen Alzheimer's Disease The unexpected finding that reducing PC levels in blood improves neurodegenerative diseases in vivo is supported by previous findings showing that the Sandoz Clinical Assessment—Geriatric score worsens more in Patients with Alzheimer's disease who receive dietary PC supplementation.

As choline uptake was considered a potential rate-limiting step in the biosynthesis of acetylcholine (ACh), oral lecithin (90-95% PC) was considered as a treatment. Outpatients with Alzheimer's disease of moderate severity completed a double-blind placebo-controlled crossover trial of lecithin. Each patient received 10 g three times daily of a placebo for 3 months. Plasma choline levels rose threefold and remained at that level throughout the lecithin administration period. A significant difference between mean baseline scores and treatment scores was found on tests of new learning ability, indicating a practice effect in there tests. However, there were no significant differences between mean placebo and lecithin scores on any of the psychological test measures. (Etienne P, Dastoor D, et al. (1981) Neurology 31:1552-4)

Twenty-one Alzheimer's disease patients completed a double-blind trial on lecithin 25 g daily. Equal improvement was noted in both the lecithin and placebo groups. Serum levels of lecithin measured 12-14 h after its administration were also not increased compared with the levels in control patients. (Fisman M, Merskey H, et al. (1981) Canadian journal of psychiatry Revue canadienne de psychiatrie 26:426-8)

A randomized, double blind, cross-over study in 10 patients with primary degenerative dementia (DSM-III), 65 to 85 years old, compared placebo and three lecithin doses (4, 12, and 20 g/d) for one week each. "In spite of [an] increase in plasma . . . choline levels, there was no improvement in memory test performance." (Brinkman S D, Pomara N, et al. (1982) J Clin Psychopharmacol 2:281-5)

A double-blind, cross-over study in 10 Alzheimer's disease patients, 54 to 78 years old, compared placebo and three lecithin doses (15.0, 22.5, 30.0 g/d) for one week each. "Lecithin did not result in any clinically significant improvement in cognitive functioning." (Dysken M W, Fovall P, et al. (1982) Neurology 32:1203-4) In fact, a novel analysis of the original data of 10 outpatients and 5 inpatients showed that the "Global Impression" (SCAG-G) not only worsened after dichotomization—"they produced a pooled odds ratio estimate of 3.0 (95% confidence interval (CI) from 0.9 to 9.8, a just non-significant finding in favor of placebo" (Higgins J P, Flicker L (2003) Cochrane Database Syst Rev CD001015), but declined with increasing dose of PC (Table 9), although the decline was not "significant" in a reanalysis performed as part of the present disclosure ($P_{ANOCA}$=0.2467)

TABLE 9

Increasing serum phosphatidylcholine levels worsens Alzheimer's disease. SCAG-G results (high values are better in patients with Alzheimer's disease receiving 2 weeks of lecithin at different levels. In some patients the assessment was repeated. Higher values are worse. Derived from (Harris CM (1981) PhD:140, Table XXI).

| SCAG-G | Placebo | Avg | Low | Avg | Medium | Avg | High | Avg |
|---|---|---|---|---|---|---|---|---|
| G4 | 5.4 | (5.40) | 6.6 | (6.60) | 6.6 | (6.60) | 5.5 | (5.50) |
| G5 | 5.5 | (5.50) | 6.5 | (6.50) | 6.5 | (6.50) | 5.6 | (5.60) |
| G12 | 6.6 | 6.6 (6.60) | 5.6 | (5.60) | 6.6 | 6.6 (6.60) | 6.5 | (6.50) |
| G15 | 5.5 | 5.5 (5.50) | 5.5 | (5.50) | 5.5 | (5.50) | 5.5 | 5.5 (5.50) |
| G16 | 2.1 | 2.2 (2.15) | 3.3 | (3.30) | 2.2 | 2.2 (2.20) | 2.2 | (2.20) |
| G20 | 4.3 | (4.30) | 4.4 | (4.40) | 4.4 | (4.40) | 4.4 | (4.40) |
| G21 | 3.1 | (3.10) | 2.2 | (2.20) | 3.3 | (3.30) | 2.3 | (2.30) |
| G22 | 5.5 | (5.50) | 5.5 | (5.50) | 4.6 | (4.60) | 5.5 | (5.50) |
| G23 | 5.6 | (5.60) | 4.6 | (4.60) | 5.4 | (5.40) | 4.4 | (4.40) |
| G24 | 2.3 | (2.30) | 2.3 | (2.30) | 2.3 | (2.30) | 3.2 | (3.20) |
| G25 | 2.3 | 2.2 (2.25) | 2.2 | (2.20) | 3.2 | 3.3 (3.25) | 2.2 | (2.20) |
| G26 | 4.4 | 4.3 (4.35) | 3.3 | 4.4 (3.85) | 3.4 | (3.40) | 4.4 | (4.40) |
| G27 | 6.6 | 6.6 (6.60) | 6.5 | (6.50) | 6.6 | 5.5 (6.05) | 6.6 | (6.60) |
| G28 | 6.4 | (6.40) | 5.5 | (5.50) | 4.4 | (4.40) | 4.4 | (4.40) |
| G29 | 4.4 | 3.3 (3.85) | 3.4 | (3.40) | 3.3 | (3.30) | 3.3 | 3.3 (3.30) |
| Avg | 4.67 | (4.63) | 4.49 | (4.53) | 4.55 | (4.52) | 4.40 | (4.40) |

A long-term, randomized, double-blind, study in Alzheimer's disease patients compared 20-25 g/d lecithin v. placebo (18 and 17 subjects with complete data, respectively) for six months with at least six months of follow-up. Lecithin treatment increased plasma choline values (depending on compliance). "As a whole there were no significant differences between the lecithin and placebo groups . . . . [If anything] it was the relatively poor compliers who did best." (Little A, Levy R, et al. (1985) J Neurol Neurosurg Psychiatry 48:736-42)

Overall, there is no evidence that lecithin (phosphatidylcholine) supplementation benefits patients with Alzheimer's disease. On the contrary, two studies provide results that are consistent with the hypothesis that PC worsens Alzheimer's disease, even when given only for a relatively short study period.

The unexpected findings of the present disclosure explain the inconsistent findings with some studies showing some improvement of dementia from dietary PC supplementation and other showing a negative effect: Reduction of overall PC may, in fact, be detrimental, but reduction of monomeric PC, which is present only "at an extremely low concentration" (Wilton D C (2005) European Journal of Lipid Science and Technology 107:193-205), provides a benefit.

Example 18: The Successful Results of Cyclodextrins in Various Animal Models are the Result of a Synergistic Effect on Inflammation an Autophagy HP-β-CD had been shown to be effective in animal models for a wide range of diseases, but scavenging cholesterol, the presumed mode of action, carried the risk of permanent hearing loss. The surprising genetic results of Example 1 and Example 2 let to the hypothesis that the mode of action of HP-β-CD was not through scavenging cholesterol, but through scavenging phospholipids (FIG. 45). Hence, HP-α-CD emerged as a safer (and more effective) alternative. The surprising results of Example 16 confirmed in FIG. 40 showed HP-α-CD to reduce systemic inflammation, in addition to improving autophagy.

In summary, α-CDs slow down several processes that are essential during early life, but can cause problems after the age of 50: (1) migration of cells during pre-natal (tissue) and early-post-natal (neuronal) development, (2) cellular uptake of nutrients during growth, and (3) innate immunity (inflammation) as a defense against pathogens not seen, yet, by the immune system. HP-α-CD achieves this by (a) reducing endocytosis and, thus, lysosomal stress (FIG. 46) and (b) inflammation, also called "inflammaging" (FIG. 47). An additional benefit is that reducing inflammation improves autophagy and, conversely, improving autophagy reduces inflammation. Hence, the effects of HP-α-CD on age-related conditions involving upregulated inflammation and down-regulated autophagy are expected to be highly synergistic.

Example 19: Study Design for Studying Neuroprotection by Alpha and Beta Cyclodextrin in Cell and Mouse Models of Alzheimer's Disease Abstract.

There is extensive evidence that cholesterol and membrane lipids play a key role in Alzheimer disease (AD) pathogenesis. Cyclodextrins (CD) are cyclic oligosaccharide compounds and hydroxypropyl-β-CD (HP-β-CD) is widely used to bind cholesterol. Since CD exerts significant beneficial effects in Niemann-Pick type C disease, which shares neuropathological features with AD, the effects of HP-β-CD were examined in cell and mouse models of AD. Cell membrane cholesterol accumulation was detected in N2a cells over-expressing Swedish mutant APP (SwN2a), and the level of membrane cholesterol was reduced by HP-β-CD treatment. HP-β-CD dramatically lowered the levels of Aβ42 in SwN2a cells, and the effects were persistent for 24 hours after withdrawal. Four months of subcutaneous HP-β-CD administration significantly improved spatial learning and memory deficits in Tg19959 mice, diminished Aβ plaque deposition, and reduced tau immunoreactive dystrophic neurites (DN). These are transgenic mice with 2 mutations in the APP gene which have been associated with human AD and beneficial effects were attributed to a reduction in cholesterol. Recently, a new GWAS analyses was used, which showed an overlap of phospholipid pathway genes in metastatic breast cancer with those found in AD cohorts. HPαCD also binds phospholipids, as does HP-β-CD, but does not bind cholesterol. HPαCD was twice as effective as HP-β-CD in slowing migration of breast cancer cells. It is therefore possible that the efficacy of HP-β-CD is not due to its effects on cholesterol but rather on phospholipids. One way to distinguish these possibilities is to test the efficacy of HPαCD both in vitro and in transgenic mice with APP mutations (Tg19959). In the present proposal we intend to determine whether HPαCD is equally efficacious, or much more efficacious, without having effects on cholesterol levels or membrane cholesterol as determined using filipin staining and mass spectroscopy. We will also determine whether the effects are dose-responsive both on beta-amyloid production in the N2a cells, as well as in vivo in the Tg19959 transgenic mice. These studies will therefore provide the ground work and scientific rationale to pursue this strategy further in clinical trials in patients with AD.

Summary of Key Supporting Data.

Previous, the effects of HP-β-CD were examined in cell and mouse models of AD. HP-β-CD dramatically lowered the levels of Aβ42 in SwN2a cells, and the effects were persistent for 24 h after withdrawal. Four months of subcutaneous HP-β-CD administration significantly improved spatial learning and memory deficits in Tg19959 mice, diminished Aβ plaque deposition, and reduced tau immunoreactive dystrophic neurites (DN). See (Sim I, Carini S, et al. (2012) AMIA Annu Symp Proc 2012:856-65). HP-β-CD lowered levels of Aβ42 in part by reducing β-cleavage of the APP protein, and it also up-regulated the expression of genes involved in cholesterol transport and Aβ clearance. This study for the first time showed neuroprotective effects of HP-β-CD in a transgenic mouse model of AD, both by reducing Aβ production and enhancing clearance mechanisms, which suggested that it could be a novel therapeutic strategy for disease modification in AD. Among the upregulated genes was ABCA1, a membrane transporter that exports cholesterol and phospholipids and is considered as a target of agonist peptides for the treatment of AD. (Bielicki J K (2016) Current opinion in lipidology 27:40-6)

Recent results, (Wittkowski K M, Dadurian C, et al. (2018) PLoS One 13:e0199012), identified several genes involved in "derailed endocytosis" of breast cancer, most of which (including ABCA1) had already been implicated in functional and gene-expression studies of AD, including ATP8A1/ATP8B1 (Arch Neurol, 65 (1), 45-53; Internat J Mol Sci, 14 (4), 7897-922; PLOS Genetics, 8 (8), e1002853).

ANO4 (Alzheimers Dement, 10 (1), 45-52).

ABCA1 (PLoS One, 11 (11), e0166195; Neurobiol Dis, 72 Pt A, 13-21; Alzheimers & Dementia, 11 (12), 1430-38; Neurobiol Dis, 72 Pt A, 54-60).

AGPAT3/AGPAT4 (J Alzheimers Dis, 23 (2), 349-59). (Sherva R, Baldwin C T, et al. (2011) J Alzheimers Dis 23:349-59)

DGKQ (Zhu, X. C., et al. (2016), 'Association of Parkinson's Disease GWAS-Linked Loci with Alzheimer's Disease in Han Chinese', Mol Neurobiol).

All of these genes are involved in transport and metabolism of phospholipids, while only few are involved in transport of cholesterol, suggesting that the effects seen in the above animal models of AD could be a consequence of reductions in phospholipids rather than cholesterol.

This hypothesis was supported by in vitro experiments in two human breast cancer cell lines, MDA-MB-231 (triple negative) and MCF-7 (estrogen receptor positive), showing 1 mM HPαCD to be more effective than 2 mM HPβCD against migration of both ER− and ER+ tumor cell migration (p=0.0252). See (Wittkowski K M, Dadurian C, et al. (2018) PLoS One 13:e0199012).

II. Aim 1 (Primary): To Test Efficacy of Equimolar HPαCD Versus HPβCD (2,000 and 4,000 mg/kg) and Control on Spatial Learning and Memory Deficits, in Tg19959 Mice Overexpressing Human Mutant APP Innovation: HPβCD is widely believed to exert its activity, including its activity in mouse models of AD, by scavenging cholesterol. See (Yao J, Ho D, et al. (2012) J Exp Med 209:2501-13). Our GWAS results, confirmed in in vitro studies, (Wittkowski K M, Dadurian C, et al. (2018) PLoS One 13:e0199012), showed association with genes already seen in functional and expression studies as implicating derailed endocytosis" in BC (Nat Rev Cancer, 8 (11), 835-50), and "driving pathogenesis in sporadic and familial [AD]". Biomed Res Int, 2014, 167024. Hence the effect of HPβCD seen in previous in vitro studies (Raghu H, Sodadasu P K, et al. (2010) BMC Cancer 10:647) was likely true to scavenging PLs, rather than cholesterol. "Derailed/deranged signaling and associated endocytosis" in AD. (Van Dooren T, Princen K, et al. (2014) Biomed Res Int 2014: 167024) If similar results were seen in in vitro models of AD, novel treatments could be sought that target PLs, rather than cholesterol.

Significance:

The initial positive in vivo results on AD in mice were not followed up with clinical trials, mainly because HPβCD was shown to carry the risk of causing permanent hearing loss from depriving outer hair cells of cholesterol. See The Journal of Experimental Medicine, 209 (13), 2501-13; (Takahashi S, Homma K, et al. (2016) Sci Rep 6:21973) The recent GWAS results shift the focus from cholesterol to PLs. This, in turn, could now open novel treatment options for AD, including HPαCD, which may be more effective than HPβCD, while avoiding the risk of permanent hearing loss from scavenging cholesterol. HPαCD is also less toxic than HPβCD in vitro. See International Journal of Pharmaceutics, 101 (1-2), 97-103.

Approach:

We will examine effects on cleavage of APP, expression of cholesterol and lipid transport genes, and Aβ clearance as well as levels of cholesterol and phospholipids. We will determine whether effects are dose-responsive by examining 2 concentrations of both HPαCD and HPβCD, and effects on lysosomes by cathepsin D immunostaining. We will perform these tests in five groups (Control, HPβCD 2g, HPβCD 4g, HPαCD 2g, HPαCD 4g) of 20 mice each.

Pitfalls and Alternatives:

Not all effects previously seen with HPβCD will be replicated with HPαCD and the differential effect will provide novel insights into the etiology. If, however, too few of the effects of HPβCD can be replicated with HPαCD, the hypothesis that the latter could become a safer treatment against AD will not be further pursued. Still, the results from Aim 2 may still provide novel insights leading to potential alternatives.

III. Aim 2: To Explore the Relative Activity of Scavenging PLs Only (HPαCD) Versus Scavenging Both PLs and Cholesterol (HPβCD) on AD Pathology . . . Aim 2a: . . . In N2a Cells Expressing the Swedish APP Mutation (Membrane Cholesterol, AP Production) Aim 2b: . . . in Tg19959 Mice Overexpressing Human Mutant APP (AP Deposition, Microgliosis, Amylogenesis, Tau and Lysosomal Abnormalities, Gene Expression)

Innovation:

Even if HPαCD spatial learning and memory by improving Aβ and tau pathology, the role of PLs v. cholesterol in the etiology of AD remains to be elucidated.

Significance:

A single drug is unlikely to become a panacea in AD. The mechanistic studies will provide insights to design studies that could lead to more specific drugs targeting cholesterol.

Approach:

We will aim to replicate the successful in vitro studies of HPβCD reducing Aβ production in N2a cells expressing the Swedish APP mutation, this time using HPαCD instead of HPβCD. To further elucidate the mechanism of action, we will use filipin staining to assess the effect of scavenging PLs on membrane cholesterol.

Pitfalls and Alternatives:

The role of cholesterol in AD is assumed, but not known. Hence, both positive and negative results on the effect of HPαCD on membrane cholesterol and Aβ production will be helpful in refining the understanding of the role of CDs in AD and provide valuable insights for the development of additional drugs.

Experimental Design and Methods

Based on the previous results showing 4,000 mg/kg HPβCD to be effective in vitro and the in vitro results showing HPαCD to be at least twice as effective as HPαCD in regulating EEC we will compare HPαCD_2g v. HPβCD_4g, but also HPαCD_2g v. HPβCD_2g, HPαCD_4g v. HPβCD_4g, HPαCD_4g v. HPαCD_2g, and HPαCD_4g v. HPαCD_2g. See The Journal of Experimental Medicine, 209 (13), 2501-13. As positive controls, we will replicate the previous results comparing Control v. HPβCD_4g.

To guard against regression to the mean (winner's curse) and account for multiplicity (five dependent comparisons) in Aim 1 and to ensure that negative results in the exploratory Aim 2 can be meaningfully interpreted, we will increase the sample size from 10 per group in the previous study of two groups ($\alpha=0.05$, power=0.80, $\delta=1.3$) to 20 per group in this study of 5 groups ($\alpha=0.01$, power=0.90). See The Journal of Experimental Medicine, 209 (13), 2501-13.

Experimental Animals.

Tg19959 mice were obtained from Dr. George Carlson (McLaughlin Research Institute, Great Falls, Mont.). Tg19959 mice are constructed by injecting FVBx129S6 F1 embryos with a cosmid insert containing human APP695 with two familial AD mutations (KM670/671NL and V717F), under control of the hamster PrP promoter. All experiments will be approved by the Institutional Animal Care and Use Committee at Weill-Cornell Medical College.

Cell Lines:

Mouse N2a neuroblastoma cells stably transfected with human APP695 carrying the 670/671 Swedish mutation (SwN2a) will be grown as described previously (Yao J, Hennessey T, et al. (2010) PLoS One 5:e15546).

HP-α-CD/HP-β-CD (HP-CD) Treatment in Cells.

10 mM HP-CD stock solution will be made in 1×PBS. SwN2a and N2a cells will be treated with HP-CD (5 mM) in serum free medium at different incubation times. To measure Aβ levels, SwN2a cells will be recovered in serum free medium for 5 or 24 h after HP-CD treatment.

Filipin Staining and Analysis.

Filipin is prepared in DMSO (50 mg/ml) and stored at −20° C. Cells will be fixed in 4% PFA for 30 min. For filipin staining, separate permeabilization of cells is not needed since filipin itself permeabilizes the cells. The stock solution will be diluted in PBS (1:100-1:500). The cells will be incubated for 15 min at room temperature and then washed in PBS 3× for 5 min. Anti-fading reagent (Fluoromount-G, SouthernBiotech) will be used in the mounting medium. Filipin is detected using $\lambda ex=360$ nm and $\lambda em=460$ nm. A fluorescence microscope connected to a CCD camera will be used, and images are taken using Metamorph (Molecular Devices). To analyze the images, we will use Image J (NIH) to apply a 70% threshold onto the images and quantify the alteration of filipin intensity of SwN2a cells with and without CD treatment. See Nat Neurosci, 9 (10), 1265-73.

Cholesterol Extraction from SwN2a Cells.

Six-well plates of SwN2a cells will be treated with and without CD for 15 min. Cells will be washed 3× with Hank's buffer and then 800 ul of hexane/isopropanol (3/2 v/v) containing β-sitosterol (internal standard, 5 ug of β-sitosterol per well) will be added. Lipids are extracted for 30 min under gentle shaking at room temperature. Lipid extracts will be transferred to 12×75 mm borosilicate glass culture tubes; and dried under Argon. The extraction will be repeated again and 50 ul hexane will be added per tube, vortexed and then transferred into glass vials for separation and analysis on GC-Mass Spec. The levels of cholesterol/mg protein will be calculated and plotted.

Cyclodextrin Administration to Mice.

Mice will be treated with HP-α-CD or HP-3-CD (HP-CD, 2000 or 4000 mg/kg) by subcutaneous injection twice weekly. HP-CD will be provided as a 20% (w/v) solution in isotonic saline with isotonic saline alone as the control. The injections of HP-CD in the mice will be started at P7, and the duration of the treatment will be four months. Twenty mice will be studied in each group.

Morris Water Maze.

Spatial learning and memory will be analyzed using the Morris water maze. See Learning and Motivation, 12 (2), 239-60. The mice are handled daily, starting 1 wk prior to behavioral testing, in order to habituate them. During the acquisition period, visual cues will be arranged in the room. The hidden platform is located in the middle of the northwest (NW) quadrant. Each day, mice were placed next to and facing the wall of the basin in 4 starting positions: north, east, south, and west, corresponding to four successive trials per day. The duration of a trial will be 60 s with an inter-trial interval of 60 min. Whenever the mouse fails to reach the platform within 60 s, it is placed on the platform by the experimenter for 10 s. Latencies before reaching the platform will be recorded for 5 d and analyzed.

A probe trial will be assessed 24 h after the last trial of the acquisition period, removing the platform from the pool. Mice will be released on the north side for a single trial of 60 s, during which the time spent in the area of the platform will be measured. The velocity will also be measured.

The visible platform testing will be performed over 2 d with 4 trials per day. In this cued test, a pole will be added on the platform, and its location was changed between each trial. The duration of a trial will be 60 s with an inter-trial interval of 60 min. Latencies before reaching the platform will be recorded and averaged.

Sample Preparation from Brains and Cells.

Mice will be deeply anesthetized with intraperitoneal sodium pentobarbital and transcardially perfused with ice-cold saline. The brains will be removed and dissected on ice. One hemisphere will be used for histological analysis and the other hemisphere will be used for subsequent protein extraction or Trizol RNA extraction (Invitrogen). Brain tissues will be homogenized in lysis buffer containing 1% SDS+0.5% NP-40 and protease inhibitors (Roche) for Western blot analysis. Cells will be homogenized and prepared in Trizol for RNA extraction and in RIPA buffer or 1% Triton in PBS for protein extraction. Protein concentrations will be determined by BCA protein assay (Thermo Scientific).

Western Blot Analysis.

Samples with equal amount of protein will be separated by Tricine-SDS gel electrophoresis and transferred to PVDF membranes using the iBlot dry blotting system (Invitrogen). Membranes will be blocked with 5% milk/0.1% Tween20 in TBS for 1 h at room temperature, followed by incubation with primary antibodies overnight at 4° C. Signals will be detected using HRP-conjugated secondary antibodies and enhanced chemiluminescence (Thermo Scientific). Blots will be scanned at 600 dpi and densitometry will be performed using ImageJ (NIH). We will use the following antibodies: mouse monoclonal anti-tubulin (Sigma, 1:10000), mouse anti-Aβ1-16 (6E10) monoclonal antibody (Covance, 1:1000), rabbit anti-APP C-terminal antibody (Calbiochem), HRP-conjugated goat anti-mouse IgG (1:2000) and goat anti-rabbit IgG (1:3000) (KPL).

Enzyme Linked Immunosorbent Assay (ELISA).

Aβ42 levels will be quantified using a commercial ELISA kit (Invitrogen, KHB3441). The manufacturer's protocol will be followed to measure Aβ levels in cell extracts, medium from SwN2a cells and brain extracts from mice. Medium from SwN2a cells will be diluted 1:1 in diluents, and brain extracts will be diluted 1:10 in diluents, and then loaded onto the plate for analysis. Each sample will be run in duplicate and the experiments will be repeated at least twice.

Immunohistology.

The mice which will have been assessed behaviorally will be deeply anesthetized with intraperitoneal sodium pentobarbital and transcardially perfused with ice-cold saline. Brains will be post-fixed in 4% paraformaldehyde in PBS for at least 24 h. The brain tissues will be cut in 35 um sections, and immunostained using the avidin-biotin complex peroxidase method and visualized after DAB (diaminobenzidine) incubation for 5 min (Vector, Burlingame, Calif., USA). For each animal, 5 sections will be analyzed. For amyloid deposits, brain sections will be labeled with the anti-Aβ42 rabbit polyclonal antibody AB5078P (1:1000, Chemicon). For microglial activation, adjacent sections are also labeled with anti-CD-11b rat monoclonal antibody (1:100, Serotec). For phosphorylated tau, sections are labeled with AT8 antibody (1:500, Thermo Scientific). For cathepsin D, sections are labeled with RU4 antibody (generous gift from Dr. Ralph Nixon, New York University School of Medicine/Nathan Kline Institute). Using NIH Image 1.63 software (National Institutes of Health, Bethesda, Md., USA), the percentage areas occupied by AB5078P immunoreactive amyloid plaques and by CD-11b immunoreactive reactive microglia per 0.75 mm$^2$ will be calculated.

Thioflavin-S Staining.

Floating sections from Tg19959 will be washed and incubated in 1% Triton-PBS for 15 min, washed with PBS, and stained for 5 min with a solution of 0.05% thioflavin S (ThS) in 50% ethanol. Finally, sections are washed in 50% ethanol and then in water. The fluorescence of ThS is detected using λex=488 nm with fluorescence microscopy. The area of ThS fluorescence is determined using Image J and expressed as a fraction of total area.

Quantitation of Genes by RT-PCR

RNA will be extracted from 4-month-old mouse brains using the Trizol protocol (Invitrogen). Total RNA (1 μg) will then be reverse transcribed into cDNA using the High Capacity cDNA Reverse Transcription kit (Applied Biosystems, USA), with the addition of nuclease-free deionized water. Reverse transcription is performed according to the manufacturer's protocol. A total of 30 ng of cDNA is loaded into each well of the PCR plate. The cDNA is analyzed in duplicate by real-time quantitative PCR using the ABI Prism 7000 Sequence Detection System (Applied Biosystems, USA) and detected with Power SYBR Green Master Mix (Applied Biosystems, USA. Primer sequences were obtained from previous publications. See Biochim Biophys Acta, 1801 (8), 831-8; Proc Natl Acad Sci USA, 106 (7), 2377-82.

ABCA1 (Fwd: 5'-CGTTTCCGGGAAGTGTCCTA-3' (SEQ ID NO: 9);

Rev: 5'-GCTAGAGATGACAAGGAGGATGGA-3' (SEQ ID NO: 10)),

ABCA2 (Fwd: 5'-AGTGCTCAGCCTTCGTACAG-3' (SEQ ID NO: 11),

Rev: 5'-AGGCGCGTACAGGATTTTGG-3') (SEQ ID NO: 12)),

ABCG1 (Fwd: 5'-TTTGAGGGATTTGGGTCTGAAC-3' (SEQ ID NO: 13),

Rev: 5'-CCCCTTTAATCGTTTTGTCTGCT-3' (SEQ ID NO: 14)),

NPC1 (Fwd: 5'-GGGATGCCCGTGCCTGCAAT-3' (SEQ ID NO: 15);

Rev: 5'-CTGGCAGCTACATGGCCCCG-3' (SEQ ID NO: 16)),

For each sample, the cycle number Ct to reach threshold fluorescence will be determined in duplicate for each mRNA and actin. To determine relative amounts of mRNA in Tg19959 mice v. wildtype mice, data are presented using the 2-ΔΔCt method (Livak K J, Schmittgen T D (2001) Methods 25:402-8).

Statistical Methods.

Unpaired comparisons between groups will be performed using generalized Friedman/Kruskal-Wallis type rank-tests with Scheffe-type multiple comparisons. (Wittkowski K M (1988) J Am Statist Assoc 83:1163-70, 87:258). Calculations will be performed using R (http://www.cran.r-project.org/) and the muStat package (https://cran.r-project.org/package=muStat).

The primary outcome for Aim 1 is a composite u-score comprising

Total time spent reaching the hidden platform on day 5 and

Total time spent in the platform area.

To guard against artifacts (outliers, skewed distributions) in the interpretation (incl. Aim 2), we will plot results as box-and-whiskers plots. See (Tukey J W (1977) Exploratory data analysis Reading, Mass.: Addison-Wesley).

Example 20: Study Design for Studying Neuroprotection by Alpha and Beta Cyclodextrin in Cell and Mouse Models of Parkinson's Disease The aggregation of a-synuclein (a-syn) is believed to play a critical role in the pathogenesis of disorders such as dementia with Lewy bodies and Parkinson's disease. The main objective of a previous study (Bar-On P, Rockenstein E, et al. (2006) J Neurochem 98:1032-45) was to determine whether methyl-b-cyclodextrin (M-β-CD), interfered with a-syn accumulation in models of synucleinopathy. See J Neurochem, 98 (4), 1032-45. The authors studied the effects of M-β-CD on the accumulation of a-syn in a transfected neuronal cell line and in transgenic mice. Immunoblot analysis showed that M-β-CD reduced the level of a-syn in the membrane fraction and detergent-insoluble fraction of transfected cells. In agreement with the in vitro studies, treatment of mice with M-β-CD resulted in decreased levels of a-syn in membrane fractions and reduced accumulation of a-syn in the neuronal cell body and synapses. Taken together, these results were interpreted as suggesting that changes in cholesterol and lipid composition using M-β-CD may become a treatment of synucleinopathies. The results of the above examples, however, suggest that the effects seen were primarily due to M-β-CD, which was seen as a "cholesterol lowering agent" were, in fact, primarily due to M-β-CD scavenging phospholipids. In the current Example, the study will be replicated, this time using HP-α-CD, rather than M-β-CD.

Effects of M-β-CD on a-Syn Levels in Non-Tg and α-Syn Tg Mice Brains.

Non-transgenic (tg) and ha-syn tg mice will be treated with M-β-CD (10 mM) for 1 week and analyzed by western blot and immunocytochemistry.

Example 21: Study Design for Testing the Efficacy of a Cyclodextrin in Breast Cancer Because women after resection of breast cancer have a definitive diagnosis, clinical trials of HP-α-CD against "derailed endocytosis" should start in this population. As a non-limiting example, a seamless phase 2b/3 clinical trial for HP-α-CD for the prevention of metastases in breast cancer could be conducted in a population of women with triple negative breast cancer (tamoxifen and herceptin do not work well in this population) and axillary lymph node metastasis (patients have established the tendency to develop metastases)

The phase 2b part of the seamless design would have futility as an outcome after the first 80 patients have been seen for at least 2 yr and continue to be treated without unblinding, so that they can contribute to the primary endpoint, which would have time to distant metastasis as the outcome. As the recurrence rate is high for the first three years only data will be collected for up to 5 yrs. See J Breast Cancer, 18 (4), 371-7. Some of the later recruited patients will be administratively censored when the last patient will have been seen for two years. Gehan's test will be used to compare treated v. placebo patients. See Biometrika, 52, 203-23.

At an effective median observation time of three years, one would expect 30% of women to have a distant recurrence and could detect a reduction in incidence by 50% (to 15%) with the standard 80% power at the 5% level with 125 subjects per group. The placebo-controlled treatment would be given on top of the standard of care (chemotherapy, radiation, . . . ).

As long-term parenteral administration of HP-β-CD (200 mg/kg) was reported to decrease bone mineral density (BMD) in rats (Toxicol Pathol, 40 (5), 742-50), the study should carefully monitor Bone density.

Human erythrocytes tolerate α-CD better then β-CD. See WHO/JECFA Food Additive Series, 48, 1030. From animal studies, which have less tolerance for cyclodextrin than humans, the dose-limiting factors are likely nephrotoxicity and hemolysis In animal studies, α-CD did not show ototoxicity (Ann Clin Transl Neurol, 3 (5), 366-80) still, the dose-finding studies should carefully screen for Ototoxicity.

Example 22: Study Design for Testing the Efficacy of a Cyclodextrin in FSGS

In one aspect, the present disclosure provides a method of treating and/or preventing focal segmental glomerulosclerosis (FSGS) and/or nephrotic swelling in a subject in need thereof, the method comprising administering to the subject an effective amount of an α-CD, or an analogue or derivative thereof, either alone or in combination with one or more additional active agents. In some embodiment the composition is a clathrate of HP-α-CD and sodium caprate or caprylate.

A study will be performed in which HP-α-CD with and without clathrate will be administered orally to rats using a model set forth in Fogo, *Semin Nephrol.* 2003 March; 23(2):161-71, which is incorporated by reference in its entirety. Other oral formulations comprising and not comprising HP-α-CD will be tested alongside HP-α-CD to measure efficacy.

Other oral formulations may include those described in WO2016105465, ORAL COMPOSITIONS FOR INSOLUBLE COMPOUNDS, also incorporated by reference in its entirety.

We expect that HP-α-CD or analogs or derivatives thereof will effectively treat and/or prevent development of FSGS in mammals as well or better than other experimental compounds without known side effects of beta-cyclodextrins.

REFERENCES CITED

U.S. Patent Documents

U.S. Pat. No. 6,890,549 B2 2003/07/29 Artiss J D, Jen C (Priority: US 40436602 P Aug. 19, 2002) Compositions Comprising Dietary Fat Complexer And Methods For Their Use.
A method for reducing the bioavailability of fat in a consumable fat-containing food product comprising determining the amount of fat in a consumable fat-containing food product and combining α-cyclodextrin with the consumable fat-containing food product such that the consumable fat-containing food product comprises a ratio of α-cyclodextrin to fat of about 1:20 to about 1:3 w/w wherein said α-cyclodextrin or α-cyclodextrin complexes are not removed from said food product prior to consumption.

Other Publications

American Cancer Society (2015) *Cancer Facts & Figures 2015*. Atlanta: American Cancer Society Deli M A (2009) Potential use of tight junction modulators to reversibly open membranous barriers and improve drug delivery. *Biochimica et Biophysica Acta (BBA)—Biomembranes* 1788: 892-910

Renukuntla J, Vadlapudi A D, Patel A, Boddu S H S, Mitra A K (2013) Approaches for Enhancing Oral Bioavailability of Peptides and Proteins. *Int J Pharm* 447: 75-93

Shaikh I, Derle N D, Bhamber R, PDF] D (2012) Permeability Enhancement Techniques for Poorly Permeable Drugs: A Review. *J Appl Pharmacol Sci* 2: 34-9

Shityakov S, Salmas R E, Salvador E, Roewer N, Broscheit J et al. (2016) Evaluation of the potential toxicity of unmodified and modified cyclodextrins on murine blood-brain barrier endothelial cells. *J Toxicol Sci* 41: 175-84

Ohtani Y, Irie T, Uekama K, Fukunaga K, Pitha J (1989) Differential effects of α-, β- and γ-cyclodextrins on human erythrocytes. *European Journal of Biochemistry* 186: 17-22

Monnaert V, Tilloy S, Bricout H, Fenart L, Cecchelli R et al. (2004) Behavior of α-, β-, and γ-Cyclodextrins and Their Derivatives on an in Vitro Model of Blood-Brain Barrier. *Journal of Pharmacology and Experimental Therapeutics* 310: 745-51

Nociari M M, Lehmann G L, Perez Bay A E, Radu R A, Jiang Z et al. (2014) Beta cyclodextrins bind, stabilize, and remove lipofuscin bisretinoids from retinal pigment epithelium. *Proceedings of the National Academy of Sciences* 111: E1402-E8

Posor Y, Eichhorn-Grunig M, Haucke V (2015) Phosphoinositides in endocytosis. *Biochim Biophys Acta* 1851: 794-804

Samie M A, Xu H (2014) Lysosomal exocytosis and lipid storage disorders. *J Lipid Res* 55: 995-1009

Schmid S L, Mettlen M (2013) Cell biology: Lipid switches and traffic control. *Nature* 499: 161-2

Bohdanowicz M, Grinstein S (2013) Role of phospholipids in endocytosis, phagocytosis, and macropinocytosis. *Physiol Rev* 93: 69-106

Hesketh G G, Perez-Dorado I, Jackson L P, Wartosch L, Schafer I B et al. (2014) VARP is recruited on to endosomes by direct interaction with retromer, where together they function in export to the cell surface. *Dev Cell* 29: 591-606

Mosesson Y, Mills G B, Yarden Y (2008) Derailed endocytosis: an emerging feature of cancer. *Nat Rev Cancer* 8: 835-50

Chen X, Hui L, Soliman M L, Geiger J D (2014) Altered Cholesterol Intracellular Trafficking and the Development of Pathological Hallmarks of Sporadic AD. *J Parkinsons Dis Alzheimers Dis* 1

Schreij A M, Fon E A, McPherson P S (2015) Endocytic membrane trafficking and neurodegenerative disease. *Cell Mol Life Sci*

Blaising J, Polyak S J, Pecheur E I (2014) Arbidol as a broad-spectrum antiviral: an update. *Antiviral research* 107: 84-94

Cole S L, Grudzien A, Manhart I O, Kelly B L, Oakley H et al. (2005) Statins cause intracellular accumulation of amyloid precursor protein, beta-secretase-cleaved fragments, and amyloid beta-peptide via an isoprenoid-dependent mechanism. *J Biol Chem* 280: 18755-70

Kilpatrick K, Zeng Y, Hancock T, Segatori L (2015) Genetic and chemical activation of TFEB mediates clearance of aggregated alpha-synuclein. *PLoS One* 10: e0120819

Davidson C D, Fishman Y I, Puskas I, Szeman J, Sohajda T et al. (2016) Efficacy and ototoxicity of different cyclodextrins in Niemann-Pick C disease. *Ann Clin Transl Neurol* 3: 366-80

McKew J, Zheng W E I, Xu M, Swaroop M, Marugan Juan J (2014). Cyclodextrin For The Treatment Of Lysosomal Storage Diseases. WO Patent No: WO 2014/022841 A1

Sole-Domenech S, Cruz D L, Capetillo-Zarate E, Maxfield F R (2016) The endocytic pathway in microglia during health, aging and Alzheimer's disease. *Ageing Res Rev* 32: 89-103

Song W, Wang F, Lotfi P, Sardiello M, Segatori L (2014) 2-Hydroxypropyl-beta-cyclodextrin promotes transcription factor EB-mediated activation of autophagy: implications for therapy. *J Biol Chem* 289: 10211-22

Kim S, Choi K J, Cho S J, Yun S M, Jeon J P et al. (2016) Fisetin stimulates autophagic degradation of phosphorylated tau via the activation of TFEB and Nrf2 transcription factors. *Sci Rep* 6: 24933

Medina D L, Ballabio A (2015) Lysosomal calcium regulates autophagy. *Autophagy* 11: 970-1

Salter M W, Stevens B (2017) Microglia emerge as central players in brain disease. *Nat Med* 23: 1018-27

Luo C, Jian C, Liao Y, Huang Q, Wu Y et al. (2017) The role of microglia in multiple sclerosis. *Neuropsychiatr Dis Treat* 13: 1661-7

Prinz M, Priller J (2014) Microglia and brain macrophages in the molecular age: from origin to neuropsychiatric disease. *Nat Rev Neurosci* 15: 300-12

Gunasekara L, Al-Saiedy M, Green F, Pratt R, Bjornson C et al. (2017) Pulmonary surfactant dysfunction in pediatric cystic fibrosis: Mechanisms and reversal with a lipid-sequestering drug. *Journal of cystic fibrosis: official journal of the European Cystic Fibrosis Society*

Hipler U C, Schonfelder U, Hipler C, Elsner P (2007) Influence of cyclodextrins on the proliferation of HaCaT keratinocytes in vitro. *J Biomed Mater Res A* 83: 70-9

Irie T, Fukunaga K, Garwood M K, Carpenter T O, Pitha J (1992) Hydroxypropylcyclodextrins in parenteral use. II: Effects on transport and disposition of lipids in rabbit and humans. *J Pharm Sci* 81: 524-8

Frank D W, Gray J E, Weaver R N (1976) Cyclodextrin nephrosis in the rat. *Am J Pathol* 83: 367-82

Wittkowski K M, Dadurian C, Seybold M P, Kim H S, Hoshino A et al. (2018) Complex polymorphisms in endocytosis genes suggest alpha-cyclodextrin as a treatment for breast cancer. *PLoS One* 13: e0199012

Wittkowski K M, Lee E, Nussbaum R, Chamian F N, Krueger J G (2004) Combining several ordinal measures in clinical studies. *Stat Med* 23: 1579-92

Tuvia S, Pelled D, Marom K, Salama P, Levin-Arama M et al. (2014) A Novel Suspension Formulation Enhances Intestinal Absorption of Macromolecules Via Transient and Reversible Transport Mechanisms. *Pharmaceutical Research* 31: 2010-21

Sardiello M (2016) Transcription factor EB: from master coordinator of lysosomal pathways to candidate therapeutic target in degenerative storage diseases. *Ann N Y Acad Sci* 1371: 3-14

Moors T E, Hoozemans J J, Ingrassia A, Beccari T, Parnetti L et al. (2017) Therapeutic potential of autophagy-enhancing agents in Parkinson's disease. *Mol Neurodegener* 12: 11

Martini-Stoica H, Xu Y, Ballabio A, Zheng H (2016) The Autophagy-Lysosomal Pathway in Neurodegeneration: A TFEB Perspective. *Trends Neurosci* 39: 221-34

Elmaleh D (2017). Methods For Treating Alzheimer's Disease And Related Disorders. WO Patent No: WO 2017/087962 A1

Michel D, Chitanda J M, Balogh R, Yang P, Singh J et al. (2012) Design and evaluation of cyclodextrin-based delivery systems to incorporate poorly soluble curcumin analogs for the treatment of melanoma. *Eur J Pharm Biopharm* 81: 548-56

Hunter R, Stellenboom N, Caira M R (2008) Efficient one-pot synthesis of unsymmetrical cysteine disulfides. *Synlett*: 252-4

Butt A M, Mohd Amin M C, Katas H (2015) Synergistic effect of pH-responsive folate-functionalized poloxamer 407-TPGS-mixed micelles on targeted delivery of anticancer drugs. *Int J Nanomedicine* 10: 1321-34

Wittkowski K M, Sonakya V, Bigio B, Tonn M K, Shic F et al. (2014) A novel computational biostatistics approach implies impaired dephosphorylation of growth factor receptors as associated with severity of autism. *Transl Psychiatry* 4: e354

Waugh M G (2015) PIPs in neurological diseases. *Biochim Biophys Acta* 1851: 1066-82

Prakash A S, Abbott P J (2001) Safety evaluation of certain food additives and contaminants: alpha-cyclodextrin. *WHO/JECFA Food Additive Series* 48: 1030

Committee for Human Medicinal Products (CHMP) (2017) Cyclodextrins used as excipients. *European Medicines Agency*: EMA/CHMP/333892/2013

European Medicines Agency (2017) Annex to the European Commission guideline on 'Excipients in the labelling and package leaflet of medicinal products for human use'. EMA/CHMP/302620/2017/EN Tatusova T A, Madden T L (1999) BLAST 2 Sequences, a new tool for comparing protein and nucleotide sequences. *FEMS microbiology letters* 174: 247-50

Ooms Lisa M, Binge Lauren C, Davies Elizabeth M, Rahman P, Conway James R W et al. (2015) The Inositol Polyphosphate 5-Phosphatase PIPP Regulates AKT1-Dependent Breast Cancer Growth and Metastasis. *Cancer cell* 28: 155-69

Ma K, Cheung S M, Marshall A J, Duronio V (2008) PI(3,4,5)P3 and PI(3,4)P2 levels correlate with PKB/akt phosphorylation at Thr308 and Ser473, respectively; PI(3,4)P2 levels determine PKB activity. *Cell Signal* 20: 684-94

Majerus P W, York J D (2009) Phosphoinositide phosphatases and disease. *Journal of Lipid Research* 50: S249-S54

Bridges D, Saltiel A R (2015) Phosphoinositides: Key modulators of energy metabolism. *Biochim Biophys Acta* 1851: 857-66

Woolley J F, Dzneladze I, Salmena L (2015) Phosphoinositide signaling in cancer: INPP4B Akt(s) out. *Trends Mol Med* 21: 530-2

Chew C L, Chen M, Pandolfi P P (2016) Endosome and INPP4B. *Oncotarget* 7: 5-6

O'Neill C (2013) PI3-kinase/Akt/mTOR signaling: impaired on/off switches in aging, cognitive decline and Alzheimer's disease. *Experimental gerontology* 48: 647-53

Mayer I A, Arteaga C L (2016) The PI3K/AKT Pathway as a Target for Cancer Treatment. *Annu Rev Med* 67: 11-28

Vecsernyes M, Fenyvesi F, Bacskay I, Deli M A, Szente L et al. (2014) Cyclodextrins, blood-brain barrier, and treatment of neurological diseases. *Arch Med Res* 45: 711-29

Rivers J R, Maggo S D, Ashton J C (2012) Neuroprotective effect of hydroxypropyl-beta-cyclodextrin in hypoxia-ischemia. *Neuroreport* 23: 134-8

Zimmer S, Grebe A, Bakke S S, Bode N, Halvorsen B et al. (2016) Cyclodextrin promotes atherosclerosis regression via macrophage reprogramming. *Sci Transl Med* 8: 333ra50

Walenbergh S M, Houben T, Hendrikx T, Jeurissen M L, van Gorp P J et al. (2015) Weekly treatment of 2-hydroxypropyl-beta-cyclodextrin improves intracellular cholesterol levels in LDL receptor knockout mice. *Int J Mol Sci* 16: 21056-69

Dos Santos A G, Bayiha J C, Dufour G, Cataldo D, Evrard B et al. (2017) Changes in membrane biophysical properties induced by the Budesonide/Hydroxypropyl-beta-cyclodextrin complex. *Biochim Biophys Acta* 1859: 1930-40

Cataldo D, Evrard B, Noel A, Foldart J-M (2015). Use Of Cyclodextrin For Treatment And Prevention Of Bronchial Inflammatory Diseases. U.S. Pat. No. 9,034,846 B2, U.S. Pat. No. 9,034,846 B2:

Llanos P, Contreras-Ferrat A, Georgiev T, Osorio-Fuentealba C, Espinosa A et al. (2015) The cholesterol-lowering agent methyl-beta-cyclodextrin promotes glucose uptake via GLUT4 in adult muscle fibers and reduces insulin resistance in obese mice. *American journal of physiology Endocrinology and metabolism* 308: E294-305

Prior M, Lehmann S, Sy M S, Molloy B, McMahon H E (2007) Cyclodextrins inhibit replication of scrapie prion protein in cell culture. *Journal of virology* 81: 11195-207

Danthi P, Chow M (2004) Cholesterol removal by methyl-beta-cyclodextrin inhibits poliovirus entry. *Journal of virology* 78: 33-41

Balla T (2013) Phosphoinositides: tiny lipids with giant impact on cell regulation. *Physiological Reviews* 93: 1019-137

Shishido T K, Jokela J, Kolehmainen C T, Fewer D P, Wahlsten M et al. (2015) Antifungal activity improved by coproduction of cyclodextrins and anabaenolysins in Cyanobacteria. *Proc Natl Acad Sci USA* 112: 13669-74

Abou Daher A, El Jalkh T, Eid A A, Fornoni A, Marples B et al. (2017) Translational Aspects of Sphingolipid Metabolism in Renal Disorders. *Int J Mol Sci* 18

Viaud J, Mansour R, Antkowiak A, Mujalli A, Valet C et al. (2016) Phosphoinositides: Important lipids in the coordination of cell dynamics. *Biochimie* 125: 250-8

Falasca M (2012, ed)^(2012, eds) *Phosphoinositides and Disease*. (Vogt, P K (ed) *Current topics in microbiology and immunology*) Dordrecht: Springer, Pages Wang C, Telpoukhovskaia M A, Bahr B A, Chen X, Gan L (2017) Endo-lysosomal dysfunction: a converging mechanism in neurodegenerative diseases. *Curr Opin Neurobiol* 48: 52-8

Bishop D V (2010) Which neurodevelopmental disorders get researched and why?*PLoS One* 5: e15112

Sullivan P M, Zhou X, Hu F (2017) Autophagy-Lysosome Dysfunction in Amyotrophic Lateral Sclerosis and Frontotemporal Lobar Degeneration. In: Sharma, PD (ed) *Lysosomes-Associated Diseases and Methods to Study Their Function*. Rijeka: InTech, 63-91

Irie T, Uekama K (1997) Pharmaceutical applications of cyclodextrins. III. Toxicological issues and safety evaluation. *J Pharm Sci* 86: 147-62

Brewster M E, Loftsson T (2007) Cyclodextrins as pharmaceutical solubilizers. *Advanced Drug Delivery Reviews* 59: 645-66

Loftsson T, Brewster M E (1996) Pharmaceutical applications of cyclodextrins. 1. Drug solubilization and stabilization. *J Pharm Sci* 85: 1017-25

Stella V J, He Q (2008) Cyclodextrins. *Toxicol Pathol* 36: 30-42

Irie T, Otagiri M, Sunada M, Uekama K, Ohtani Y et al. (1982) Cyclodextrin-induced hemolysis and shape changes of human erythrocytes in vitro. *J Pharmacobiodyn* 5: 741-4

Roka E, Ujhelyi Z, Deli M, Bocsik A, Fenyvesi E et al. (2015) Evaluation of the Cytotoxicity of alpha-Cyclodextrin Derivatives on the Caco-2 Cell Line and Human Erythrocytes. *Molecules* 20: 20269-85

Ono N, Arima H, Hirayama F, Uekama K (2001) A moderate interaction of maltosyl-alpha-cyclodextrin with Caco-2 cells in comparison with the parent cyclodextrin. *Biol Pharm Bull* 24: 395-402

Ward S, O'Donnell P, Fernandez S, Vite C H (2010) 2-hydroxypropyl-beta-cyclodextrin raises hearing threshold in normal cats and in cats with Niemann-Pick type C disease. *Pediatr Res* 68: 52-6

Ory D S, Ottinger E A, Farhat N Y, King K A, Jiang X et al. (2017) Intrathecal 2-hydroxypropyl-beta-cyclodextrin decreases neurological disease progression in Niemann-Pick disease, type C1: a non-randomised, open-label, phase 1-2 trial. *Lancet* 390: 1758-68

Vance J E, Karten B (2014) Niemann-Pick C disease and mobilization of lysosomal cholesterol by cyclodextrin. *Journal of Lipid Research* 55: 1609-21

Liu B, Turley S D, Burns D K, Miller A M, Repa J J et al. (2009) Reversal of defective lysosomal transport in NPC disease ameliorates liver dysfunction and neurodegeneration in the npc1–/– mouse. *Proc Natl Acad Sci USA* 106: 2377-82

NIH (2015) Study of 2-hydroxypropyl-β-cyclodextrin (VTS-270) to Treat Niemann-Pick Type C1 (NPC1) Disease. *ClinicalTrialsgov*: NCT02534844

Zarzycki P K, Ohta H, Saito Y, Jinno K (2008) Interaction of native alpha-cyclodextrin, beta-cyclodextrin and gamma-cyclodextrin and their hydroxypropyl derivatives with selected organic low molecular mass compounds at elevated and subambient temperature under RP-HPLC conditions. *Anal Bioanal Chem* 391: 2793-801

Fauvelle F, Debouzy J C, Crouzy S, Goschl M, Chapron Y (1997) Mechanism of alpha-cyclodextrin-induced hemolysis. 1. The two-step extraction of phosphatidylinositol from the membrane. *J Pharm Sci* 86: 935-43

Cai W, Du A, Feng K, Zhao X, Qian L et al. (2013) Adenylyl cyclase 6 activation negatively regulates TLR4 signaling through lipid raft-mediated endocytosis. *J Immunol* 191: 6093-100

Huang Z, London E (2013) Effect of cyclodextrin and membrane lipid structure upon cyclodextrin-lipid interaction. *Langmuir* 29: 14631-8

Takahashi S, Homma K, Zhou Y, Nishimura S, Duan C et al. (2016) Susceptibility of outer hair cells to cholesterol chelator 2-hydroxypropyl-beta-cyclodextrine is prestindependent. *Sci Rep* 6: 21973

Kamar R I, Organ-Darling L E, Raphael R M (2012) Membrane Cholesterol Strongly Influences Confined Diffusion of Prestin. *Biophysical Journal* 103: 1627-36

Kantner I, Erben R G (2012) Long-term parenteral administration of 2-hydroxypropyl-beta-cyclodextrin causes bone loss. *Toxicol Pathol* 40: 742-50

Liu X-M, Wiswall A T, Rutledge J E, Akhter M P, Cullen D M et al. (2008) Osteotropic β-cyclodextrin for local bone regeneration. *Biomaterials* 29: 1686-92

Booij L H (2009) Cyclodextrins and the emergence of sugammadex. *Anaesthesia* 64 Suppl 1: 31-7

Merkus F W, Verhoef J C, Romeijn S G, Schipper N G (1991) Absorption enhancing effect of cyclodextrins on intranasally administered insulin in rats. *Pharm Res* 8: 588-92

Shao Z, Krishnamoorthy R, Mitra A K (1992) CYCLODEXTRINS AS NASAL ABSORPTION PROMOTERS OF INSULIN—MECHANISTIC EVALUATIONS. *Pharmaceutical Research* 9: 1157-63

Sakurai T, Sakurai A, Chen Y, Vaisman B L, Amar M J et al. (2017) Dietary alpha-cyclodextrin reduces atherosclerosis and modifies gut flora in apolipoprotein E-deficient mice. *Mol Nutr Food Res* 61

Liu Z C, Samanta A, Lei J Y, Sun J L, Wang Y P et al. (2016) Cation-Dependent Gold Recovery with a-Cyclodextrin Facilitated by Second-Sphere Coordination. *Journal of the American Chemical Society* 138: 11643-53

Szente L, Fenyvesi E (2017) Cyclodextrin-Lipid Complexes: Cavity Size Matters. *Structural Chemistry* 28: 479-92

Maarup T J, Chen A H, Porter F D, Farhat N Y, Ory D S et al. (2015) Intrathecal 2-hydroxypropyl-beta-cyclodextrin in a single patient with Niemann-Pick C1. *Mol Genet Metab* 116: 75-9

Tiribuzi R, Orlacchio A, Crispoltoni L, Maiotti M, Zampolini M et al. (2011) Lysosomal beta-galactosidase and beta-hexosaminidase activities correlate with clinical stages of dementia associated with Alzheimer's disease and type 2 diabetes mellitus. *J Alzheimers Dis* 24: 785-97

Haldar K, Alam S (2017). Methods For Detection And Treatment Of Neurodegenerative Diseases. US Patent No: US 2017/0044590 A1

Kim T-W, Di Paolo G, Kang Min S U K, Berman D, McIntire Laura Beth J (2012). Phosphoinositide Modulation For The Treatment Of Neurodegenerative Diseases. U.S. Pat. No. 8,288,378 B2, U.S. Pat. No. 8,288,378:

Wittkowski K M (2014). Treatment and prevention of autism and autism spectrum disorders. U.S., US 2016/0206581 A1:

Michailidou K, Lindstrom S, Dennis J, Beesley J, Hui S et al. (2017) Association analysis identifies 65 new breast cancer risk loci. *Nature* 551: 92-4

Hunter D J, Kraft P, Jacobs K B, Cox D G, Yeager M et al. (2007) A genome-wide association study identifies alleles in FGFR2 associated with risk of sporadic postmenopausal breast cancer. *Nature Genet* 39: 870-4

Garcia-Closas M, Couch F J, Lindstrom S, Michailidou K, Schmidt M K et al. (2013) Genome-wide association studies identify four ER negative-specific breast cancer risk loci. *Nat Genet* 45: 392-8, 8e1-2

Mann H B, Whitney D R (1947) On a test of whether one of two random variables is stochastically larger than the other. *Ann Math Stat* 18: 50-60

Wilcoxon F (1954) Individual comparisons by ranking methods. *Biometrics* 1: 80-3

Armitage P (1955) Tests for linear trends in proportions and frequencies. *Biometrics* 11: 375-86

Hoeffding W (1948) A class of statistics with asymptotically normal distribution. *Ann Math Stat* 19: 293-325

Wittkowski K M, Sonakya V, Song T, Seybold M P, Keddache M et al. (2013) From single-SNP to wide-locus: genome-wide association studies identifying functionally related genes and intragenic regions in small sample studies. *Pharmacogenomics* 14: 391-401

Pearson T A, Manolio T A (2008) How to interpret a genome-wide association study. *JAMA* 299: 1335-44

Cleveland W S, Devlin S J (1988) Locally Weighted Regression: An Approach to Regression Analysis by Local Fitting. *J Am Statist Assoc* 83: 596-610

Tukey J W (1980) We Need Both Exploratory and Confirmatory. *American Statistician* 34: 23-5

Fisher R A (1956) *Statistical Methods and Scientific Inference*. New York: Hafner Gigerenzer G (2004) Dread risk, September 11, and fatal traffic accidents. *Psychol Sci* 15: 286-7

Tukey J W (1977) *Exploratory data analysis*. Reading, Mass.: Addison-Wesley

Tukey J W (1962) The future of data-analysis. *Ann Math Stat* 33: 1-67

Cicek M S, Cunningham J M, Fridley B L, Serie D J, Bamlet W R et al. (2012) Colorectal cancer linkage on chromosomes 4q21, 8q13, 12q24, and 15q22. *PLoS One* 7: e38175

Shulga Y V, Myers D S, Ivanova P T, Milne S B, Brown H A et al. (2010) Molecular species of phosphatidylinositol-cycle intermediates in the endoplasmic reticulum and plasma membrane. *Biochemistry* 49: 312-7

Busa W B (1988) Roles for the phosphatidylinositol cycle in early development. *Philos Trans R Soc Lond B Biol Sci* 320: 415-26

Kerr W G (2011) Inhibitor and activator: dual functions for SHIP in immunity and cancer. *Ann N Y Acad Sci* 1217: 1-17

Bosch A, Li Z, Bergamaschi A, Ellis H, Toska E et al. (2015) PI3K inhibition results in enhanced estrogen receptor function and dependence in hormone receptor-positive breast cancer. *Sci Transl Med* 7: 283ra51-ra51

Sengelaub C A, Navrazhina K, Ross J B, Halberg N, Tavazoie S F (2015) PTPRN2 and PLCβ1 promote metastatic breast cancer cell migration through PI(4,5)P2☐dependent actin remodeling. *The EMBO Journal*

Mellman I, Yarden Y (2013) Endocytosis and Cancer. *Cold Spring Harbor Perspectives in Biology* 5

Crews L, Tsigelny I, Hashimoto M, Masliah E (2009) Role of synucleins in Alzheimer's disease. *Neurotox Res* 16: 306-17

Tsigelny I F, Crews L, Desplats P, Shaked G M, Sharikov Y et al. (2008) Mechanisms of hybrid oligomer formation in the pathogenesis of combined Alzheimer's and Parkinson's diseases. *PLoS One* 3: e3135

Feldman A L, Johansson A L, Lambert P C, Sieurin J, Yang F et al. (2014) Familial coaggregation of Alzheimer's disease and Parkinson's disease: systematic review and meta-analysis. *Neuroepidemiology* 42: 69-80

Moskvina V, Harold D, Russo G, et al. (2013) Analysis of genome-wide association studies of alzheimer disease and of parkinson disease to determine if these 2 diseases share a common genetic risk. *JAMA Neurology* 70: 1268-76

Guerreiro R, Escott-Price V, Darwent L, Parkkinen L, Ansorge O et al. (2016) Genome-wide analysis of genetic correlation in dementia with Lewy bodies, Parkinson's and Alzheimer's diseases. *Neurobiol Aging* 38: 214 e7-10

Bras J, Guerreiro R, Darwent L, Parkkinen L, Ansorge O et al. (2014a) Genetic analysis implicates APOE, SNCA and suggests lysosomal dysfunction in the etiology of dementia with Lewy bodies. *Hum Mol Genet* 23: 6139-46

Disse M, Reich H, Lee P K, Schram S S (2016) A Review of the Association Between Parkinson Disease and Malignant Melanoma. *Dermatol Surg* 42: 141-6

Hanson H A, Horn K P, Rasmussen K M, Hoffman J M, Smith K R (2016) Is Cancer Protective for Subsequent Alzheimer's Disease Risk? Evidence From the Utah Population Database. *J Gerontol B Psychol Sci Soc Sci*

Malkki H (2016) Alzheimer disease: Cancer immunotherapy drug reduces symptoms of Alzheimer disease in mice. *Nat Rev Neurol* 12: 126-

Cai R, Hao Z, Winslett M, Xiao X, Yang Y et al. (2015) Deterministic identification of specific individuals from GWAS results. *Bioinformatics* 31: 1701-7

Rouzier R, Rajan R, Wagner P, Hess K R, Gold D L et al. (2005) Microtubule-associated protein tau: A marker of paclitaxel sensitivity in breast cancer. *Proc Natl Acad Sci USA* 102: 8315-20

Lopez Gonzalez I, Garcia-Esparcia P, Llorens F, Ferrer I (2016) Genetic and Transcriptomic Profiles of Inflammation in Neurodegenerative Diseases: Alzheimer, Parkinson, Creutzfeldt-Jakob and Tauopathies. *Int J Mol Sci* 17: 206

Kawate T, Iwaya K, Koshikawa K, Moriya T, Yamasaki T et al. (2015) High levels of DJ-1 protein and isoelectric point 6.3 isoform in sera of breast cancer patients. *Cancer Sci* 106: 938-43

Rivero-Rios P, Gomez-Suaga P, Fernandez B, Madero-Perez J, Schwab A J et al. (2015) Alterations in late endocytic trafficking related to the pathobiology of LRRK2-linked Parkinson's disease. *Biochem Soc Trans* 43: 390-5

Agalliu I, San Luciano M, Mirelman A, Giladi N, Waro B et al. (2015) Higher frequency of certain cancers in LRRK2 G2019S mutation carriers with Parkinson disease: a pooled analysis. *JAMA Neurol* 72: 58-65

Farge E, Ojcius D M, Subtil A, Dautry-Varsat A (1999) Enhancement of endocytosis due to aminophospholipid transport across the plasma membrane of living cells. *Am J Physiol* 276: C725-33

Levano K, Sobocki T, Jayman F, Debata P R, Sobocka M B et al. (2009) A genetic strategy involving a glycosyltransferase promoter and a lipid translocating enzyme to eliminate cancer cells. *Glycoconj J* 26: 739-48

Levano K, Punia V, Raghunath M, Debata P R, Curcio G M et al. (2012) Atp8a1 deficiency is associated with phosphatidylserine externalization in hippocampus and delayed hippocampus-dependent learning. *J Neurochem* 120: 302-13

Andersen J P, Vestergaard A L, Mikkelsen S A, Mogensen L S, Chalat M et al. (2016) P4-ATPases as Phospholipid Flippases-Structure, Function, and Enigmas. *Front Physiol* 7: 275 da Costa A, Lenze D, Hummel M, Kohn B, Gruber A D et al. (2012) Identification of six potential markers for the detection of circulating canine mammary tumour cells in the peripheral blood identified by microarray analysis. *J Comp Pathol* 146: 143-51

Sjöblom T, Jones S, Wood L D, Parsons D W, Lin J et al. (2006) The Consensus Coding Sequences of Human Breast and Colorectal Cancers. *Science* 314: 268-74

Lee B H, Taylor M G, Robinet P, Smith J D, Schweitzer J et al. (2013) Dysregulation of cholesterol homeostasis in human prostate cancer through loss of ABCA1. *Cancer Res* 73: 1211-8

Sekine Y, Demosky S J, Stonik J A, Furuya Y, Koike H et al. (2010) High-density lipoprotein induces proliferation and migration of human prostate androgen-independent cancer cells by an ABCA1-dependent mechanism. *Mol Cancer Res* 8: 1284-94

Trasino S E, Kim Y S, Wang T T (2009) Ligand, receptor, and cell type-dependent regulation of ABCA1 and ABCG1 mRNA in prostate cancer epithelial cells. *Mol Cancer Ther* 8: 1934-45

Zhu X, Libby R T, de Vries W N, Smith R S, Wright D L et al. (2012) Mutations in a P-Type ATPase Gene Cause Axonal Degeneration. *PLOS Genetics* 8: e1002853

Soderberg M, Edlund C, Alafuzoff I, Kristensson K, Dallner G (1992) Lipid composition in different regions of the brain in Alzheimer's disease/senile dementia of Alzheimer's type. *J Neurochem* 59: 1646-53

Li H, Wetten S, Li L, St Jean P L, Upmanyu R et al. (2008) Candidate single-nucleotide polymorphisms from a genomewide association study of Alzheimer disease. *Arch Neurol* 65: 45-53

Picollo A, Malvezzi M, Accardi A (2015) TMEM16 proteins: unknown structure and confusing functions. *J Mol Biol* 427: 94-105

Weber G F (2015) Molecular Analysis of a Recurrent Sarcoma Identifies a Mutation in FAF1. *Sarcoma* 2015: 839182

Sherva R, Tripodis Y, Bennett D A, Chibnik L B, Crane P K et al. (2014) Genome-wide association study of the rate of cognitive decline in Alzheimer's disease. *Alzheimers Dement* 10: 45-52

Hamon Y, Trompier D, Ma Z, Venegas V, Pophillat M et al. (2006) Cooperation between Engulfment Receptors: The Case of ABCA1 and MEGF10. *PLoS One* 1: e120

Zhao W, Prijic S, Urban B C, Tisza M J, Zuo Y et al. (2016) Candidate Antimetastasis Drugs Suppress the Metastatic Capacity of Breast Cancer Cells by Reducing Membrane Fluidity. *Cancer Res* 76: 2037-49

Schimanski S, Wild P J, Treeck O, Horn F, Sigruener A et al. (2010) Expression of the lipid transporters ABCA3 and ABCA1 is diminished in human breast cancer tissue. *Horm Metab Res* 42: 102-9

Dong Y, Gou Y, Li Y, Liu Y, Bai J (2015) Synaptojanin cooperates in vivo with endophilin through an unexpected mechanism. *Elife* 4

Pinho R, Guedes L C, Soreq L, Lobo P P, Mestre T et al. (2016) Gene Expression Differences in Peripheral Blood of Parkinson's Disease Patients with Distinct Progression Profiles. *PLoS One* 11: e0157852

Dong X, Liu T, Xu S, Zhu L, Zhang P et al. (2016) The relevance of ABCA1 R219K polymorphisms and serum ABCA1 protein concentration to Parkinson's disease pathogenesis and classification: a case-control study. *Genes & Genomics* 38: 243-50

Loane D J, Washington P M, Vardanian L, Pocivavsek A, Hoe H S et al. (2011) Modulation of ABCA1 by an LXR agonist reduces beta-amyloid levels and improves outcome after traumatic brain injury. *J Neurotrauma* 28: 225-36

Koldamova R, Fitz N F, Lefterov I (2014) ATP-binding cassette transporter A1: from metabolism to neurodegeneration. *Neurobiol Dis* 72 Pt A: 13-21

Pahnke J, Langer O, Krohn M (2014) Alzheimer's and ABC transporters—new opportunities for diagnostics and treatment. *Neurobiol Dis* 72 Pt A: 54-60

Boehm-Cagan A, Bar R, Harats D, Shaish A, Levkovitz H et al. (2016) Differential Effects of apoE4 and Activation of ABCA1 on Brain and Plasma Lipoproteins. *PLoS One* 11: e0166195

Nordestgaard L T, Tybjaerg-Hansen A, Nordestgaard B G, Frikke-Schmidt R (2015) Loss-of-function mutation in ABCA1 and risk of Alzheimer's disease and cerebrovascular disease. *Alzheimers & Dementia* 11: 1430-8

Valenza M, Marullo M, Di Paolo E, Cesana E, Zuccato C et al. (2015) Disruption of astrocyte-neuron cholesterol cross talk affects neuronal function in Huntington's disease. *Cell Death Differ* 22: 690-702

Bradley R M, Marvyn P M, Aristizabal Henao J J, Mardian E B, George S et al. (2015) Acylglycerophosphate acyltransferase 4 (AGPAT4) is a mitochondrial lysophosphatidic acid acyltransferase that regulates brain phosphatidylcholine, phosphatidylethanolamine, and phosphatidylinositol levels. *Biochimica et Biophysica Acta (BBA)—Molecular and Cell Biology of Lipids* 1851: 1566-76

Sahay D, Leblanc R, Grunewald T G, Ambatipudi S, Ribeiro J et al. (2015) The LPA1/ZEB1/miR-21-activation pathway regulates metastasis in basal breast cancer. *Oncotarget* 6: 20604-20

Hopkins M M, Zhang Z, Liu Z, Meier K E (2016) Eicosopentaneoic Acid and Other Free Fatty Acid Receptor Agonists Inhibit Lysophosphatidic Acid- and Epidermal Growth Factor-Induced Proliferation of Human Breast Cancer Cells. *J Clin Med* 5

Gatto F, Miess H, Schulze A, Nielsen J (2015) Flux balance analysis predicts essential genes in clear cell renal cell carcinoma metabolism. *Sci Rep* 5: 10738

Cheng D, Jenner A M, Shui G, Cheong W F, Mitchell T W et al. (2011) Lipid Pathway Alterations in Parkinson's Disease Primary Visual Cortex. *PLoS One* 6: e17299

Sherva R, Baldwin C T, Inzelberg R, Vardarajan B, Cupples L A et al. (2011) Identification of novel candidate genes for Alzheimer's disease by autozygosity mapping using genome wide SNP data. *J Alzheimers Dis* 23: 349-59

Sakane F, Kanoh H (1997) Molecules in focus: diacylglycerol kinase. *Int J Biochem Cell Biol* 29: 1139-43

Filigheddu N, Cutrupi S, Porporato P E, Riboni F, Baldanzi G et al. (2007) Diacylglycerol kinase is required for HGF-induced invasiveness and anchorage-independent growth of MDA-MB-231 breast cancer cells. *Anticancer Res* 27: 1489-92

Bektas M, Payne S G, Liu H, Goparaju S, Milstien S et al. (2005) A novel acylglycerol kinase that produces lysophosphatidic acid modulates cross talk with EGFR in prostate cancer cells. *J Cell Biol* 169: 801-11

Lill C M, Roehr J T, McQueen M B, Kavvoura F K, Bagade S et al. (2012) Comprehensive research synopsis and systematic meta-analyses in Parkinson's disease genetics: The PDGene database. *PLoS Genet* 8: e1002548

Nails M A, Pankratz N, Lill C M, Do C B, Hernandez D G et al. (2014) Large-scale meta-analysis of genome-wide association data identifies six new risk loci for Parkinson's disease. *Nat Genet* 46: 989-93

Zhu X C, Cao L, Tan M S, Jiang T, Wang H F et al. (2016) Association of Parkinson's Disease GWAS-Linked Loci with Alzheimer's Disease in Han Chinese. *Mol Neurobiol*

Yu P, Agbaegbu C, Malide D A, Wu X, Katagiri Y et al. (2015) Cooperative interactions of LPPR family members in membrane localization and alteration of cellular morphology. *Journal of Cell Science* 128: 3210-22

Moran L B, Duke D C, Deprez M, Dexter D T, Pearce R K et al. (2006) Whole genome expression profiling of the medial and lateral substantia nigra in Parkinson's disease. *Neurogenetics* 7: 1-11

Ben-Chetrit N, Chetrit D, Russell R, Korner C, Mancini M et al. (2015) Synaptojanin 2 is a druggable mediator of metastasis and the gene is overexpressed and amplified in breast cancer. *Sci Signal* 8: ra7

Rossi M R, Hawthorn L, Platt J, Burkhardt T, Cowell J K et al. (2005) Identification of inactivating mutations in the JAK1, SYNJ2, and CLPTM1 genes in prostate cancer cells using inhibition of nonsense-mediated decay and microarray analysis. *Cancer Genet Cytogenet* 161: 97-103

Cao J, Gaamouch F E, Meabon J S, Meeker K D, Zhu L et al. (2017) ApoE4-associated phospholipid dysregulation contributes to development of Tau hyper-phosphorylation after traumatic brain injury. *Sci Rep* 7: 11372

Koran M E, Hohman T J, Meda S A, Thornton-Wells T A (2014) Genetic interactions within inositol-related pathways are associated with longitudinal changes in ventricle size. *J Alzheimers Dis* 38: 145-54

Erneux C, Ghosh S, Ramos A R, Edimo W E (2016) New Functions of the Inositol Polyphosphate 5-Phosphatases in Cancer. *Curr Pharm Des* 22: 2309-14

Zhang H-Y, Liang F, Jia Z-L, Song S-T, Jiang Z-F (2013) PTEN mutation, methylation and expression in breast cancer patients. *Oncology Letters* 6: 161-8

Pourmand G, Ziaee A A, Abedi A R, Mehrsai A, Alavi H A et al. (2007) Role of PTEN gene in progression of prostate cancer. *Urology journal* 4: 95-100

Choubey V, Cagalinec M, Liiv J, Safiulina D, Hickey M A et al. (2014) BECN1 is involved in the initiation of mitophagy: it facilitates PARK2 translocation to mitochondria. *Autophagy* 10: 1105-19

Frere S, Slutsky I (2016) Targeting PTEN interactions for Alzheimer's disease. *Nat Neurosci* 19: 416-8

Khalil B, El Fissi N, Aouane A, Cabirol-Pol M J, Rival T et al. (2015) PINK1-induced mitophagy promotes neuroprotection in Huntington's disease. *Cell Death Dis* 6: e1617

Wilson P M, Fryer R H, Fang Y, Hatten M E (2010) Astn2, A Novel Member of the Astrotactin Gene Family, Regulates the Trafficking of ASTN1 during Glial-Guided Neuronal Migration. *The Journal of Neuroscience* 30: 8529-40

Solecki D J (2012) Sticky situations: recent advances in control of cell adhesion during neuronal migration. *Curr Opin Neurobiol* 22: 791-8

Kawauchi T (2012) Cell adhesion and its endocytic regulation in cell migration during neural development and cancer metastasis. *Int J Mol Sci* 13: 4564-90

Wang K S, Tonarelli S, Luo X, Wang L, Su B et al. (2015) Polymorphisms within ASTN2 gene are associated with age at onset of Alzheimer's disease. *J Neural Transm (Vienna)* 122: 701-8

Anazi S, Maddirevula S, Faqeih E, Alsedairy H, Alzahrani F et al. (2016) Clinical genomics expands the morbid genome of intellectual disability and offers a high diagnostic yield. *Mol Psychiatry*

Rainero E, Howe J D, Caswell P T, Jamieson N B, Anderson K et al. (2015) Ligand-Occupied Integrin Internalization Links Nutrient Signaling to Invasive Migration. *Cell Rep* 10: 398-413

McCleverty C J, Lin D C, Liddington R C (2007) Structure of the PTB domain of tensin1 and a model for its recruitment to fibrillar adhesions. *Protein Science: A Publication of the Protein Society* 16: 1223-9

Burghel G J, Lin W-Y, Whitehouse H, Brock I, Hammond D et al. (2013) Identification of Candidate Driver Genes in Common Focal Chromosomal Aberrations of Microsatellite Stable Colorectal Cancer. *PLoS One* 8: e83859

Hall E H, Daugherty A E, Choi C K, Horwitz A F, Brautigan D L (2009) Tensin1 requires protein phosphatase-1alpha in addition to RhoGAP DLC-1 to control cell polarization, migration, and invasion. *J Biol Chem* 284: 34713-22

Shen Q, He B, Lu N, Conradt B, Grant B D et al. (2013) Phagocytic receptor signaling regulates clathrin and epsin-mediated cytoskeletal remodeling during apoptotic cell engulfment in *C. elegans*. *Development* 140: 3230-43

Singh T D, Park S Y, Bae J S, Yun Y, Bae Y C et al. (2010) MEGF10 functions as a receptor for the uptake of amyloid-beta. *FEBS Lett* 584: 3936-42

Baietti M F, Zhang Z, Mortier E, Melchior A, Degeest G et al. (2012) Syndecan-syntenin-ALIX regulates the biogenesis of exosomes. *Nat Cell Biol* 14: 677-85

Hurley J H, Odorizzi G (2012) Get on the exosome bus with ALIX. *Nat Cell Biol* 14: 654-5

Yang Y, Hong Q, Shi P, Liu Z, Luo J et al. (2013) Elevated expression of syntenin in breast cancer is correlated with lymph node metastasis and poor patient survival. *Breast Cancer Res* 15: R50

Tomlinson P R, Zheng Y, Fischer R, Heidasch R, Gardiner C et al. (2015) Identification of distinct circulating exosomes in Parkinson's disease. *Ann Clin Transl Neurol* 2: 353-61

Leonova E I, Galzitskaya O V (2015) Role of Syndecans in Lipid Metabolism and Human Diseases. *Adv Exp Med Biol* 855: 241-58

Persaud A, Alberts P, Hayes M, Guettler S, Clarke I et al. (2011) Nedd4-1 binds and ubiquitylates activated FGFR1 to control its endocytosis and function. *EMBO J* 30: 3259-73

Jung S, Li C, Jeong D, Lee S, Ohk J et al. (2013) Oncogenic function of p34SEI-1 via NEDD41mediated PTEN ubiquitination/degradation and activation of the PI3K/AKT pathway. *Int J Oncol* 43: 1587-95

Minn A J, Gupta G P, Siegel P M, Bos P D, Shu W et al. (2005) Genes that mediate breast cancer metastasis to lung. *Nature* 436: 518-24

Liao C J, Chi H C, Tsai C Y, Chen C D, Wu S M et al. (2015) A novel small-form NEDD4 regulates cell invasiveness and apoptosis to promote tumor metastasis. *Oncotarget* 6: 9341-54

Perrett R M, Alexopoulou Z, Tofaris G K (2015) The endosomal pathway in Parkinson's disease. *Mol Cell Neurosci* 66: 21-8

Rodrigues E M, Scudder S L, Goo M S, Patrick G N (2016) Abeta-Induced Synaptic Alterations Require the E3 Ubiquitin Ligase Nedd4-1. *J Neurosci* 36: 1590-5

Salminen A, Kaarniranta K, Kauppinen A, Ojala J, Haapasalo A et al. (2013) Impaired autophagy and APP processing in Alzheimer's disease: The potential role of Beclin 1 interactome. *Prog Neurobiol* 106-107: 33-54

Jounai N, Kobiyama K, Shiina M, Ogata K, Ishii K J et al. (2011) NLRP4 negatively regulates autophagic processes through an association with beclin1. *J Immunol* 186: 1646-55

Zhang Y, Sauler M, Shinn A S, Gong H, Haslip M et al. (2014) Endothelial PINK1 Mediates the Protective Effects of NLRP3 Deficiency during Lethal Oxidant Injury. *The Journal of Immunology* 192: 5296-304

Rohatgi R A, Shaw L M (2016) An autophagy-independent function for Beclin 1 in cancer. *Mol Cell Oncol* 3

Zhiyu W, Wang N, Wang Q, Peng C, Zhang J et al. (2016) The inflammasome: an emerging therapeutic oncotarget for cancer prevention. *Oncotarget* 7: 50766

Wang J D, Cao Y L, Li Q, Yang Y P, Jin M et al. (2015) A pivotal role of FOS-mediated BECN1/Beclin 1 upregulation in dopamine D2 and D3 receptor agonist-induced autophagy activation. *Autophagy* 11: 2057-73

Antonell A, Llado A, Sanchez-Valle R, Sanfeliu C, Casserras T et al. (2015) Altered Blood Gene Expression of Tumor-Related Genes (PRKCB, BECN1, and CDKN2A) in Alzheimer's Disease. *Mol Neurobiol*

Swaminathan G, Zhu W, Plowey E D (2016) BECN1/Beclin 1 sorts cell-surface APP/amyloid beta precursor protein for lysosomal degradation. *Autophagy* 12: 2404-19

Inabe K, Ishiai M, Scharenberg A M, Freshney N, Downward J et al. (2002) Vav3 modulates B cell receptor responses by regulating phosphoinositide 3-kinase activation. *J Exp Med* 195: 189-200

Malhotra S, Kovats S, Zhang W, Coggeshall K M (2009) Vav and Rac Activation in B Cell Antigen Receptor Endocytosis Involves Vav Recruitment to the Adapter Protein LAB. *The Journal of Biological Chemistry* 284: 36202-12

Chen X I N, Chen S I, Liu X-A, Zhou W-B, Ma R-R et al. (2015) Vav3 oncogene is upregulated and a poor prognostic factor in breast cancer patients. *Oncology Letters* 9: 2143-8

Wilkinson B L, Cramer P E, Varvel N H, Reed-Geaghan E, Jiang Q et al. (2012) Ibuprofen attenuates oxidative damage through NOX2 inhibition in Alzheimer's Disease. *Neurobiology of Aging* 33: 197.e21-.e32

Haddad S A, Ruiz-Narvaez E A, Haiman C A, Sucheston-Campbell L E, Bensen J T et al. (2016) An exome-wide analysis of low frequency and rare variants in relation to risk of breast cancer in African American Women: the AMBER Consortium. *Carcinogenesis*

Lin D-C, Xu L, Ding L-W, Sharma A, Liu L-Z et al. (2013) Genomic and functional characterizations of phosphodiesterase subtype 4D in human cancers. *Proc Natl Acad Sci USA* 110: 6109-14

Yang L, Calingasan N Y, Lorenzo B J, Beal M F (2008) Attenuation of MPTP neurotoxicity by rolipram, a specific inhibitor of phosphodiesterase IV. *Exp Neurol* 211: 311-4

Gurney M E, D'Amato E C, Burgin A B (2015) Phosphodiesterase-4 (PDE4) molecular pharmacology and Alzheimer's disease. *Neurotherapeutics* 12: 49-56

Pfeffer S R (1999) Motivating endosome motility. *Nat Cell Biol* 1: E145-E7

Walter J, Fluhrer R, Hartung B, Willem M, Kaether C et al. (2001) Phosphorylation regulates intracellular trafficking of beta-secretase. *J Biol Chem* 276: 14634-41

Armstrong A, Mattsson N, Appelqvist H, Janefjord C, Sandin L et al. (2014) Lysosomal network proteins as potential novel CSF biomarkers for Alzheimer's disease. *Neuromolecular Med* 16: 150-60

Waschbusch D, Michels H, Strassheim S, Ossendorf E, Kessler D et al. (2014) LRRK2 transport is regulated by its novel interacting partner Rab32. *PLoS One* 9: e111632

Bultema J J, Ambrosio A L, Burek C L, Di Pietro S M (2012) BLOC-2, AP-3, and AP-1 proteins function in concert with Rab38 and Rab32 proteins to mediate protein trafficking to lysosome-related organelles. *J Biol Chem* 287: 19550-63

Fukuda M (2016) Multiple Roles of VARP in Endosomal Trafficking: Rabs, Retromer Components and R-SNARE VAMP7 Meet on VARP. *Traffic* 17: 709-19

Wang X, Huang T, Bu G, Xu H (2014) Dysregulation of protein trafficking in neurodegeneration. *Molecular Neurodegeneration* 9: 1-9 van Weering J R, Verkade P, Cullen P J (2012) SNX-BAR-mediated endosome tubulation is co-ordinated with endosome maturation. *Traffic* 13: 94-107

Zhang Q Y, Tan M S, Yu J T, Tan L (2015) The Role of Retromer in Alzheimer's Disease. *Mol Neurobiol*

Rivera J, Megias D, Bravo J (2010) Sorting nexin 6 interacts with breast cancer metastasis suppressor-1 and promotes transcriptional repression. *J Cell Biochem* 111: 1464-72

Small S A, Petsko G A (2015) Retromer in Alzheimer disease, Parkinson disease and other neurological disorders. *Nat Rev Neurosci* 16: 126-32

Reitz C (2012) The role of intracellular trafficking and the VPS10d receptors in Alzheimer's disease. *Future Neurol* 7: 423-31

Gonzalez A, Valeiras M, Sidransky E, Tayebi N (2014) Lysosomal integral membrane protein-2: a new player in lysosome-related pathology. *Mol Genet Metab* 111: 84-91

Nishimura Y, Yoshioka K, Bernard O, Bereczky B, Itoh K (2006) A role of LIM kinase 1/cofilin pathway in regulating endocytic trafficking of EGF receptor in human breast cancer cells. *Histochem Cell Biol* 126: 627-38

Nishimura Y, Itoh K, Yoshioka K, Tokuda K, Himeno M (2003) Overexpression of ROCK in human breast cancer cells: evidence that ROCK activity mediates intracellular membrane traffic of lysosomes. *Pathol Oncol Res* 9: 83-95

Alcalay R N, Levy O A, Wolf P, Oliva P, Zhang X K et al. (2016) SCARB2 variants and glucocerebrosidase activity in Parkinson's disease. *NPJ Parkinsons Dis* 2

Shimizu E, Kawahara K, Kajizono M, Sawada M, Nakayama H (2008) IL-4-induced selective clearance of oligomeric beta-amyloid peptide(1-42) by rat primary type 2 microglia. *J Immunol* 181: 6503-13

Bras J, Guerreiro R, Darwent L, Parkkinen L, Ansorge O et al. (2014b) Genetic analysis implicates APOE, SNCA and suggests lysosomal dysfunction in the etiology of dementia with Lewy bodies. *Hum Mol Genet* 23: 6139-46

Ahmed H, AlSadek D M (2015) Galectin-3 as a Potential Target to Prevent Cancer Metastasis. *Clin Med Insights Oncol* 9: 113-21

O'Reilly E A, Gubbins L, Sharma S, Tully R, Guang M H et al. (2015) The fate of chemoresistance in triple negative breast cancer (TNBC). *BBA Clin* 3: 257-75 van Dijk K D, Persichetti E, Chiasserini D, Eusebi P, Beccari T et al. (2013) Changes in endolysosomal enzyme activities in cerebrospinal fluid of patients with Parkinson's disease. *Mov Disord* 28: 747-54

Parnell E, Palmer T M, Yarwood S J (2015) The future of EPAC-targeted therapies: agonism versus antagonism. *Trends Pharmacol Sci* 36: 203-14

Almahariq M, Tsalkova T, Mei F C, Chen H, Zhou J et al. (2013) A novel EPAC-specific inhibitor suppresses pancreatic cancer cell migration and invasion. *Mol Pharmacol* 83: 122-8

Jiang H L, Sun H F, Gao S P, Li L D, Hu X et al. (2015) Loss of RAB1B promotes triple-negative breast cancer metastasis by activating TGF-beta/SMAD signaling. *Oncotarget* 6: 16352-65

Winslow A R, Chen C W, Corrochano S, Acevedo-Arozena A, Gordon D E et al. (2010) alpha-Synuclein impairs macroautophagy: implications for Parkinson's disease. *J Cell Biol* 190: 1023-37

Puthiyedth N, Riveros C, Berretta R, Moscato P (2016) Identification of Differentially Expressed Genes through Integrated Study of Alzheimer's Disease Affected Brain Regions. *PLoS One* 11: e0152342

Bereczki E, Francis P T, Howlett D, Pereira J B, Hoglund K et al. (2016) Synaptic proteins predict cognitive decline in Alzheimer's disease and Lewy body dementia. *Alzheimers Dement*

Betz A, Okamoto M, Benseler F, Brose N (1997) Direct interaction of the rat unc-13 homologue Munc13-1 with the N terminus of syntaxin. *J Biol Chem* 272: 2520-6

Martin T F (2015) PI(4,5)P(2)-binding effector proteins for vesicle exocytosis. *Biochim Biophys Acta* 1851: 785-93

Fernandez-Nogueira P, Bragado P, Almendro V, Ametller E, Rios J et al. (2016) Differential expression of neurogenes among breast cancer subtypes identifies high risk patients. *Oncotarget* 7: 5313-26

Keogh M J, Daud D, Pyle A, Duff J, Griffin H et al. (2015) A novel de novo STXBP1 mutation is associated with mitochondrial complex I deficiency and late-onset juvenile-onset parkinsonism. *Neurogenetics* 16: 65-7

Campbell I M, Yatsenko S A, Hixson P, Reimschisel T, Thomas M et al. (2012) Novel 9q34.11 gene deletions encompassing combinations of four Mendelian disease genes: STXBP1, SPTAN1, ENG, and TOR1A. *Genet Med* 14: 868-76

Miller J A, Woltjer R L, Goodenbour J M, Horvath S, Geschwind D H (2013) Genes and pathways underlying regional and cell type changes in Alzheimer's disease. *Genome Med* 5: 48

Takahashi M, Iseki E, Kosaka K (2000) Cdk5 and munc-18/p67 co-localization in early stage neurofibrillary tangles-bearing neurons in Alzheimer type dementia brains. *J Neurol Sci* 172: 63-9

Law C, Schaan Profes M, Levesque M, Kaltschmidt J A, Verhage M et al. (2016) Normal Molecular Specification and Neurodegenerative Disease-Like Death of Spinal Neurons Lacking the SNARE-Associated Synaptic Protein Munc18-1. *J Neurosci* 36: 561-76

Antoniou A C, Beesley J, McGuffog L, Sinilnikova O M, Healey S et al. (2010) Common breast cancer susceptibility alleles and the risk of breast cancer for BRCA1 and BRCA2 mutation carriers: implications for risk prediction. *Cancer Res* 70: 9742-54

Day P, Riggs K A, Hasan N, Corbin D, Humphrey D et al. (2011) Syntaxins 3 and 4 mediate vesicular trafficking of alpha5beta1 and alpha3beta1 integrins and cancer cell migration. *Int J Oncol* 39: 863-71

Diao J, Burre J, Vivona S, Cipriano D J, Sharma M et al. (2013) Native alpha-synuclein induces clustering of synaptic-vesicle mimics via binding to phospholipids and synaptobrevin-2/VAMP2. *Elife* 2: e00592

Russell C L, Semerdjieva S, Empson R M, Austen B M, Beesley P W et al. (2012) Amyloid-beta acts as a regulator of neurotransmitter release disrupting the interaction between synaptophysin and VAMP2. *PLoS One* 7: e43201

Lizarbe M A, Barrasa J I, Olmo N, Gavilanes F, Turnay J (2013) Annexin-phospholipid interactions. Functional implications. *Int J Mol Sci* 14: 2652-83

Willshaw A, Grant K, Yan J, Rockliffe N, Ambavarapu S et al. (2004) Identification of a novel protein complex containing annexin A4, rabphilin and synaptotagmin. *FEBS Lett* 559: 13-21

Wei B, Guo C, Liu S, Sun M Z (2015) Annexin A4 and cancer. *Clin Chim Acta* 447: 72-8

Yao H, Sun C, Hu Z, Wang W (2016) The role of annexin A4 in cancer. *Front Biosci (Landmark Ed)* 21: 949-57

Matigian N, Abrahamsen G, Sutharsan R, Cook A L, Vitale A M et al. (2010) Disease-specific, neurosphere-derived cells as models for brain disorders. *Disease Models & Mechanisms* 3: 785-98

Kuzuya A, Zoltowska K M, Post K L, Arimon M, Li X et al. (2016) Identification of the novel activity-driven interaction between synaptotagmin 1 and presenilin 1 links calcium, synapse, and amyloid beta. *BMC Biol* 14: 25

Tan M G, Lee C, Lee J H, Francis P T, Williams R J et al. (2014) Decreased rabphilin 3A immunoreactivity in Alzheimer's disease is associated with Abeta burden. *Neurochem Int* 64: 29-36

Valencia A, Sapp E, Kimm J S, McClory H, Ansong K A et al. (2013) Striatal synaptosomes from Hdh140Q/140Q knock-in mice have altered protein levels, novel sites of methionine oxidation, and excess glutamate release after stimulation. *Journal of Huntington's disease* 2: 459-75

Chin H, Choi S H, Jang Y S, Cho S M, Kim H S et al. (2006) Protein kinase A-dependent phosphorylation of B/K protein. *Exp Mol Med* 38: 144-52

Fukuda M (2013) The role of synaptotagmin and synaptotagmin-like protein (Slp) in regulated exocytosis. *Madame Curie Regulated Database [Internet]*

Weng L, Ziliak D, Im H K, Gamazon E R, Philips S et al. (2013) Genome-wide discovery of genetic variants affecting tamoxifen sensitivity and their clinical and functional validation. *Annals of Oncology*

Gautam V, D'Avanzo C, Berezovska O, Tanzi R E, Kovacs D M (2015) Synaptotagmins interact with APP and promote Abeta generation. *Mol Neurodegener* 10: 31

Cha S H, Choi Y R, Heo C H, Kang S J, Joe E H et al. (2015) Loss of parkin promotes lipid rafts-dependent endocytosis through accumulating caveolin-1: implications for Parkinson's disease. *Mol Neurodegener* 10: 63

Ahmed M R, Zhan X, Song X, Kook S, Gurevich V V et al. (2011) Ubiquitin ligase parkin promotes Mdm2-arrestin interaction but inhibits arrestin ubiquitination. *Biochemistry* 50: 3749-63

Wang H, Liu B, Zhang C, Peng G, Liu M et al. (2009) Parkin regulates paclitaxel sensitivity in breast cancer via a microtubule-dependent mechanism. *J Pathol* 218: 76-85

Feng D D, Cai W, Chen X (2015) The associations between Parkinson's disease and cancer: the plot thickens. *Transl Neurodegener* 4: 20

Kitada T, Asakawa S, Hattori N, Matsumine H, Yamamura Y et al. (1998) Mutations in the parkin gene cause autosomal recessive juvenile parkinsonism. *Nature* 392: 605-8

Martin-Maestro P, Gargini R, Perry G, Avila J, Garcia-Escudero V (2016) PARK2 enhancement is able to compensate mitophagy alterations found in sporadic Alzheimer's disease. *Hum Mol Genet* 25: 792-806

Michailidou K, Hall P, Gonzalez-Neira A, Ghoussaini M, Dennis J et al. (2013) Large-scale genotyping identifies 41 new loci associated with breast cancer risk. *Nat Genet* 45: 353-61, 61e1-2

Chen C-L, Hou W-H, Liu I-H, Hsiao G, Huang S S et al. (2009) Inhibitors of clathrin-dependent endocytosis enhance TGFβ signaling and responses. *Journal of Cell Science* 122: 1863-71

Seaman M, Freeman C L (2014) Analysis of the Retromer complex-WASH complex interaction illuminates new avenues to explore in Parkinson disease. *Commun Integr Biol* 7: e29483

Vilarino-Guell C, Rajput A, Milnerwood A J, Shah B, Szu-Tu C et al. (2014) DNAJC13 mutations in Parkinson disease. *Hum Mol Genet* 23: 1794-801

Hsu W C, Wang H K, Lee L C, Fung H C, Lin J C et al. (2008) Promoter polymorphisms modulating HSPA5 expression may increase susceptibility to Taiwanese Alzheimer's disease. *J Neural Transm* (Vienna) 115: 1537-43

Kim S, Sato Y, Mohan P S, Peterhoff C, Pensalfini A et al. (2016) Evidence that the rab5 effector APPL1 mediates APP-betaCTF-induced dysfunction of endosomes in Down syndrome and Alzheimer's disease. *Mol Psychiatry* 21: 707-16

Van Dooren T, Princen K, De Witte K, Griffioen G (2014) Derailed intraneuronal signalling drives pathogenesis in sporadic and familial Alzheimer's disease. *Biomed Res Int* 2014: 167024

Di Fiore P P, von Zastrow M (2014) Endocytosis, Signaling, and Beyond. *Cold Spring Harbor Perspectives in Biology* 6

Colacurcio D J, Nixon R A (2016) Disorders of lysosomal acidification—The emerging role of v-ATPase in aging and neurodegenerative disease. *Ageing Res Rev*

Schroeder B, McNiven M A (2014) Importance of endocytic pathways in liver function and disease. *Compr Physiol* 4: 1403-17

Cooper A, Shaul Y (2006) Clathrin-mediated endocytosis and lysosomal cleavage of hepatitis B virus capsid-like core particles. *J Biol Chem* 281: 16563-9

Pecheur E I, Borisevich V, Halfmann P, Morrey J D, Smee D F et al. (2016) The Synthetic Antiviral Drug Arbidol Inhibits Globally Prevalent Pathogenic Viruses. *Journal of virology* 90: 3086-92

Mitra S, Cheng K W, Mills G B (2012) Rab25 in cancer: a brief update. *Biochem Soc Trans* 40: 1404-8

Zhang Q, Furukawa K, Chen H H, Sakakibara T, Urano T (2006) Metastatic potential of mouse Lewis lung cancer cells is regulated via ganglioside GM1 by modulating the matrix metalloprotease-9 localization in lipid rafts. *J Biol Chem* 281: 18145-55

Li Y C, Park M J, Ye S K, Kim C W, Kim Y N (2006) Elevated levels of cholesterol-rich lipid rafts in cancer cells are correlated with apoptosis sensitivity induced by cholesterol-depleting agents. *Am J Pathol* 168: 1107-18; quiz 404-5

Storch C H, Ehehalt R, Haefeli W E, Weiss J (2007) Localization of the human breast cancer resistance protein (BCRP/ABCG2) in lipid rafts/caveolae and modulation of its activity by cholesterol in vitro. *J Pharmacol Exp Ther* 323: 257-64

Daleke D L (2007) Phospholipid flippases. *J Biol Chem* 282: 821-5

Raghu H, Sodadasu P K, Malla R R, Gondi C S, Estes N et al. (2010) Localization of uPAR and MMP-9 in lipid rafts is critical for migration, invasion and angiogenesis in human breast cancer cells. *BMC Cancer* 10: 647

Palaniyandi K, Pockaj B A, Gendler S J, Chang X-B (2012) Human Breast Cancer Stem Cells Have Significantly Higher Rate of Clathrin-Independent and Caveolin-Independent Endocytosis than the Differentiated Breast Cancer Cells. *Journal of cancer science & therapy* 4: 214-22

Guerra F S, Sampaio LdS, Konig S, Bonamino M, Rossi M I D et al. (2016) Membrane cholesterol depletion reduces breast tumor cell migration by a mechanism that involves non-canonical Wnt signaling and IL-10 secretion. *Translational Medicine Communications* 1: 3

Resnik N, Repnik U, Kreft M E, Sepcic K, Macek P et al. (2015) Highly Selective Anti-Cancer Activity of Cholesterol-Interacting Agents Methyl-beta-Cyclodextrin and Ostreolysin A/Pleurotolysin B Protein Complex on Urothelial Cancer Cells. *PLoS One* 10: e0137878

Yamaguchi R, Perkins G, Hirota K (2015) Targeting cholesterol with beta-cyclodextrin sensitizes cancer cells for apoptosis. *FEBS Lett* 589: 4097-105

Yokoo M, Kubota Y, Motoyama K, Higashi T, Taniyoshi M et al. (2015) 2-Hydroxypropyl-beta-Cyclodextrin Acts as a Novel Anticancer Agent. *PLoS One* 10: e0141946

Simons M, Keller P, De Strooper B, Beyreuther K, Dotti C G et al. (1998) Cholesterol depletion inhibits the generation of beta-amyloid in hippocampal neurons. *Proc Natl Acad Sci USA* 95: 6460-4

Kojro E, Gimpl G, Lammich S, Marz W, Fahrenholz F (2001) Low cholesterol stimulates the nonamyloidogenic pathway by its effect on the alpha-secretase ADAM 10. *Proc Natl Acad Sci USA* 98: 5815-20

Yao J, Ho D, Calingasan N Y, Pipalia N H, Lin M T et al. (2012) Neuroprotection by cyclodextrin in cell and mouse models of Alzheimer disease. *J Exp Med* 209: 2501-13

Fortin D L, Troyer M D, Nakamura K, Kubo S, Anthony M D et al. (2004) Lipid rafts mediate the synaptic localization of alpha-synuclein. *J Neurosci* 24: 6715-23

Grosse P Y, Bressolle F, Pinguet F (1998) Antiproliferative effect of methyl-beta-cyclodextrin in vitro and in human tumour xenografted athymic nude mice. *Br J Cancer* 78: 1165-9

Gotoh K, Kariya R, Alam M M, Matsuda K, Hattori S et al. (2014) The antitumor effects of methyl-beta-cyclodextrin against primary effusion lymphoma via the depletion of cholesterol from lipid rafts. *Biochem Biophys Res Commun* 455: 285-9

Rocks N, Bekaert S, Coia I, Paulissen G, Gueders M et al. (2012) Curcumin-cyclodextrin complexes potentiate gemcitabine effects in an orthotopic mouse model of lung cancer. *Br J Cancer* 107: 1083-92

Agardan N B, Degim Z, Yilmaz S, Altintas L, Topal T (2015) The Effectiveness of Raloxifene-Loaded Liposomes and Cochleates in Breast Cancer Therapy. *AAPS PharmSciTech*

Jameson L P, Smith N W, Dzyuba S V (2012) Dye-binding assays for evaluation of the effects of small molecule inhibitors on amyloid (abeta) self-assembly. *ACS Chem Neurosci* 3: 807-19

Bar-On P, Rockenstein E, Adame A, Ho G, Hashimoto M et al. (2006) Effects of the cholesterol-lowering compound methyl-beta-cyclodextrin in models of alpha-synucleinopathy. *J Neurochem* 98: 1032-45

Gautam S, Karmakar S, Bose A, Chowdhury P K (2014) beta-cyclodextrin and curcumin, a potent cocktail for disaggregating and/or inhibiting amyloids: a case study with alpha-synuclein. *Biochemistry* 53: 4081-3

Song Y, Stampfer M J, Liu S (2004) Meta-analysis: apolipoprotein E genotypes and risk for coronary heart disease. *Ann Intern Med* 141: 137-47

Tan Z S, Seshadri S, Beiser A, Wilson P W, Kiel D P et al. (2003) Plasma total cholesterol level as a risk factor for Alzheimer disease: the Framingham Study. *Archives of internal medicine* 163: 1053-7

Cronin S, Lin A, Thompson K, Hoenerhoff M, Duncan R K (2015) Hearing Loss and Otopathology Following Systemic and Intracerebroventricular Delivery of 2-Hydroxypropyl-Beta-Cyclodextrin. *J Assoc Res Otolaryngol* 16: 599-611

Crumling M A, Liu L, Thomas P V, Benson J, Kanicki A et al. (2012) Hearing loss and hair cell death in mice given the cholesterol-chelating agent hydroxypropyl-beta-cyclodextrin. *PLoS One* 7: e53280

Vite C H, Bagel J H, Swain G P, Prociuk M, Sikora T U et al. (2015) Intracisternal cyclodextrin prevents cerebellar dysfunction and Purkinje cell death in feline Niemann-Pick type C1 disease. *Sci Transl Med* 7: 276ra26

Yamashita T, Hakizimana P, Wu S, Hassan A, Jacob S et al. (2015) Outer Hair Cell Lateral Wall Structure Constrains the Mobility of Plasma Membrane Proteins. *PLoS Genet* 11: e1005500

Lowry M C, Gallagher W M, O'Driscoll L (2015) The Role of Exosomes in Breast Cancer. *Clin Chem* 61: 1457-65

Peinado H, Lavotshkin S, Lyden D (2011) The secreted factors responsible for pre-metastatic niche formation: old sayings and new thoughts. *Semin Cancer Biol* 21: 139-46

Hoshino A, Costa-Silva B, Shen T-L, Rodrigues G, Hashimoto A et al. (2015) Tumour exosome integrins determine organotropic metastasis. *Nature* 527: 329-35

Koumangoye R B, Sakwe A M, Goodwin J S, Patel T, Ochieng J (2011) Detachment of Breast Tumor Cells Induces Rapid Secretion of Exosomes Which Subsequently Mediate Cellular Adhesion and Spreading. *PLoS One* 6: e24234

Strandvik B (2010) Fatty acid metabolism in cystic fibrosis. *Prostaglandins, leukotrienes, and essential fatty acids* 83: 121-9

Skolnik K, Levy R D, Wilcox P G, Quon B S (2016) Coronary artery disease in cystic fibrosis: An emerging concern? *Journal of cystic fibrosis: official journal of the European Cystic Fibrosis Society* 15: e70-e1

Dai S, Dulcey A E, Hu X, Wassif C A, Porter F D et al. (2017) Methyl-beta-cyclodextrin restores impaired autophagy flux in Niemann-Pick C1-deficient cells through activation of AMPK. *Autophagy* 13: 1435-51

Liu B, Li H, Repa J J, Turley S D, Dietschy J M (2008) Genetic variations and treatments that affect the lifespan of the NPC1 mouse. *J Lipid Res* 49: 663-9

Shvartsman D E, Gutman O, Tietz A, Henis Y I (2006) Cyclodextrins but not compactin inhibit the lateral diffusion of membrane proteins independent of cholesterol. *Traffic* 7: 917-26

Whyte L S, Lau A A, Hemsley K M, Hopwood J J, Sargeant T J (2017) Endo-lysosomal and autophagic dysfunction: a driving factor in Alzheimer's disease? *J Neurochem* 140: 703-17

Tan Y Q, Zhang J, Zhou G (2017) Autophagy and its implication in human oral diseases. *Autophagy* 13: 225-36

Pugazhendhi S, Baskaran K, Santhanam S, Ramakrishna B S (2017) Association of ATG16L1 gene haplotype with inflammatory bowel disease in Indians. *PLoS One* 12: e0178291

Plaza-Zabala A, Sierra-Torre V, Sierra A (2017) Autophagy and Microglia: Novel Partners in Neurodegeneration and Aging. *Int J Mol Sci* 18

Moloudizargari M, Asghari M H, Ghobadi E, Fallah M, Rasouli S et al. (2017) Autophagy, its mechanisms and regulation: Implications in neurodegenerative diseases. *Ageing Res Rev* 40: 64-74

Chen Y, Yu L (2017) Recent progress in autophagic lysosome reformation. *Traffic* 18: 358-61

Settembre C, Di Malta C, Polito V A, Garcia Arencibia M, Vetrini F et al. (2011) TFEB links autophagy to lysosomal biogenesis. *Science* 332: 1429-33

Decressac M, Mattsson B, Weikop P, Lundblad M, Jakobsson J et al. (2013) TFEB-mediated autophagy rescues midbrain dopamine neurons from alpha-synuclein toxicity. *Proc Natl Acad Sci USA* 110: E1817-26

Dehay B, Bove J, Rodriguez-Muela N, Perier C, Recasens A et al. (2010) Pathogenic lysosomal depletion in Parkinson's disease. *J Neurosci* 30

Cheng J, Ohsaki Y, Tauchi-Sato K, Fujita A, Fujimoto T (2006) Cholesterol depletion induces autophagy. *Biochem Biophys Res Commun* 351: 246-52

Yang H O, Ko W K, Kim J Y, Ro H S (2004) Paeoniflorin: an antihyperlipidemic agent from *Paeonia lactiflora*. *Fitoterapia* 75: 45-9

Li J Z, Wu J H, Yu S Y, Shao Q R, Dong X M (2013) Inhibitory effects of paeoniflorin on lysophosphatidylcholine-induced inflammatory factor production in human umbilical vein endothelial cells. *Int J Mol Med* 31: 493-7

Ma Z, Chu L, Liu H, Wang W, Li J et al. (2017) Beneficial effects of paeoniflorin on non-alcoholic fatty liver disease induced by high-fat diet in rats. *Sci Rep* 7: 44819

Ma Z, Liu H, Wang W, Guan S, Yi J et al. (2017) Paeoniflorin suppresses lipid accumulation and alleviates insulin resistance by regulating the Rho kinase/IRS-1 pathway in palmitate-induced HepG2Cells. *Biomed Pharmacother* 90: 361-7

Li H, Jiao Y, Xie M (2017) Paeoniflorin Ameliorates Atherosclerosis by Suppressing TLR4-Mediated N F-kappaB Activation. *Inflammation* 40: 2042-51

Cuzner M L, Davison A N (1973) Changes in cerebral lysosomal enzyme activity and lipids in multiple sclerosis. *J Neurol Sci* 19: 29-36

Riekkinen P J, Rinne U K, Arstila A U (1972) Neurochemical and morphological studies on demyelination in multiple sclerosis with special reference to etiological aspects. *Zeitschrift fur Neurologie* 203: 91-104

McKeown S R, Allen I V (1977) Lysosomal involvement in the pathogenesis of multiple sclerosis [proceedings]. *Biochem Soc Trans* 5: 1416-8

McKeown S R, Allen I V (1979) The fragility of cerebral lysosomes in multiple sclerosis. *Neuropathol Appl Neurobiol* 5: 405-15

Hultberg B, Olsson J E (1978) Diagnostic value of determinations of lysosomal hydrolases in CSF of patients with neurological diseases. *Acta Neurol Scand* 57: 201-15

Hultberg B, Olsson J E (1979) Lysosomal hydrolases in CSF of patients with multiple sclerosis. *Acta Neurol Scand* 59: 23-30

Rastogi S C, Clausen J (1980) Loss of lysosomal neutral proteinase from leucocytes induced by the action of multiple sclerosis-specific brain antigens. *Clin Exp Immunol* 42: 50-6

Allen I V (1981) The pathology of multiple sclerosis—fact, fiction and hypothesis. *Neuropathol Appl Neurobiol* 7: 169-82

Schwyzer R U, Henzi H (1983) Multiple sclerosis: plaques caused by 2-step demyelination? *Med Hypotheses* 12: 129-42

Tulpule K, Dringen R (2013) Formaldehyde in brain: an overlooked player in neurodegeneration? *Journal of Neurochemistry* 127: 7-21

Li H, Cuzner M L, Newcombe J (1996) Microglia-derived macrophages in early multiple sclerosis plaques. *Neuropathol Appl Neurobiol* 22: 207-15

George M F, Briggs F B, Shao X, Gianfrancesco M A, Kockum I et al. (2016) Multiple sclerosis risk loci and disease severity in 7,125 individuals from 10 studies. *Neurology Genetics* 2: e87

Bogie J F, Jorissen W, Mailleux J, Nijland P G, Zelcer N et al. (2013) Myelin alters the inflammatory phenotype of macrophages by activating PPARs. *Acta Neuropathol Commun* 1: 43

Germain D P (2010) Fabry disease. *Orphanet journal of rare diseases* 5: 30

Bottcher T, Rolfs A, Tanislav C, Bitsch A, Kohler W et al. (2013) Fabry disease-underestimated in the differential diagnosis of multiple sclerosis? *PLoS One* 8: e71894

Cammarata G, Fatuzzo P, Rodolico M S, Colomba P, Sicurella L et al. (2015) High variability of Fabry disease manifestations in an extended Italian family. *Biomed Res Int* 2015: 504784

Tettey P, Simpson S, Jr., Taylor B V, van der Mei I A (2014) Vascular comorbidities in the onset and progression of multiple sclerosis. *J Neurol Sci* 347: 23-33 von Tresckow B, Kallen K J, von Strandmann E P, Borchmann P, Lange H et al. (2004) Depletion of cellular cholesterol and lipid rafts increases shedding of CD30. *Journal of Immunology* 172: 4324-31

Kim T W, Di Paolo G, Kang M S, Berman D, McIntire L B J (2012). Phosphoinositide modulation for the treatment of neurodegenerative diseases.

Alanko J, Ivaska J (2016) Endosomes: Emerging Platforms for Integrin-Mediated FAK Signalling. *Trends Cell Biol* 26: 391-8

Symeonides S N, Anderton S M, Serrels A (2017) FAK-inhibition opens the door to checkpoint immunotherapy in Pancreatic Cancer. *Journal for immunotherapy of cancer* 5: 17

Rodal S K, Skretting G, Garred Ø, Vilhardt F, van Deurs B et al. (1999) Extraction of Cholesterol with Methyl-β-Cyclodextrin Perturbs Formation of Clathrin-coated Endocytic Vesicles. *Molecular Biology of the Cell* 10: 961-74

Rajendran L, Knolker H-J, Simons K (2010) Subcellular targeting strategies for drug design and delivery. *Nat Rev Drug Discov* 9: 29-42

Ben Halima S, Mishra S, Raja K M, Willem M, Baici A et al. (2016) Specific Inhibition of beta-Secretase Processing of the Alzheimer Disease Amyloid Precursor Protein. *Cell Rep* 14: 2127-41

Wadman M (2016) Battle over rare disease drug ensnares NIH. *Science* 354: 18-9

Pitha J (1981) Enhanced water solubility of vitamins A, D, E, and K by substituted cycloamyloses. *Life Sci* 29: 307-11

Perrin J H, Field F P, Hansen D A, Mufson R A, Torosian G (1978) beta-Cyclodextrin as an aid to peritoneal dialysis. Renal toxicity of beta-cyclodextrin in the rat. *Research communications in chemical pathology and pharmacology* 19: 373-6

Rajewski R A, Stella V J (1996) Pharmaceutical applications of cyclodextrins. 2. In vivo drug delivery. *J Pharm Sci* 85: 1142-69

Del Valle E M M (2004) Cyclodextrins and their uses: a review. *Process Biochemistry* 39: 1033-46

Bilensoy E, Hincal A A (2009) Recent advances and future directions in amphiphilic cyclodextrin nanoparticles. *Expert Opin Drug Deliv* 6: 1161-73

Liu B (2012) Therapeutic potential of cyclodextrins in the treatment of Niemann-Pick type C disease. *Clinical lipidology* 7: 289-301

De Schaepdrijver L, Marien D, Rhimi C, Voets M, van Heerden M et al. (2015) Juvenile animal testing of hydroxypropyl-beta-cyclodextrin in support of pediatric drug development. *Reproductive toxicology* (Elmsford, N Y) 56: 87-96

Pitha J, Szente L (1981) Cyclodextrins and Congeners in Parenteral Applications. In: *Proceedings of the First International Symposium on Cyclodextrins*. Springer Netherlands, 457-66

Hastings C (2010) Request for intrathecal delivery of HPbCD for Niemann-Pick type C patients. *FDA-Filing* 2010

Loftsson T, Brewster M E (2010) Pharmaceutical applications of cyclodextrins: basic science and product development. *J Pharm Pharmacol* 62: 1607-21

Loftsson T, Moya-Ortega M D, Alvarez-Lorenzo C, Concheiro A (2016) Pharmacokinetics of cyclodextrins and drugs after oral and parenteral administration of drug/cyclodextrin complexes. *J Pharm Pharmacol* 68: 544-55

Gould S, Scott R C (2005) 2-Hydroxypropyl-beta-cyclodextrin (HP-beta-CD): a toxicology review. *Food Chem Toxicol* 43: 1451-9

Riebeek W M (1990a) Determination of the acute intravenous toxicity of alphacyclodextrin in mice. *TNO-CIV Institute* V90

Riebeek W M (1990b) Determination of the acute intravenous toxicity of alphacyclodextrin in rats. *TNO-CIV Institute* V90

Prinsen M K (1991) Acute intraperitoneal toxicity studies with alpha-cyclodextrin in rats. *TNO-CIV Institute* V91

Leroy-Lechat F, Wouessidjewe D, Andreux J P, Puisieux F, Duchene D (1994) Evaluation of the cytotoxicity of cyclodextrins and hydroxypropylated derivatives. *International Journal of Pharmaceutics* 101: 97-103

Frijlink H W, Eissens A C, Hefting N R, Poelstra K, Lerk C F et al. (1991) The effect of parenterally administered cyclodextrins on cholesterol levels in the rat. *Pharm Res* 8: 9-16

Binkowski-Machut C, Hapiot F, Martin P, Cecchelli R, Monflier E (2006) How cyclodextrins can mask their toxic effect on the blood-brain barrier. *Bioorganic & Medicinal Chemistry Letters* 16: 1784-7

Okada S S, Kuo A, Muttreja M R, Hozakowska E, Weisz P B et al. (1995) Inhibition of human vascular smooth muscle cell migration and proliferation by beta-cyclodextrin tetradecasulfate. *J Pharmacol Exp Ther* 273: 948-54

Guo F, Liu X, Cai H, Le W (2018) Autophagy in neurodegenerative diseases: pathogenesis and therapy. *Brain Pathol* 28: 3-13

Van Ommen B, De Bie A T, Bar A (2004) Disposition of 14C-alpha-cyclodextrin in germ-free and conventional rats. *Regul Toxicol Pharmacol* 39 Suppl 1: 57-66

Duchene D, Wouessidjewe D (1990) Pharmaceutical uses of cyclodextrins and derivatives. *Drug Dev Ind Pharm* 16: 2487-99

Wagner E M, Jen K L, Artiss J D, Remaley A T (2008) Dietary alpha-cyclodextrin lowers low-density lipoprotein cholesterol and alters plasma fatty acid profile in low-density lipoprotein receptor knockout mice on a high-fat diet. *Metabolism* 57: 1046-51

Yoshitomi H, Nishihata T, Frederick G, Dillsaver M, Higuchi T (1987) Effect of triglyceride on small intestinal absorption of cefoxitin in rats. *J Pharm Pharmacol* 39: 887-91

Cunningham T J, Yao L, Oetinger M, Cort L, Blankenhorn E P et al. (2006) Secreted phospholipase A2 activity in experimental autoimmune encephalomyelitis and multiple sclerosis. *J Neuroinflammation* 3: 26

Chalbot S, Zetterberg H, Blennow K, Fladby T, Andreasen N et al. (2011) Blood-cerebrospinal fluid barrier permeability in Alzheimer's disease. *J Alzheimers Dis* 25: 505-15

Klavins K, Koal T, Dallmann G, Marksteiner J, Kemmler G et al. (2015) The ratio of phosphatidylcholines to lysophosphatidylcholines in plasma differentiates healthy controls from patients with Alzheimer's disease and mild cognitive impairment. *Alzheimer's & dementia* (Amsterdam, Netherlands) 1: 295-302

Cunningham T J, Yao L, Lucena A (2008) Product inhibition of secreted phospholipase A2 may explain lysophosphatidylcholines' unexpected therapeutic properties. *Journal of inflammation* (London, England) 5: 17

Dong Z, Meller J, Succop P, Wang J, Wikenheiser-Brokamp K et al. (2014) Secretory phospholipase A2-IIa upregulates HER/HER2-elicited signaling in lung cancer cells. *Int J Oncol* 45: 978-84

Hernandez M, Martin R, Garcia-Cubillas M D, Maeso-Hernandez P, Nieto M L (2010) Secreted PLA2 induces proliferation in astrocytoma through the EGF receptor: another inflammation-cancer link. *Neuro-oncology* 12: 1014-23

Yarla N S, Bishayee A, Vadlakonda L, Chintala R, Duddukuri G R et al. (2016) Phospholipase A2 Isoforms as Novel Targets for Prevention and Treatment of Inflammatory and Oncologic Diseases. *Curr Drug Targets* 17: 1940-62

Mallat Z, Lambeau G, Tedgui A (2010) Lipoprotein-associated and secreted phospholipases A(2) in cardiovascular disease: roles as biological effectors and biomarkers. *Circulation* 122: 2183-200

Saegusa J, Akakura N, Wu C Y, Hoogland C, Ma Z et al. (2008) Pro-inflammatory secretory phospholipase A2 type IIA binds to integrins alphavbeta3 and alpha4beta1 and induces proliferation of monocytic cells in an integrin-dependent manner. *J Biol Chem* 283: 26107-15

Fujita M, Zhu K, Fujita C K, Zhao M, Lam K S et al. (2015) Proinflammatory secreted phospholipase A2 type IIA (sPLA-IIA) induces integrin activation through direct binding to a newly identified binding site (site 2) in integrins alphavbeta3, alpha4beta1, and alpha5beta1. *J Biol Chem* 290: 259-71

Nicholls S J, Kastelein J J, Schwartz G G, Bash D, Rosenson R S et al. (2014) Varespladib and cardiovascular events in patients with an acute coronary syndrome: the VISTA-16 randomized clinical trial. *JAMA* 311: 252-62

Etienne P, Dastoor D, Gauthier S, Ludwick R, Collier B (1981) Alzheimer disease: lack of effect of lecithin treatment for 3 months. *Neurology* 31: 1552-4

Fisman M, Merskey H, Helmes E, McCready J, Colhoun E H et al. (1981) Double blind study of lecithin in patients with Alzheimer's disease. *Canadian journal of psychiatry Revue canadienne de psychiatrie* 26: 426-8

Brinkman S D, Pomara N, Goodnick P J, Barnett N, Domino E F (1982) A dose-ranging study of lecithin in the treatment of primary degenerative dementia (Alzheimer disease). *J Clin Psychopharmacol* 2: 281-5

Dysken M W, Fovall P, Harris C M, Davis J M, Noronha A (1982) Lecithin administration in Alzheimer dementia. *Neurology* 32: 1203-4

Higgins J P, Flicker L (2003) Lecithin for dementia and cognitive impairment. *Cochrane Database Syst Rev*: CD001015

Harris C M (1981) *Test of the memory-enhancing effect of phosphatidylcholine in humans*. Chicago, Ill.: University of Illinois, 140

Little A, Levy R, Chuaqui-Kidd P, Hand D (1985) A double-blind, placebo controlled trial of high-dose lecithin in Alzheimer's disease. *J Neurol Neurosurg Psychiatry* 48: 736-42

Wilton D C (2005) Phospholipases A2: structure and function. *European Journal of Lipid Science and Technology* 107: 193-205

Sim I, Carini S, Tu S W, Detwiler L T, Brinkley J et al. (2012) Ontology-based federated data access to human studies information. *AMIA Annu Symp Proc* 2012: 856-65

Bielicki J K (2016) ABCA1 agonist peptides for the treatment of disease. *Current opinion in lipidology* 27: 40-6

Yao J, Hennessey T, Flynt A, Lai E, Beal M F et al. (2010) MicroRNA-related cofilin abnormality in Alzheimer's disease. *PLoS One* 5: e15546

Livak K J, Schmittgen T D (2001) Analysis of relative gene expression data using real-time quantitative PCR and the 2(-Delta Delta C(T)) Method. *Methods* 25: 402-8

Wittkowski K M (1988) Friedman-type statistics and consistent multiple comparisons for unbalanced designs. *J Am Statist Assoc* 83: 1163-70, 87:258

Gaspar J T, Mathieu J, Alvarez P J J, De Grey A (2016). Cyclodextrin Compounds For The Prevention And Treatment Of Aging. WO Patent No: WO 2016/168772 A1

Gaspar J, Mathieu J, Alvarez P (2017) 2-Hydroxypropyl-beta-cyclodextrin (HPβCD) reduces age-related lipofuscin accumulation through a cholesterol-associated pathway. *Scientific Reports* 7: 2197

Mohammad N, Malvi P, Meena A S, Singh S V, Chaube B et al. (2014) Cholesterol depletion by methyl-beta-cyclodextrin augments tamoxifen induced cell death by enhancing its uptake in melanoma. *Mol Cancer* 13: 204

Goetz J G, Minguet S, Navarro-Lerida I, Lazcano J J, Samaniego R et al. (2011) Biomechanical remodeling of the microenvironment by stromal caveolin-1 favors tumor invasion and metastasis. *Cell* 146: 148-63

Yamaguchi H, Takeo Y, Yoshida S, Kouchi Z, Nakamura Y et al. (2009) Lipid rafts and caveolin-1 are required for invadopodia formation and extracellular matrix degradation by human breast cancer cells. *Cancer Res* 69: 8594-602

Antalis C J, Uchida A, Buhman K K, Siddiqui R A (2011) Migration of MDA-MB-231 breast cancer cells depends on the availability of exogenous lipids and cholesterol esterification. *Clin Exp Metastasis* 28: 733-41

Hashimoto S, Mikami S, Sugino H, Yoshikawa A, Hashimoto A et al. (2016) Lysophosphatidic acid activates Arf6 to promote the mesenchymal malignancy of renal cancer. *Nat Commun* 7: 10656

The present invention is also further described by the following claims.

The invention claimed is:

1. A method of reducing levels of serum phospholipids in a subject in need thereof, the method comprising administering to the subject a therapeutically effective amount of a pharmaceutical composition comprising a clathrate comprising an alpha-cyclodextrin, or a salt thereof; and a medium chain fatty acid, or a salt thereof, and wherein the clathrate is administered at a dose of from about 1 g/day to about 20 g/day.

2. The method of claim 1, wherein the subject has been diagnosed as having a malignant, neurodegenerative, vascular, metabolic, inflammatory, autoimmune, pulmonary, fibrotic, hepatic, lysosomal storage, age-related, or viral disease or disorder.

3. The method of claim 1, wherein the composition comprises a clathrate comprising hydroxypropyl-alpha-cyclodextrin in an amount of from about 80 wt % to about 90 wt % and sodium caprate in an amount of change the recitation "from about 5 wt % to about 15 wt %" (line 3) to "from about 10 wt % to about 20 wt %.

4. The method of claim 1, wherein the molar ratio of alpha-cyclodextrin to the medium chain fatty acid is from about 0.5 to about 5.

5. The method of claim 1, wherein the alpha-cyclodextrin is present in an amount of from about 80 wt % to about 90 wt %, based on the total weight of the composition.

6. The method of claim 1, wherein the alpha-cyclodextrin is 2-hydroxypropyl-alpha-cyclodextrin.

7. The method of claim 1, wherein the medium chain fatty acid is present in an amount of from about 10 wt % to about 20 wt %, based on the total weight of the composition.

8. The method of claim 1, wherein the medium chain fatty acid comprises a saturated aliphatic tail.

9. The method of claim 1, wherein the medium chain fatty acid comprises an aliphatic tail having from about 6 to about 12 carbon atoms.

10. The method of claim 1, wherein the medium chain fatty acid is caproic acid.

11. The method of claim 1, wherein the medium chain fatty acid is capric acid.

12. The method of claim 1, wherein the medium chain fatty acid is sodium caprate.

13. The method of claim 1, wherein the composition is formulated as an oral dosage form.

14. The method of claim 1, further comprising a penetration enhancer.

* * * * *

SEQUENCE LISTING

<160> NUMBER OF SEQ ID NOS: 16

<210> SEQ ID NO 1
<211> LENGTH: 1164
<212> TYPE: PRT
<213> ORGANISM: Homo sapiens

<400> SEQUENCE: 1

```
Met Pro Thr Met Arg Arg Thr Val Ser Glu Ile Arg Ser Arg Ala Glu
1               5                   10                  15

Gly Tyr Glu Lys Thr Asp Asp Val Ser Glu Lys Thr Ser Leu Ala Asp
            20                  25                  30

Gln Glu Glu Val Arg Thr Ile Phe Ile Asn Gln Pro Gln Leu Thr Lys
        35                  40                  45

Phe Cys Asn Asn His Val Ser Thr Ala Lys Tyr Asn Ile Ile Thr Phe
    50                  55                  60

Leu Pro Arg Phe Leu Tyr Ser Gln Phe Arg Arg Ala Ala Asn Ser Phe
65                  70                  75                  80

Phe Leu Phe Ile Ala Leu Leu Gln Gln Ile Pro Asp Val Ser Pro Thr
                85                  90                  95

Gly Arg Tyr Thr Thr Leu Val Pro Leu Leu Phe Ile Leu Ala Val Ala
            100                 105                 110

Ala Ile Lys Glu Ile Ile Glu Asp Ile Lys Arg His Lys Ala Asp Asn
        115                 120                 125

Ala Val Asn Lys Lys Gln Thr Gln Val Leu Arg Asn Gly Ala Trp Glu
    130                 135                 140

Ile Val His Trp Glu Lys Val Ala Val Gly Glu Ile Val Lys Val Thr
145                 150                 155                 160

Asn Gly Glu His Leu Pro Ala Asp Leu Ile Ser Leu Ser Ser Ser Glu
                165                 170                 175

Pro Gln Ala Met Cys Tyr Ile Glu Thr Ser Asn Leu Asp Gly Glu Thr
            180                 185                 190

Asn Leu Lys Ile Arg Gln Gly Leu Pro Ala Thr Ser Asp Ile Lys Asp
        195                 200                 205

Val Asp Ser Leu Met Arg Ile Ser Gly Arg Ile Glu Cys Glu Ser Pro
    210                 215                 220

Asn Arg His Leu Tyr Asp Phe Val Gly Asn Ile Arg Leu Asp Gly His
225                 230                 235                 240

Gly Thr Val Pro Leu Gly Ala Asp Gln Ile Leu Leu Arg Gly Ala Gln
                245                 250                 255

Leu Arg Asn Thr Gln Trp Val His Gly Ile Val Val Tyr Thr Gly His
            260                 265                 270

Asp Thr Lys Leu Met Gln Asn Ser Thr Ser Pro Pro Leu Lys Leu Ser
        275                 280                 285

Asn Val Glu Arg Ile Thr Asn Val Gln Ile Leu Ile Leu Phe Cys Ile
    290                 295                 300

Leu Ile Ala Met Ser Leu Val Cys Ser Val Gly Ser Ala Ile Trp Asn
305                 310                 315                 320

Arg Arg His Ser Gly Lys Asp Trp Tyr Leu Asn Leu Asn Tyr Gly Gly
                325                 330                 335

Ala Ser Asn Phe Gly Leu Asn Phe Leu Thr Phe Ile Ile Leu Phe Asn
            340                 345                 350

Asn Leu Ile Pro Ile Ser Leu Leu Val Thr Leu Glu Val Val Lys Phe
        355                 360                 365
```

```
Thr Gln Ala Tyr Phe Ile Asn Trp Asp Leu Asp Met His Tyr Glu Pro
    370             375             380
Thr Asp Thr Ala Ala Met Ala Arg Thr Ser Asn Leu Asn Glu Glu Leu
385             390             395                             400
Gly Gln Val Lys Tyr Ile Phe Ser Asp Lys Thr Gly Thr Leu Thr Cys
                405             410             415
Asn Val Met Gln Phe Lys Lys Cys Thr Ile Ala Gly Val Ala Tyr Gly
            420             425             430
His Val Pro Glu Pro Glu Asp Tyr Gly Cys Ser Pro Asp Glu Trp Gln
            435             440             445
Asn Ser Gln Phe Gly Asp Glu Lys Thr Phe Ser Asp Ser Ser Leu Leu
450             455             460
Glu Asn Leu Gln Asn Asn His Pro Thr Ala Pro Ile Ile Cys Glu Phe
465             470             475                             480
Leu Thr Met Met Ala Val Cys His Thr Ala Val Pro Glu Arg Glu Gly
                485             490             495
Asp Lys Ile Ile Tyr Gln Ala Ala Ser Pro Asp Glu Gly Ala Leu Val
            500             505             510
Arg Ala Ala Lys Gln Leu Asn Phe Val Phe Thr Gly Arg Thr Pro Asp
            515             520             525
Ser Val Ile Ile Asp Ser Leu Gly Gln Glu Glu Arg Tyr Glu Leu Leu
530             535             540
Asn Val Leu Glu Phe Thr Ser Ala Arg Lys Arg Met Ser Val Ile Val
545             550             555             560
Arg Thr Pro Ser Gly Lys Leu Arg Leu Tyr Cys Lys Gly Ala Asp Thr
                565             570             575
Val Ile Tyr Asp Arg Leu Ala Glu Thr Ser Lys Tyr Lys Glu Ile Thr
            580             585             590
Leu Lys His Leu Glu Gln Phe Ala Thr Glu Gly Leu Arg Thr Leu Cys
            595             600             605
Phe Ala Val Ala Glu Ile Ser Glu Ser Asp Phe Gln Glu Trp Arg Ala
            610             615             620
Val Tyr Gln Arg Ala Ser Thr Ser Val Gln Asn Arg Leu Leu Lys Leu
625             630             635                             640
Glu Glu Ser Tyr Glu Leu Ile Glu Lys Asn Leu Gln Leu Leu Gly Ala
                645             650             655
Thr Ala Ile Glu Asp Lys Leu Gln Asp Gln Val Pro Glu Thr Ile Glu
            660             665             670
Thr Leu Met Lys Ala Asp Ile Lys Ile Trp Ile Leu Thr Gly Asp Lys
            675             680             685
Gln Glu Thr Ala Ile Asn Ile Gly His Ser Cys Lys Leu Leu Lys Lys
            690             695             700
Asn Met Gly Met Ile Val Ile Asn Glu Gly Ser Leu Asp Gly Thr Arg
705             710             715                             720
Glu Thr Leu Ser Arg His Cys Thr Thr Leu Gly Asp Ala Leu Arg Lys
                725             730             735
Glu Asn Asp Phe Ala Leu Ile Ile Asp Gly Lys Thr Leu Lys Tyr Ala
            740             745             750
Leu Thr Phe Gly Val Arg Gln Tyr Phe Leu Asp Leu Ala Leu Ser Cys
            755             760             765
Lys Ala Val Ile Cys Cys Arg Val Ser Pro Leu Gln Lys Ser Glu Val
            770             775             780
Val Glu Met Val Lys Lys Gln Val Lys Val Val Thr Leu Ala Ile Gly
```

```
            785                 790                 795                 800
Asp Gly Ala Asn Asp Val Ser Met Ile Gln Thr Ala His Val Gly Val
                    805                 810                 815

Gly Ile Ser Gly Asn Glu Gly Leu Gln Ala Ala Asn Ser Ser Asp Tyr
            820                 825                 830

Ser Ile Ala Gln Phe Lys Tyr Leu Lys Asn Leu Leu Met Ile His Gly
        835                 840                 845

Ala Trp Asn Tyr Asn Arg Val Ser Lys Cys Ile Leu Tyr Cys Phe Tyr
    850                 855                 860

Lys Asn Ile Val Leu Tyr Ile Glu Ile Trp Phe Ala Phe Val Asn
865                 870                 875                 880

Gly Phe Ser Gly Gln Ile Leu Phe Glu Arg Trp Cys Ile Gly Leu Tyr
                885                 890                 895

Asn Val Met Phe Thr Ala Met Pro Pro Leu Thr Leu Gly Ile Phe Glu
            900                 905                 910

Arg Ser Cys Arg Lys Glu Asn Met Leu Lys Tyr Pro Glu Leu Tyr Lys
        915                 920                 925

Thr Ser Gln Asn Ala Leu Asp Phe Asn Thr Lys Val Phe Trp Val His
    930                 935                 940

Cys Leu Asn Gly Leu Phe His Ser Val Ile Leu Phe Trp Phe Pro Leu
945                 950                 955                 960

Lys Ala Leu Gln Tyr Gly Thr Ala Phe Gly Asn Gly Lys Thr Ser Asp
                965                 970                 975

Tyr Leu Leu Leu Gly Asn Phe Val Tyr Thr Phe Val Val Ile Thr Val
            980                 985                 990

Cys Leu Lys Ala Gly Leu Glu Thr Ser Tyr Trp Thr Trp Phe Ser His
        995                 1000                1005

Ile Ala Ile Trp Gly Ser Ile Ala Leu Trp Val Val Phe Phe Gly
    1010                1015                1020

Ile Tyr Ser Ser Leu Trp Pro Ala Ile Pro Met Ala Pro Asp Met
    1025                1030                1035

Ser Gly Glu Ala Ala Met Leu Phe Ser Ser Gly Val Phe Trp Met
    1040                1045                1050

Gly Leu Leu Phe Ile Pro Val Ala Ser Leu Leu Leu Asp Val Val
    1055                1060                1065

Tyr Lys Val Ile Lys Arg Thr Ala Phe Lys Thr Leu Val Asp Glu
    1070                1075                1080

Val Gln Glu Leu Glu Ala Lys Ser Gln Asp Pro Gly Ala Val Val
    1085                1090                1095

Leu Gly Lys Ser Leu Thr Glu Arg Ala Gln Leu Leu Lys Asn Val
    1100                1105                1110

Phe Lys Lys Asn His Val Asn Leu Tyr Arg Ser Glu Ser Leu Gln
    1115                1120                1125

Gln Asn Leu Leu His Gly Tyr Ala Phe Ser Gln Asp Glu Asn Gly
    1130                1135                1140

Ile Val Ser Gln Ser Glu Val Ile Arg Ala Tyr Asp Thr Thr Lys
    1145                1150                1155

Gln Arg Pro Asp Glu Trp
    1160

<210> SEQ ID NO 2
<211> LENGTH: 1251
<212> TYPE: PRT
<213> ORGANISM: Homo sapiens
```

<400> SEQUENCE: 2

```
Met Ser Thr Glu Arg Asp Ser Glu Thr Thr Phe Asp Glu Asp Ser Gln
1               5                   10                  15

Pro Asn Asp Glu Val Val Pro Tyr Ser Asp Glu Thr Glu Asp Glu
            20                  25                  30

Leu Asp Asp Gln Gly Ser Ala Val Glu Pro Glu Gln Asn Arg Val Asn
            35                  40                  45

Arg Glu Ala Glu Glu Asn Arg Glu Pro Phe Arg Lys Glu Cys Thr Trp
    50                  55                  60

Gln Val Lys Ala Asn Asp Arg Lys Tyr His Glu Gln Pro His Phe Met
65                  70                  75                  80

Asn Thr Lys Phe Leu Cys Ile Lys Glu Ser Lys Tyr Ala Asn Asn Ala
                85                  90                  95

Ile Lys Thr Tyr Lys Tyr Asn Ala Phe Thr Phe Ile Pro Met Asn Leu
            100                 105                 110

Phe Glu Gln Phe Lys Arg Ala Ala Asn Leu Tyr Phe Leu Ala Leu Leu
            115                 120                 125

Ile Leu Gln Ala Val Pro Gln Ile Ser Thr Leu Ala Trp Tyr Thr Thr
130                 135                 140

Leu Val Pro Leu Leu Val Val Leu Gly Val Thr Ala Ile Lys Asp Leu
145             150                 155                 160

Val Asp Asp Val Ala Arg His Lys Met Asp Lys Glu Ile Asn Asn Arg
                165                 170                 175

Thr Cys Glu Val Ile Lys Asp Gly Arg Phe Lys Val Ala Lys Trp Lys
            180                 185                 190

Glu Ile Gln Val Gly Asp Val Ile Arg Leu Lys Lys Asn Asp Phe Val
            195                 200                 205

Pro Ala Asp Ile Leu Leu Leu Ser Ser Ser Glu Pro Asn Ser Leu Cys
210                 215                 220

Tyr Val Glu Thr Ala Glu Leu Asp Gly Glu Thr Asn Leu Lys Phe Lys
225                 230                 235                 240

Met Ser Leu Glu Ile Thr Asp Gln Tyr Leu Gln Arg Glu Asp Thr Leu
                245                 250                 255

Ala Thr Phe Asp Gly Phe Ile Glu Cys Glu Glu Pro Asn Asn Arg Leu
            260                 265                 270

Asp Lys Phe Thr Gly Thr Leu Phe Trp Arg Asn Thr Ser Phe Pro Leu
            275                 280                 285

Asp Ala Asp Lys Ile Leu Leu Arg Gly Cys Val Ile Arg Asn Thr Asp
290                 295                 300

Phe Cys His Gly Leu Val Ile Phe Ala Gly Ala Asp Thr Lys Ile Met
305                 310                 315                 320

Lys Asn Ser Gly Lys Thr Arg Phe Lys Arg Thr Lys Ile Asp Tyr Leu
                325                 330                 335

Met Asn Tyr Met Val Tyr Thr Ile Phe Val Val Leu Ile Leu Leu Ser
            340                 345                 350

Ala Gly Leu Ala Ile Gly His Ala Tyr Trp Glu Ala Gln Val Gly Asn
            355                 360                 365

Ser Ser Trp Tyr Leu Tyr Asp Gly Glu Asp Asp Thr Pro Ser Tyr Arg
            370                 375                 380

Gly Phe Leu Ile Phe Trp Gly Tyr Ile Ile Val Leu Asn Thr Met Val
385                 390                 395                 400

Pro Ile Ser Leu Tyr Val Ser Val Glu Val Ile Arg Leu Gly Gln Ser
```

-continued

```
                405                 410                 415
His Phe Ile Asn Trp Asp Leu Gln Met Tyr Tyr Ala Glu Lys Asp Thr
            420                 425                 430

Pro Ala Lys Ala Arg Thr Thr Thr Leu Asn Glu Gln Leu Gly Gln Ile
            435                 440                 445

His Tyr Ile Phe Ser Asp Lys Thr Gly Thr Leu Thr Gln Asn Ile Met
        450                 455                 460

Thr Phe Lys Lys Cys Cys Ile Asn Gly Gln Ile Tyr Gly Asp His Arg
465                 470                 475                 480

Asp Ala Ser Gln His Asn His Asn Lys Ile Glu Gln Val Asp Phe Ser
                485                 490                 495

Trp Asn Thr Tyr Ala Asp Gly Lys Leu Ala Phe Tyr Asp His Tyr Leu
            500                 505                 510

Ile Glu Gln Ile Gln Ser Gly Lys Glu Pro Glu Val Arg Gln Phe Phe
        515                 520                 525

Phe Leu Leu Ala Val Cys His Thr Val Met Val Asp Arg Thr Asp Gly
        530                 535                 540

Gln Leu Asn Tyr Gln Ala Ala Ser Pro Asp Glu Gly Ala Leu Val Asn
545                 550                 555                 560

Ala Ala Arg Asn Phe Gly Phe Ala Phe Leu Ala Arg Thr Gln Asn Thr
                565                 570                 575

Ile Thr Ile Ser Glu Leu Gly Thr Glu Arg Thr Tyr Asn Val Leu Ala
            580                 585                 590

Ile Leu Asp Phe Asn Ser Asp Arg Lys Arg Met Ser Ile Ile Val Arg
        595                 600                 605

Thr Pro Glu Gly Asn Ile Lys Leu Tyr Cys Lys Gly Ala Asp Thr Val
610                 615                 620

Ile Tyr Glu Arg Leu His Arg Met Asn Pro Thr Lys Gln Glu Thr Gln
625                 630                 635                 640

Asp Ala Leu Asp Ile Phe Ala Asn Glu Thr Leu Arg Thr Leu Cys Leu
                645                 650                 655

Cys Tyr Lys Glu Ile Glu Glu Lys Glu Phe Thr Glu Trp Asn Lys Lys
            660                 665                 670

Phe Met Ala Ala Ser Val Ala Ser Thr Asn Arg Asp Glu Ala Leu Asp
        675                 680                 685

Lys Val Tyr Glu Glu Ile Glu Lys Asp Leu Ile Leu Leu Gly Ala Thr
        690                 695                 700

Ala Ile Glu Asp Lys Leu Gln Asp Gly Val Pro Glu Thr Ile Ser Lys
705                 710                 715                 720

Leu Ala Lys Ala Asp Ile Lys Ile Trp Val Leu Thr Gly Asp Lys Lys
                725                 730                 735

Glu Thr Ala Glu Asn Ile Gly Phe Ala Cys Glu Leu Leu Thr Glu Asp
            740                 745                 750

Thr Thr Ile Cys Tyr Gly Glu Asp Ile Asn Ser Leu Leu His Ala Arg
        755                 760                 765

Met Glu Asn Gln Arg Asn Arg Gly Gly Val Tyr Ala Lys Phe Ala Pro
        770                 775                 780

Pro Val Gln Glu Ser Phe Phe Pro Pro Gly Gly Asn Arg Ala Leu Ile
785                 790                 795                 800

Ile Thr Gly Ser Trp Leu Asn Glu Ile Leu Leu Glu Lys Lys Thr Lys
                805                 810                 815

Arg Asn Lys Ile Leu Lys Leu Lys Phe Pro Arg Thr Glu Glu Glu Arg
            820                 825                 830
```

-continued

Arg Met Arg Thr Gln Ser Lys Arg Arg Leu Glu Ala Lys Lys Glu Gln
        835                 840                 845

Arg Gln Lys Asn Phe Val Asp Leu Ala Cys Glu Cys Ser Ala Val Ile
    850                 855                 860

Cys Cys Arg Val Thr Pro Lys Gln Lys Ala Met Val Val Asp Leu Val
865                 870                 875                 880

Lys Arg Tyr Lys Lys Ala Ile Thr Leu Ala Ile Gly Asp Gly Ala Asn
                885                 890                 895

Asp Val Asn Met Ile Lys Thr Ala His Ile Gly Val Gly Ile Ser Gly
                900                 905                 910

Gln Glu Gly Met Gln Ala Val Met Ser Ser Asp Tyr Ser Phe Ala Gln
                915                 920                 925

Phe Arg Tyr Leu Gln Arg Leu Leu Leu Val His Gly Arg Trp Ser Tyr
    930                 935                 940

Ile Arg Met Cys Lys Phe Leu Arg Tyr Phe Phe Tyr Lys Asn Phe Ala
945                 950                 955                 960

Phe Thr Leu Val His Phe Trp Tyr Ser Phe Phe Asn Gly Tyr Ser Ala
                965                 970                 975

Gln Thr Ala Tyr Glu Asp Trp Phe Ile Thr Leu Tyr Asn Val Leu Tyr
                980                 985                 990

Thr Ser Leu Pro Val Leu Leu Met Gly Leu Leu Asp Gln Asp Val Ser
                995                 1000                1005

Asp Lys Leu Ser Leu Arg Phe Pro Gly Leu Tyr Ile Val Gly Gln
    1010                1015                1020

Arg Asp Leu Leu Phe Asn Tyr Lys Arg Phe Phe Val Ser Leu Leu
    1025                1030                1035

His Gly Val Leu Thr Ser Met Ile Leu Phe Phe Ile Pro Leu Gly
    1040                1045                1050

Ala Tyr Leu Gln Thr Val Gly Gln Asp Gly Glu Ala Pro Ser Asp
    1055                1060                1065

Tyr Gln Ser Phe Ala Val Thr Ile Ala Ser Ala Leu Val Ile Thr
    1070                1075                1080

Val Asn Phe Gln Ile Gly Leu Asp Thr Ser Tyr Trp Thr Phe Val
    1085                1090                1095

Asn Ala Phe Ser Ile Phe Gly Ser Ile Ala Leu Tyr Phe Gly Ile
    1100                1105                1110

Met Phe Asp Phe His Ser Ala Gly Ile His Val Leu Phe Pro Ser
    1115                1120                1125

Ala Phe Gln Phe Thr Gly Thr Ala Ser Asn Ala Leu Arg Gln Pro
    1130                1135                1140

Tyr Ile Trp Leu Thr Ile Ile Leu Thr Val Ala Val Cys Leu Leu
    1145                1150                1155

Pro Val Val Ala Ile Arg Phe Leu Ser Met Thr Ile Trp Pro Ser
    1160                1165                1170

Glu Ser Asp Lys Ile Gln Lys His Arg Lys Arg Leu Lys Ala Glu
    1175                1180                1185

Glu Gln Trp Gln Arg Arg Gln Gln Val Phe Arg Arg Gly Val Ser
    1190                1195                1200

Thr Arg Arg Ser Ala Tyr Ala Phe Ser His Gln Arg Gly Tyr Ala
    1205                1210                1215

Asp Leu Ile Ser Ser Gly Arg Ser Ile Arg Lys Lys Arg Ser Pro
    1220                1225                1230

Leu Asp Ala Ile Val Ala Asp Gly Thr Ala Glu Tyr Arg Arg Thr
1235                1240                1245

Gly Asp Ser
    1250

<210> SEQ ID NO 3
<211> LENGTH: 2736
<212> TYPE: DNA
<213> ORGANISM: Homo sapiens

<400> SEQUENCE: 3

| | | | | | |
|---|---|---|---|---|---|
| aaaaactcca | ttcgaaccca | tggagcagaa | aaccaccgac | atctactcta | tgagtgctgg | 60 |
| gcctcctggg | gcgtgtggta | taaataccaa | cctttggatc | ttgtaaggcg | gtactttgga | 120 |
| gagaagattg | ggttatattt | tgcctggttg | ggctggtaca | ccggcatgct | cttcccagct | 180 |
| gccttcattg | gattgtttgt | cttttgtat | ggcgtcacca | ctctggatca | cagccaagtc | 240 |
| agtaaagaag | tctgccaagc | tacagatatc | atcatgtgtc | ctgtgtgtga | taaatactgt | 300 |
| ccattcatga | ggctgtcaga | cagctgtgta | tatgccaagg | taacccacct | ttttgacaat | 360 |
| ggagccactg | tcttctttgc | tgttttcatg | gcagtctggg | caacagtttt | cctggagttt | 420 |
| tggaaaagac | ggcgagcagt | aattgctat | gactgggatt | tgatagactg | ggaagaagag | 480 |
| gaggaagaaa | tacgacccca | gtttgaagcc | aagtattcca | agaaagagcg | gatgaatcca | 540 |
| atttctggaa | agccagaacc | ttatcaagca | tttacagata | aatgcagcag | acttatcgtt | 600 |
| tctgcatctg | gaatattttt | tatgatctgc | gtggtgattg | ctgccgtgtt | cgggatcgtc | 660 |
| atttaccggg | tggtgactgt | cagcactttc | gctgccttta | gtgggcgtt | aatcaggaat | 720 |
| aactctcagg | ttgcaaccac | agggactgct | gtgtgcatca | acttctgtat | cattatgttg | 780 |
| ctgaatgtgc | tctatgaaaa | agttgccctg | cttctgacga | atttagaaca | gcctcgcaca | 840 |
| gagtctgagt | gggagaacag | cttcacccctg | aaaatgtttc | ttttcagtt | tgtcaatctg | 900 |
| aacagctcca | cattttacat | cgcattcttc | ctcggaagat | ttacaggaca | cccaggtgcc | 960 |
| tacttgaggc | tgataaacag | gtggagacta | aagagtgcc | accctagtgg | atgccttatt | 1020 |
| gatctgtgta | tgcaaatggg | tattataatg | gtgctaaagc | agacctggaa | taatttcatg | 1080 |
| gaacttggct | acccgttaat | tcagaattgg | tggactagaa | gaaagtacg | acaagaacat | 1140 |
| ggacctgaaa | ggaaaataag | tttcccacaa | tgggaaaagg | actataacct | tcagccgatg | 1200 |
| aatgcctatg | gactcttcga | tgaatactta | gaaatgattc | ttcagtttgg | attcacaact | 1260 |
| atctttgtgg | cagcttttcc | cctagccaca | cttctggcct | tactgaataa | cataattgaa | 1320 |
| attcgacttg | atgcttacaa | atttgtcaca | cagtggagga | gaccttagc | ttcaagggcc | 1380 |
| aaagacatag | gaatttggta | tggaattctt | gaaggcattg | gaattctctc | tgttatcaca | 1440 |
| aatgcatttg | tcatagcgat | aacatctgac | tttatccctc | gcttggtgta | tgcttataag | 1500 |
| tatgaccctt | gtgcaggcca | aggagaagct | gggcaaaagt | gcatggttgg | ctatgtgaat | 1560 |
| gccagcttgt | ctgtatttcg | aatttctgac | tttgagaacc | gatctgagcc | tgaatctgat | 1620 |
| ggcagtgagt | tctcggggac | tcctcttaag | tactgcagat | accgggacta | ccgtgacccg | 1680 |
| cctcattcac | tggtgcccta | tggctacaca | ctgcagtttt | ggcatgtcct | agctgctcga | 1740 |
| ttagcttttta | tcattgtctt | tgagcacctc | gtgttttgta | taaagcacct | catttcgtat | 1800 |
| ctgatcccag | acctcccaaa | agacctaagg | gatcgaatga | aagagagaa | gtacttgatt | 1860 |
| caggagatga | tgtatgaagc | agaactgaa | cgtctccaga | aggaacgaaa | ggagaggaag | 1920 |
| aagaatggaa | aagcacacca | caacgagtgg | ccgtgaccat | aaaatagtcc | ctttccaggc | 1980 |

-continued

```
caaggacctg aattctgttt acttcttctg gctgtgcaaa agcacactca agtgaatgac    2040
taaaaatgca accacagtgc atgttgcaga taccggcggc cgcaggaggg gcagcatcca    2100
gtagaggact ggcgttggag tcacactgct gtgaaatcac gttgcagtcc agcgcacaat    2160
tgctatctat ccatagacca ttcttgacca agcaagcatg cacattatgg gcagttacat    2220
tctcaagttt ttaaaatcaa ggggaacttg tatactgggc ctgttttca gcctgtttgc     2280 tacctttttt gcattctatc ccatgtgaat tttacagaca ctgggctaaa aagggtattc    2340
agacacatgg acacacattc ctagaatgtc atcatatggt cctaattcca tgtcaccaag    2400
aacacagaca agaccctgtt tacaacttt tctttccttt tttttaattt tagacctttc     2460
tgagaagatt attatatatg acatatctat agctatgtgt atggccatag atgtatttct    2520
gtgtgtacat atgtatagtc atgtattcct gcatatgtac atacaaatac agagatatat   2580
aaagtacata gaaattcctt acttgtaaat agccaaaaag tactgacatg agtgaatttt    2640
cacatttaaa tagtcatcaa tatgaagcca tgattaatgc ttgtataatg tgatgcaata    2700
aaatttaaaa taaatttctg cacatggaat attttc                              2736
```

```
<210> SEQ ID NO 4
<211> LENGTH: 2261
<212> TYPE: PRT
<213> ORGANISM: Homo sapiens
<220> FEATURE:
<221> NAME/KEY: misc_feature
<222> LOCATION: (780)..(780)
<223> OTHER INFORMATION: Xaa can be any naturally occurring amino acid
<220> FEATURE:
<221> NAME/KEY: misc_feature
<222> LOCATION: (1555)..(1555)
<223> OTHER INFORMATION: Xaa can be any naturally occurring amino acid
<220> FEATURE:
<221> NAME/KEY: misc_feature
<222> LOCATION: (1648)..(1648)
<223> OTHER INFORMATION: Xaa can be any naturally occurring amino acid
<220> FEATURE:
<221> NAME/KEY: misc_feature
<222> LOCATION: (1974)..(1974)
<223> OTHER INFORMATION: Xaa can be any naturally occurring amino acid
<220> FEATURE:
<221> NAME/KEY: misc_feature
<222> LOCATION: (2168)..(2168)
<223> OTHER INFORMATION: Xaa can be any naturally occurring amino acid

<400> SEQUENCE: 4

Met Ala Cys Trp Pro Gln Leu Arg Leu Leu Trp Lys Asn Leu Thr
1               5                   10                  15

Phe Arg Arg Arg Gln Thr Cys Gln Leu Leu Glu Val Ala Trp Pro
                20                  25                  30

Leu Phe Ile Phe Leu Ile Leu Ile Ser Val Arg Leu Ser Tyr Pro Pro
            35                  40                  45

Tyr Glu Gln His Glu Cys His Phe Pro Asn Lys Ala Met Pro Ser Ala
        50                  55                  60

Gly Thr Leu Pro Trp Val Gln Gly Ile Ile Cys Asn Ala Asn Asn Pro
65                  70                  75                  80

Cys Phe Arg Tyr Pro Thr Pro Gly Glu Ala Pro Gly Val Val Gly Asn
                85                  90                  95

Phe Asn Lys Ser Ile Val Ala Arg Leu Phe Ser Asp Ala Arg Arg Leu
            100                 105                 110

Leu Leu Tyr Ser Gln Lys Asp Thr Ser Met Lys Asp Met Arg Lys Val
        115                 120                 125
```

Leu Arg Thr Leu Gln Gln Ile Lys Lys Ser Ser Asn Leu Lys Leu
130                 135                 140

Gln Asp Phe Leu Val Asp Asn Glu Thr Phe Ser Gly Phe Leu Tyr His
145                 150                 155                 160

Asn Leu Ser Leu Pro Lys Ser Thr Val Asp Lys Met Leu Arg Ala Asp
                165                 170                 175

Val Ile Leu His Lys Val Phe Leu Gln Gly Tyr Gln Leu His Leu Thr
                180                 185                 190

Ser Leu Cys Asn Gly Ser Lys Ser Glu Glu Met Ile Gln Leu Gly Asp
                195                 200                 205

Gln Glu Val Ser Glu Leu Cys Gly Leu Pro Arg Glu Lys Leu Ala Ala
210                 215                 220

Ala Glu Arg Val Leu Arg Ser Asn Met Asp Ile Leu Lys Pro Ile Leu
225                 230                 235                 240

Arg Thr Leu Asn Ser Thr Ser Pro Phe Pro Ser Lys Glu Leu Ala Glu
                245                 250                 255

Ala Thr Lys Thr Leu Leu His Ser Leu Gly Thr Leu Ala Gln Glu Leu
                260                 265                 270

Phe Ser Met Arg Ser Trp Ser Asp Met Arg Gln Glu Val Met Phe Leu
                275                 280                 285

Thr Asn Val Asn Ser Ser Ser Ser Thr Gln Ile Tyr Gln Ala Val
290                 295                 300

Ser Arg Ile Val Cys Gly His Pro Glu Gly Gly Leu Lys Ile Lys
305                 310                 315                 320

Ser Leu Asn Trp Tyr Glu Asp Asn Asn Tyr Lys Ala Leu Phe Gly Gly
                325                 330                 335

Asn Gly Thr Glu Glu Asp Ala Glu Thr Phe Tyr Asp Asn Ser Thr Thr
                340                 345                 350

Pro Tyr Cys Asn Asp Leu Met Lys Asn Leu Glu Ser Ser Pro Leu Ser
                355                 360                 365

Arg Ile Ile Trp Lys Ala Leu Lys Pro Leu Leu Val Gly Lys Ile Leu
                370                 375                 380

Tyr Thr Pro Asp Thr Pro Ala Thr Arg Gln Val Met Ala Glu Val Asn
385                 390                 395                 400

Lys Thr Phe Gln Glu Leu Ala Val Phe His Asp Leu Glu Gly Met Trp
                405                 410                 415

Glu Glu Leu Ser Pro Lys Ile Trp Thr Phe Met Glu Asn Ser Gln Glu
                420                 425                 430

Met Asp Leu Val Arg Met Leu Leu Asp Ser Arg Asp Asn Asp His Phe
                435                 440                 445

Trp Glu Gln Gln Leu Asp Gly Leu Asp Trp Thr Ala Gln Asp Ile Val
450                 455                 460

Ala Phe Leu Ala Lys His Pro Glu Asp Val Gln Ser Ser Asn Gly Ser
465                 470                 475                 480

Val Tyr Thr Trp Arg Glu Ala Phe Asn Glu Thr Asn Gln Ala Ile Arg
                485                 490                 495

Thr Ile Ser Arg Phe Met Glu Cys Val Asn Leu Asn Lys Leu Glu Pro
                500                 505                 510

Ile Ala Thr Glu Val Trp Leu Ile Asn Lys Ser Met Glu Leu Leu Asp
                515                 520                 525

Glu Arg Lys Phe Trp Ala Gly Ile Val Phe Thr Gly Ile Thr Pro Gly
                530                 535                 540

Ser Ile Glu Leu Pro His His Val Lys Tyr Lys Ile Arg Met Asp Ile

```
             545                 550                 555                 560
Asp Asn Val Glu Arg Thr Asn Lys Ile Lys Asp Gly Tyr Trp Asp Pro
                 565                 570                 575
Gly Pro Arg Ala Asp Pro Phe Glu Asp Met Arg Tyr Val Trp Gly Gly
                 580                 585                 590
Phe Ala Tyr Leu Gln Asp Val Glu Gln Ala Ile Ile Arg Val Leu
                 595                 600                 605
Thr Gly Thr Glu Lys Lys Thr Gly Val Tyr Met Gln Gln Met Pro Tyr
                 610                 615                 620
Pro Cys Tyr Val Asp Asp Ile Phe Leu Arg Val Met Ser Arg Ser Met
625                 630                 635                 640
Pro Leu Phe Met Thr Leu Ala Trp Ile Tyr Ser Val Ala Val Ile Ile
                 645                 650                 655
Lys Gly Ile Val Tyr Glu Lys Glu Ala Arg Leu Lys Glu Thr Met Arg
                 660                 665                 670
Ile Met Gly Leu Asp Asn Ser Ile Leu Trp Phe Ser Trp Phe Ile Ser
                 675                 680                 685
Ser Leu Ile Pro Leu Leu Val Ser Ala Gly Leu Leu Val Ile Leu
         690                 695                 700
Lys Leu Gly Asn Leu Leu Pro Tyr Ser Asp Pro Ser Val Val Phe Val
705                 710                 715                 720
Phe Leu Ser Val Phe Ala Val Val Thr Ile Leu Gln Cys Phe Leu Ile
                 725                 730                 735
Ser Thr Leu Phe Ser Arg Ala Asn Leu Ala Ala Ala Cys Gly Gly Ile
                 740                 745                 750
Ile Tyr Phe Thr Leu Tyr Leu Pro Tyr Val Leu Cys Val Ala Trp Gln
             755                 760                 765
Asp Tyr Val Gly Phe Thr Leu Lys Ile Phe Ala Xaa Leu Leu Ser Pro
             770                 775                 780
Val Ala Phe Gly Phe Gly Cys Glu Tyr Phe Ala Leu Phe Glu Glu Gln
785                 790                 795                 800
Gly Ile Gly Val Gln Trp Asp Asn Leu Phe Glu Ser Pro Val Glu Glu
                 805                 810                 815
Asp Gly Phe Asn Leu Thr Thr Ser Val Ser Met Met Leu Phe Asp Thr
                 820                 825                 830
Phe Leu Tyr Gly Val Met Thr Trp Tyr Ile Glu Ala Val Phe Pro Gly
                 835                 840                 845
Gln Tyr Gly Ile Pro Arg Pro Trp Tyr Phe Pro Cys Thr Lys Ser Tyr
             850                 855                 860
Trp Phe Gly Glu Glu Ser Asp Glu Lys Ser His Pro Gly Ser Asn Gln
865                 870                 875                 880
Lys Arg Ile Ser Glu Ile Cys Met Glu Glu Pro Thr His Leu Lys
                 885                 890                 895
Leu Gly Val Ser Ile Gln Asn Leu Val Lys Val Tyr Arg Asp Gly Met
                 900                 905                 910
Lys Val Ala Val Asp Gly Leu Ala Leu Asn Phe Tyr Glu Gly Gln Ile
             915                 920                 925
Thr Ser Phe Leu Gly His Asn Gly Ala Gly Lys Thr Thr Thr Met Ser
             930                 935                 940
Ile Leu Thr Gly Leu Phe Pro Pro Thr Ser Gly Thr Ala Tyr Ile Leu
945                 950                 955                 960
Gly Lys Asp Ile Arg Ser Glu Met Ser Thr Ile Arg Gln Asn Leu Gly
                 965                 970                 975
```

-continued

```
Val Cys Pro Gln His Asn Val Leu Phe Asp Met Leu Thr Val Glu Glu
            980                 985                 990

His Ile Trp Phe Tyr Ala Arg Leu Lys Gly Leu Ser Glu Lys His Val
        995                1000                1005

Lys Ala Glu Met Glu Gln Met Ala Leu Asp Val Gly Leu Pro Ser
    1010                1015                1020

Ser Lys Leu Lys Ser Lys Thr Ser Gln Leu Ser Gly Gly Met Gln
    1025                1030                1035

Arg Lys Leu Ser Val Ala Leu Ala Phe Val Gly Gly Ser Lys Val
    1040                1045                1050

Val Ile Leu Asp Glu Pro Thr Ala Gly Val Asp Pro Tyr Ser Arg
    1055                1060                1065

Arg Gly Ile Trp Glu Leu Leu Leu Lys Tyr Arg Gln Gly Arg Thr
    1070                1075                1080

Ile Ile Leu Ser Thr His His Met Asp Glu Ala Asp Val Leu Gly
    1085                1090                1095

Asp Arg Ile Ala Ile Ile Ser His Gly Lys Leu Cys Cys Val Gly
    1100                1105                1110

Ser Ser Leu Phe Leu Lys Asn Gln Leu Gly Thr Gly Tyr Tyr Leu
    1115                1120                1125

Thr Leu Val Lys Lys Asp Val Glu Ser Ser Leu Ser Ser Cys Arg
    1130                1135                1140

Asn Ser Ser Ser Thr Val Ser Tyr Leu Lys Lys Glu Asp Ser Val
    1145                1150                1155

Ser Gln Ser Ser Ser Asp Ala Gly Leu Gly Ser Asp His Glu Ser
    1160                1165                1170

Asp Thr Leu Thr Ile Asp Val Ser Ala Ile Ser Asn Leu Ile Arg
    1175                1180                1185

Lys His Val Ser Glu Ala Arg Leu Val Glu Asp Ile Gly His Glu
    1190                1195                1200

Leu Thr Tyr Val Leu Pro Tyr Glu Ala Ala Lys Glu Gly Ala Phe
    1205                1210                1215

Val Glu Leu Phe His Glu Ile Asp Asp Arg Leu Ser Asp Leu Gly
    1220                1225                1230

Ile Ser Ser Tyr Gly Ile Ser Glu Thr Thr Leu Glu Glu Ile Phe
    1235                1240                1245

Leu Lys Val Ala Glu Glu Ser Gly Val Asp Ala Glu Thr Ser Asp
    1250                1255                1260

Gly Thr Leu Pro Ala Arg Arg Asn Arg Arg Ala Phe Gly Asp Lys
    1265                1270                1275

Gln Ser Cys Leu Arg Pro Phe Thr Glu Asp Asp Ala Ala Asp Pro
    1280                1285                1290

Asn Asp Ser Asp Ile Asp Pro Glu Ser Arg Glu Thr Asp Leu Leu
    1295                1300                1305

Ser Gly Met Asp Gly Lys Gly Ser Tyr Gln Val Lys Gly Trp Lys
    1310                1315                1320

Leu Thr Gln Gln Gln Phe Val Ala Leu Leu Trp Lys Arg Leu Leu
    1325                1330                1335

Ile Ala Arg Arg Ser Arg Lys Gly Phe Phe Ala Gln Ile Val Leu
    1340                1345                1350

Pro Ala Val Phe Val Cys Ile Ala Leu Val Phe Ser Leu Ile Val
    1355                1360                1365
```

```
Pro Pro Phe Gly Lys Tyr Pro Ser Leu Glu Leu Gln Pro Trp Met
1370                1375                1380

Tyr Asn Glu Gln Tyr Thr Phe Val Ser Asn Asp Ala Pro Glu Asp
    1385                1390                1395

Thr Gly Thr Leu Glu Leu Leu Asn Ala Leu Thr Lys Asp Pro Gly
1400                1405                1410

Phe Gly Thr Arg Cys Met Glu Gly Asn Pro Ile Pro Asp Thr Pro
    1415                1420                1425

Cys Gln Ala Gly Glu Glu Trp Thr Thr Ala Pro Val Pro Gln
1430                1435                1440

Thr Ile Met Asp Leu Phe Gln Asn Gly Asn Trp Thr Met Gln Asn
    1445                1450                1455

Pro Ser Pro Ala Cys Gln Cys Ser Ser Asp Lys Ile Lys Lys Met
1460                1465                1470

Leu Pro Val Cys Pro Pro Gly Ala Gly Leu Pro Pro Pro Gln
    1475                1480                1485

Arg Lys Gln Asn Thr Ala Asp Ile Leu Gln Asp Leu Thr Gly Arg
1490                1495                1500

Asn Ile Ser Asp Tyr Leu Val Lys Thr Tyr Val Gln Ile Ile Ala
    1505                1510                1515

Lys Ser Leu Lys Asn Lys Ile Trp Val Asn Glu Phe Arg Tyr Gly
1520                1525                1530

Gly Phe Ser Leu Gly Val Ser Asn Thr Gln Ala Leu Pro Pro Ser
    1535                1540                1545

Gln Glu Val Asn Asp Ala Xaa Lys Gln Met Lys Lys His Leu Lys
1550                1555                1560

Leu Ala Lys Asp Ser Ser Ala Asp Arg Phe Leu Asn Ser Leu Gly
    1565                1570                1575

Arg Phe Met Thr Gly Leu Asp Thr Arg Asn Asn Val Lys Val Trp
1580                1585                1590

Phe Asn Asn Lys Gly Trp His Ala Ile Ser Ser Phe Leu Asn Val
    1595                1600                1605

Ile Asn Asn Ala Ile Leu Arg Ala Asn Leu Gln Lys Gly Glu Asn
1610                1615                1620

Pro Ser His Tyr Gly Ile Thr Ala Phe Asn His Pro Leu Asn Leu
    1625                1630                1635

Thr Lys Gln Gln Leu Ser Glu Val Ala Xaa Met Thr Thr Ser Val
1640                1645                1650

Asp Val Leu Val Ser Ile Cys Val Ile Phe Ala Met Ser Phe Val
    1655                1660                1665

Pro Ala Ser Phe Val Val Phe Leu Ile Gln Glu Arg Val Ser Lys
1670                1675                1680

Ala Lys His Leu Gln Phe Ile Ser Gly Val Lys Pro Val Ile Tyr
    1685                1690                1695

Trp Leu Ser Asn Phe Val Trp Asp Met Cys Asn Tyr Val Val Pro
1700                1705                1710

Ala Thr Leu Val Ile Ile Ile Phe Ile Cys Phe Gln Gln Lys Ser
    1715                1720                1725

Tyr Val Ser Ser Thr Asn Leu Pro Val Leu Ala Leu Leu Leu Leu
1730                1735                1740

Leu Tyr Gly Trp Ser Ile Thr Pro Leu Met Tyr Pro Ala Ser Phe
    1745                1750                1755

Val Phe Lys Ile Pro Ser Thr Ala Tyr Val Val Leu Thr Ser Val
```

```
                1760                1765                1770
Asn Leu Phe Ile Gly Ile Asn Gly Ser Val Ala Thr Phe Val Leu
    1775                1780                1785
Glu Leu Phe Thr Asp Asn Lys Leu Asn Asn Ile Asn Asp Ile Leu
    1790                1795                1800
Lys Ser Val Phe Leu Ile Phe Pro His Phe Cys Leu Gly Arg Gly
    1805                1810                1815
Leu Ile Asp Met Val Lys Asn Gln Ala Met Ala Asp Ala Leu Glu
    1820                1825                1830
Arg Phe Gly Glu Asn Arg Phe Val Ser Pro Leu Ser Trp Asp Leu
    1835                1840                1845
Val Gly Arg Asn Leu Phe Ala Met Ala Val Glu Gly Val Val Phe
    1850                1855                1860
Phe Leu Ile Thr Val Leu Ile Gln Tyr Arg Phe Phe Ile Arg Pro
    1865                1870                1875
Arg Pro Val Asn Ala Lys Leu Ser Pro Leu Asn Asp Glu Asp Glu
    1880                1885                1890
Asp Val Arg Arg Glu Arg Gln Arg Ile Leu Asp Gly Gly Gly Gln
    1895                1900                1905
Asn Asp Ile Leu Glu Ile Lys Glu Leu Thr Lys Ile Tyr Arg Arg
    1910                1915                1920
Lys Arg Lys Pro Ala Val Asp Arg Ile Cys Val Gly Ile Pro Pro
    1925                1930                1935
Gly Glu Cys Phe Gly Leu Leu Gly Val Asn Gly Ala Gly Lys Ser
    1940                1945                1950
Ser Thr Phe Lys Met Leu Thr Gly Asp Thr Thr Val Thr Arg Gly
    1955                1960                1965
Asp Ala Phe Leu Asn Xaa Asn Ser Ile Leu Ser Asn Ile His Glu
    1970                1975                1980
Val His Gln Asn Met Gly Tyr Cys Pro Gln Phe Asp Ala Ile Thr
    1985                1990                1995
Glu Leu Leu Thr Gly Arg Glu His Val Glu Phe Phe Ala Leu Leu
    2000                2005                2010
Arg Gly Val Pro Glu Lys Glu Val Gly Lys Val Gly Glu Trp Ala
    2015                2020                2025
Ile Arg Lys Leu Gly Leu Val Lys Tyr Gly Glu Lys Tyr Ala Gly
    2030                2035                2040
Asn Tyr Ser Gly Gly Asn Lys Arg Lys Leu Ser Thr Ala Met Ala
    2045                2050                2055
Leu Ile Gly Gly Pro Pro Val Val Phe Leu Asp Glu Pro Thr Thr
    2060                2065                2070
Gly Met Asp Pro Lys Ala Arg Arg Phe Leu Trp Asn Cys Ala Leu
    2075                2080                2085
Ser Val Val Lys Glu Gly Arg Ser Val Val Leu Thr Ser His Ser
    2090                2095                2100
Met Glu Glu Cys Glu Ala Leu Cys Thr Arg Met Ala Ile Met Val
    2105                2110                2115
Asn Gly Arg Phe Arg Cys Leu Gly Ser Val Gln His Leu Lys Asn
    2120                2125                2130
Arg Phe Gly Asp Gly Tyr Thr Ile Val Val Arg Ile Ala Gly Ser
    2135                2140                2145
Asn Pro Asp Leu Lys Pro Val Gln Asp Phe Phe Gly Leu Ala Phe
    2150                2155                2160
```

```
Pro Gly Ser Val Xaa Lys Glu Lys His Arg Asn Met Leu Gln Tyr
    2165            2170                2175

Gln Leu Pro Ser Ser Leu Ser Ser Leu Ala Arg Ile Phe Ser Ile
    2180            2185                2190

Leu Ser Gln Ser Lys Lys Arg Leu His Ile Glu Asp Tyr Ser Val
    2195            2200                2205

Ser Gln Thr Thr Leu Asp Gln Val Phe Val Asn Phe Ala Lys Asp
    2210            2215                2220

Gln Ser Asp Asp Asp His Leu Lys Asp Leu Ser Leu His Lys Asn
    2225            2230                2235

Gln Thr Val Val Asp Val Ala Val Leu Thr Ser Phe Leu Gln Asp
    2240            2245                2250

Glu Lys Val Lys Glu Ser Tyr Val
    2255            2260

<210> SEQ ID NO 5
<211> LENGTH: 1660
<212> TYPE: DNA
<213> ORGANISM: Homo sapiens

<400> SEQUENCE: 5
tctatgaaac caacatacat ggcgtttgca tcacagttgg agtcagatgt gagcccggag      60
ggcaggtgtc tggcttgtcc acccggaagc cctgagggca gctgttccca ctggctctgc     120
tgaccttgtg ccttggacgg ctgtcctcag cgaggggccg tgcacccgct cctgagcagc     180
gccatgggcc tgctggcctt cctgaagacc cagttcgtgc tgcacctgct ggtcggcttt     240
gtcttcgtgg tgagtggtct ggtcatcaac ttcgtccagc tgtgcacgct ggcgctctgg     300
ccggtcagca agcagctcta ccgccgcctc aactgccgcc tcgcatactc actctggagc     360
caactggtca tgctgctgga gtggtggtcc tgcacggagt gtacactgtt cacggaccag     420
gccacggtag agcgctttgg gaaggagcac gcagtcatca tcctcaacca aacttcgag     480
atcgacttcc tctgtgggtg gaccatgtgt gagcgcttcg gagtgctggg gagctccaag     540
gtcctcgcta agaaggagct gctctacgtg cccctcatcg gctggacgtg gtactttctg     600
gagattgtgt tctgcaagcg gaagtgggag gaggaccggg acaccgtggt cgaagggctg     660
aggcgcctgt cggactaccc cgagtacatg tggtttctcc tgtactgcga ggggacgcgc     720
ttcacggaga ccaagcaccg cgttagcatg gaggtggcgg ctgctaaggg gcttcctgtc     780
ctcaagtacc acctgctgcc gcggaccaag ggcttcacca ccgcagtcaa gtgcctccgg     840
gggacagtcg cagctgtcta tgatgtaacc ctgaacttca gaggaaacaa gaacccgtcc     900
ctgctgggga tcctctacgg gaagaagtac gaggcggaca tgtgcgtgag agatttcct     960
ctggaagaca tcccgctgga tgaaaaggaa gcagctcagt ggcttcataa actgtaccag    1020
gagaaggacg cgctccagga gatatataat cagaagggca tgtttccagg ggagcagttt    1080
aagcctgccc ggaggccgtg gaccctcctg aacttcctgt cctgggccac cattctcctg    1140
tctcccctct tcagttttgt cttgggcgtc tttgccagcg atcacctct cctgatcctg    1200
actttcttgg ggtttgtggg agcagcttcc tttggagttc gcagactgat aggagtaact    1260
gagatagaaa aaggctccag ctacggaaac caagagttta agaaaaagga ataattaatg    1320
gctgtgactg aacacacgcg gccctgacgg tggtatccag ttaactcaaa accaacacac    1380
agagtgcagg aaaagacaat tagaaactat ttttcttatt aactggtgac taatattaac    1440
aaaacttgag ccaagagtaa agaattcaga aggcctgtca ggtgaagtct tcagcctccc    1500
```

-continued

| | |
|---|---|
| acagcgcagg gtcccagcat ctccacgcgc gcccgtggga ggtgggtccg gccggagagg | 1560 |
| cctcccgcgg acgccgtctc tccagaactc cgcttccaag agggacccttt ggctgctttc | 1620 |
| tctccttaaa cttagatcaa attttaaaaa aaaaaaaaaa | 1660 |

<210> SEQ ID NO 6
<211> LENGTH: 1774
<212> TYPE: DNA
<213> ORGANISM: Homo sapiens

<400> SEQUENCE: 6

| | |
|---|---|
| tgaacccagc cggctccatc tcagcttctg gtttctaagt ccatgtgcca aaggctgcca | 60 |
| ggaaggagac gccttcctga gtcctggatc tttcttcctt ctggaaatct ttgactgtgg | 120 |
| gtagttattt atttctgaat aagagcgtcc acgcatcatg gacctcgcgg gactgctgaa | 180 |
| gtctcagttc ctgtgccacc tggtcttctg ctacgtcttt attgcctcag gctaatcat | 240 |
| caacaccatt cagctcttca ctctcctcct ctggcccatt aacaagcagc tcttccggaa | 300 |
| gatcaactgc agactgtcct attgcatctc aagccagctg gtgatgctgc tggagtggtg | 360 |
| gtcgggcacg gaatgcacca tcttcacgga cccgcgcgcc tacctcaagt atgggaagga | 420 |
| aaatgccatc gtggttctca accacaagtt tgaaattgac tttctgtgtg ctggagcct | 480 |
| gtccgaacgc tttgggctgt tagggggctc caaggtcctg gccaagaaag agctggccta | 540 |
| tgtcccaatt atcggctgga tgtggtactt caccgagatg gtcttctgtt cgcgcaagtg | 600 |
| ggagcaggat cgcaagacgg ttgccaccag tttgcagcac ctccgggact accccgagaa | 660 |
| gtatttttc ctgattcact gtgagggcac acggttcacg gagaagaagc atgagatcag | 720 |
| catgcaggtg gcccgggcca aggggctgcc tcgcctcaag catcacctgt tgccacgaac | 780 |
| caagggcttc gccatcaccg tgaggagctt gagaaatgta gtttcagctg tatatgactg | 840 |
| tacactcaat ttcagaaata tgaaaatcc aacactgctg ggagtcctaa acggaaagaa | 900 |
| ataccatgca gatttgtatg ttaggaggat cccactggaa gacatccctg aagacgatga | 960 |
| cgagtgctcg gcctggctgc acaagctcta ccaggagaag gatgcctttc aggaggagta | 1020 |
| ctacaggacg ggcaccttcc cagagacgcc catggtgccc cccggcggc cctggaccct | 1080 |
| cgtgaactgg ctgtttggg cctcgctggt gctctaccct tcttccagt cctggtcag | 1140 |
| catgatcagg agcgggtctt ccctgacgct ggccagcttc atcctcgtct ctttgtggc | 1200 |
| ctccgtggga gttcgatgga tgattggtgt gacggaaatt gacaagggct ctgcctacgg | 1260 |
| caactctgac agcaagcaga aactgaatga ctgactcagg gaggtgtcac catccgaagg | 1320 |
| gaaccttggg gaactggtgg cctctgcata tcctccttag tgggacacgg tgacaaaggc | 1380 |
| tgggtgagcc cctgctgggc acggcggaag tcacgacctc tccagccagg gagtctggtc | 1440 |
| tcaaggccgg atggggagga agatgttttg taatcttttt ttccccatgt gctttagtgg | 1500 |
| gctttggttt tcttttgtg cgagtgtgtg tgagaatggc tgtgtggtga gtgtgaactt | 1560 |
| tgttctgtga tcatagaaag ggtattttag gctgcagggg agggcagggc tggggaccga | 1620 |
| aggggacaag ttccccttc atcctttggt gctgagtttt ctgtaaccct tggttgccag | 1680 |
| agataaagtg aaaagtgctt taggtgagat gactaaatta tgcctccaag aaaaaaaaat | 1740 |
| taaagtgctt ttctgggtca aaaaaaaaaa aaaa | 1774 |

<210> SEQ ID NO 7
<211> LENGTH: 3000
<212> TYPE: DNA

```
<213> ORGANISM: Homo sapiens
<220> FEATURE:
<221> NAME/KEY: misc_feature
<222> LOCATION: (173)..(173)
<223> OTHER INFORMATION: n is a, c, g, or t

<400> SEQUENCE: 7
```

| | | | | | |
|---|---|---|---|---|---|
| gggcggacct | aaagggcctc | gggccgctcg | ggccgggaat | ggcggcggcg | gccgagcccg | 60 |
| gggcccgcgc | ctggctgggc | ggcggctccc | cgcgccccgg | cagcccggcc | tgcagccccg | 120 |
| tgctgggctc | aggaggccgc | gcgcgcccgg | ggccggggcc | ggggccggga | cgngaccgag | 180 |
| cgggcggcgt | cagagcccgg | gcccgtgccg | cgccgggaca | cagcttccgg | aaggtgacgc | 240 |
| tcaccaagcc | caccttctgc | cacctctgct | ccgacttcat | ctgggggctg | gccggcttcc | 300 |
| tgtgcgacgt | ctgcaatttc | atgtctcatg | agaagtgcct | gaagcacgtg | aggatcccgt | 360 |
| gcacgagtgt | ggcacccagc | ctggtccggg | ttcctgtagc | ccactgcttc | ggccccggg | 420 |
| ggctccacaa | gcgcaagttc | tgtgctgtct | gccgcaaggt | cctggaggca | ccggcgctcc | 480 |
| actgcgaagt | gtgtgagctg | cacctccacc | cagactgtgt | gcccttcgcc | tgcagtgact | 540 |
| gccgccagtg | ccaccaggat | gggcaccagg | atcacgacac | ccatcaccac | cactggcggg | 600 |
| aggggaacct | gccctcggga | gcgcgctgcg | aggtctgcag | gaagacgtgc | ggctcctctg | 660 |
| acgtgctggc | cggcgtgcgc | tgcgagtggt | gcggggtcca | ggcgcactcc | ctctgctccg | 720 |
| cggcactggc | tcccgagtgt | ggcttcgggc | gtctgcgctc | cctggtcctg | cctcccgcgt | 780 |
| gcgtgcgcct | tctgcccggc | ggcttcagca | agacgcagag | cttccgcatc | gtggaggccg | 840 |
| cggagccggc | cgagggggc | gacggcgccg | acggagcgc | tgccgtgggt | ccaggcagag | 900 |
| agacacaggc | aactccggag | tccgggaagc | aaacgctgaa | gatctttgat | ggcgacgacg | 960 |
| cggtgagaag | aagccagttc | cgcctcgtca | cggtgtcccg | cctggccggt | gccgaggagg | 1020 |
| tgctggaggc | cgcactgcgg | gcccaccaca | tccccgagga | ccctggccac | ctggagctgt | 1080 |
| gccgctgccc | cccttcctct | caggcctgtg | acgcctgggc | tggggcaag | ctgggagtg | 1140 |
| ctgtgatctc | ggaggagggc | agaagccccg | ggtccggcga | ggccacgcca | gaggcctggg | 1200 |
| tcatccgggc | tctgccgcgg | gcccaggagg | tcctgaagat | ctaccctggc | tggctcaagg | 1260 |
| tgggcgtggc | ctacgtgtcc | gtgcgagtga | cccctaagag | cacggctcgc | tctgtggtgc | 1320 |
| tggaggtcct | gccgctgctc | ggccgccagg | ccgagagtcc | cgagagcttc | cagctggtgg | 1380 |
| aggtggcgat | gggctgcagg | cacgtccagc | ggacgatgct | gatggacgaa | cagcccctgc | 1440 |
| tggaccggct | acaggacatc | cggcagatgt | ctgtgcggca | ggtgagccag | acgcggttct | 1500 |
| acgtggcaga | gagcagggat | gtagccccgc | acgtctccct | gtttgttggc | ggcctgcctc | 1560 |
| ccggcctgtc | tcccgaggag | tacagcagcc | tgctgcatga | ggccgggct | accaaagcca | 1620 |
| ccgtggtgtc | cgtgagtcac | atctactcct | cccaaggcgc | ggtagtgttg | gacgttgcct | 1680 |
| gctttgcgga | ggccgagcgg | ctgtacatgc | tgctgaagga | catggctgtg | cggggccggc | 1740 |
| tgctcactgc | cctggtgctc | cccgacctgc | tgcacgcgaa | gctgccccca | gacagctgtc | 1800 |
| ccctccttgt | gttcgtgaac | cccaagagtg | gaggcctcaa | gggccgagac | ctgctctgca | 1860 |
| gcttccggaa | gctactgaac | cctcatcagg | tcttcgacct | gaccaacgga | ggtcctcttc | 1920 |
| ccgggctcca | cctgttctcc | caggtgccct | gcttccgggt | gctggtgtgt | ggtggcgatg | 1980 |
| gcactgtggg | ctgggtgctt | ggcgccctgg | aggagacacg | gtaccgactg | gcctgcccgg | 2040 |
| agccttctgt | ggccatcctg | cccctgggca | cagggaatga | ccttggtcga | gtcctccgct | 2100 |
| gggggggcgg | ctacagcggc | gaggacccgt | tctccgtact | gctgtctgtg | gacgaggccg | 2160 |

```
acgccgtgct catggaccgc tggaccatcc tgctggatgc ccacgaagct ggcagtgcag    2220
agaacgacac ggcagacgca gagccccca agatcgtgca gatgagtaac tactgtggca    2280
ttggcatcga cgcggagctg agcctggact ccaccaggc acgggaagag gagcctggca    2340
agttcacaag caggctgcac aacaagggtg tgtacgtgcg ggtggggctg cagaagatca    2400
gtcactctcg gagcctgcac aagcagatcc ggctgcaggt ggagcggcag gaggtggagc    2460
tgcccagtat tgaaggcctc atcttcatca acatccccag ctggggctcg ggggccgacc    2520 tgtgggctc cgacagcgac accaggtttg agaagccacg catggacgac gggctgctgg    2580
aggttgtggg cgtgacgggc gtcgtgcaca tgggccaggt ccagggtggg ctgcgctccg    2640
gaatccggat tgcccagggt tcctacttcc gagtcacgct cctcaaggcc accccggtgc    2700
aggtggacgg ggagccctgg gtccaggccc cggggcacat gatcatctca gctgctggcc    2760
ctaaggtgca catgctgagg aaggccaagc agaagccgag gagggccggg accaccaggg    2820
atgcccgggc ggatcgtgcg cctgcccctg agagcgatcc taggtagggg tggctggggc    2880
agcccaaggg ctcgagccat ctctgctccc gccagccttg ttttcaggtg gtctggaggc    2940
agctccacgt cacacagtgg ctgtcatata ttgaagttac cttcccactg gaaaaaaat    3000
```

<210> SEQ ID NO 8
<211> LENGTH: 2215
<212> TYPE: DNA
<213> ORGANISM: Homo sapiens

<400> SEQUENCE: 8

```
gtggctcgga ccgccgcctg aatgtacctc gctcccggga gccggacggc ccagtagggc      60
gcactggagg acgctccgct gcgggagcct ggacagtttt tgacggtgca gtcttgctat     120
atggtgtgag aaatggctgt aggaaacaac actcaacgaa gttattccat catcccgtgt     180
tttatatttg ttgagcttgt catcatggct gggacagtgc tgcttgccta ctacttcgaa     240
tgcactgaca cttttcaggt gcatatccaa ggattcttct gtcaggacgg agacttaatg     300
aagccttacc cagggacaga ggaagaaagc ttcatcaccc ctctggtgct ctattgtgtg     360
ctggctgcca ccccaactgc tattattttt attggtgaga tatccatgta tttcataaaa     420
tcaacaagag aatccctgat tgctcaggag aaaacaattc tgaccggaga atgctgttac     480
ctgaacccct tacttcgaag gatcataaga ttcacagggg tgtttgcatt tggacttttt     540
gctactgaca tttttgtaaa cgccggacaa gtggtcactg ggcacttaac gccatacttc     600
ctgactgtgt gcaagccaaa ctacaccagt gcagactgcc aagcgcacca ccagtttata     660
aacaatggga acatttgtac tggggacctg gaagtgatag aaaaggctcg gagatccttt     720
ccctccaaac acgctgctct gagcatttac tccgccttat atgccacgat gtatattaca     780
agcacaatca agacgaagag cagtcgactg gccaagccgg tgctgtgcct cggaactctc     840
tgcacagcct tcctgacagg cctcaaccgg gtctctgagt atcggaacca ctgctcggac     900
gtgattgctg gtttcatcct gggcactgca gtggccctgt tctgggaat gtgtgtggtt     960 cataacttta aaggaacgca aggatctcct tccaaaccca gcctgaggga tccccgtgga    1020
gtacccctaa tggctttccc aaggatagaa agccctctgg aaaccttaag tgcacagaat    1080
cactctgcgt ccatgaccga agttacctga cgacgatgat gtgtcacaag ctgttttta    1140 aaatcatctt ccaattctat acttcaaaac acacagttgc tcaatgtcaa actgtgatga    1200
caaatattac gtttatctag ttagaagcta atgttttgta catttttgt atgaggaagt    1260
```

-continued

```
gatgtagctt gccctgattt ttttttttttt ttttggtcag ctttaatata tttatgccag    1320
aattttaaaa ccaacaaaat tttcttgttc aagcgtgcat tgaagaacca catttattca    1380
atggttgacg ttgttttgtg atatttgtac acaaattttc ttttctcagt tttataaaca    1440
cagaagtaaa tataacaatt cactttaaac ttttattacc acagttgctg cctcctccag    1500 aattttgaa ttttaataaa aggcaaactt ttgagctgca ggaaggacaa tgttggttaa     1560
taataaatct caaagtcaat tgtagaaaaa aaattgtctt caaaagaat gttgcactct      1620 gatctcttaa caaattgtta cgttcaaagt ttaaagtgat atattaacaa agtcacctag    1680
ttatacaaac aattgtcaga gaattctgga tttggagggt attggggtta tatgattctt    1740
tcttagataa tggcctctac taaataactc aagatctttc tggaatgtct tctggcaggc    1800
aggtgccact gtcagctttt ctccaaaaag cagccaacat cagcctcccc tgtcaactca    1860
acagttttgt atctcatatt atatggactt tatatgaaaa tgaatatttt acagtttgca    1920
cagtattatt ttacagaaaa ggaatcagag aatctacaac atagggcccc agaacaacag    1980
tttcactttg tggcttttaa ttattctaga attttaactg catctcattt ttctagcatg    2040
gtgagaacta atatgtaact cctttgattg aaggagctct tttgtccgta cctatcagaa    2100
tgttttcttg acacttccat gttggctctt ctcagctttt tttgtacata ttttttttt    2160 ctaaagagaa gaaaagtta tcacaaaatg taaaaaaga aaaaaaaaaa aaaaa          2215
```

<210> SEQ ID NO 9
<211> LENGTH: 20
<212> TYPE: DNA
<213> ORGANISM: Artificial Sequence
<220> FEATURE:
<223> OTHER INFORMATION: synthetic construct; primer

<400> SEQUENCE: 9
cgtttccggg aagtgtccta                                                20

<210> SEQ ID NO 10
<211> LENGTH: 24
<212> TYPE: DNA
<213> ORGANISM: Artificial Sequence
<220> FEATURE:
<223> OTHER INFORMATION: synthetic construct; primer

<400> SEQUENCE: 10
gctagagatg acaaggagga tgga                                           24

<210> SEQ ID NO 11
<211> LENGTH: 20
<212> TYPE: DNA
<213> ORGANISM: Artificial Sequence
<220> FEATURE:
<223> OTHER INFORMATION: synthetic construct; primer

<400> SEQUENCE: 11
agtgctcagc cttcgtacag                                                20

<210> SEQ ID NO 12
<211> LENGTH: 20
<212> TYPE: DNA
<213> ORGANISM: Artificial Sequence
<220> FEATURE:
<223> OTHER INFORMATION: synthetic construct; primer

<400> SEQUENCE: 12
aggcgcgtac aggattttgg                                                20

```
<210> SEQ ID NO 13
<211> LENGTH: 22
<212> TYPE: DNA
<213> ORGANISM: Artificial Sequence
<220> FEATURE:
<223> OTHER INFORMATION: synthetic construct; primer

<400> SEQUENCE: 13
tttgagggat ttgggtctga ac                                              22

<210> SEQ ID NO 14
<211> LENGTH: 23
<212> TYPE: DNA
<213> ORGANISM: Artificial Sequence
<220> FEATURE:
<223> OTHER INFORMATION: synthetic construct; primer

<400> SEQUENCE: 14
cccctttaat cgttttgtct gct                                             23

<210> SEQ ID NO 15
<211> LENGTH: 20
<212> TYPE: DNA
<213> ORGANISM: Artificial Sequence
<220> FEATURE:
<223> OTHER INFORMATION: synthetic construct; primer

<400> SEQUENCE: 15
gggatgcccg tgcctgcaat                                                 20

<210> SEQ ID NO 16
<211> LENGTH: 20
<212> TYPE: DNA
<213> ORGANISM: Artificial Sequence
<220> FEATURE:
<223> OTHER INFORMATION: synthetic construct; primer

<400> SEQUENCE: 16
ctggcagcta catggccccg                                                 20
```